US009301808B2

(12) United States Patent
Butler et al.

(10) Patent No.: US 9,301,808 B2
(45) Date of Patent: Apr. 5, 2016

(54) APPARATUS FOR INSERTING A SURGICAL DEVICE AT LEAST PARTIALLY THROUGH A WOUND OPENING

(71) Applicant: ATROPOS LIMITED, County Wicklow (IE)

(72) Inventors: John Butler, County Dublin (IE); Trevor Vaugh, County Offaly (IE); Frank Bonadio, County Wicklow (IE); Catherine Deegan, Dublin (IE); Shane J. MacNally, County Wicklow (IE)

(73) Assignee: Atropos Limited, Bray, County Wicklow (IE)

( * ) Notice: Subject to any disclaimer, the term of this patent is extended or adjusted under 35 U.S.C. 154(b) by 0 days.

(21) Appl. No.: 13/894,172

(22) Filed: May 14, 2013

(65) Prior Publication Data

US 2013/0338646 A1    Dec. 19, 2013

Related U.S. Application Data

(63) Continuation of application No. 11/347,803, filed on Feb. 6, 2006, now Pat. No. 8,465,494, which is a continuation-in-part of application No. 10/665,395, filed on Sep. 22, 2003, now Pat. No. 7,867,164, which (Continued)

(30) Foreign Application Priority Data

| Dec. 1, 1998 | (IE) | 980997 |
|---|---|---|
| Dec. 1, 1998 | (IE) | 980999 |
| Feb. 15, 1999 | (IE) | 990107 |
| Feb. 15, 1999 | (IE) | 990108 |
| Feb. 15, 1999 | (IE) | 990110 |
| Feb. 15, 1999 | (IE) | 990111 |
| Feb. 15, 1999 | (IE) | 990112 |
| May 24, 1999 | (IE) | 990416 |
| Oct. 14, 1999 | (IE) | 990861 |
| Dec. 16, 1999 | (IE) | 991053 |
| Feb. 18, 2000 | (EP) | 00650010 |
| Sep. 19, 2002 | (IE) | 20020754 |

(51) Int. Cl.
*A61B 1/32* (2006.01)
*A61B 19/00* (2006.01)

(Continued)

(52) U.S. Cl.
CPC .......... *A61B 19/22* (2013.01); *A61B 17/06109* (2013.01); *A61B 17/3417* (2013.01);
(Continued)

(58) Field of Classification Search
CPC .................. A61B 17/92; A61F 2/4611; A61F 2220/0025
USPC ............................. 606/99, 104, 916; 600/208
See application file for complete search history.

(56) References Cited

U.S. PATENT DOCUMENTS

| 4,705,040 A | 11/1987 | Mueller et al. |
|---|---|---|
| 5,085,661 A * | 2/1992 | Moss .......................... 606/139 |

(Continued)

FOREIGN PATENT DOCUMENTS

| DE | 199 15 061 A1 | 10/2000 |
|---|---|---|
| EP | 1 500 382 A1 | 1/2005 |

(Continued)

OTHER PUBLICATIONS

International Search Report in PCT/IE2006/000007 mailed May 8, 2006.

(Continued)

*Primary Examiner* — Sameh Boles
(74) *Attorney, Agent, or Firm* — Bookoff McAndrews, PLLC

(57) ABSTRACT

An apparatus (650) for inserting a distal ring (9) of a wound retractor device (2) through a wound opening comprises a bladeless tip (641) for creating the wound opening by forcing tissue apart, and a conveying device (5) for conveying the distal ring (9) through the wound opening. The conveying device (5) comprises a hook element (6) for engaging the distal ring (9) to convey the distal ring (9) through the wound opening, and a receiver housing (651) for receiving a seal (652) and a proximal ring (653) of the wound retractor device (2) to hold the seal (652) and the proximal ring (653) externally of the wound opening, and thus maintain a sleeve portion of the wound retractor device (2) in tension, during conveying of the distal ring (9) through the wound opening.

19 Claims, 108 Drawing Sheets

Related U.S. Application Data is a continuation-in-part of application No. 10/374,523, filed on Feb. 27, 2003, now Pat. No. 7,445,597, which is a continuation of application No. 09/849,341, filed on May 7, 2001, now Pat. No. 6,582,364, which is a continuation of application No. 09/688,138, filed on Oct. 16, 2000, now Pat. No. 6,254,534, said application No. 11/347,803 is a continuation-in-part of application No. 10/902,440, filed on Jul. 30, 2004, now abandoned, which is a continuation-in-part of application No. 10/736,234, filed on Dec. 16, 2003, now abandoned, said application No. 10/902,440 is a continuation-in-part of application No. 10/678,653, filed on Oct. 6, 2003, now Pat. No. 7,559,893, which is a continuation-in-part of application No. 10/133,979, filed on Apr. 29, 2002, now Pat. No. 6,846,287, which is a continuation of application No. 09/801,826, filed on Mar. 9, 2001, now abandoned, which is a continuation of application No. PCT/IE99/00122, filed on Dec. 1, 1999, said application No. 10/678,653 is a continuation-in-part of application No. 10/374,523, filed on Feb. 27, 2003, now Pat. No. 7,445,597, which is a continuation of application No. 09/849,341, filed on May 7, 2001, now Pat. No. 6,582,364, which is a continuation of application No. 09/688,138, filed on Oct. 16, 2000, now Pat. No. 6,254,534, said application No. 10/902,440 is a continuation-in-part of application No. 10/665,395, filed on Sep. 22, 2003, now Pat. No. 7,867,164, which is a continuation-in-part of application No. 10/374,523, filed on Feb. 27, 2003, now Pat. No. 7,445,597, which is a continuation of application No. 09/849,341, filed on May 7, 2001, now Pat. No. 6,582,364, which is a continuation of application No. 09/688,138, filed on Oct. 16, 2000, now Pat. No. 6,254,534, said application No. 10/902,440 is a continuation-in-part of application No. 10/374,523, filed on Feb. 27, 2003, now Pat. No. 7,445,597, which is a continuation of application No. 09/849,341, filed on May 7, 2001, now Pat. No. 6,582,364, which is a continuation of application No. 09/688,138, filed on Oct. 16, 2000, now Pat. No. 6,254,534, said application No. 10/902,440 is a continuation-in-part of application No. 10/315,233, filed on Dec. 10, 2002, now abandoned, which is a continuation of application No. 09/804,552, which is a continuation of application No. PCT/IE99/00123, filed on Dec. 1, 1999, now Pat. No. 6,578,577, said application No. 10/902,440 is a continuation-in-part of application No. 10/133,979, filed on Apr. 29, 2002, now Pat. No. 6,846,287, which is a continuation of application No. 09/801,826, which is a continuation of application No. PCT/IE99/00122, filed on Dec. 1, 1999, now abandoned.

(60) Provisional application No. 60/490,909, filed on Jul. 30, 2003, provisional application No. 60/433,603, filed on Dec. 16, 2002, provisional application No. 60/453,200, filed on Mar. 11, 2003, provisional application No. 60/428,215, filed on Nov. 22, 2002, provisional application No. 60/415,780, filed on Oct. 4, 2002, provisional application No. 60/650,197, filed on Feb. 4, 2005, provisional application No. 60/724,775, filed on Oct. 11, 2005, provisional application No. 60/740,634, filed on Nov. 30, 2005.

(51) Int. Cl.
| | |
|---|---|
| A61B 17/06 | (2006.01) |
| A61B 17/29 | (2006.01) |
| A61B 17/3209 | (2006.01) |
| A61B 17/34 | (2006.01) |
| A61B 18/04 | (2006.01) |
| A61B 18/14 | (2006.01) |
| A61B 17/00 | (2006.01) |
| A61B 17/32 | (2006.01) |

(52) U.S. Cl.
CPC ......... *A61B17/3421* (2013.01); *A61B 17/3423* (2013.01); *A61B 17/3431* (2013.01); *A61B 17/3468* (2013.01); *A61B 17/3476* (2013.01); *A61B 17/29* (2013.01); *A61B 17/32093* (2013.01); *A61B 17/3415* (2013.01); *A61B 17/3496* (2013.01); *A61B 18/04* (2013.01); *A61B 18/1487* (2013.01); *A61B 2017/00353* (2013.01); *A61B 2017/00473* (2013.01); *A61B 2017/06042* (2013.01); *A61B 2017/320044* (2013.01); *A61B 2017/3443* (2013.01); *A61B 2017/3484* (2013.01); *A61B 2017/3492* (2013.01); *A61B 2019/306* (2013.01); *A61B 2019/481* (2013.01)

(56) References Cited

U.S. PATENT DOCUMENTS

| | | | |
|---|---|---|---|
| 5,092,868 | A | 3/1992 | Mehdian |
| 5,391,156 | A | 2/1995 | Hildwein et al. |
| 5,395,309 | A | 3/1995 | Tanaka et al. |
| 5,738,628 | A | 4/1998 | Sierocuk et al. |
| 5,810,721 | A | 9/1998 | Mueller et al. |
| 5,817,111 | A | 10/1998 | Riza |
| 5,904,699 | A | 5/1999 | Schwemberger et al. |
| 5,916,232 | A | 6/1999 | Hart |
| 5,948,002 | A | 9/1999 | Bonutti |
| 6,048,309 | A | 4/2000 | Flom et al. |
| 6,059,816 | A | 5/2000 | Moenning |
| 6,171,282 | B1 | 1/2001 | Ragsdale |
| 6,582,364 | B2 | 6/2003 | Butler et al. |
| 6,884,253 | B1 | 4/2005 | McFarlane |
| 2001/0003791 | A1 | 6/2001 | Burbank et al. |
| 2001/0037053 | A1 | 11/2001 | Bonadio et al. |
| 2002/0151954 | A1 | 10/2002 | Brenneman |
| 2003/0009181 | A1 | 1/2003 | Gellman et al. |
| 2003/0073883 | A1 | 4/2003 | Stiles |
| 2004/0143158 | A1 | 7/2004 | Hart et al. |
| 2004/0181246 | A1 | 9/2004 | Heppler |
| 2005/0090717 | A1 | 4/2005 | Bonadio et al. |
| 2006/0074445 | A1* | 4/2006 | Gerber et al. ............... 606/191 |
| 2006/0111715 | A1* | 5/2006 | Jackson ............... 606/61 |

FOREIGN PATENT DOCUMENTS

| | | |
|---|---|---|
| JP | 2002-224129 A | 8/2002 |
| WO | WO 95/15123 A1 | 6/1995 |
| WO | WO 01/54588 A1 | 8/2001 |
| WO | WO 01/91652 A1 | 12/2001 |
| WO | WO 03/026512 A1 | 4/2003 |
| WO | WO 2004/026153 A1 | 4/2004 |
| WO | WO 2004/030547 A1 | 4/2004 |
| WO | WO 2005/009257 A2 | 2/2005 |
| WO | WO 2006/040748 A1 | 4/2006 |
| WO | WO 2006/082572 A1 | 8/2006 |

OTHER PUBLICATIONS

International Search Report and Written Opinion in PCT/IE2006/000007 mailed on Jul. 18, 2006.

\* cited by examiner

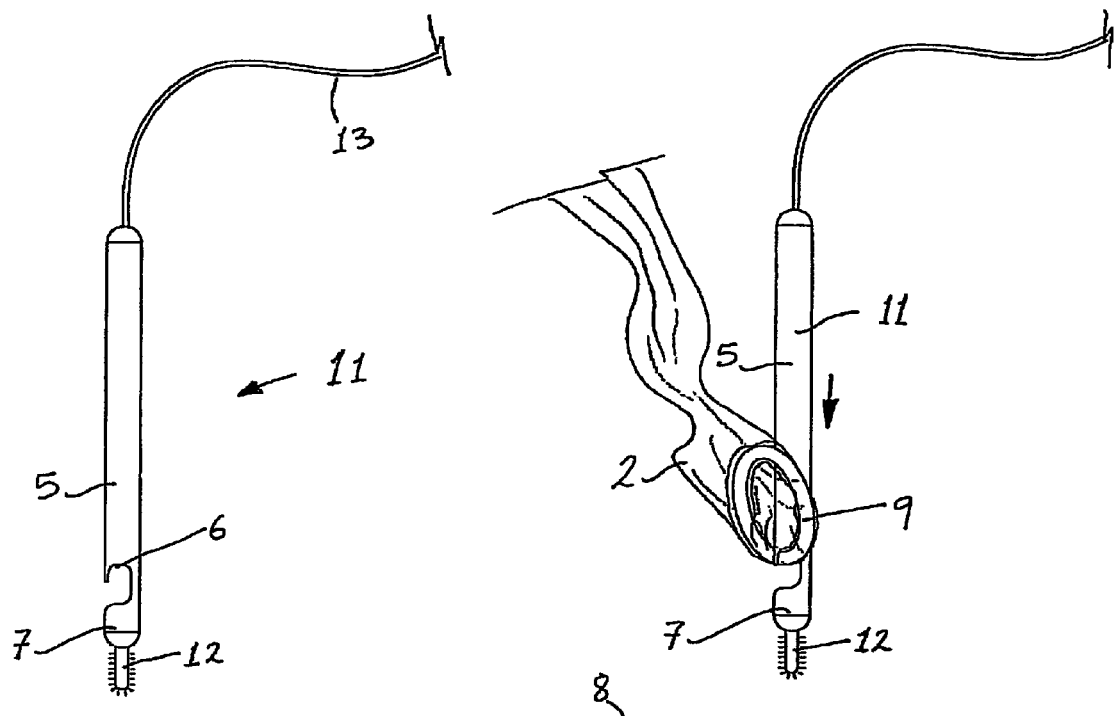

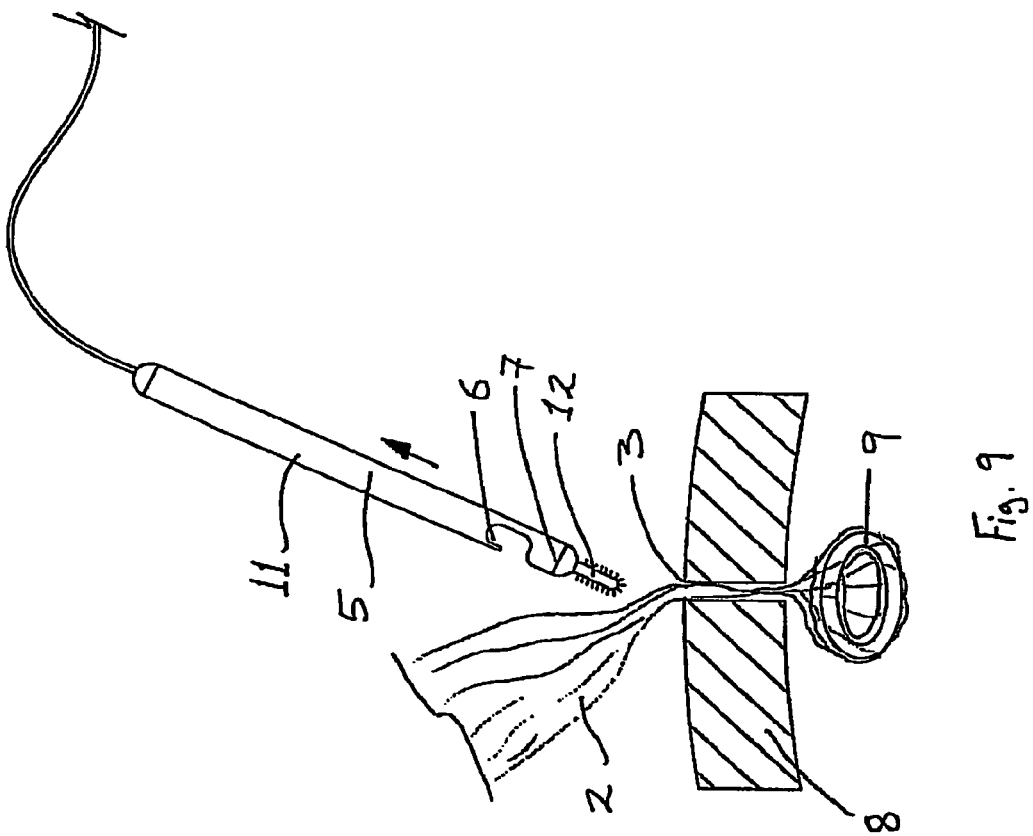
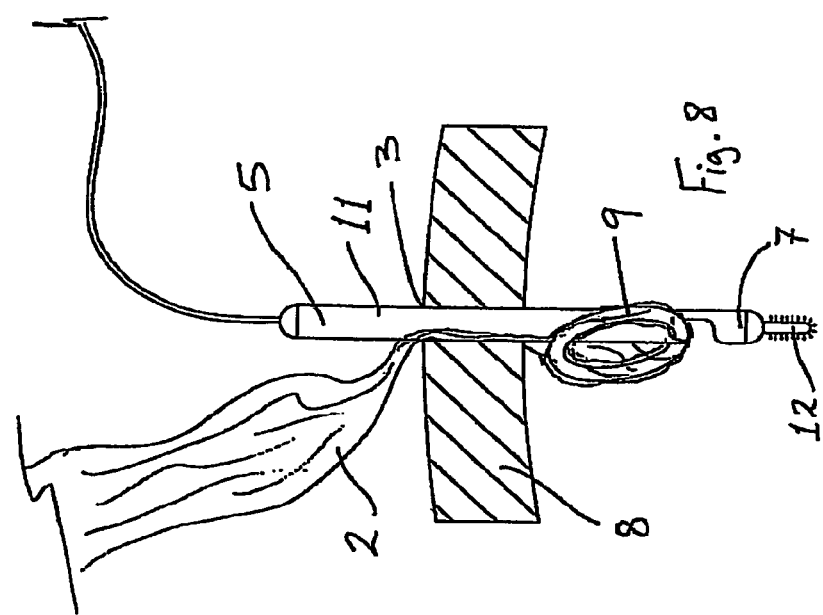

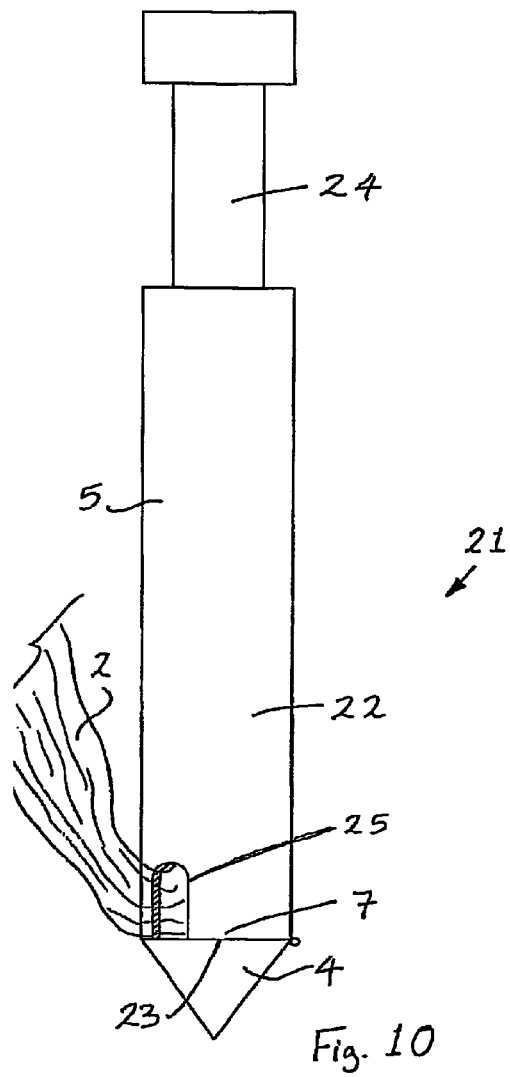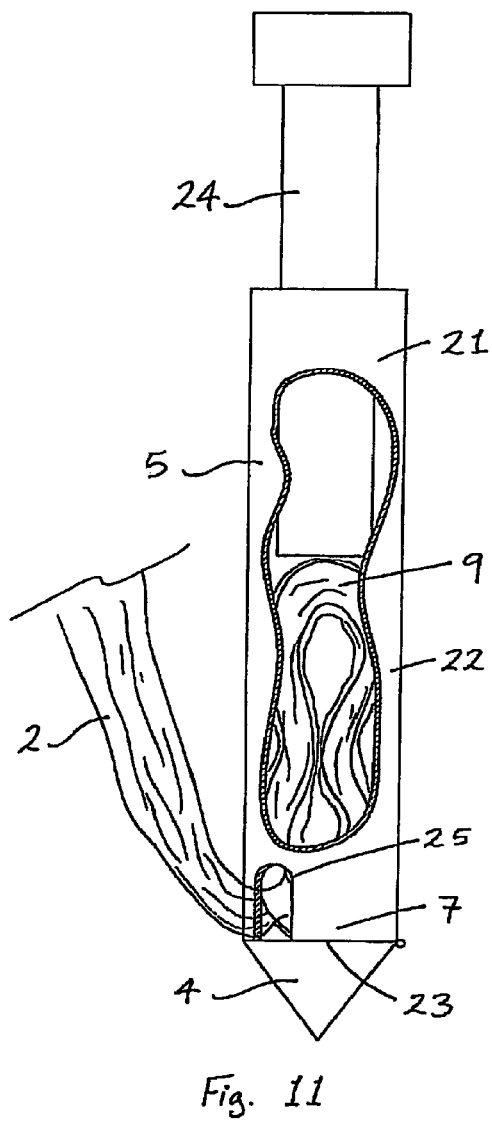
Fig. 10
Fig. 11

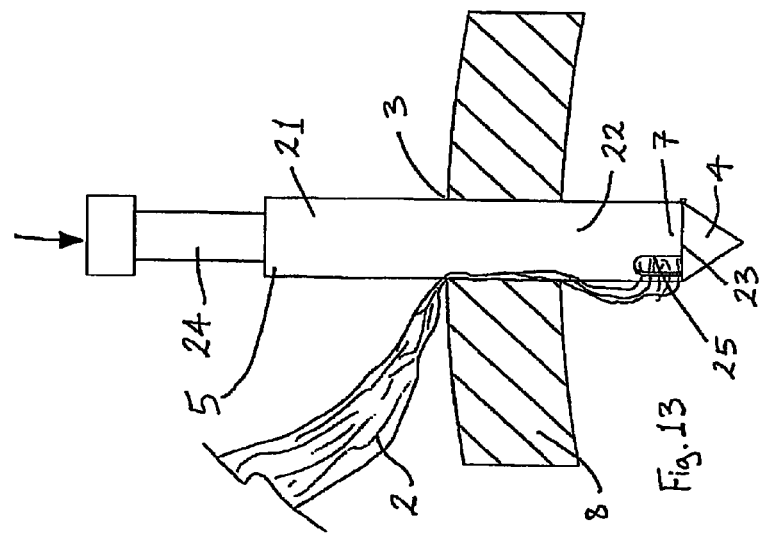
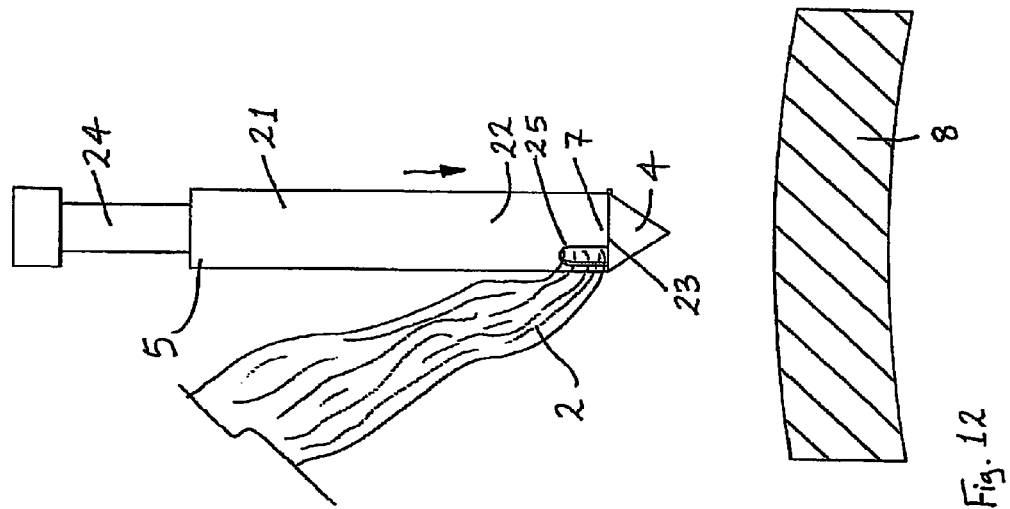

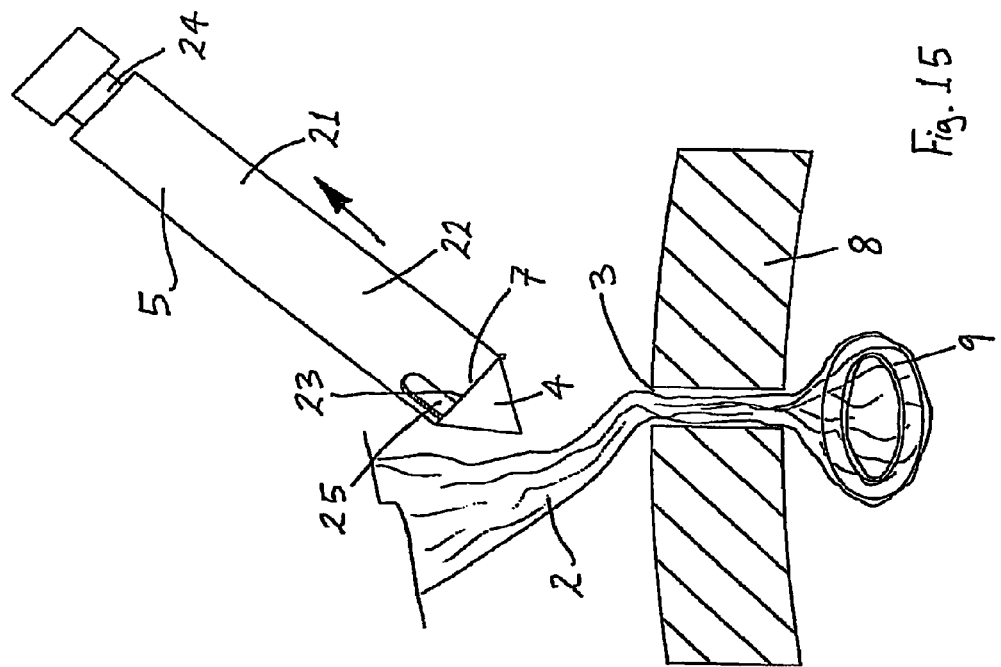
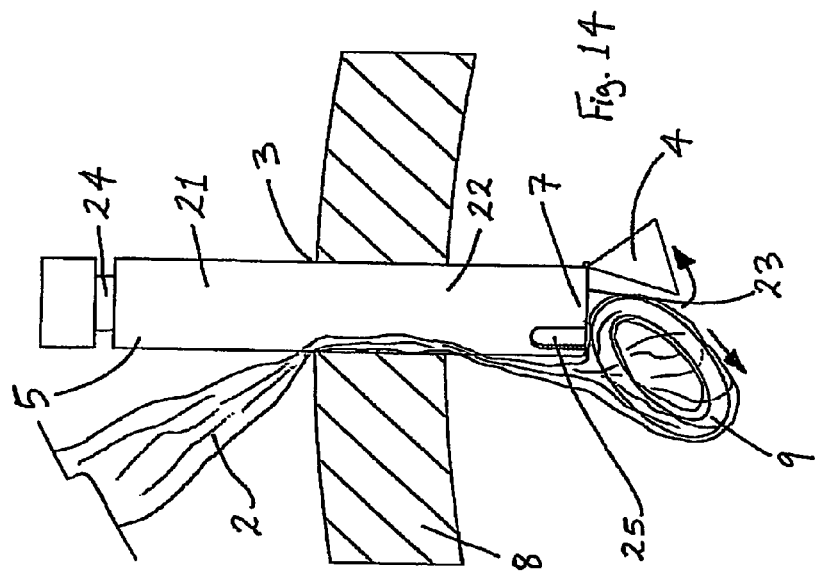

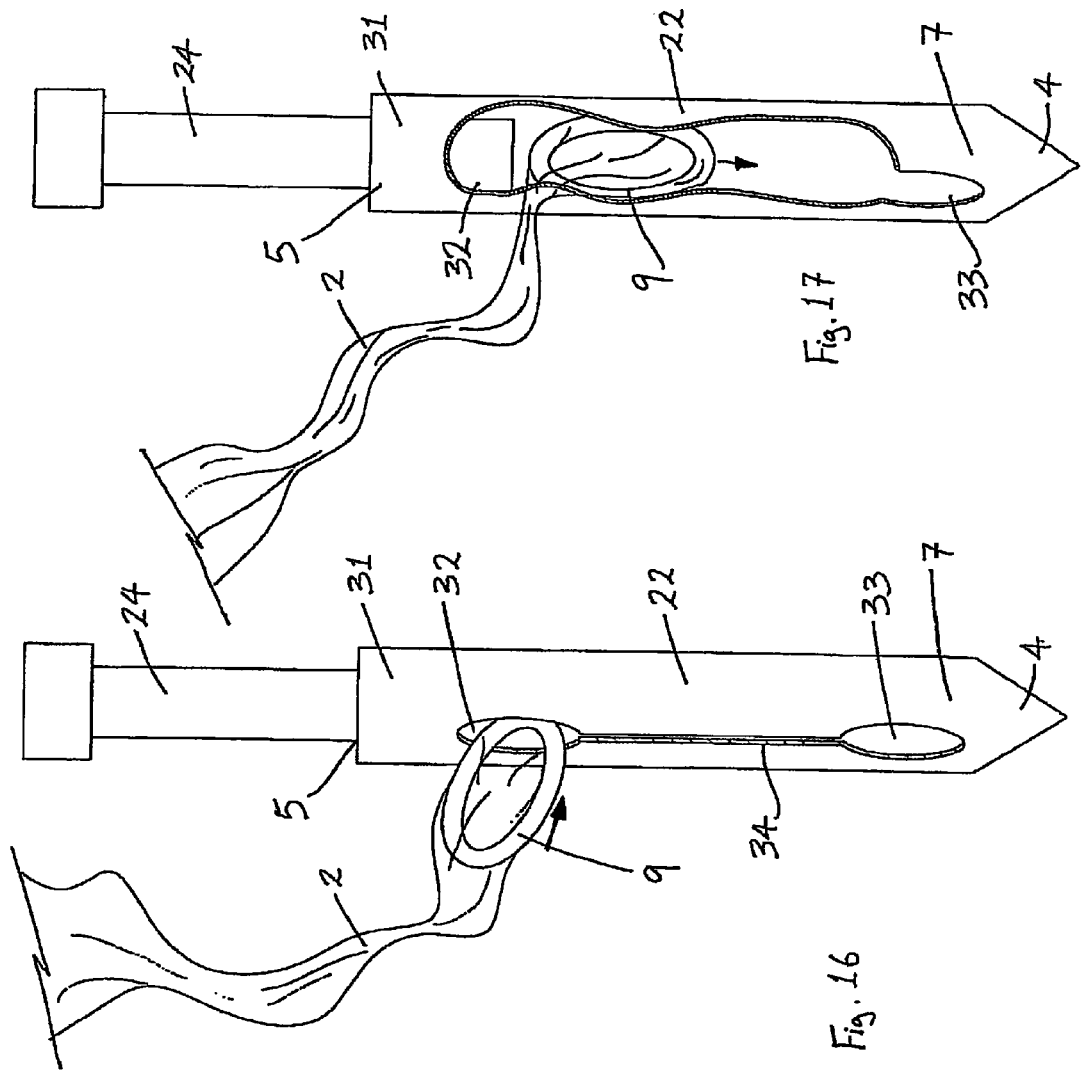

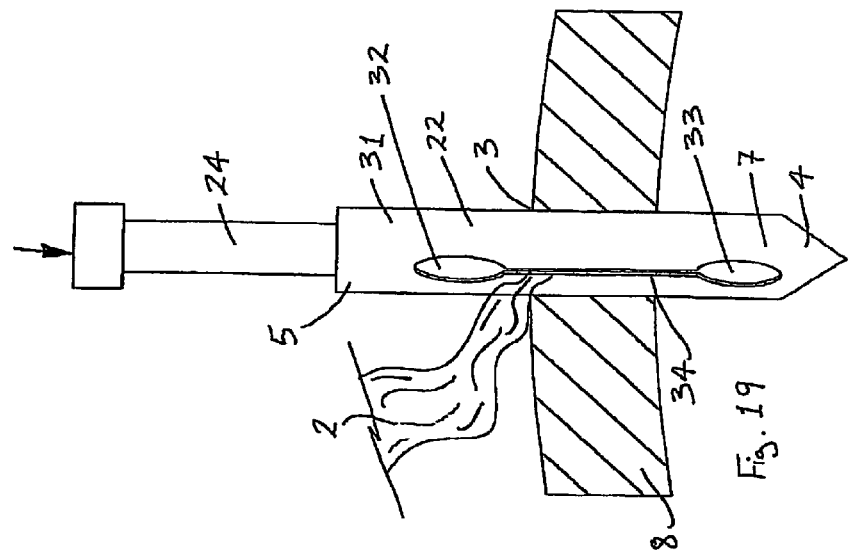
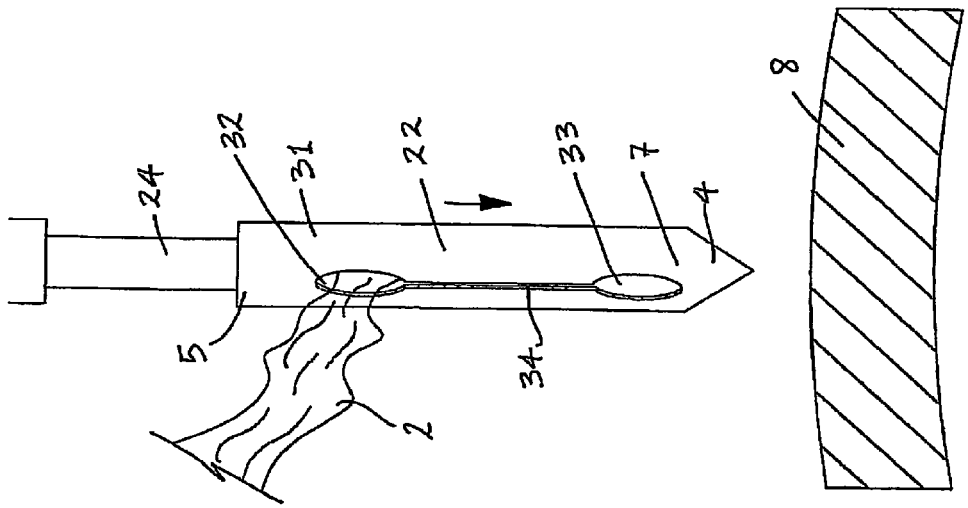

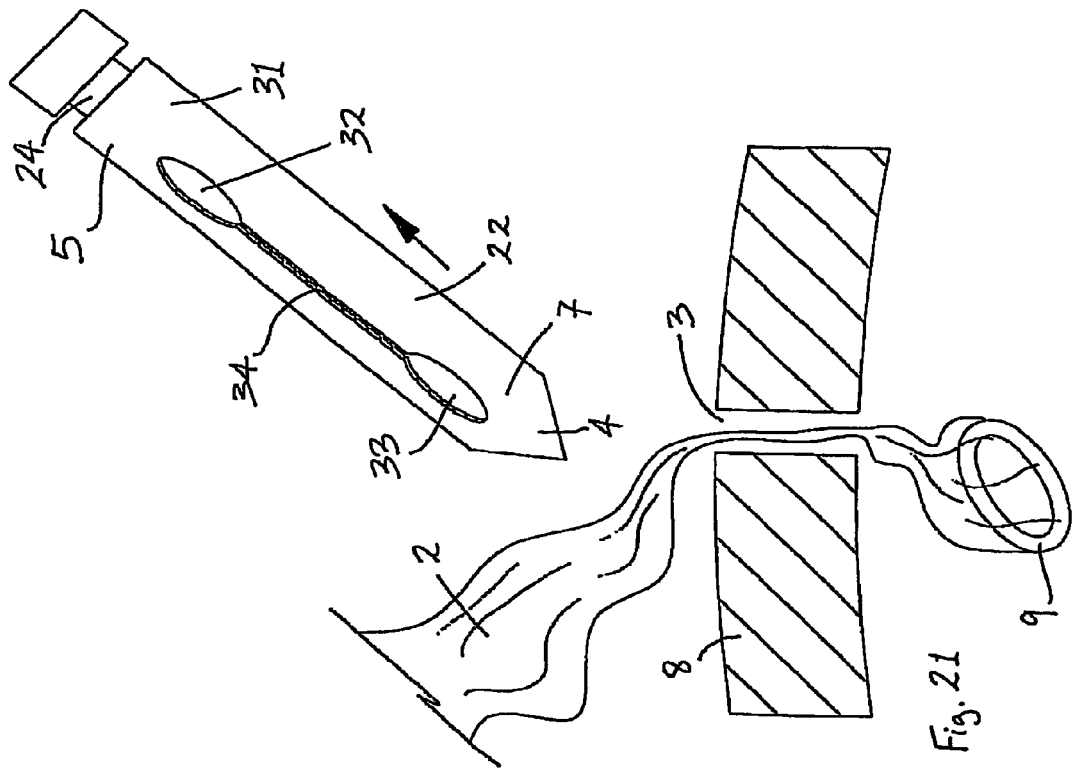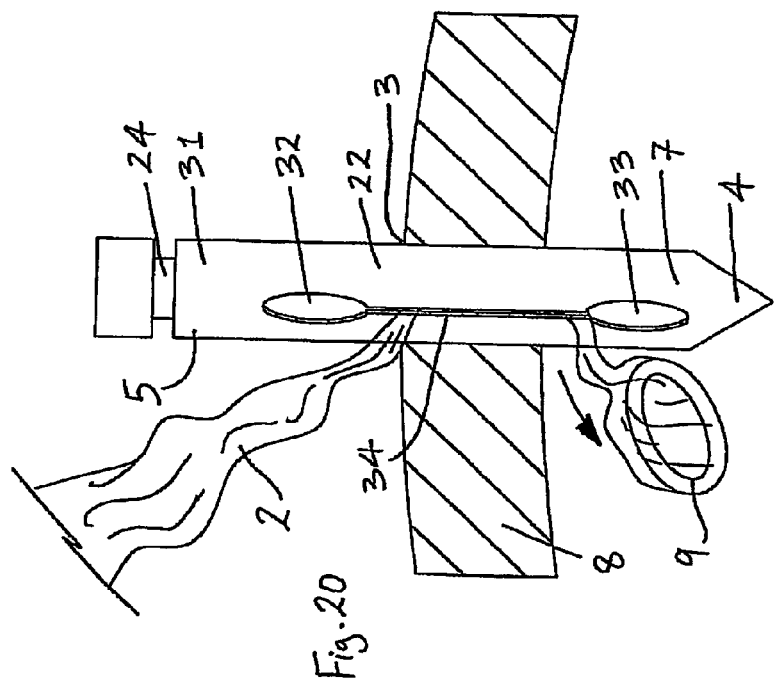

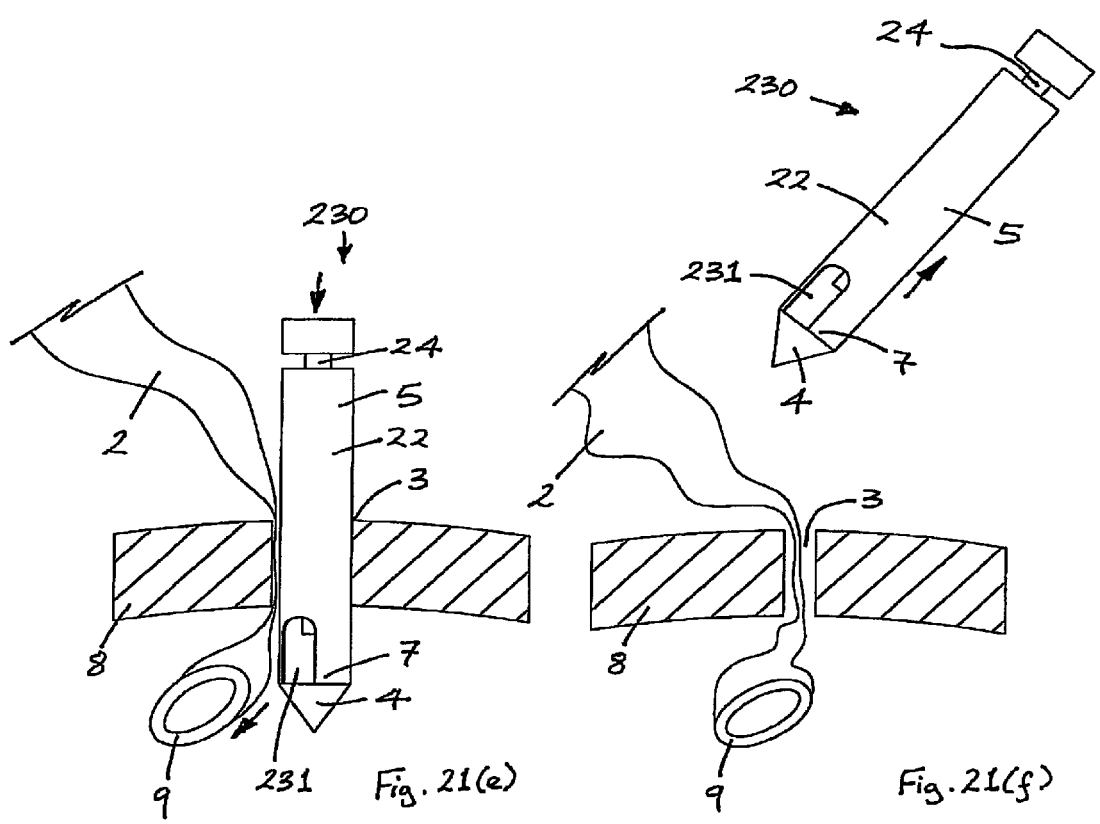

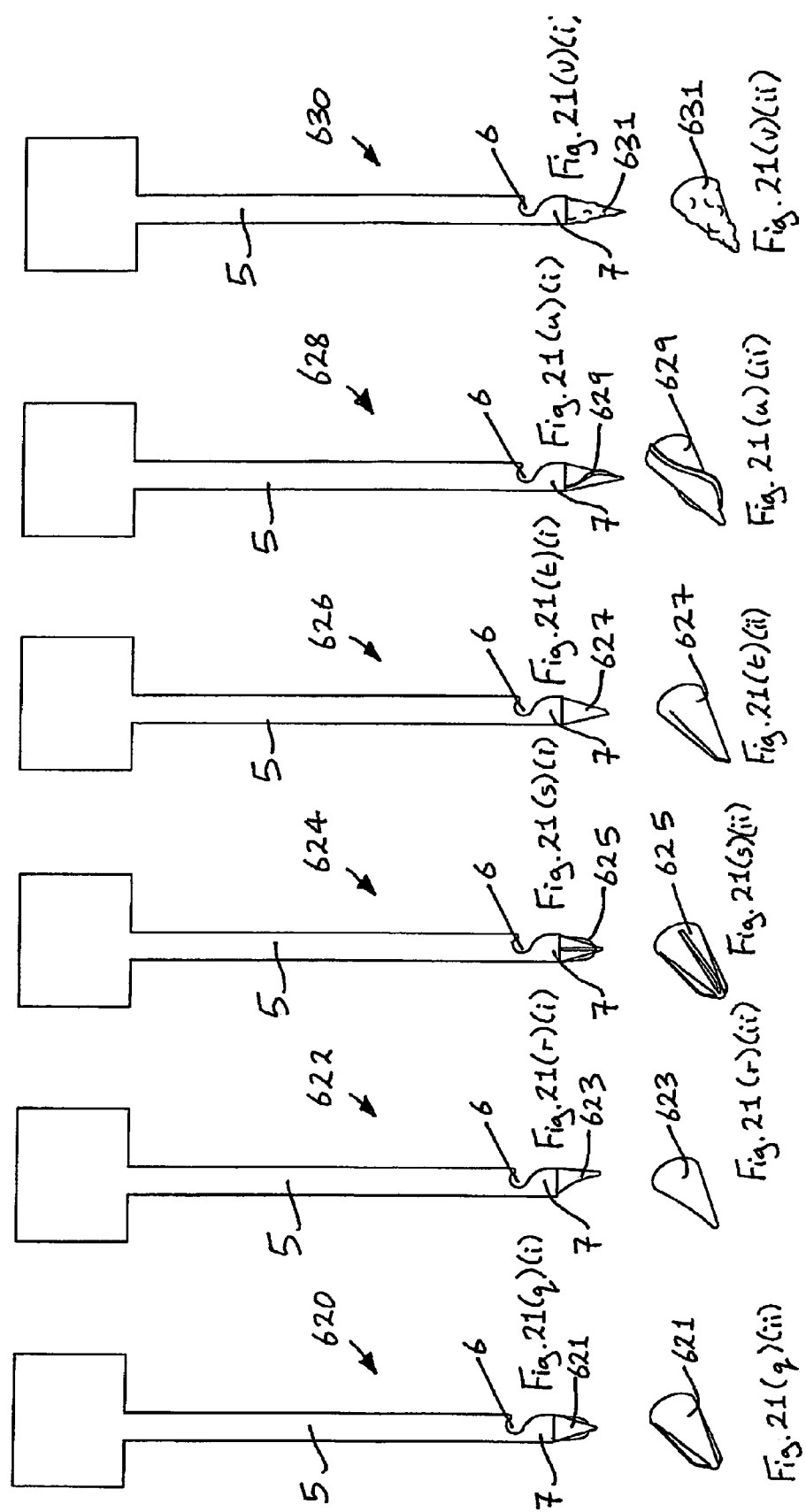

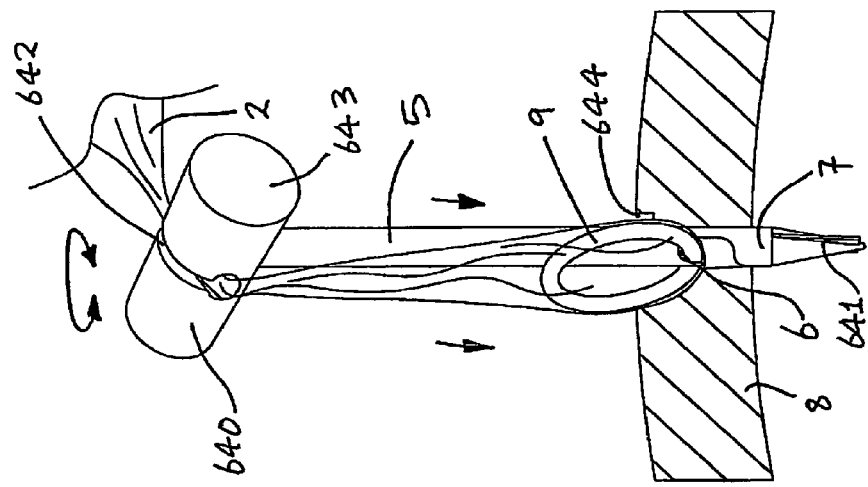
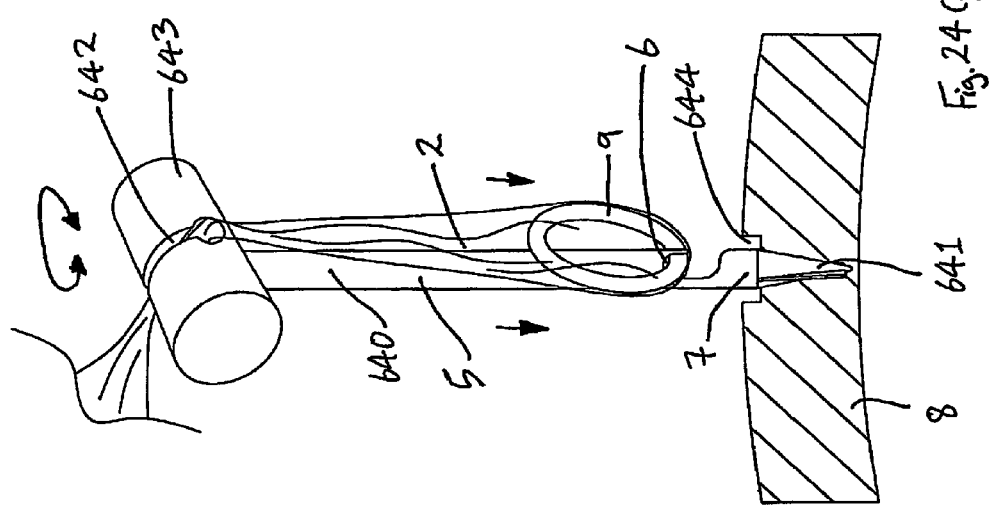
Fig. 24(g)
Fig. 24(h)

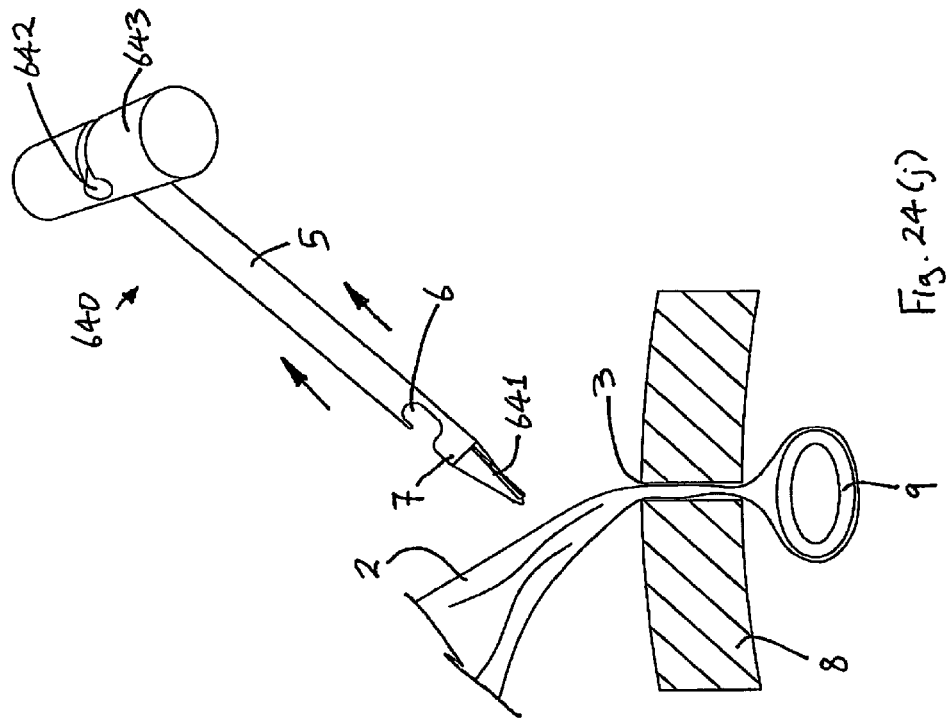
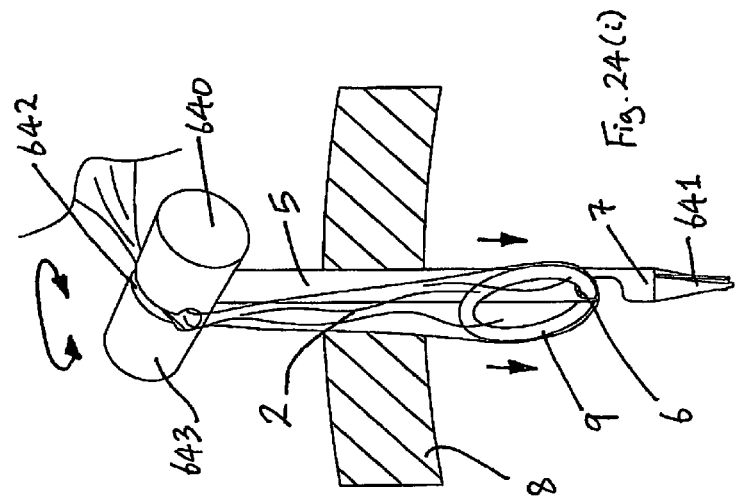
Fig. 24(i)
Fig. 24(j)

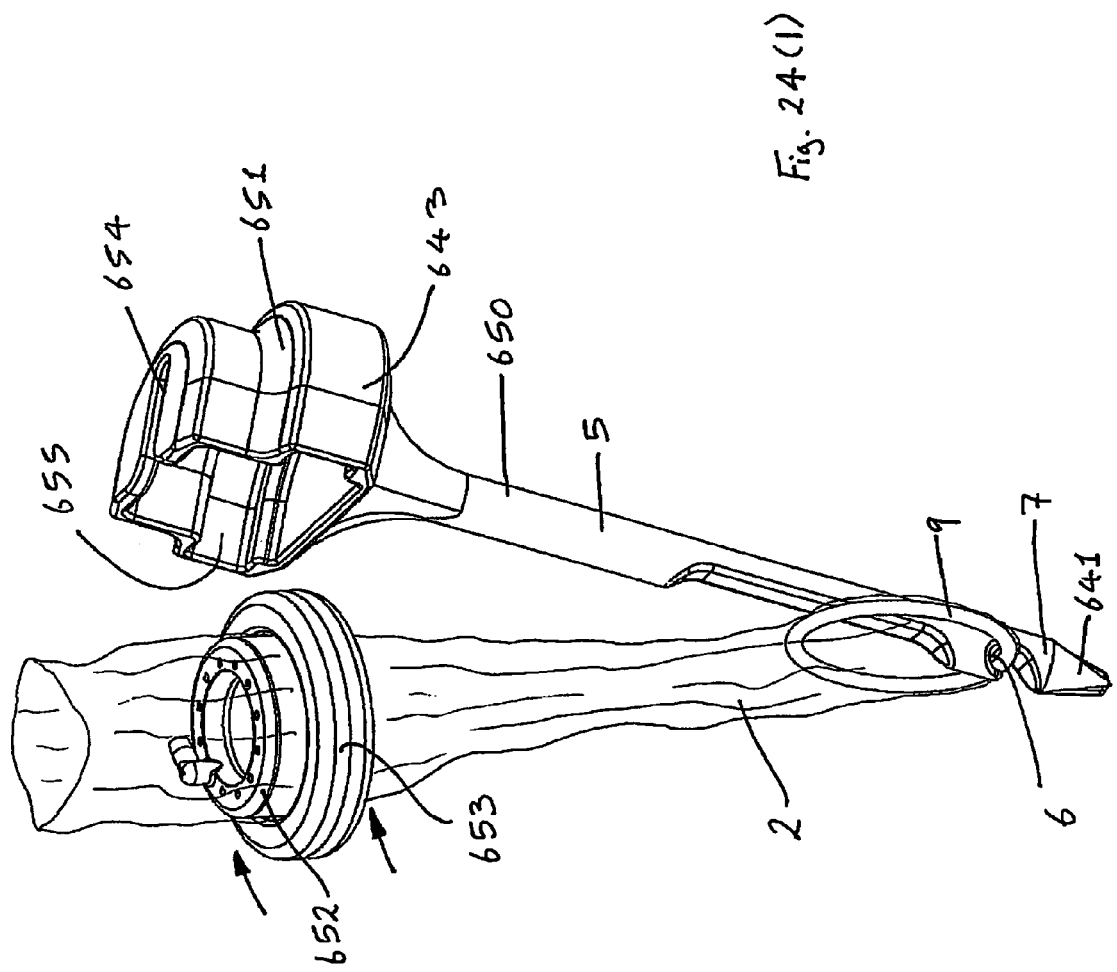

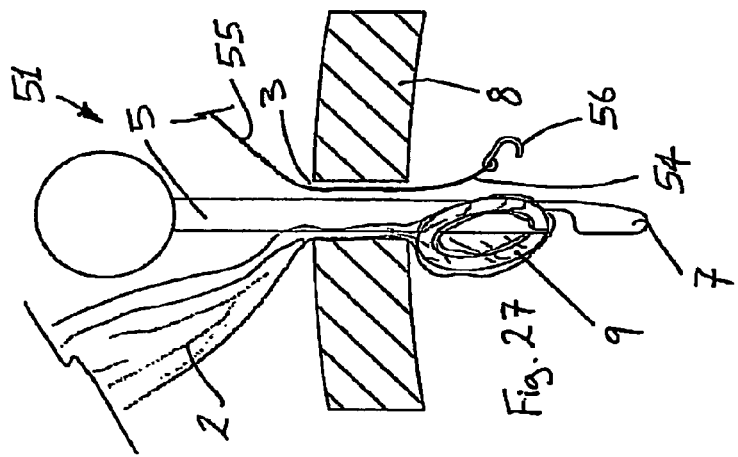
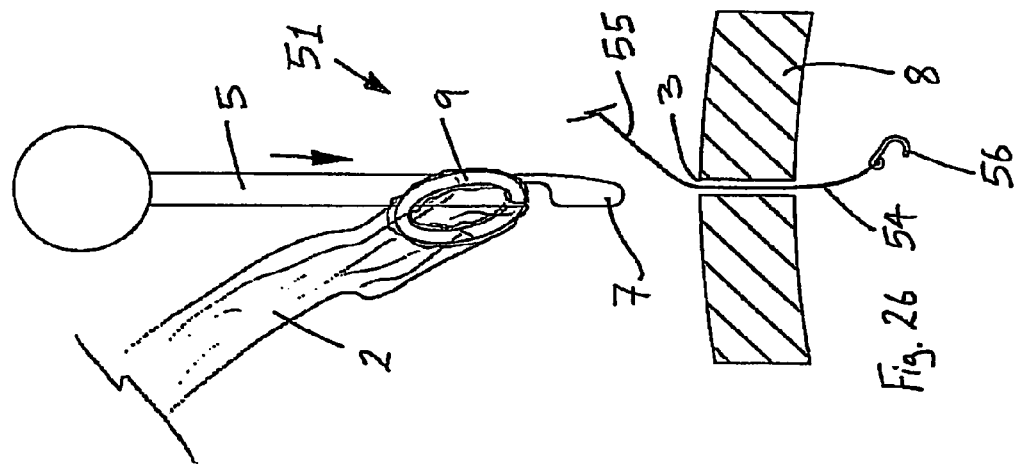
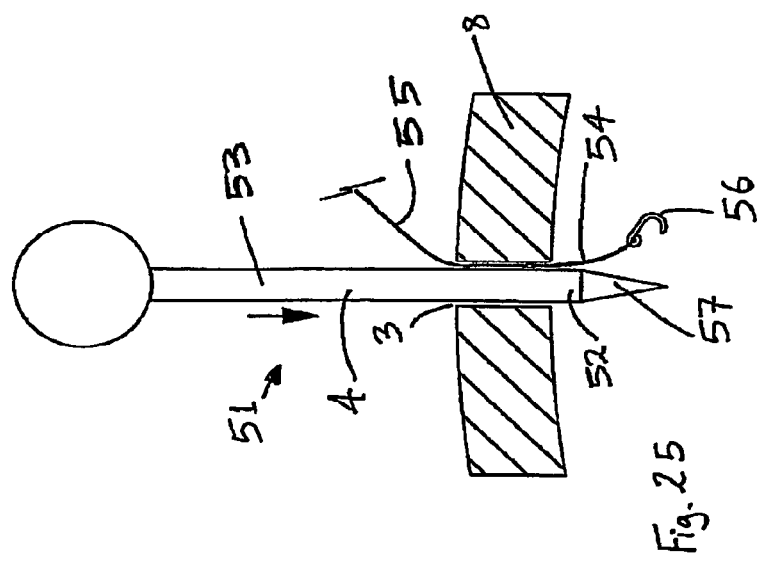

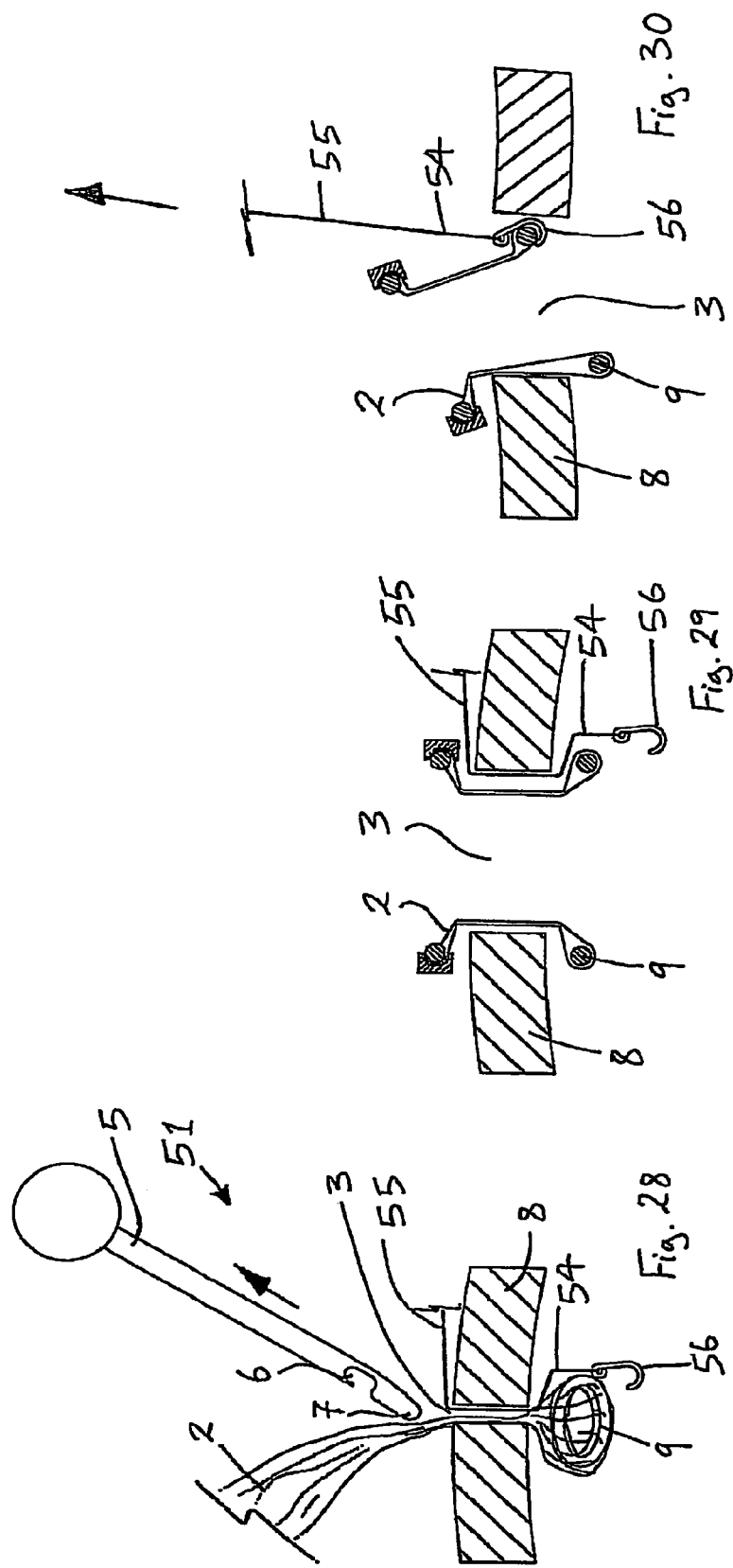

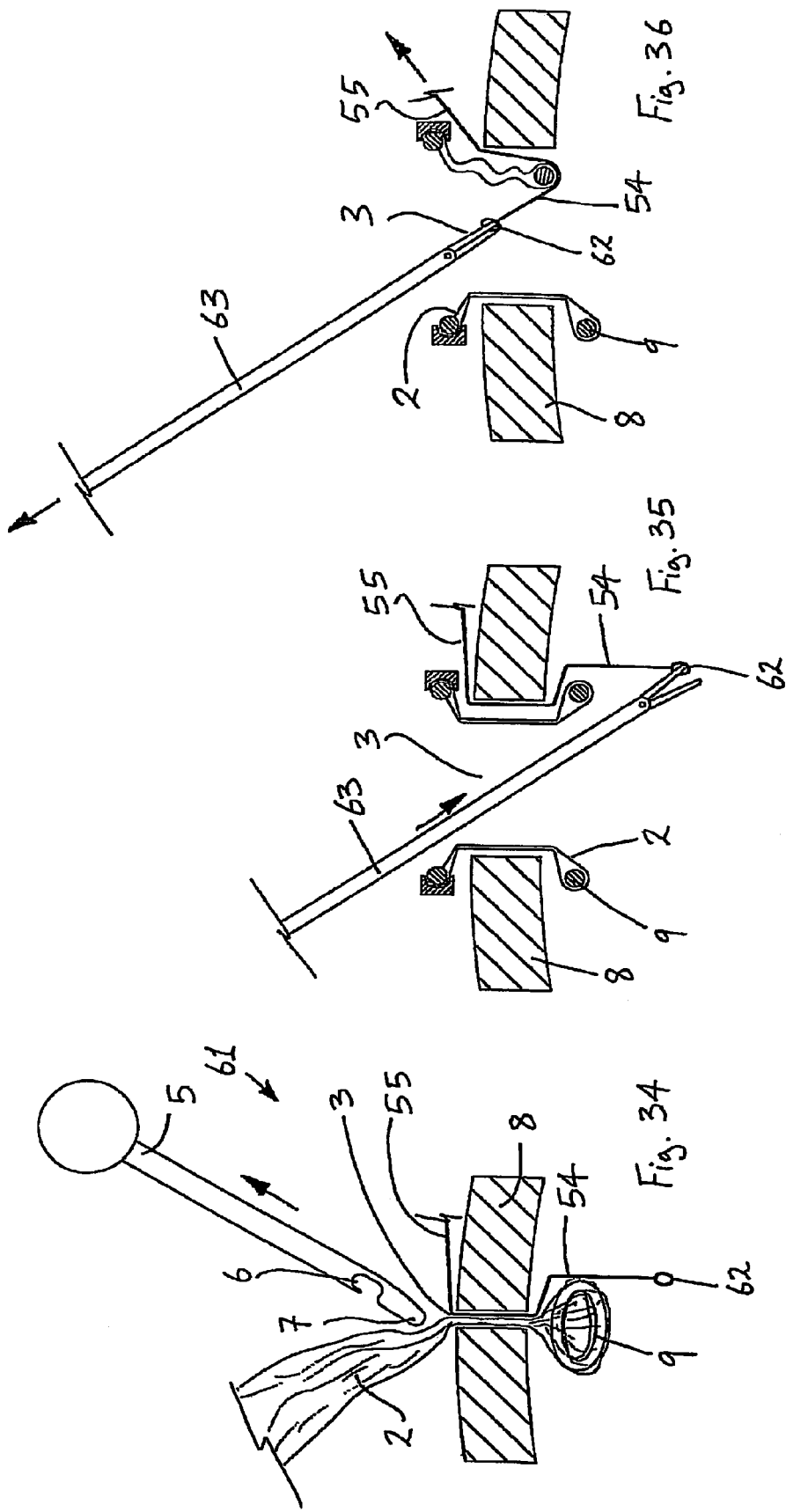

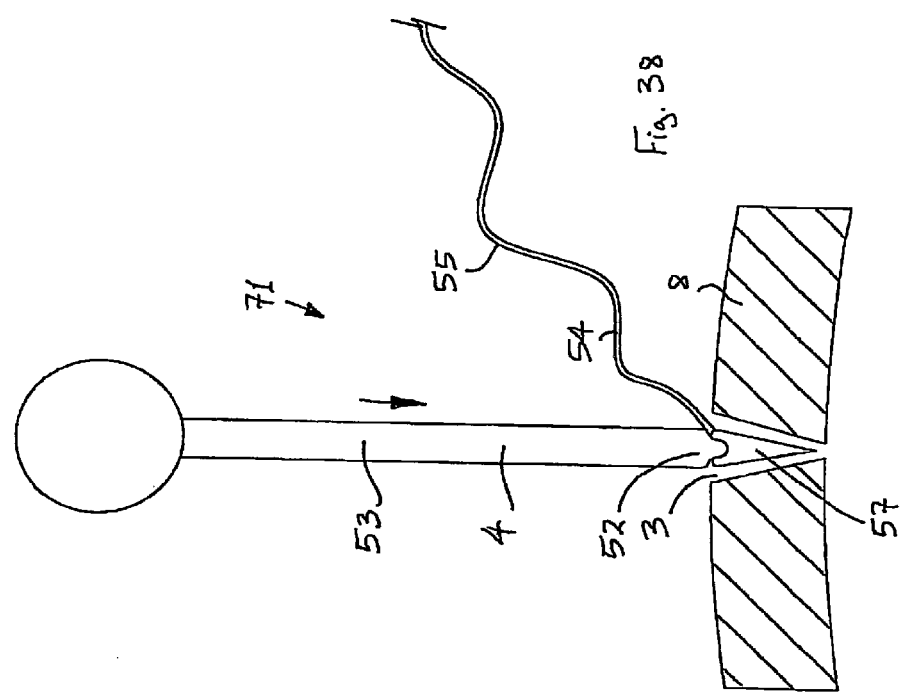
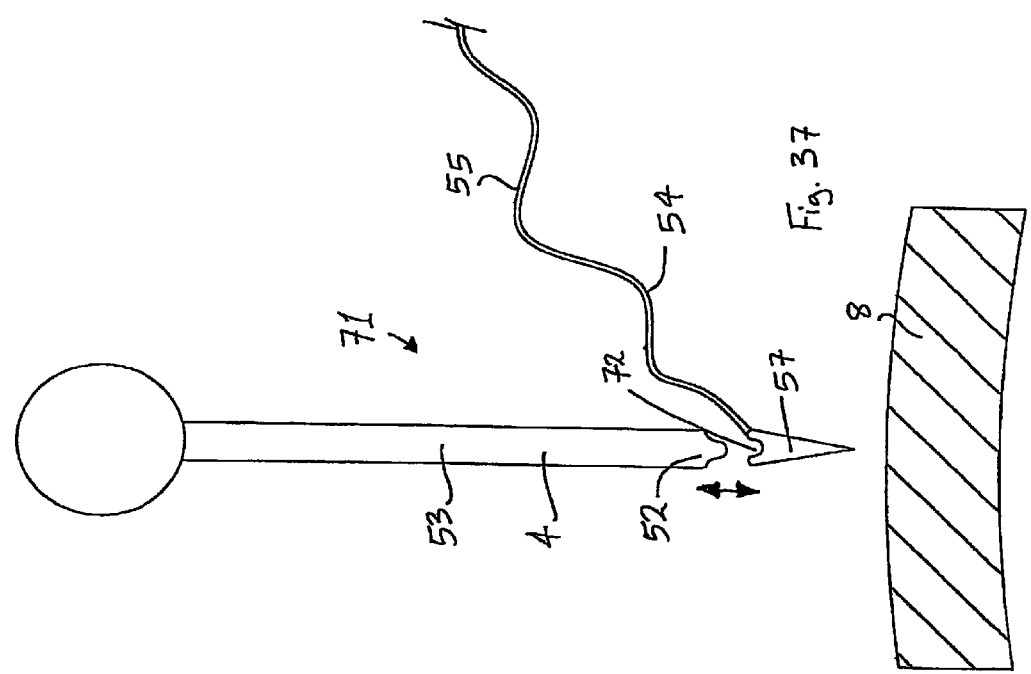

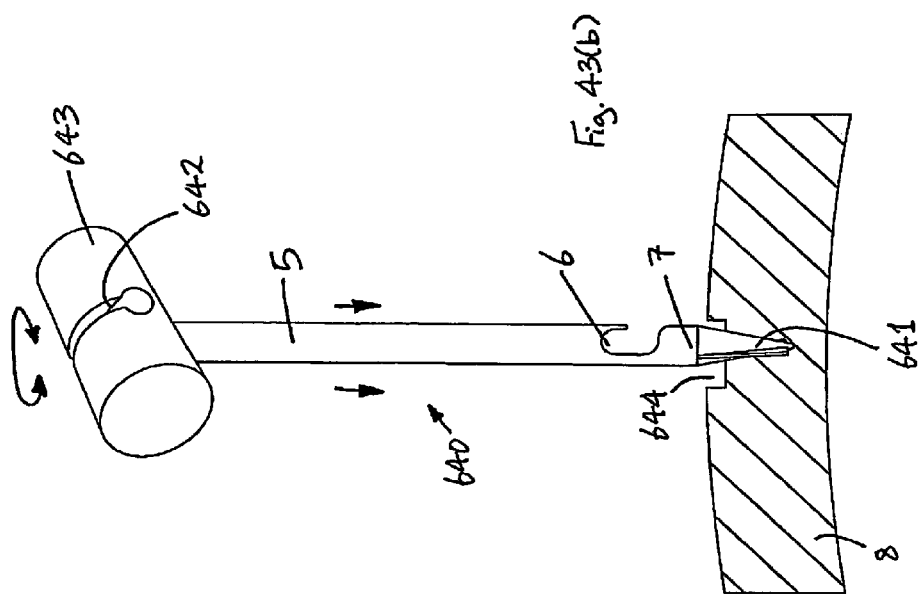
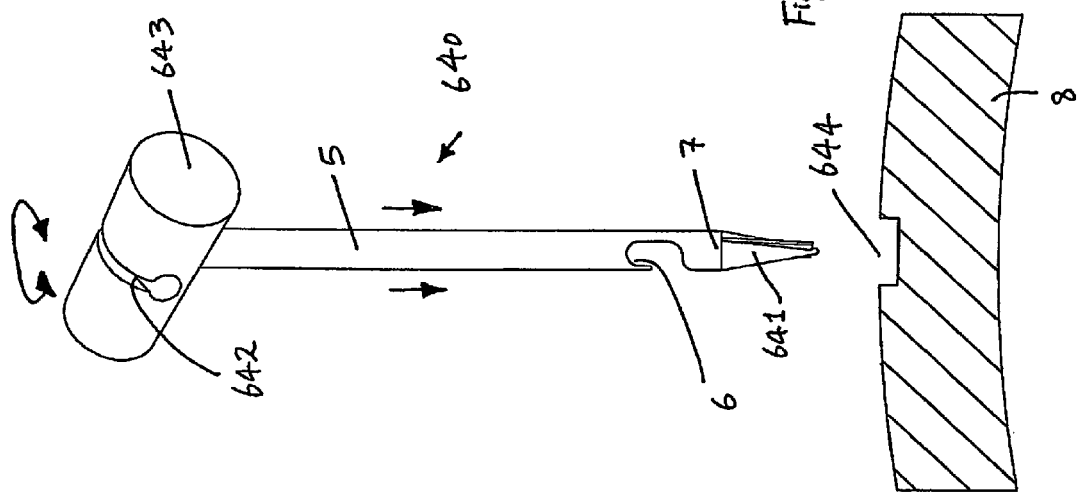

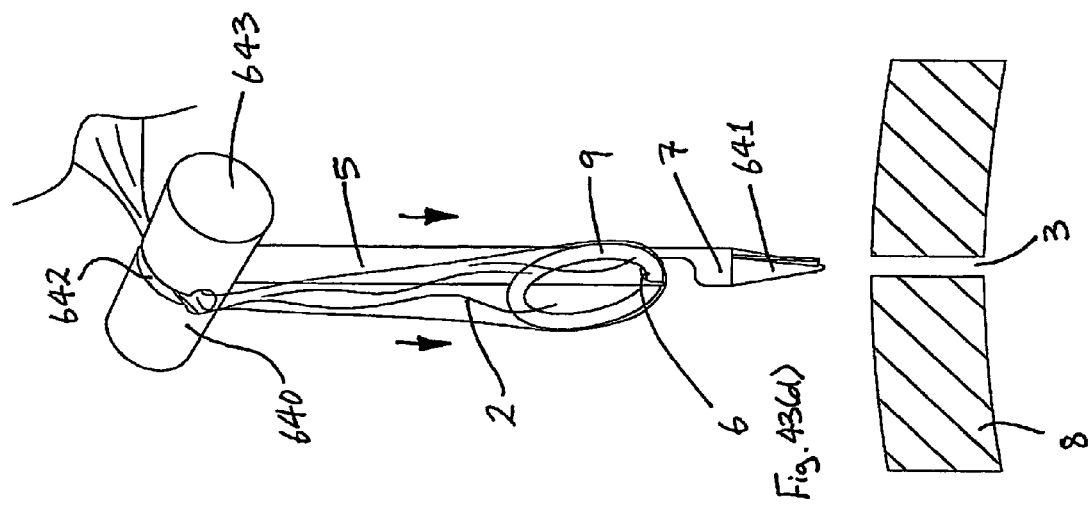
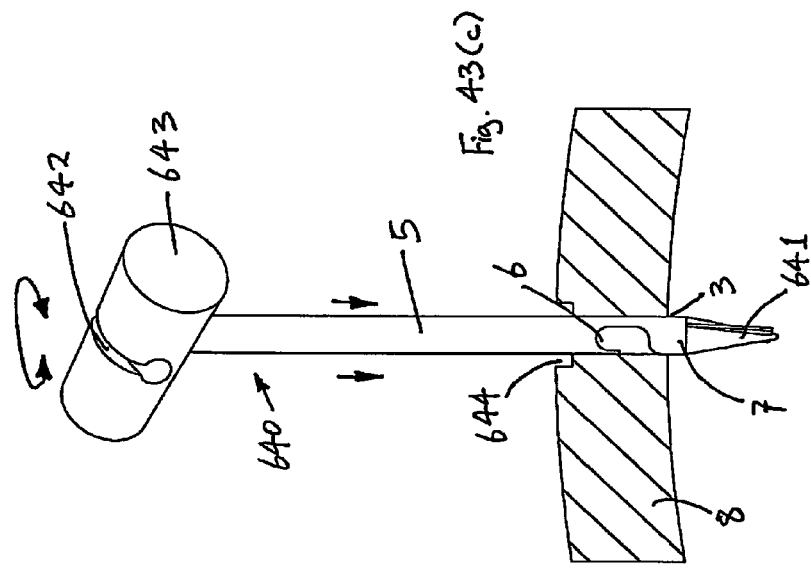

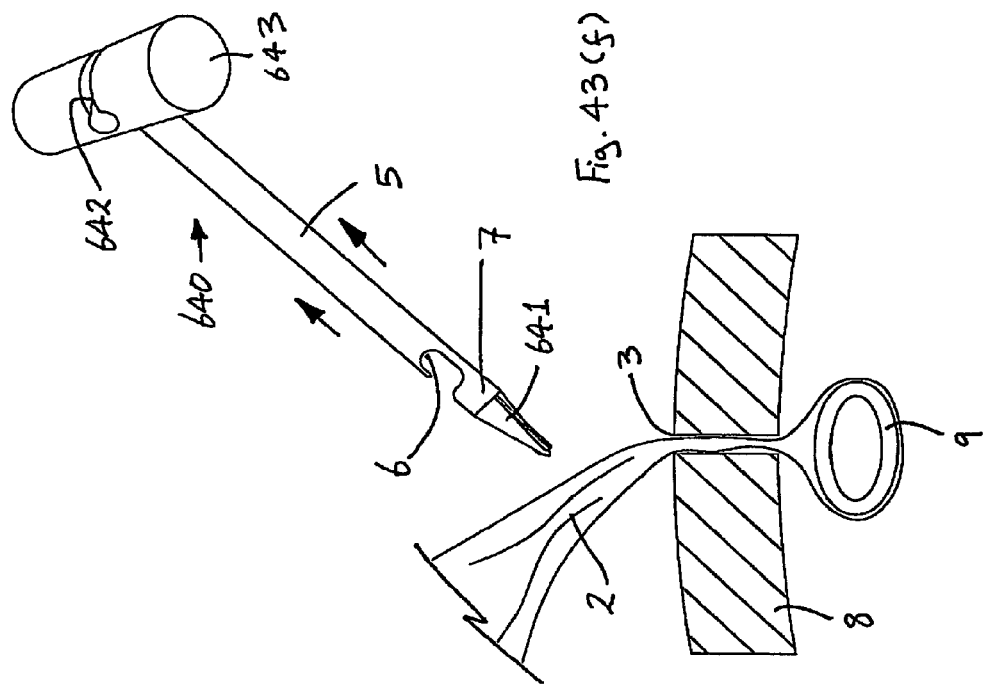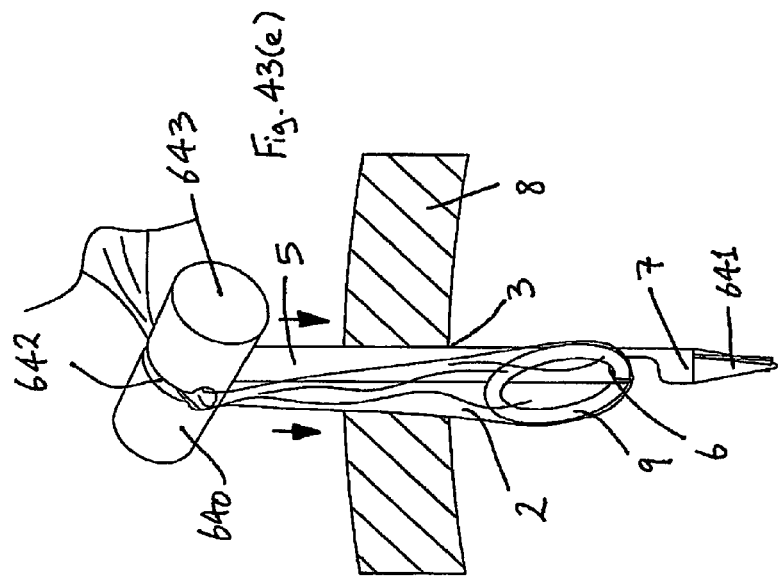

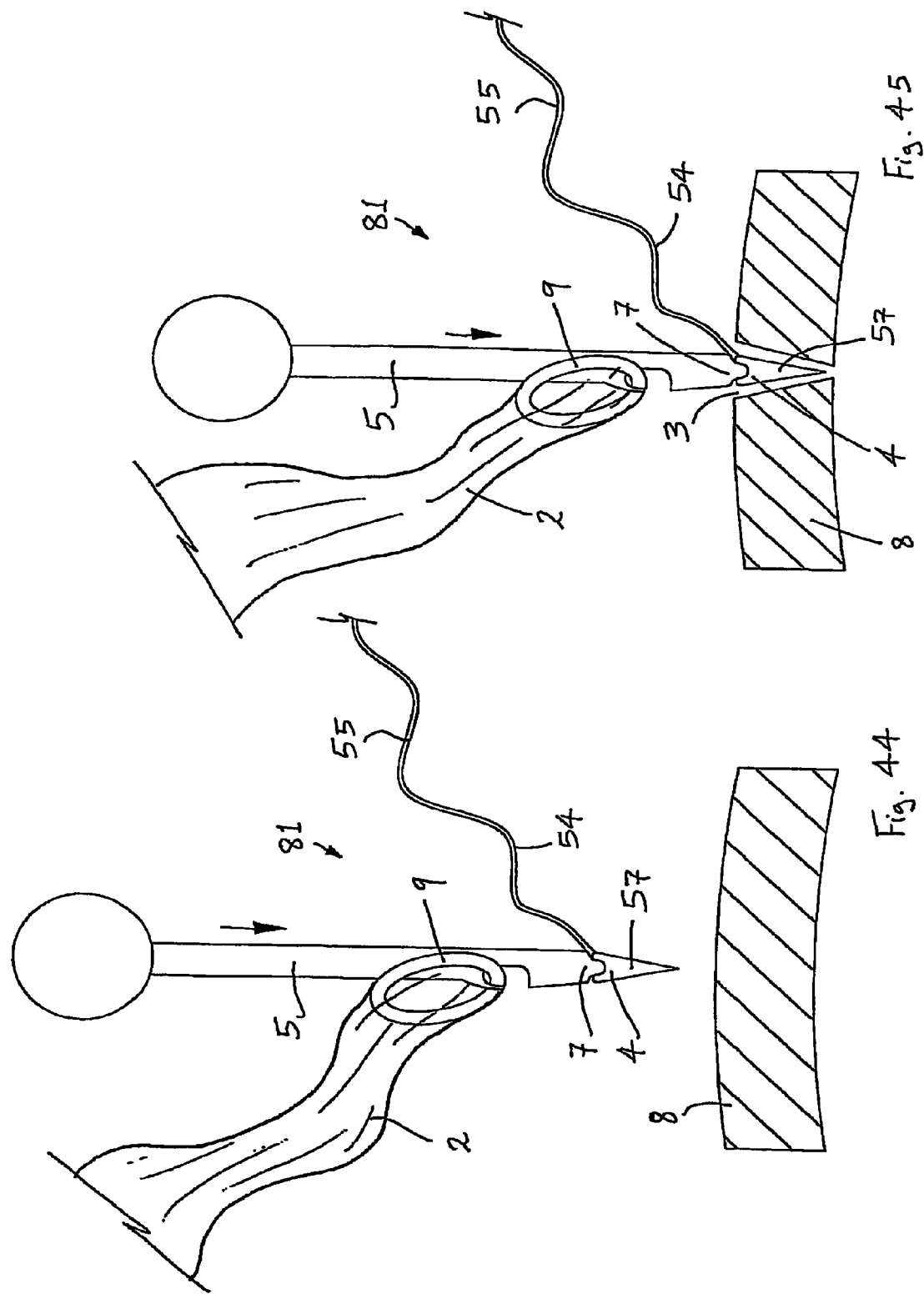

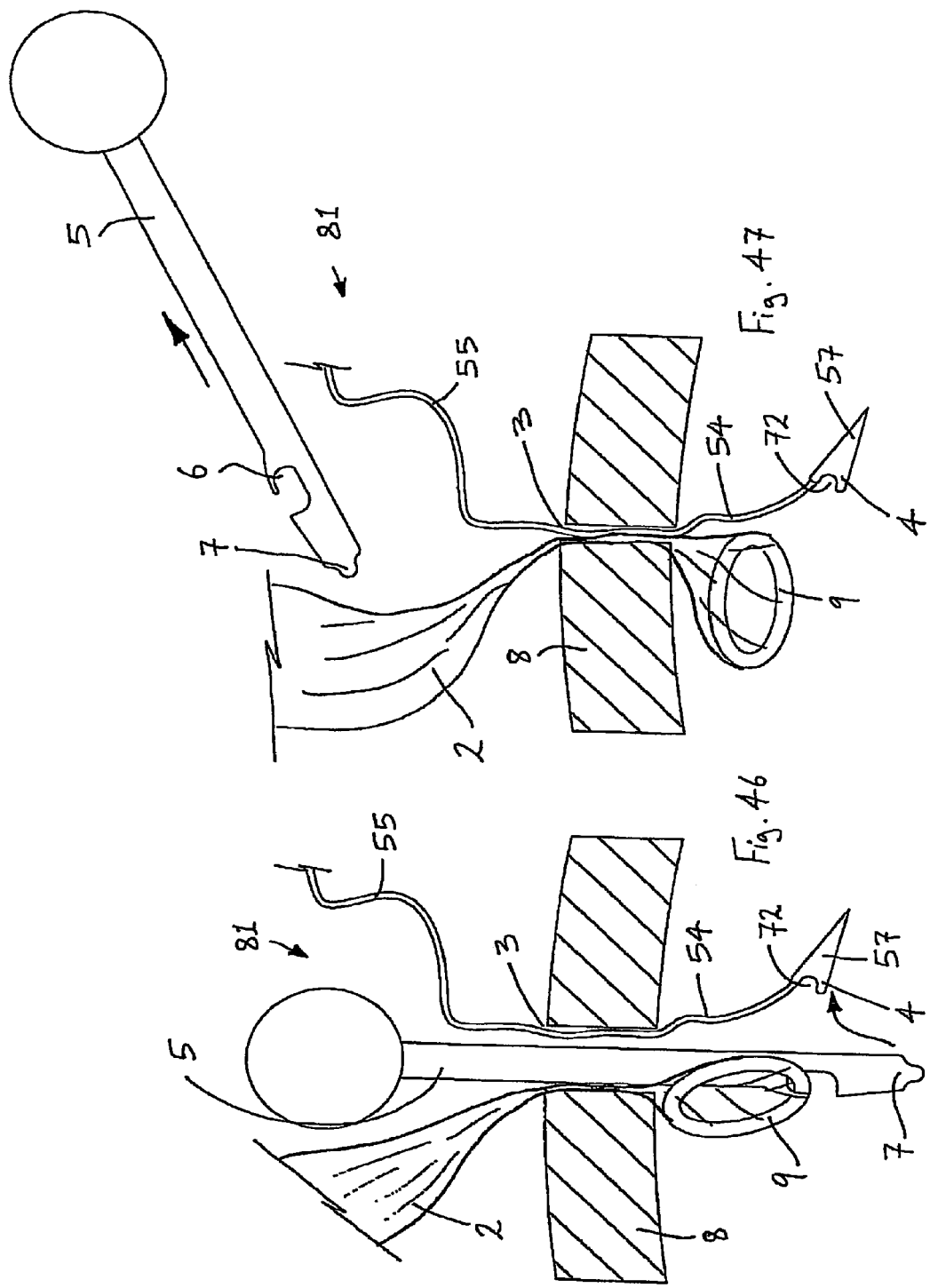

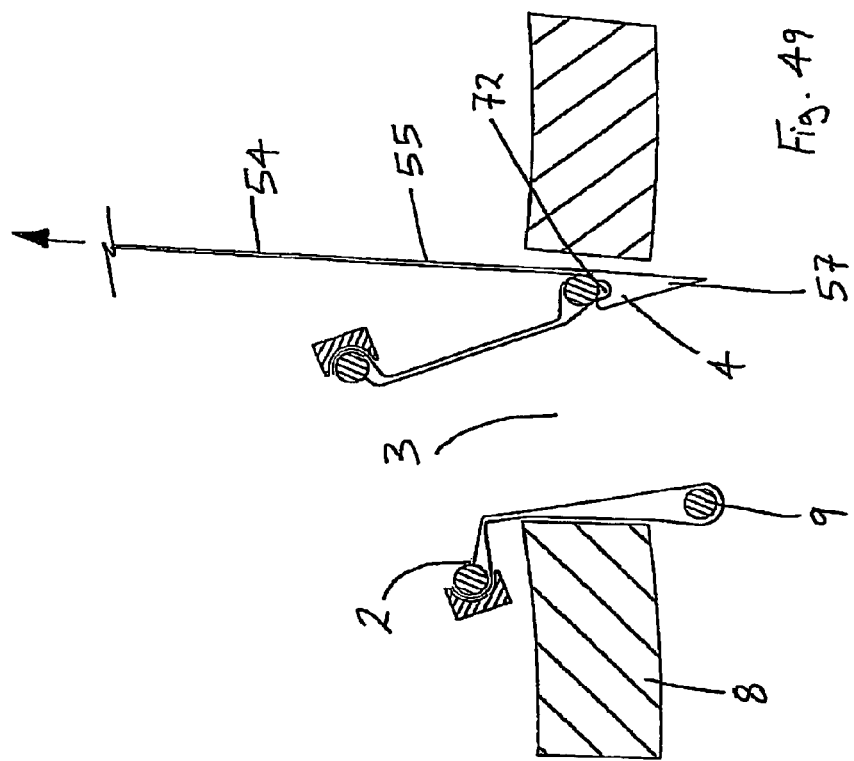
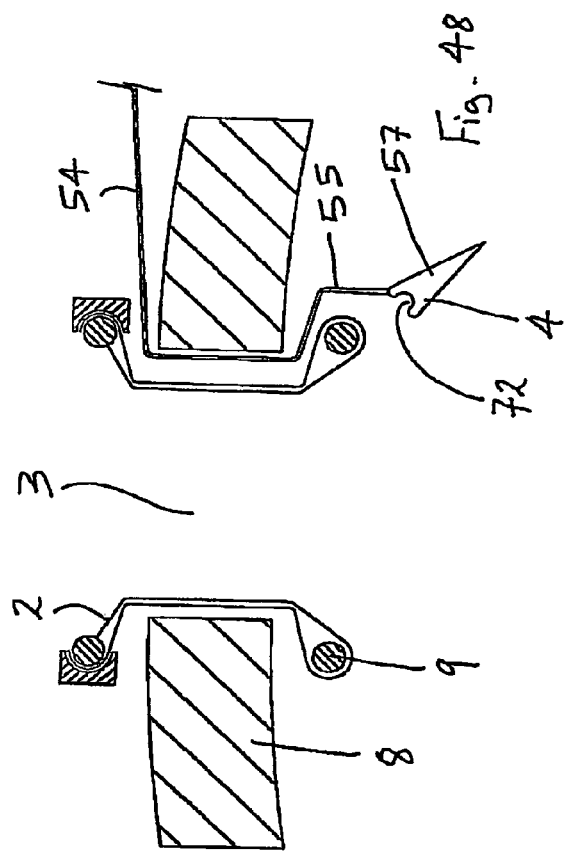

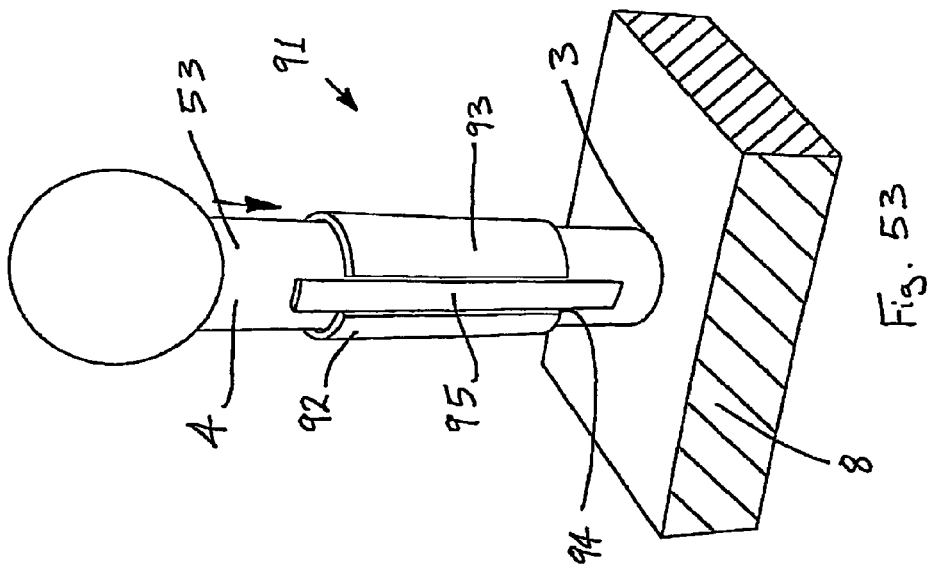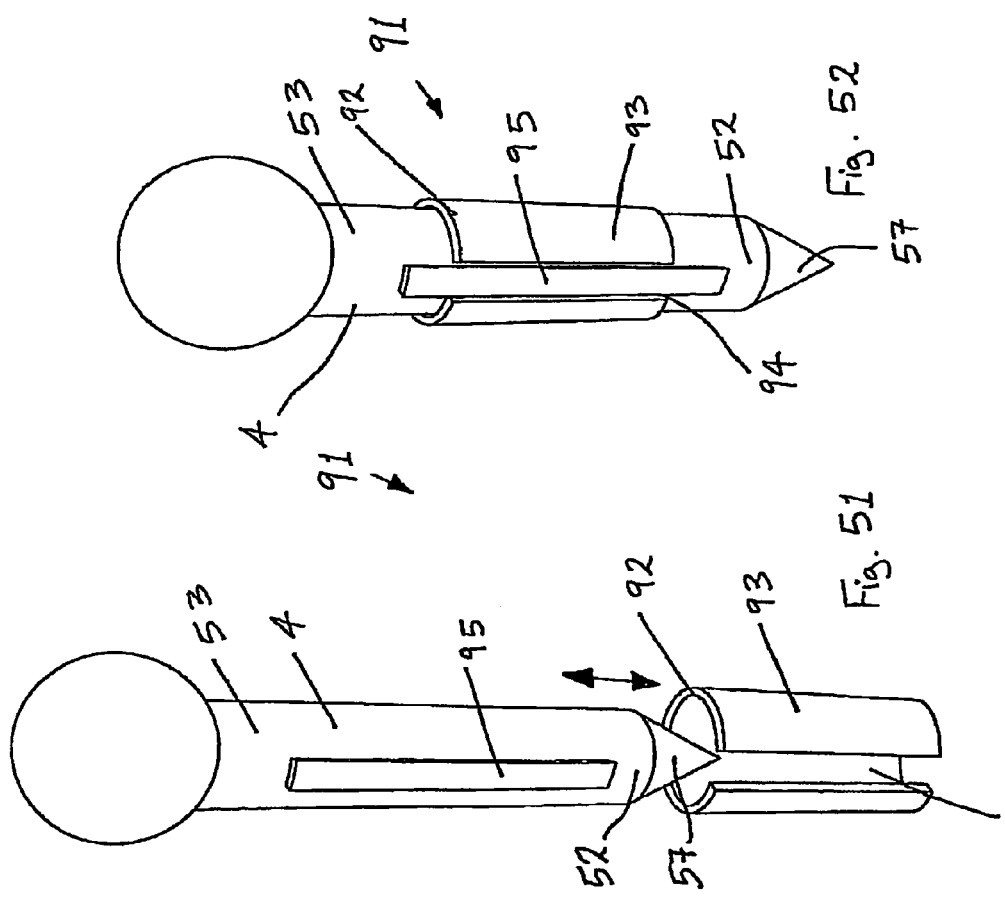

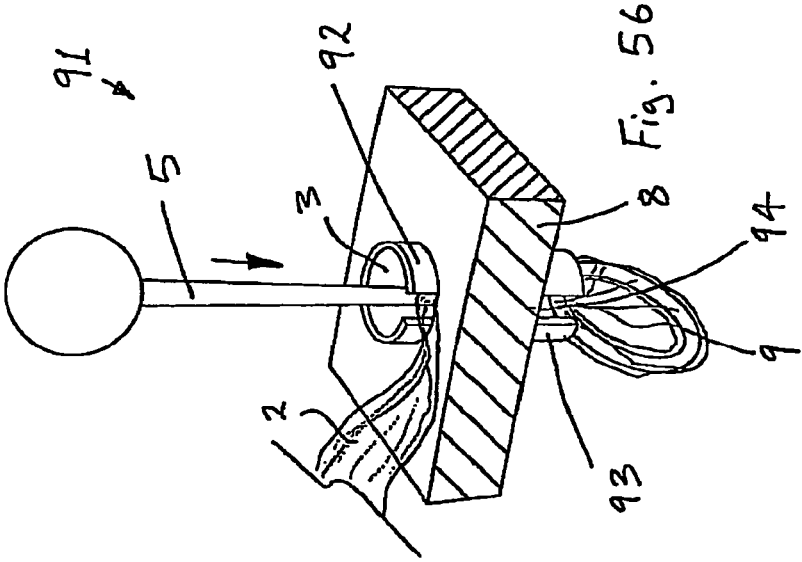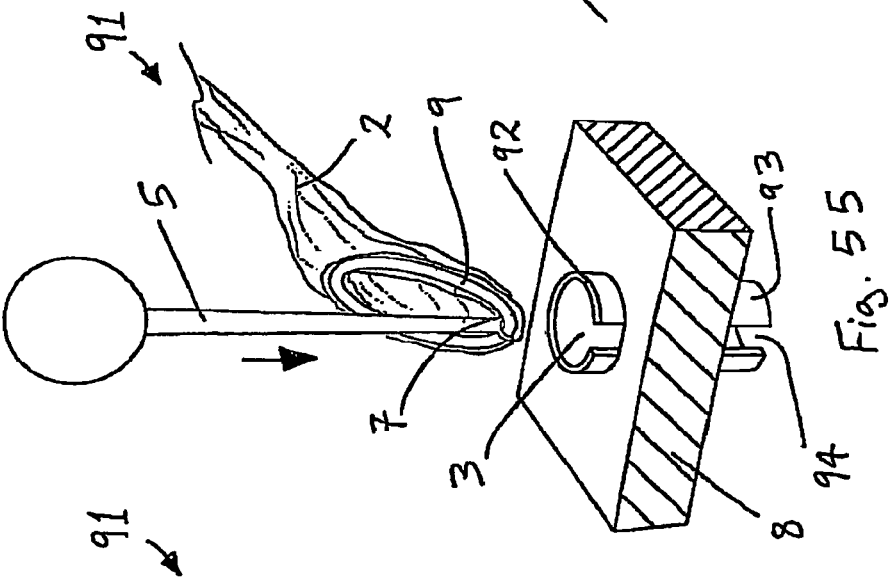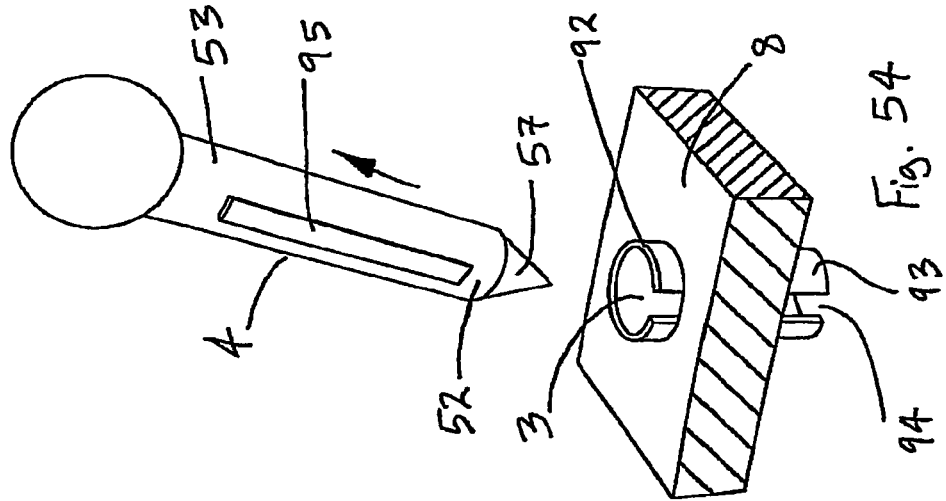

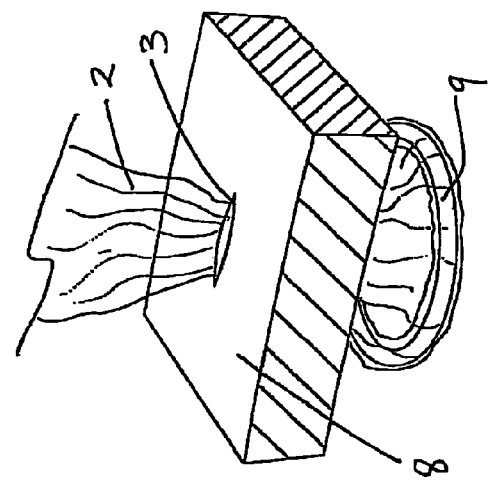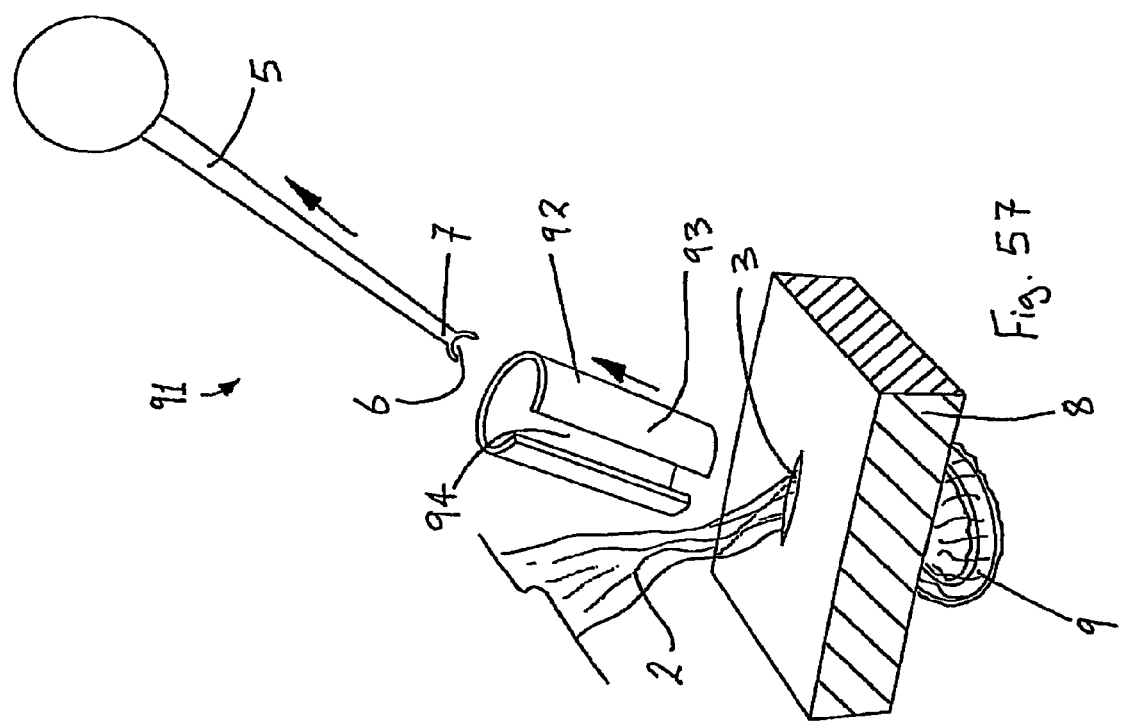

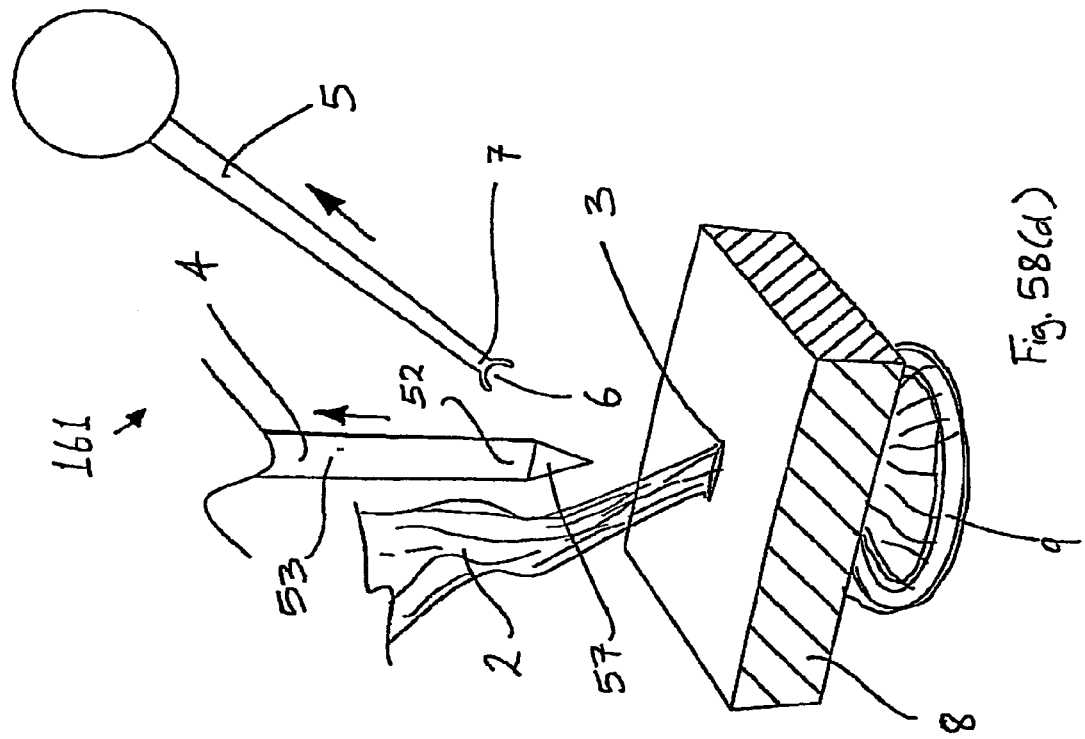
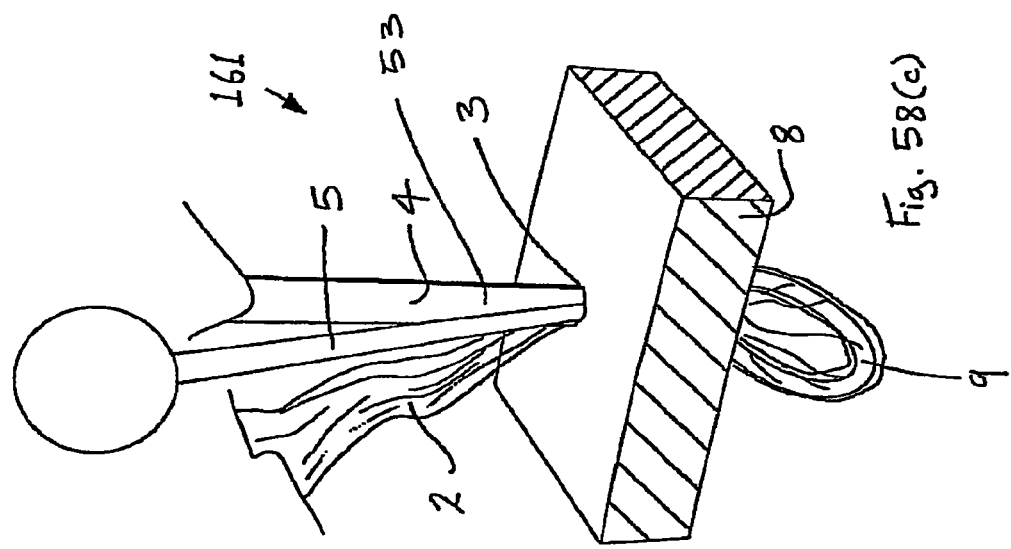
Fig. 58(d)
Fig. 58(c)

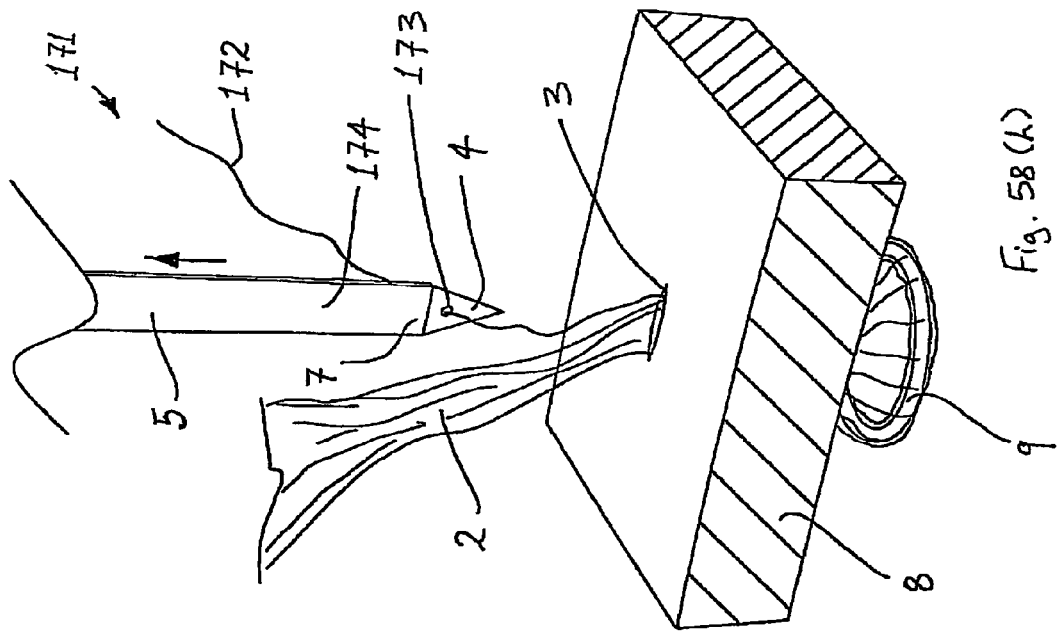
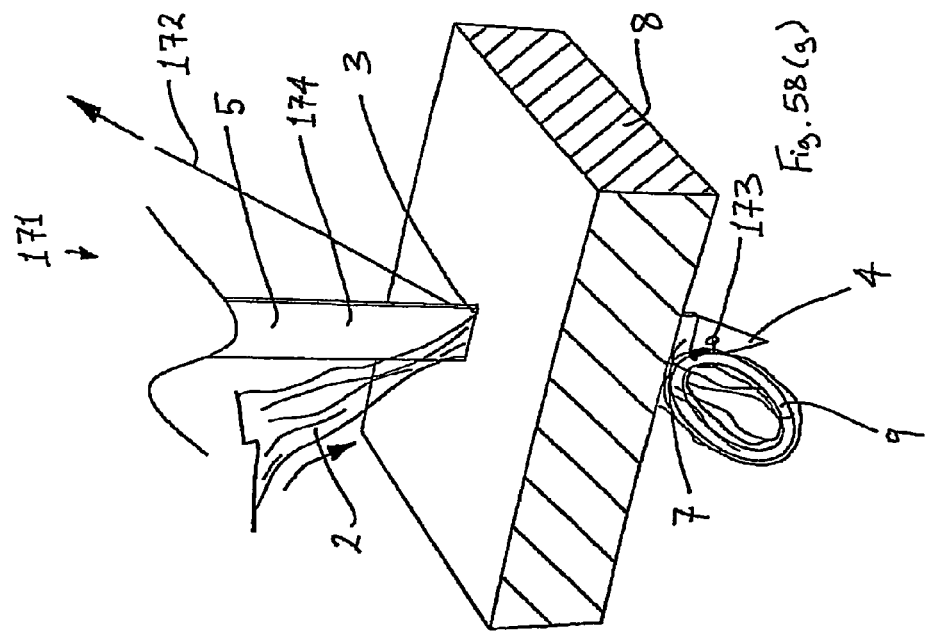
Fig. 58(h)
Fig. 58(g)

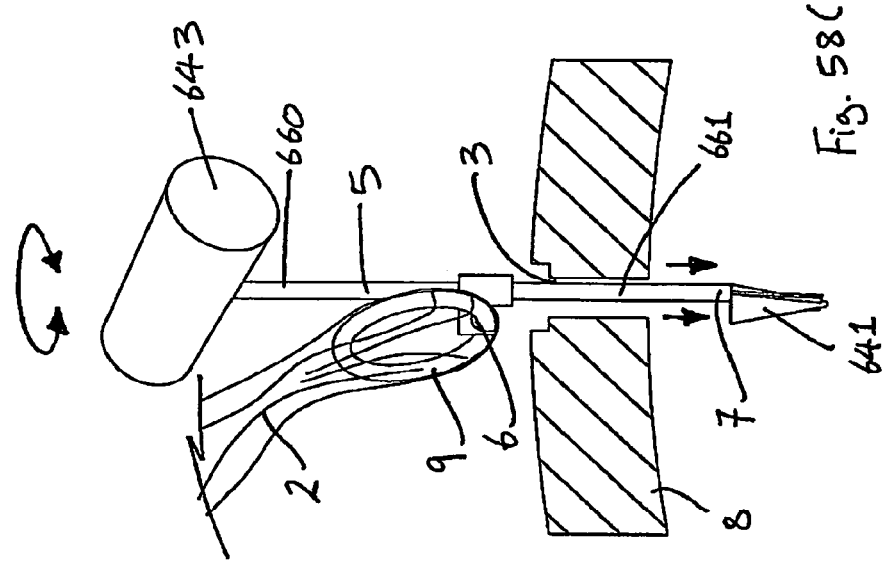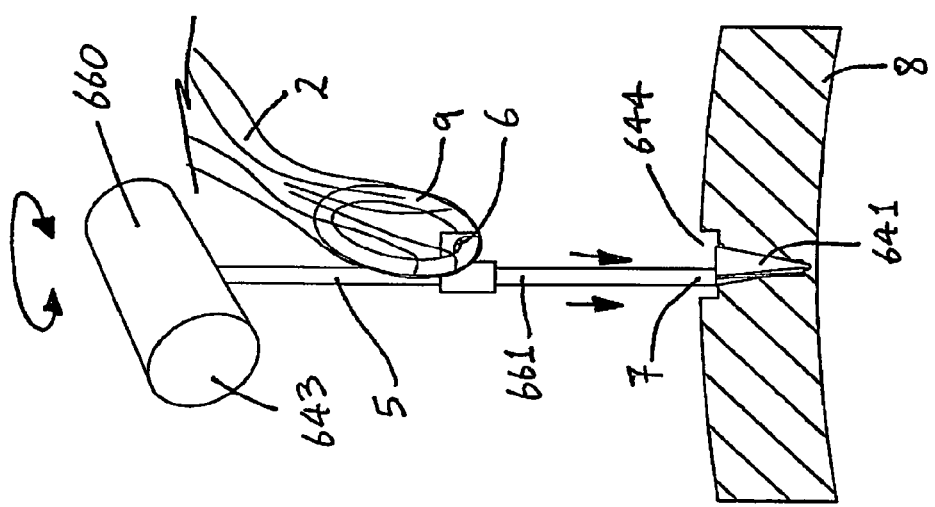

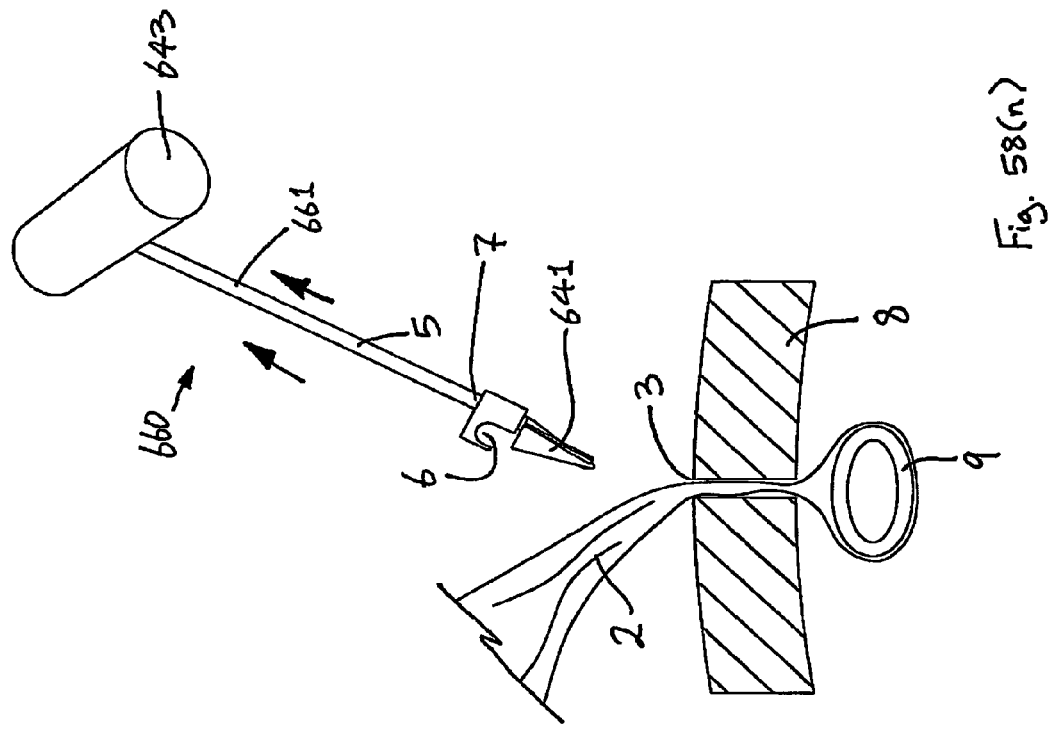
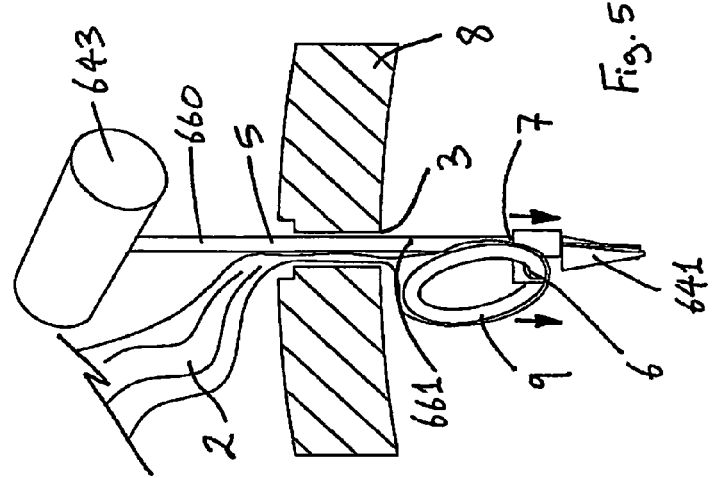
Fig. 58(n)
Fig. 58(m)

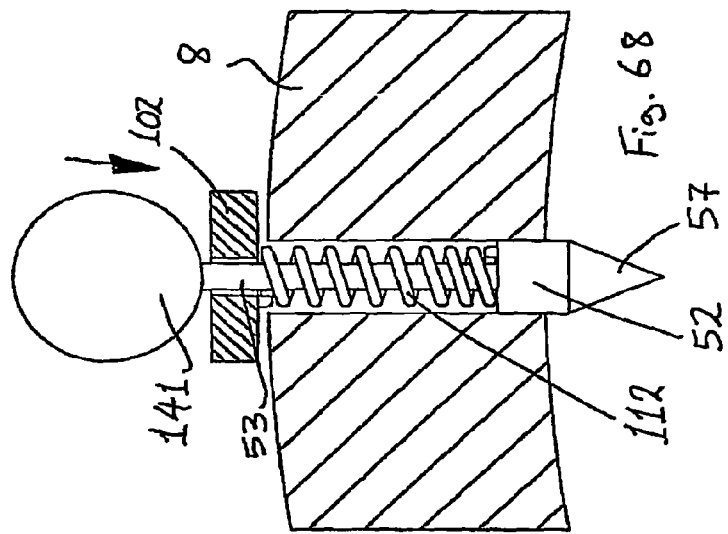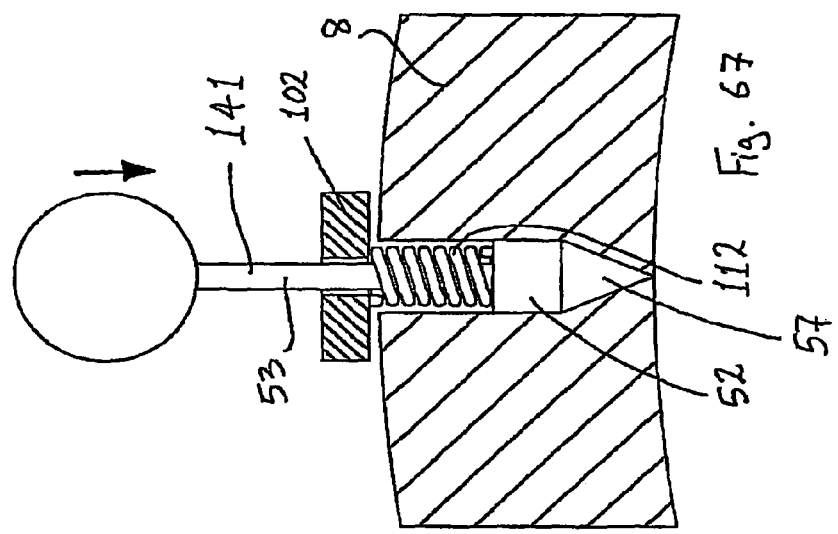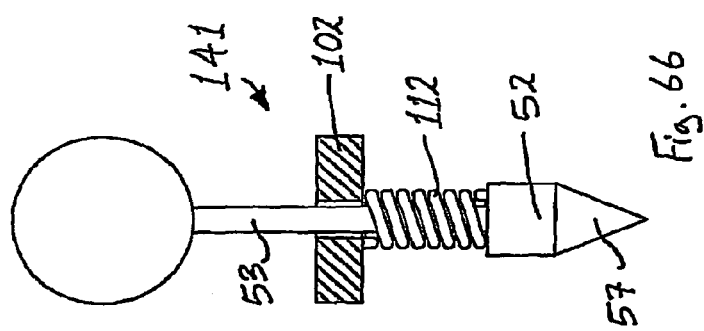

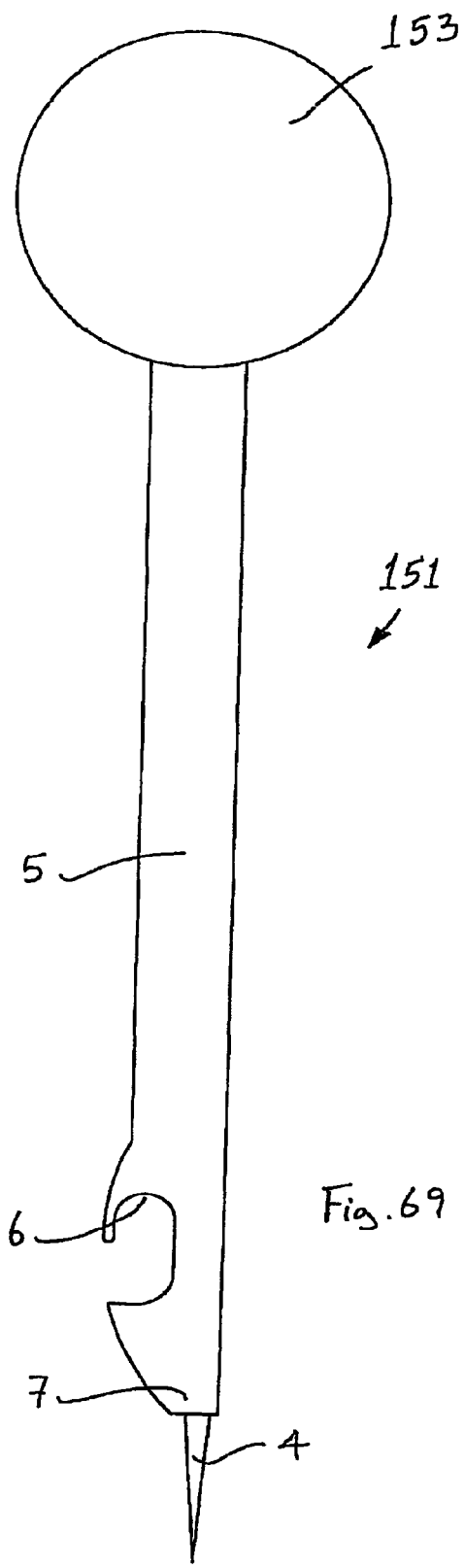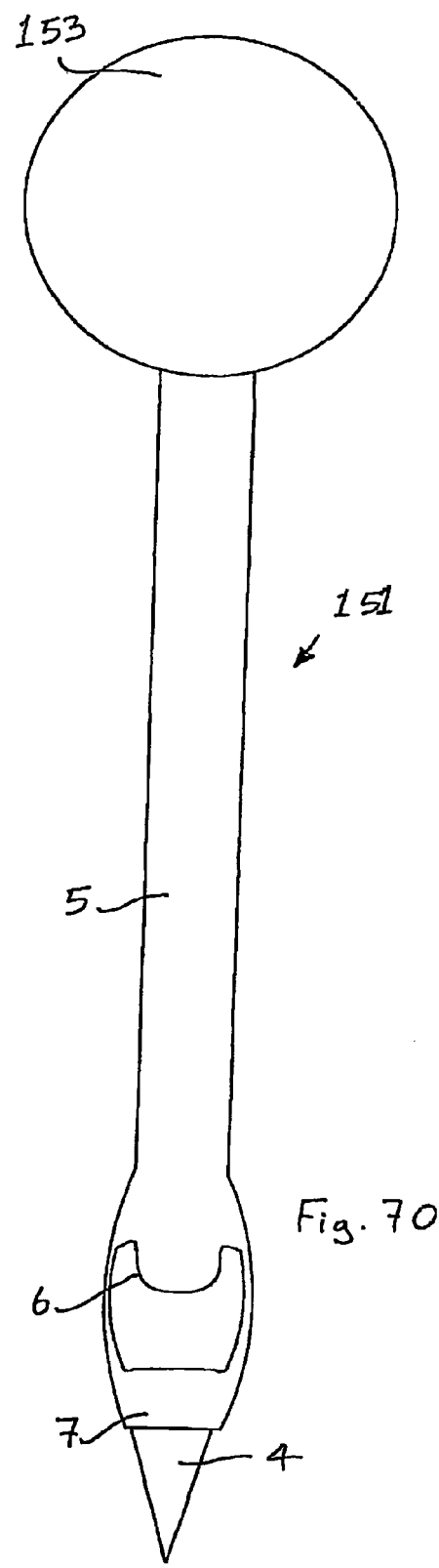

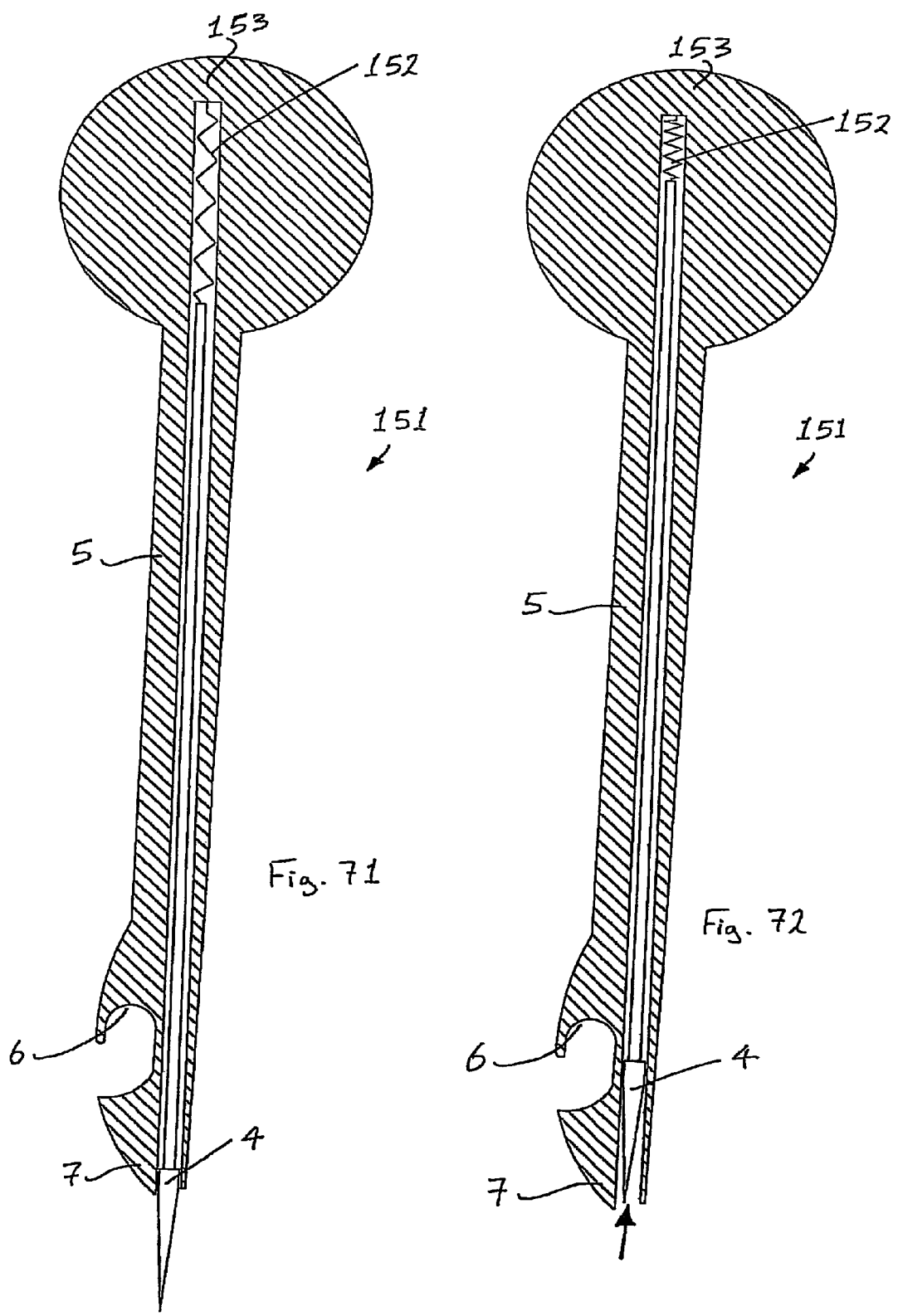

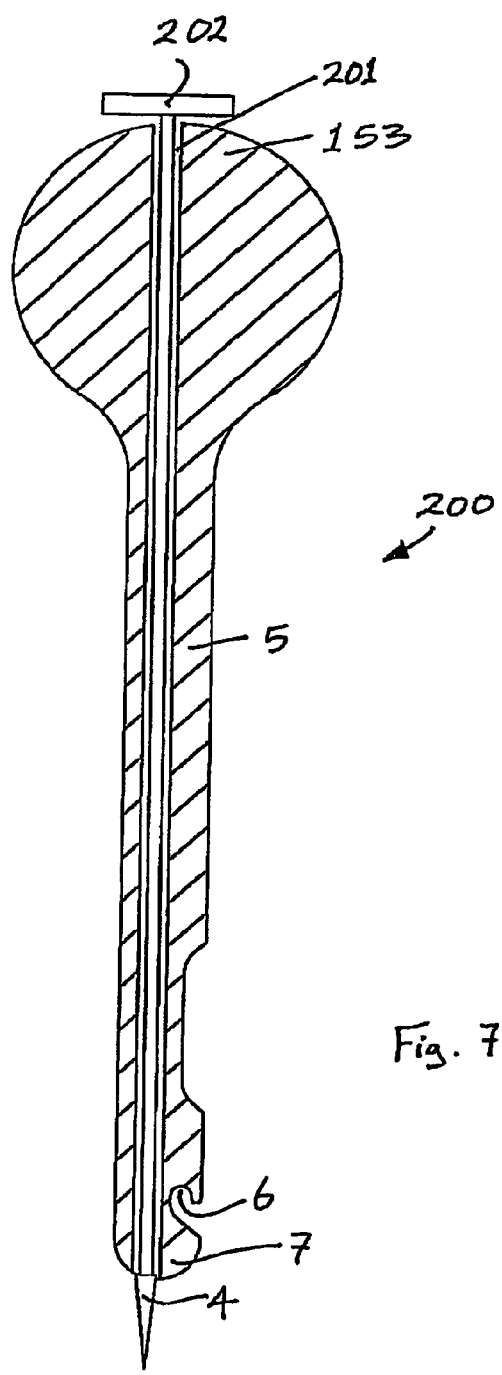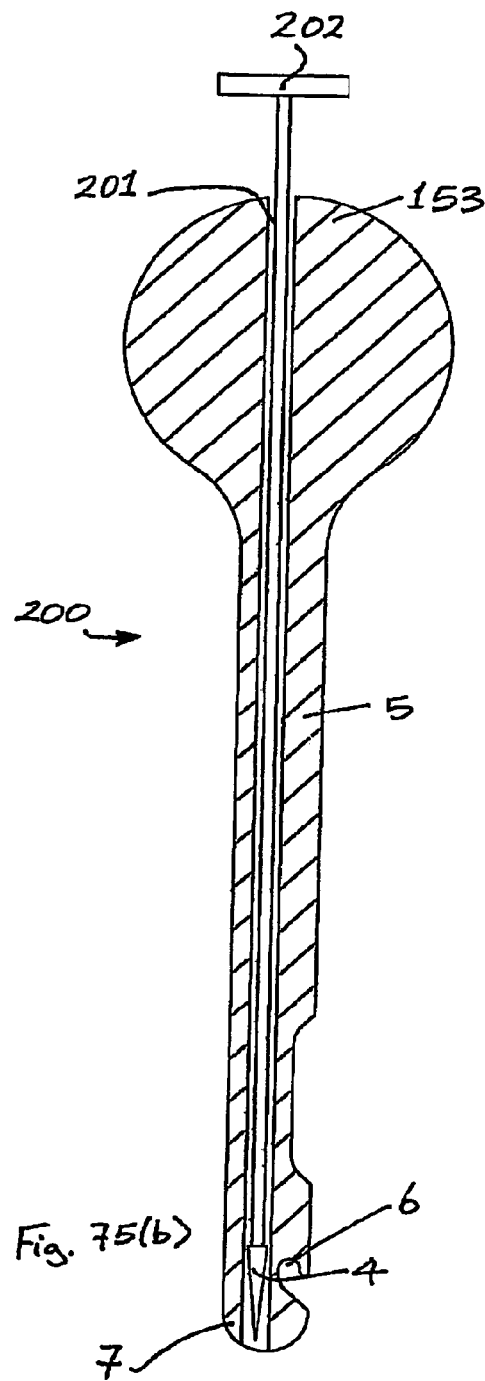
Fig. 75(a)
Fig. 75(b)

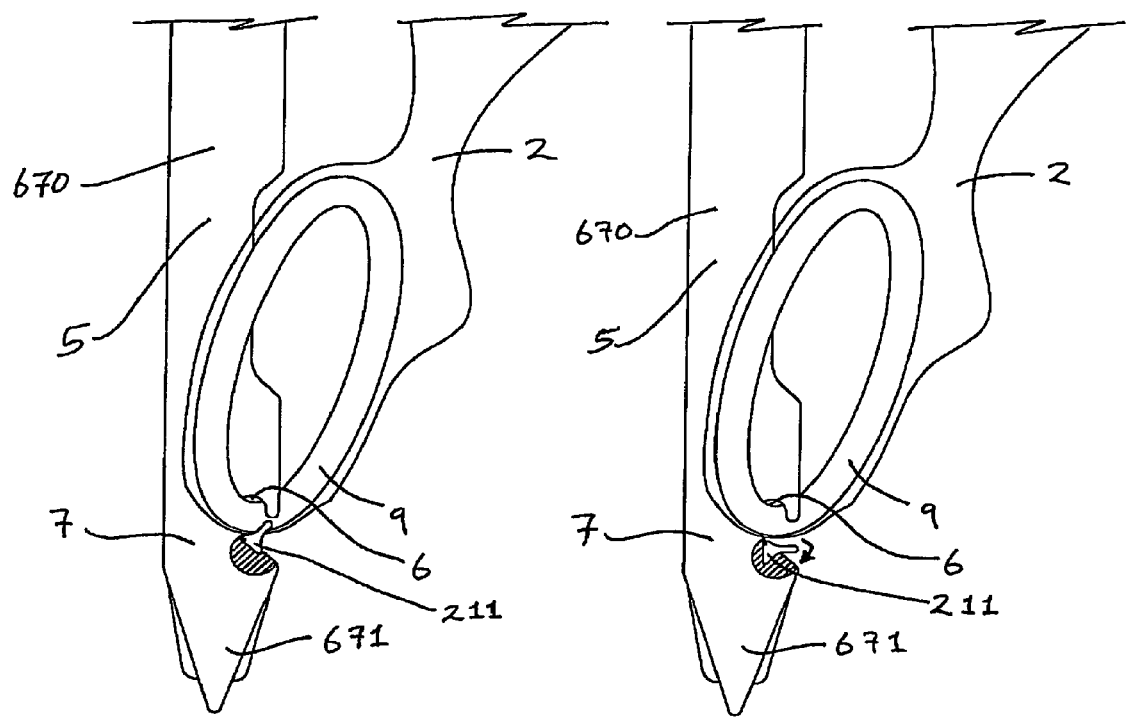
Fig. 75(k)(i)   Fig. 75(k)(ii)

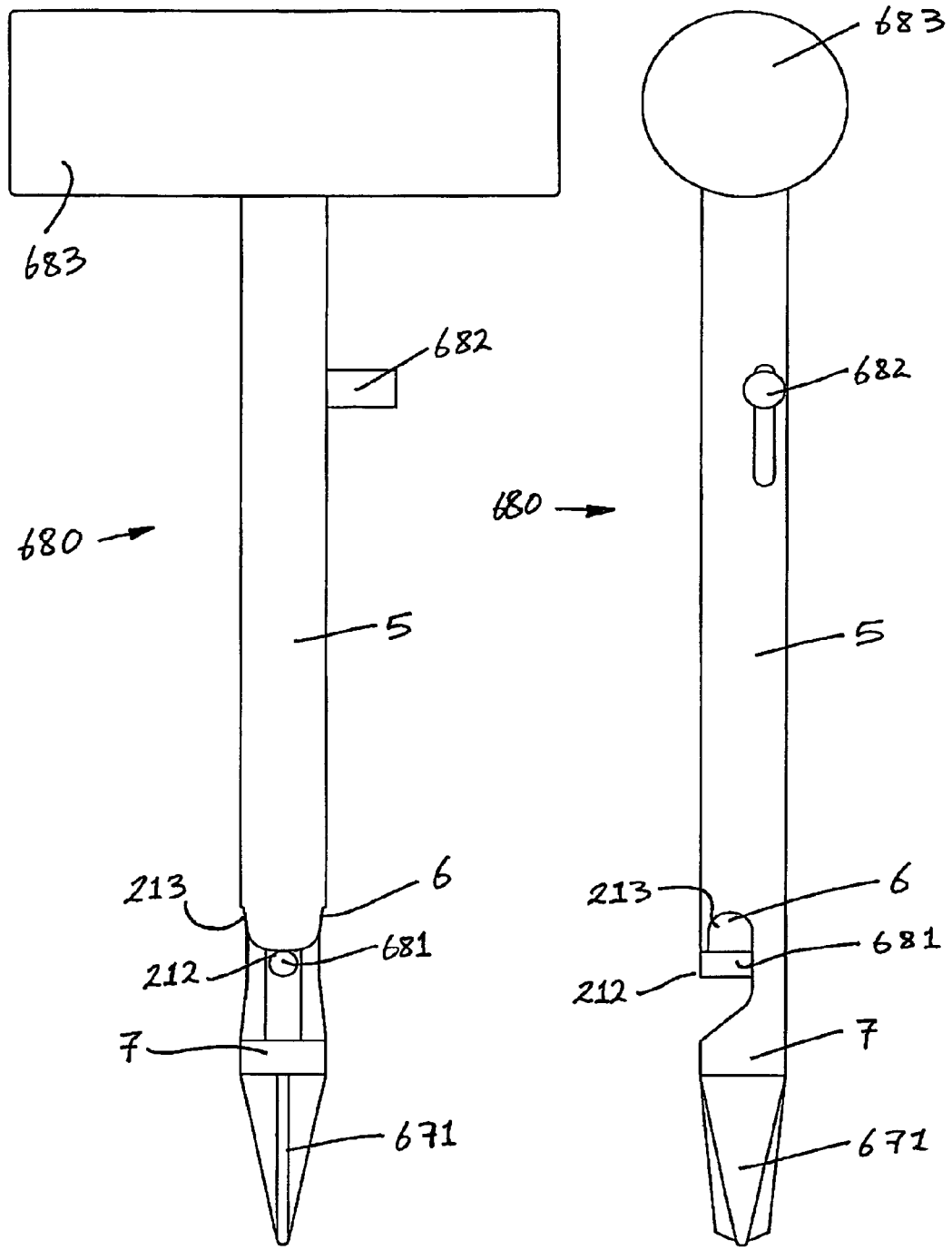
Fig. 75(k)(iii)     Fig. 75(K)(iv)

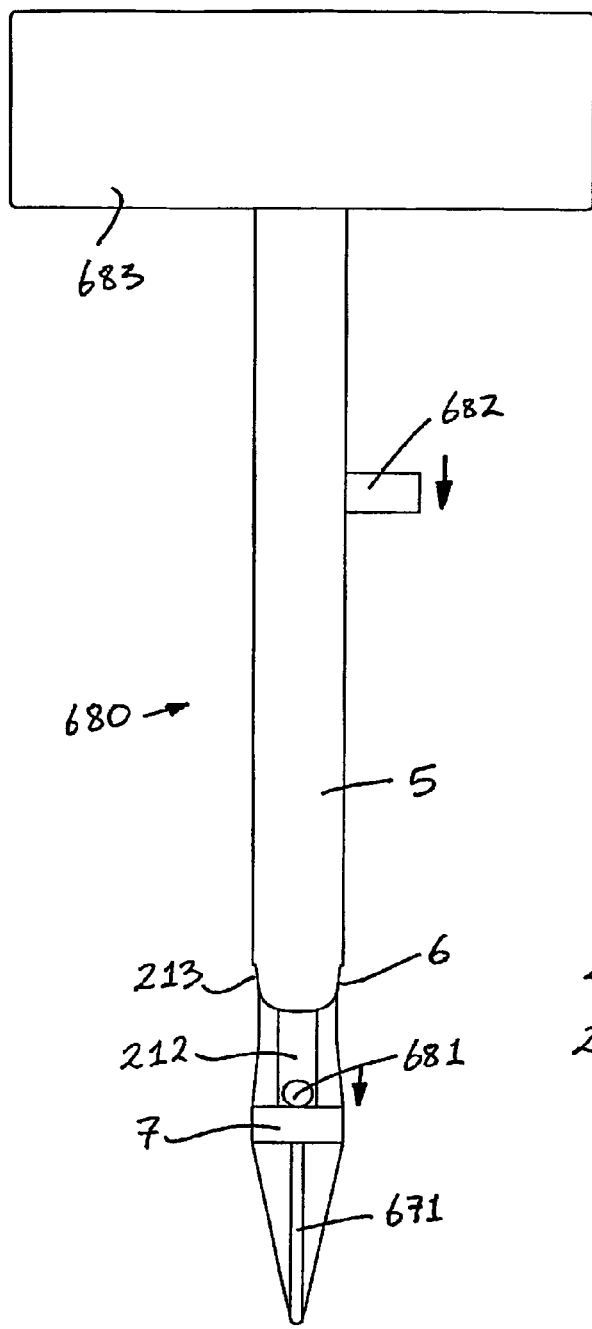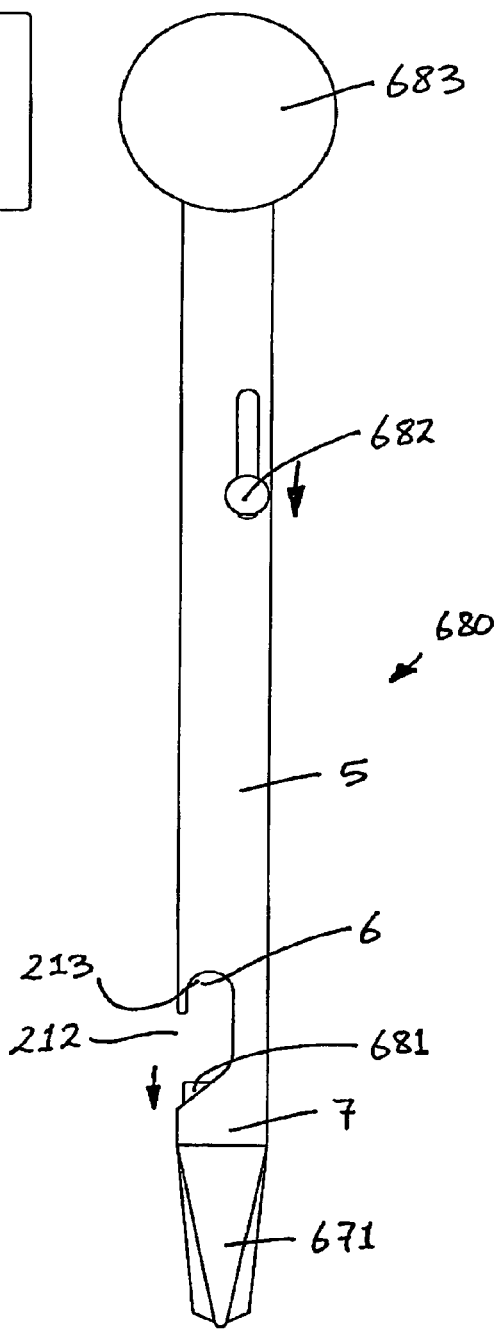
Fig. 75(k)(v)  Fig. 75(k)(vi)

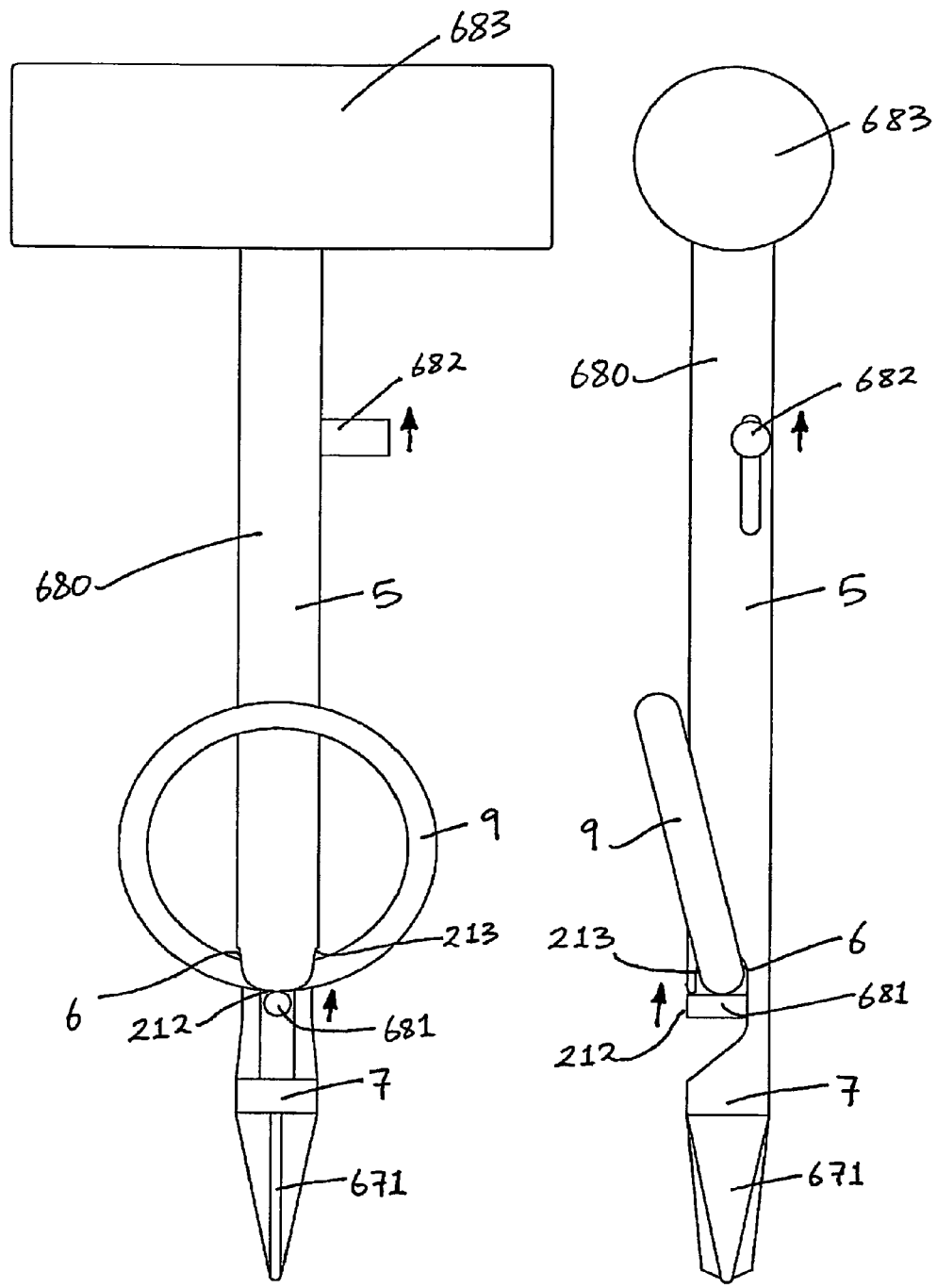
Fig. 75(k)(vii)        Fig. 75(k)(viii)

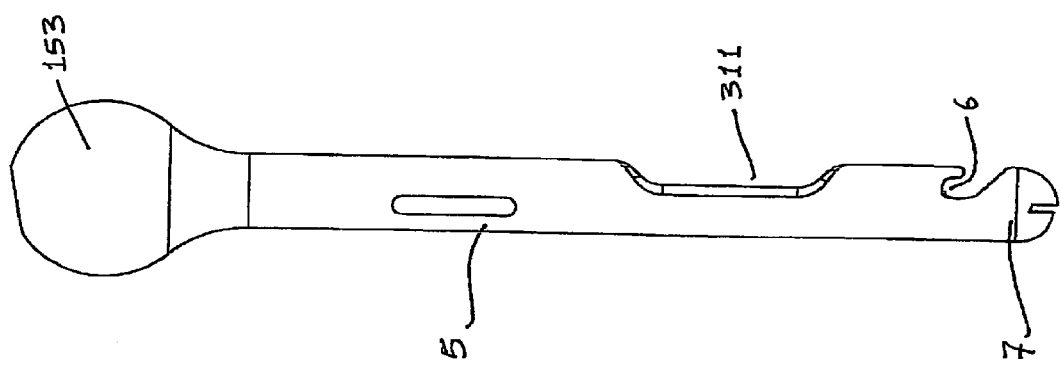

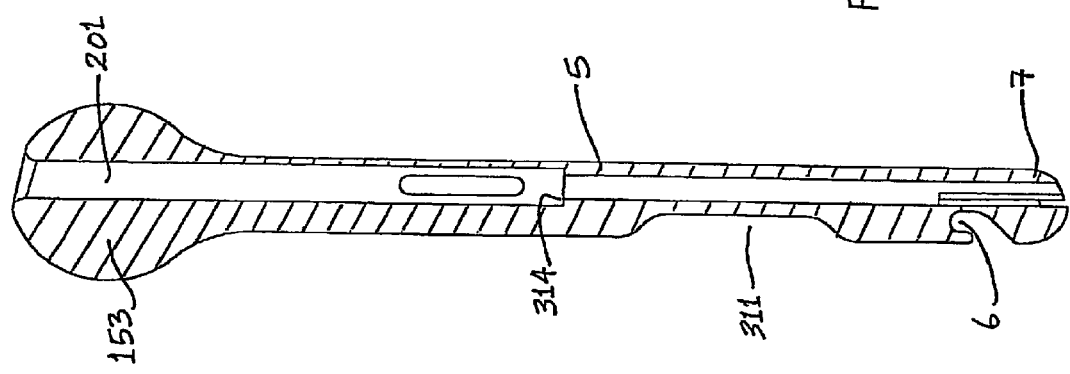

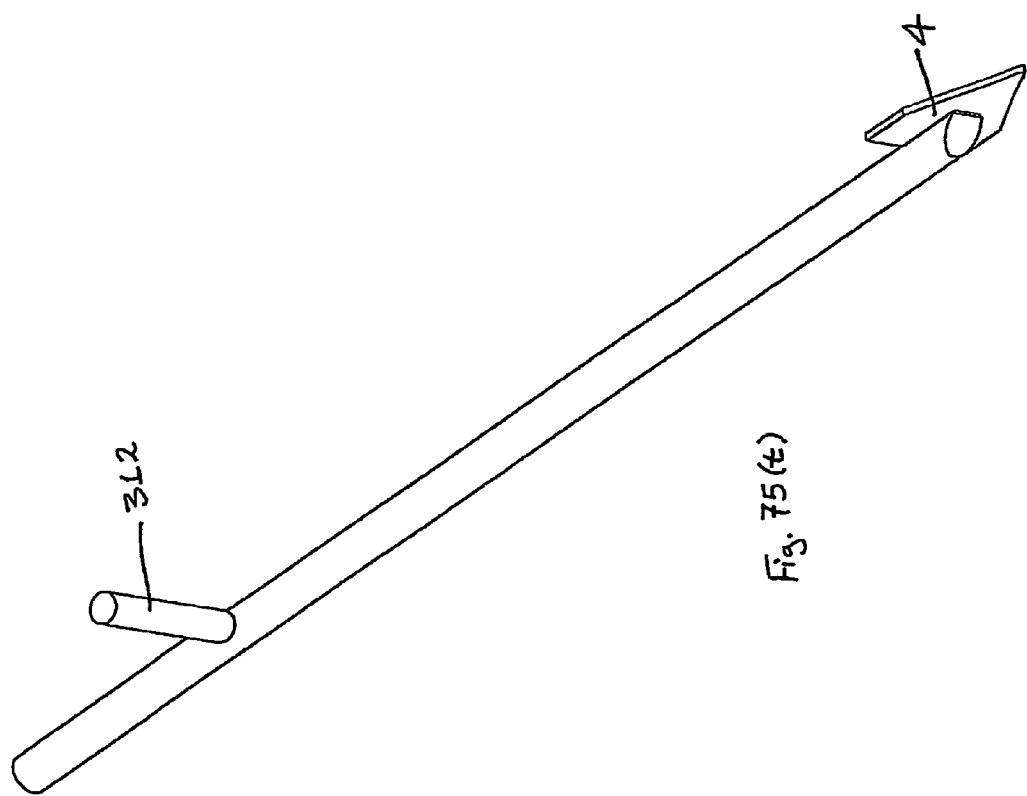

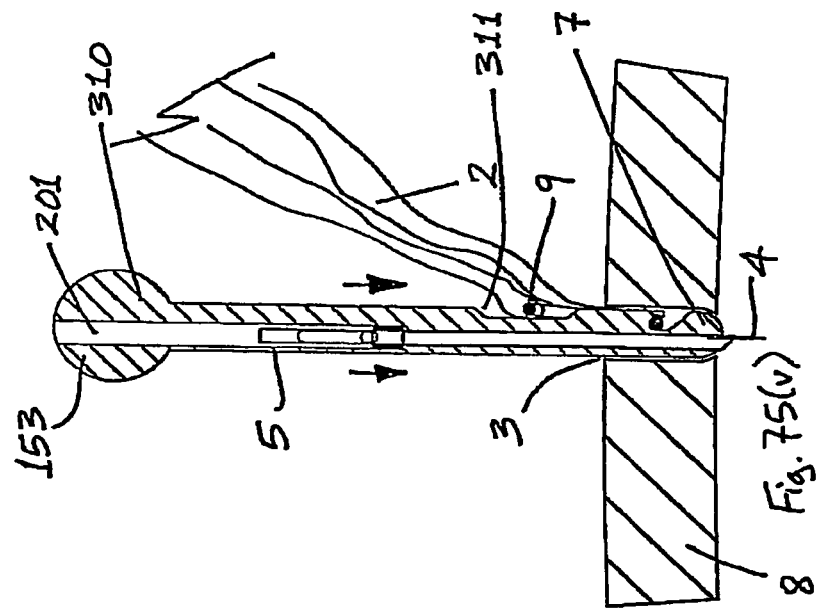
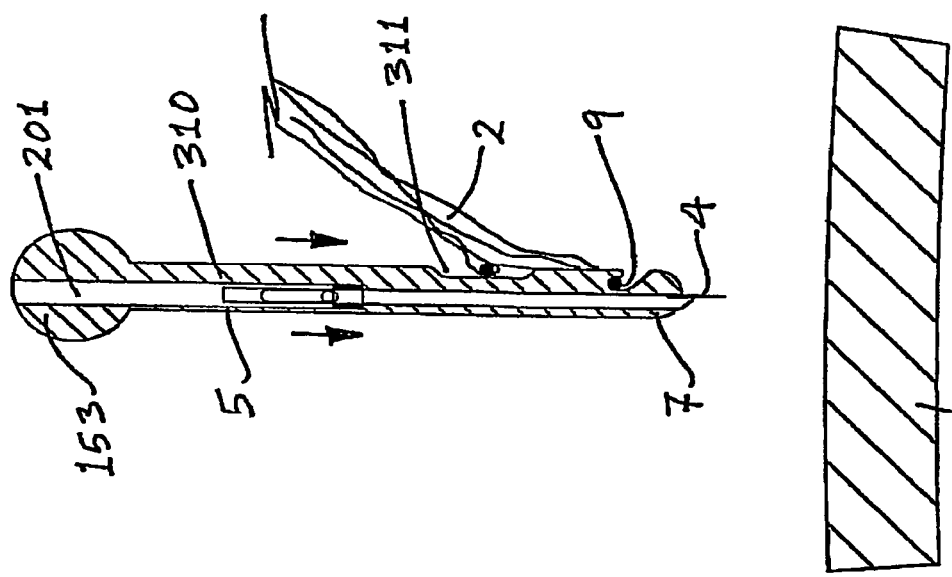

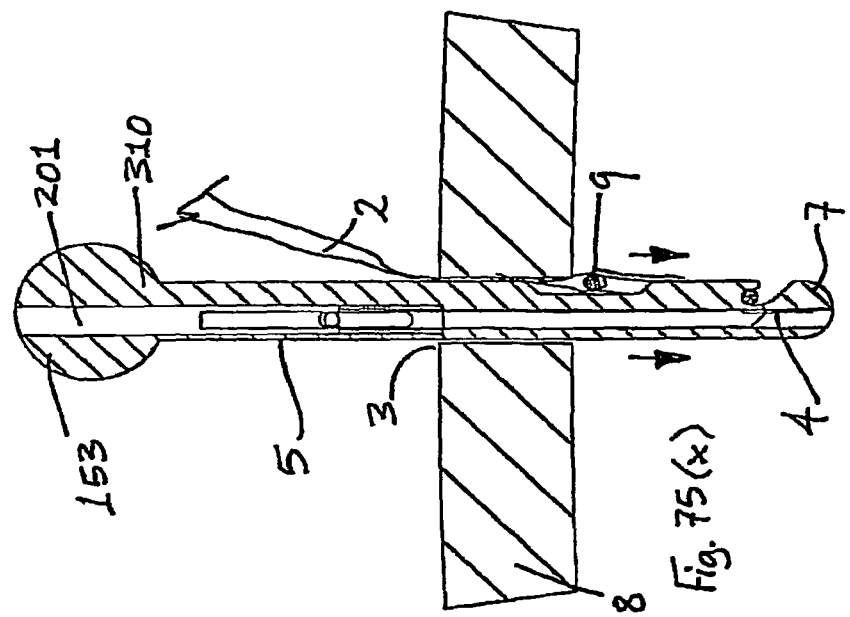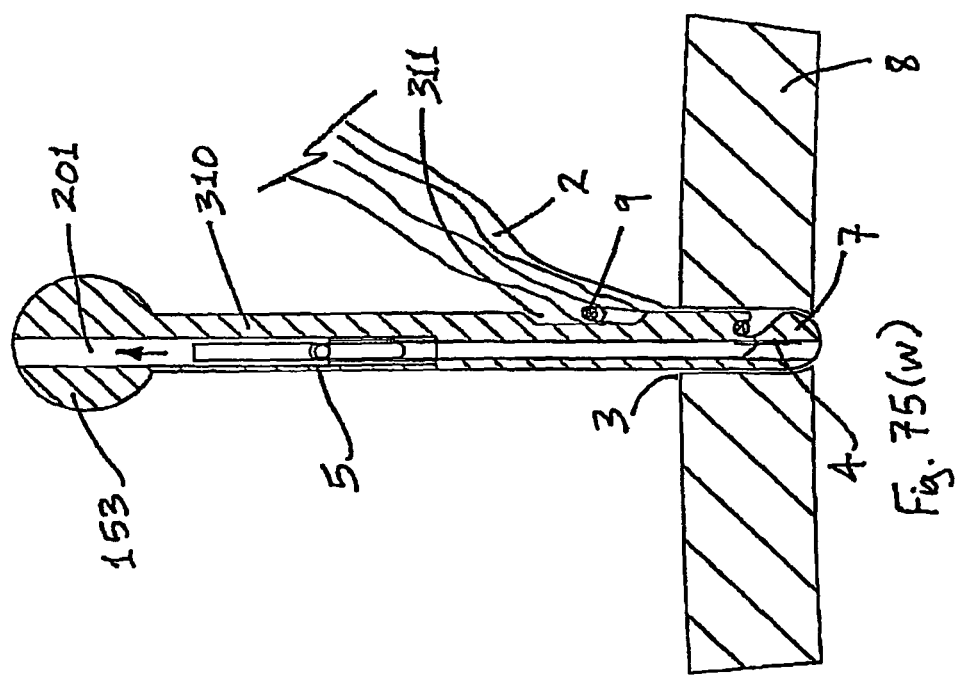

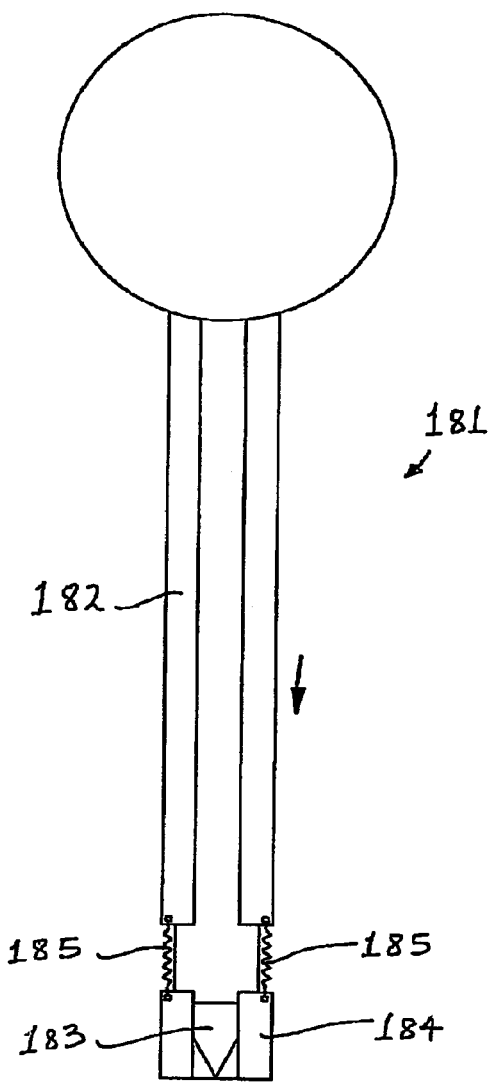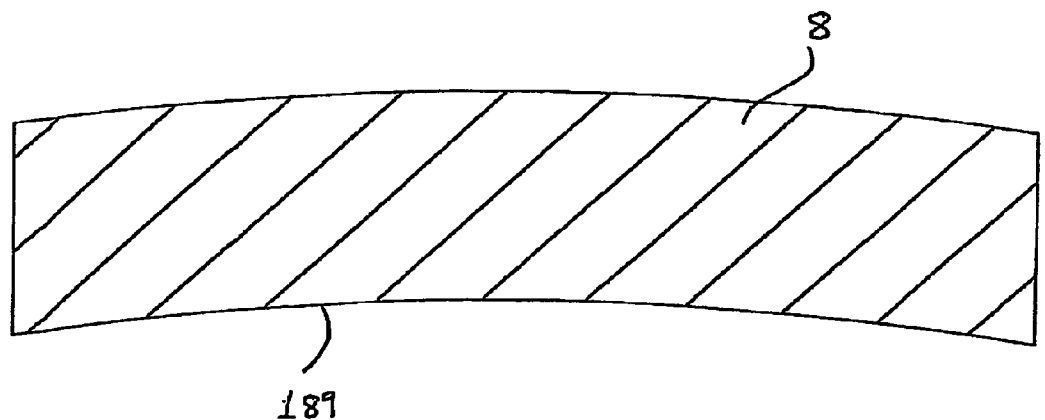
Fig. 76

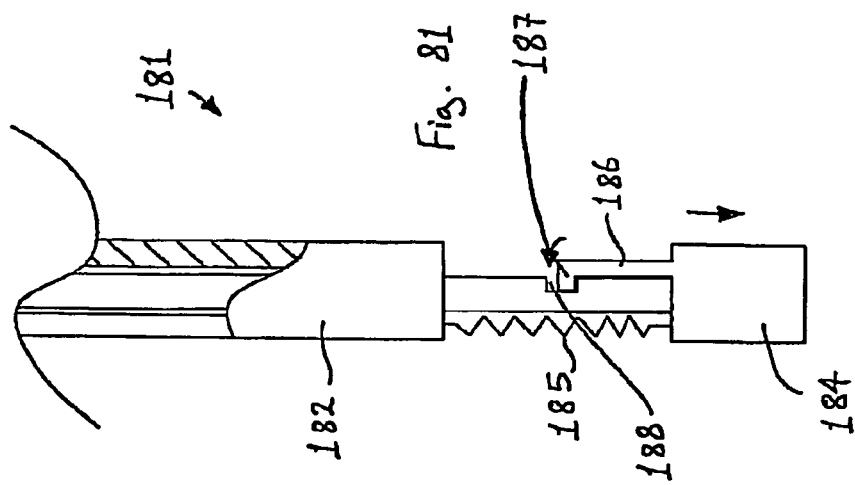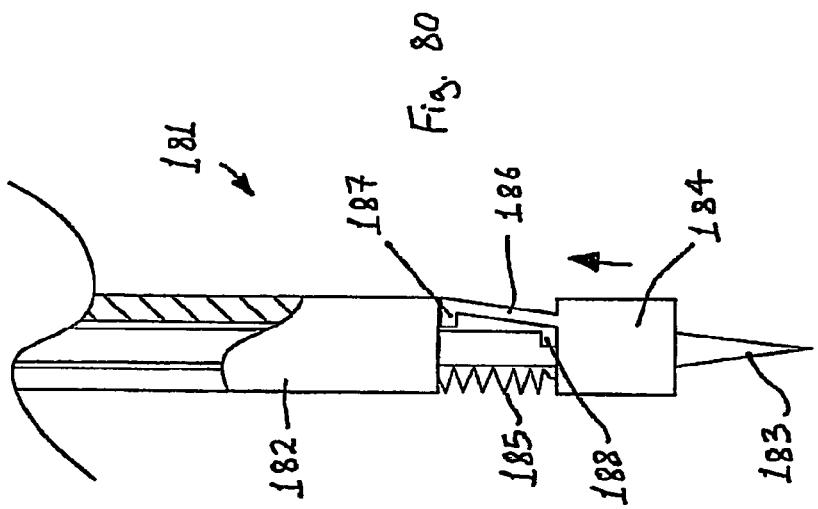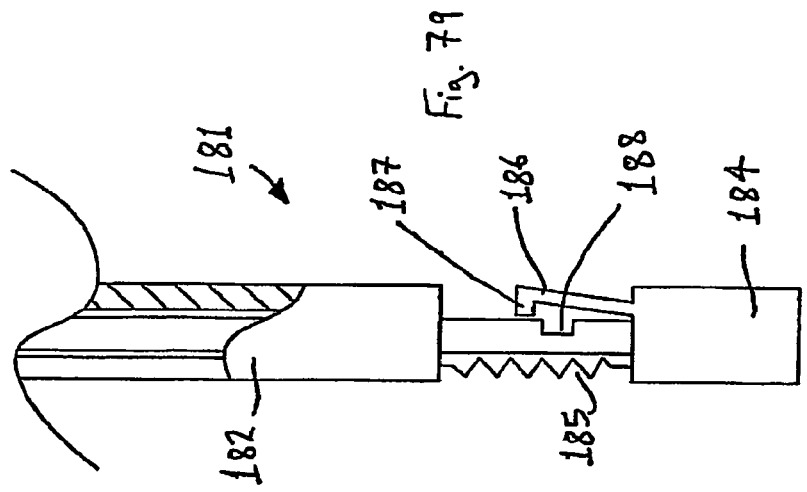

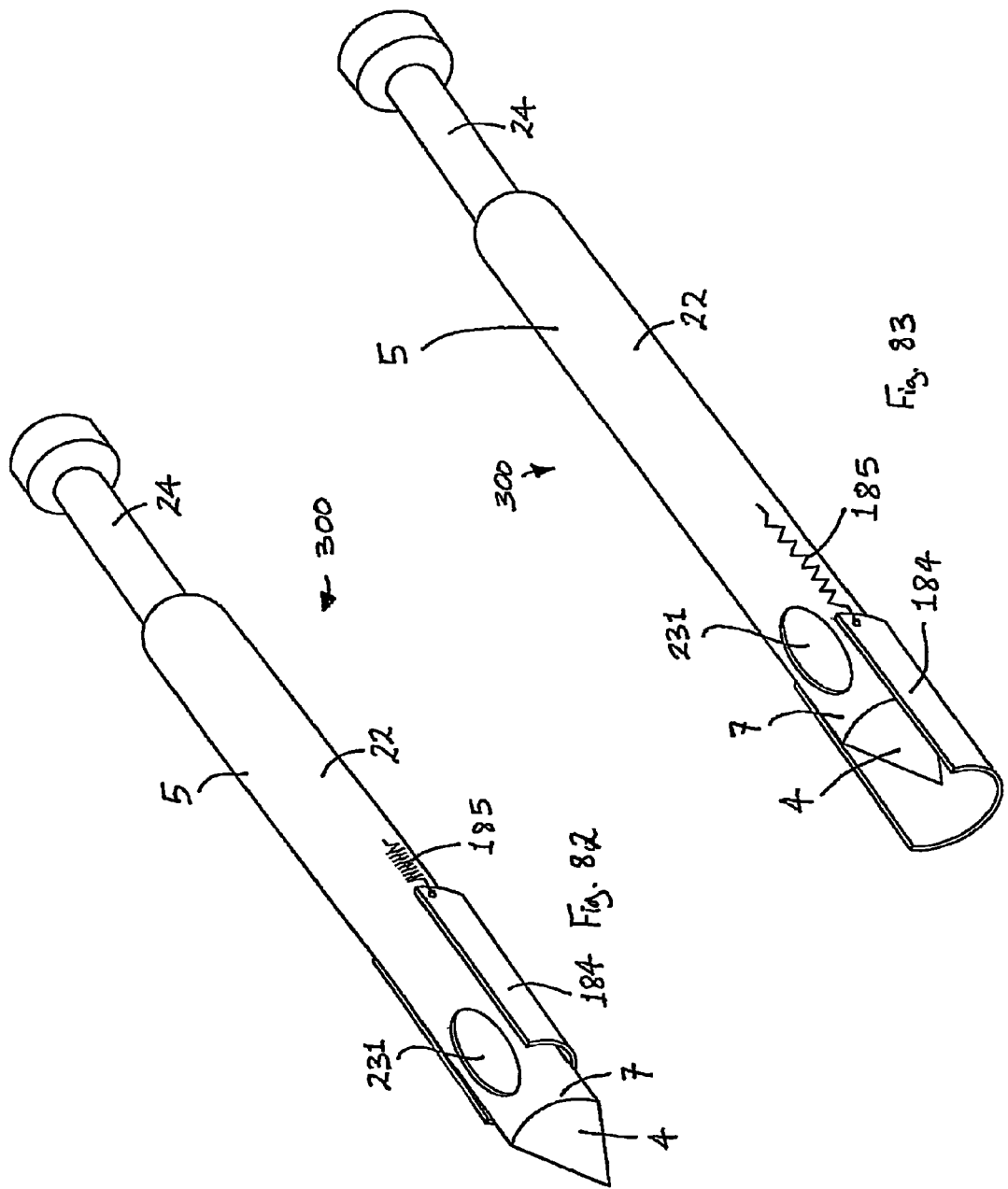

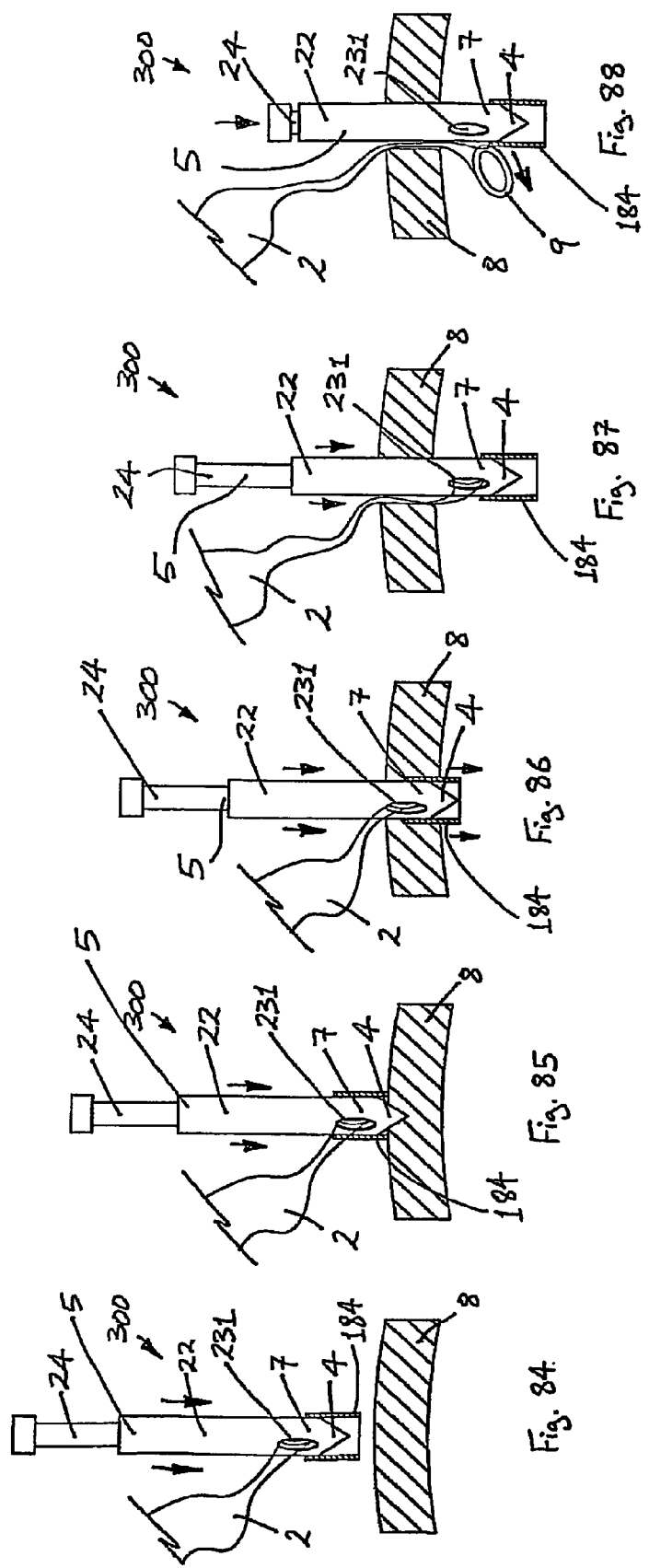

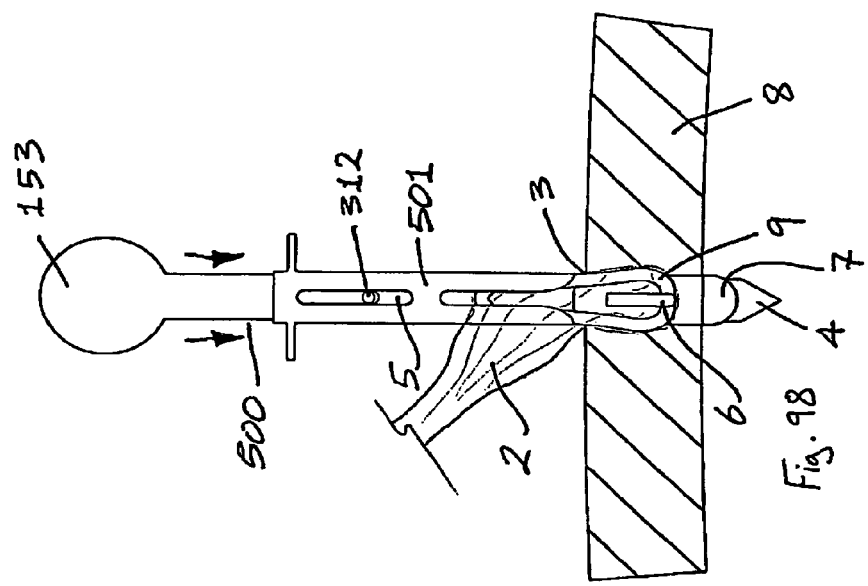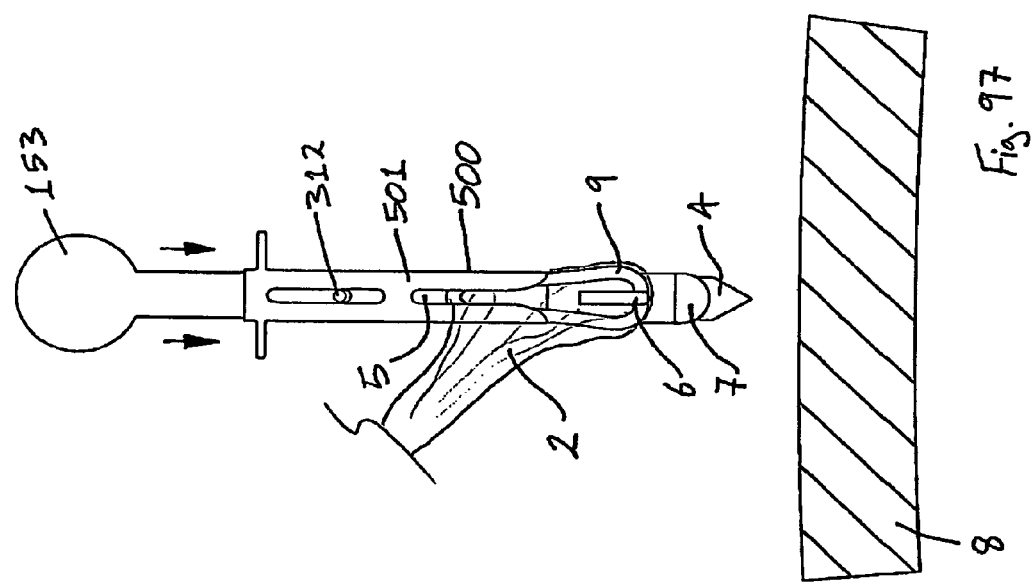

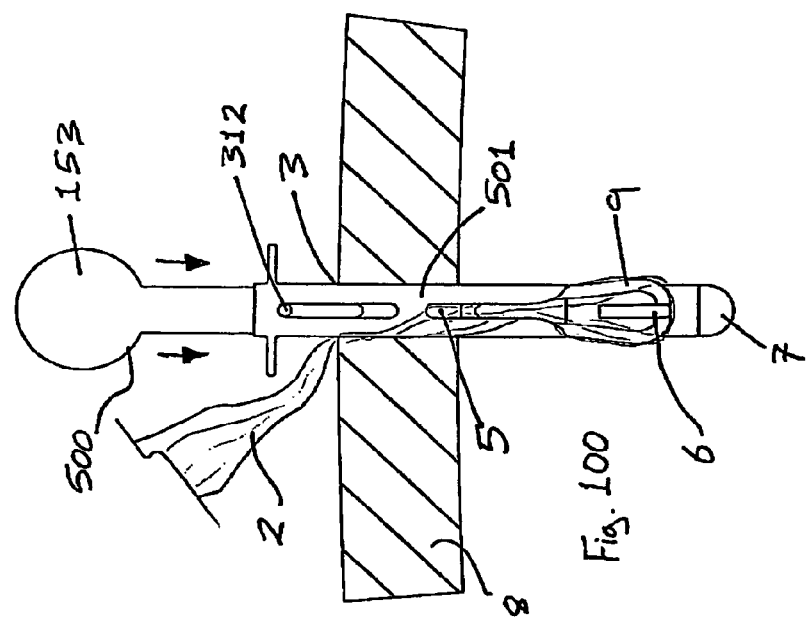
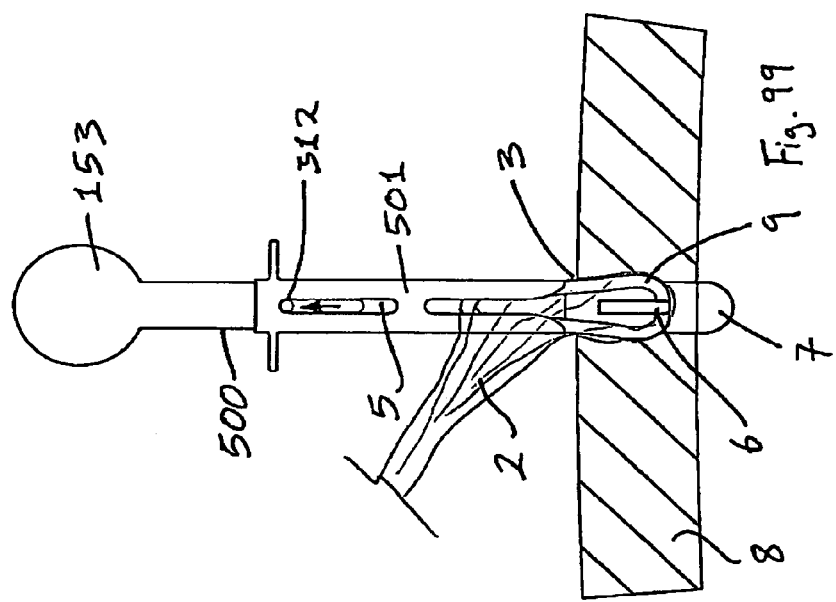

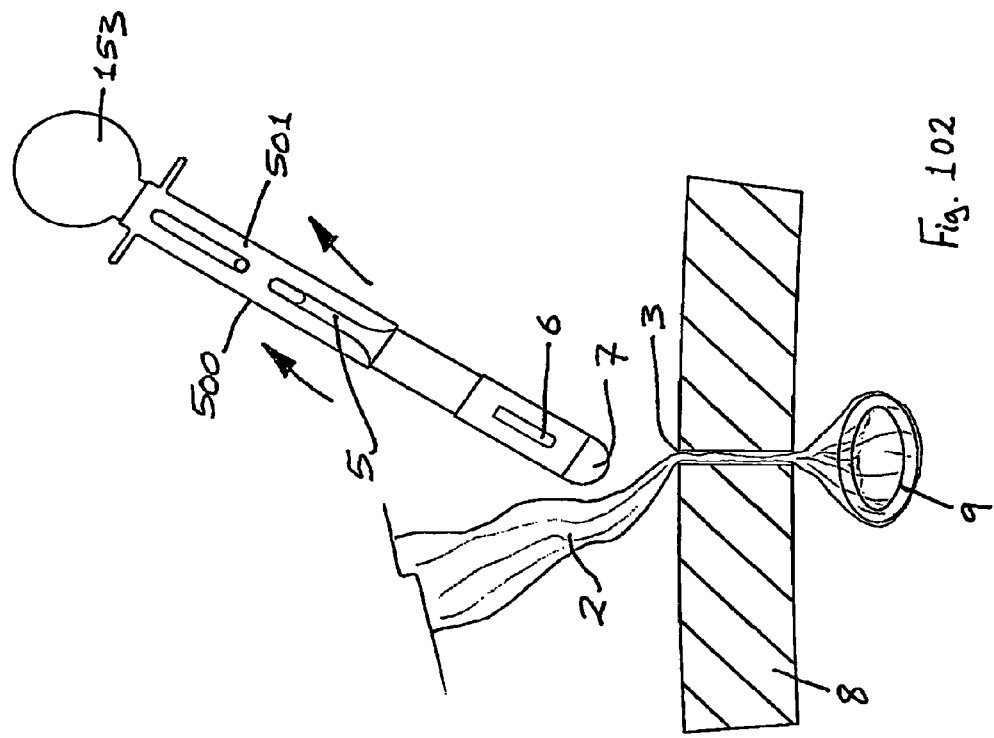
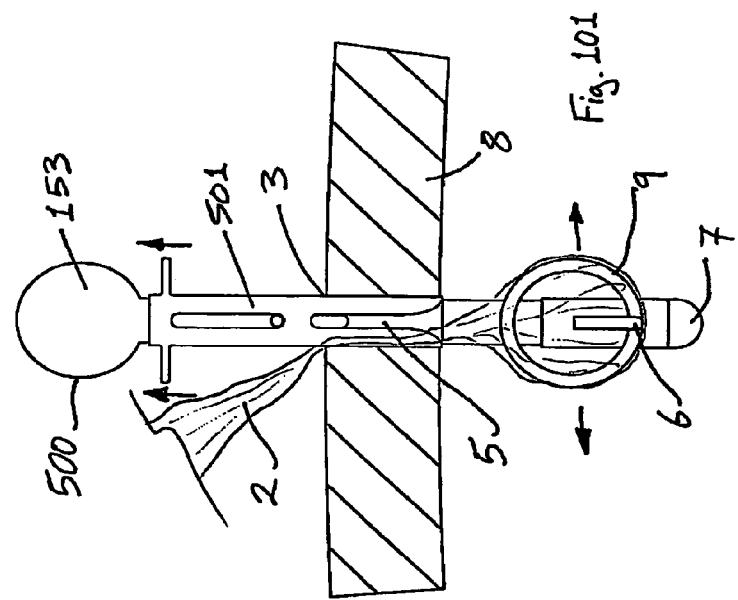

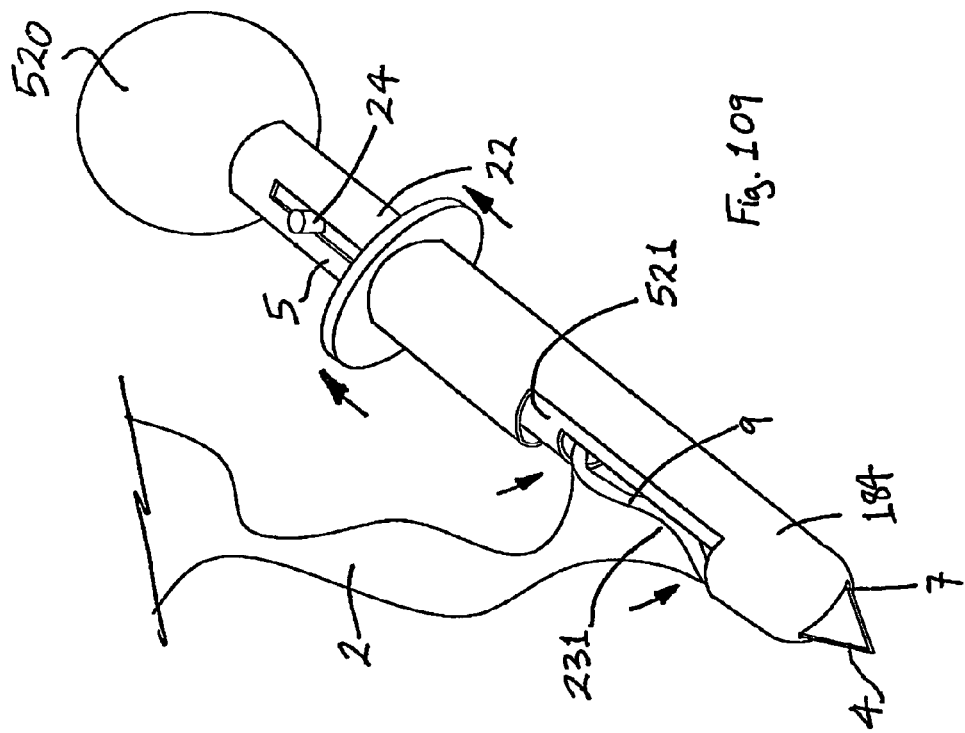
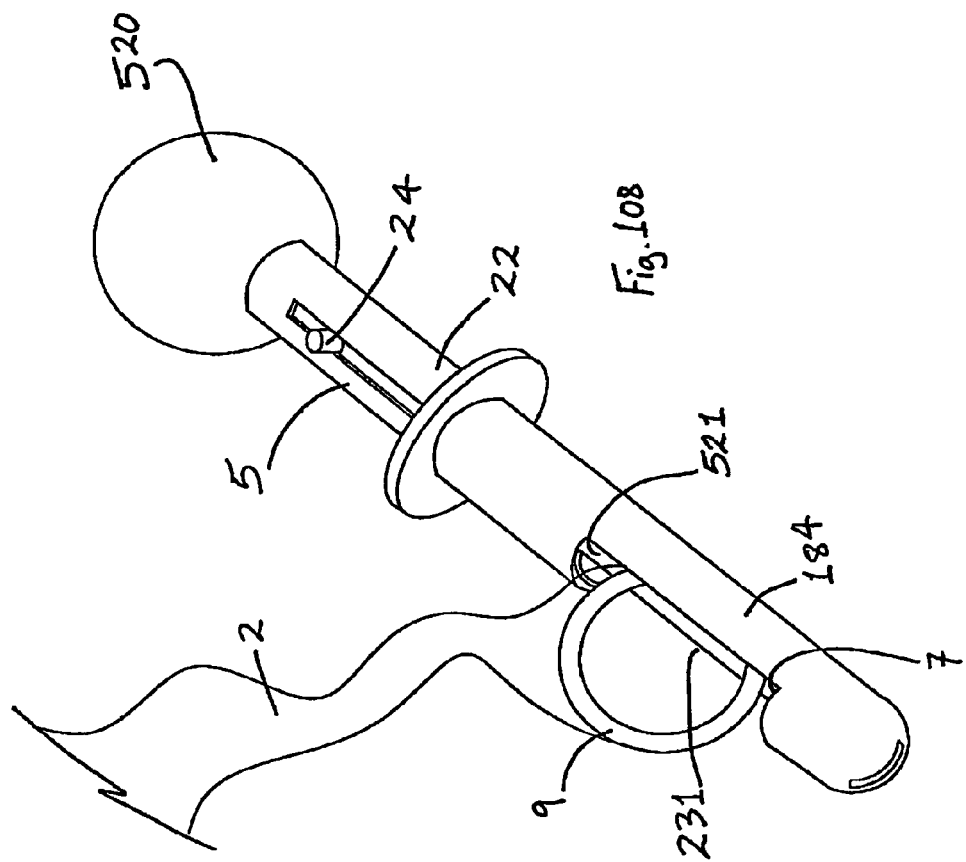

APPARATUS FOR INSERTING A SURGICAL DEVICE AT LEAST PARTIALLY THROUGH A WOUND OPENING

CROSS-REFERENCE TO RELATED APPLICATIONS

This application is a Continuation of U.S. patent application Ser. No. 11/1347,803, filed Feb. 6, 2006, which is a Continuation-In-Part of U.S. application Ser. No. 10/665,395, filed Sep. 22, 2003, now U.S. Pat. No. 7,867,164, which is a Continuation-In-Part of U.S. application Ser. No. 10/374,523, filed Feb. 27, 2003, now U.S. Pat. No. 7,445,597, which is a Continuation of U.S. application Ser. No. 09/849,341, filed May 7, 2001, now U.S. Pat. No. 6,582,364, which is a Continuation of U.S. application Ser. No. 09/688,138, filed Oct. 16, 2000, now U.S. Pat. No. 6,254,534.

Application Ser. No. 10/665,395 claims the benefit of U.S. Provisional Application No. 60/490,909, filed Jul. 30, 2003.

Application Ser. No. 11/347,803 is a Continuation-In-Part of U.S. application Ser. No. 10/902,440 filed Jul. 30, 2004, now abandoned, which is a Continuation-In-Part of U.S. application Ser. No. 10/736,234, filed Dec. 16, 2003, now abandoned, which claims the benefit of U.S. Provisional Application Nos. 60/433,603, filed Dec. 16, 2002, and 60/453,200, filed Mar. 11, 2003.

Application Ser. No. 10/902,440 is a Continuation-in-Part of U.S. application Ser. No. 10/678,653, filed Oct. 6, 2003, now U.S. Pat. No. 7,559,893, which is a Continuation-in-Part of U.S. application Ser. No. 10/133,979, filed Apr. 29, 2002, now U.S. Pat. No. 6,846,287, which is a Continuation of U.S. application Ser. No. 09/801,826, filed Mar. 9, 2001, now abandoned, which is a Continuation of PCT/IE99/00122, filed Dec. 1, 1999.

Application Ser. No. 10/678,653 is a Continuation-In-Part of U.S. application Ser. No. 10/374,523, filed Feb. 27, 2003, now U.S. Pat. No. 7,445,597, which is a Continuation of U.S. application Ser. No. 09/849,341, filed May 7, 2001, now U.S. Pat. No. 6,582,364, which is a Continuation of U.S. application Ser. No. 09/688,138, filed Oct. 16, 2000, now U.S. Pat. No. 6,254,534.

Application Ser. No. 10/678,653 claims the benefit of U.S. Provisional Application Nos. 60/415,780, filed Oct. 4, 2002, 60/428,215, filed Nov. 22, 2002, and 60/490,909, filed Jul. 30, 2003.

Application Ser. No. 10/902,440 is a Continuation-In-Part of U.S. application Ser. No. 10/665,395, filed Sep. 22, 2003, now U.S. Pat. No. 7,867,164, which is a Continuation-In-Part of U.S. application Ser. No. 10/374,523, filed Feb. 27, 2003, now U.S Pat. No. 7,445,597, which is a Continuation of U.S. application Ser. No. 09/849,341, filed May 7, 2001, now U.S. Pat. No. 6,582,364, which is a Continuation of U.S. application Ser. No. 09/688,138, filed Oct. 16, 2000, now U.S. Pat. No. 6,254,534.

Application Ser. No. 10/665,395 claims the benefit of U.S. Provisional Application No. 60/490,909, filed Jul. 30, 2003.

Application Ser. No. 10/902,440 is a Continuation-in-Part of U.S. application Ser. No. 10/374,523, filed Feb. 27, 2003, now U.S. Pat. No. 7,445,597, which is a Continuation of U.S. application Ser. No. 09/849,341, filed May 7, 2001, now U.S. Pat. No. 6,582,364, which is a Continuation of U.S. application Ser. No. 09/688,138, filed Oct. 16, 2000, now U.S. Pat. No. 6,254,534.

Application Ser. No. 10/902,440 is a Continuation-in-Part of U.S. application Ser. No. 10/315,233, filed Dec. 10 2002, now abandoned, which is a Continuation of U.S. application Ser. No. 09/804,552, filed Mar. 13, 2001, now U.S. Pat. No. 6,578,577, which is a Continuation of PCT/IE99/00123, filed Dec. 1, 1999.

Application Ser. No. 10/902,440 is a Continuation-In-Part of U.S. application Ser. No. 10/133,979, filed Apr. 29, 2002, now U.S. Pat. No. 6,846,287, which is a Continuation of U.S. application Ser. No. 09/801,826, filed Mar. 9, 2001, now abandoned, which is a Continuation of PCT/IE99/00122, filed Dec. 1, 1999.

Application Ser. No. 10/902,440 claims the benefit of U.S. Provisional Application No. 60/490,909, filed Jul. 30, 2003.

Application Ser. No. 11/347,803 claims the benefit of U.S. Provisional Application Nos. 60/650,197, filed Feb. 4, 2005, 60/724,775, filed Oct. 11, 2005, and 60/740,634, filed Nov. 30, 2005.

All the above applications are incorporated by reference herein in their entirety.

INTRODUCTION

This invention relates to an apparatus for inserting a surgical device at least partially through a wound opening, and to a method of inserting the surgical device at least partially through the wound opening.

STATEMENTS OF INVENTION

According to the invention there is provided an apparatus for inserting a surgical device at least partially through a wound opening, the apparatus comprising:—
a conveying device insertable at least partially through a wound opening to convey a surgical device at least partially through the wound opening.

In one embodiment of the invention the conveying device is configured to engage a surgical device to couple the surgical device to the conveying device. The conveying device may comprise a hook element to engage a surgical device. A concave portion of the hook element may face distally. The hook element may be provided in the region of a distal end of the conveying device. The conveying device may comprise a body portion, and the hook element may be movable relative to the body portion.

In one embodiment the conveying device comprises a retaining element to retain a surgical device in engagement with the conveying device. The conveying device may comprise a passageway to facilitate location of a surgical device in engagement with the conveying device. The passageway may facilitate location of at least part of a surgical device in the concave portion of the hook element. The retaining element may be configured to selectively obstruct at least part of the passageway.

In one case the retaining element is movable between an obstructing configuration obstructing at least part of the passageway and a passage configuration facilitating passage of a surgical device through the passageway. The retaining element may be pivotably movable between the obstructing configuration and the passage configuration. The retaining element may be biased towards the obstructing configuration. The retaining element may comprise a resilient arm. The conveying device may comprise a control element to control movement of the retaining element between the obstructing configuration and the passage configuration.

In one embodiment the apparatus is configured to insert a surgical device at least partially through a wound opening with at least part of the surgical device in a low-profile configuration. The apparatus may comprise a holder element for holding at least part of a surgical device in a low-profile configuration. The holder element may be movable relative to the conveying device between a holding configuration in which at least part of a surgical device is held in a low-profile configuration and a release configuration in which the surgical device is released. The holder element may be mounted to the conveying device. The holder element may be concentrically mounted around the conveying device.

In one case the apparatus is configured to hold a first part of a surgical device externally of a wound opening during conveying of a second part of the surgical device through the wound opening. The apparatus may be configured to maintain part of a surgical device in tension. The apparatus may comprise a receiver portion for receiving a first part of a surgical device to hold the first part. The receiver portion may comprise a slot. The receiver portion may comprise a housing portion. The receiver portion may be provided at a proximal end of the conveying device.

In another embodiment the conveying device comprises a housing portion for receiving at least part of a surgical device to couple the surgical device to the conveying device. The housing portion may have an exit opening to facilitate ejection of at least part of a surgical device from within the housing portion. The housing portion may have an entry opening to facilitate insertion of at least part of a surgical device into the housing portion. The housing portion may have an opening which acts as both the exit opening and the entry opening. The exit opening and/or the entry opening may be provided at a distal end of the housing portion. The exit opening and/or the entry opening may face distally.

The exit opening and/or the entry opening may be provided along at least part of a sidewall of the housing portion. In one case the exit opening and/or the entry opening faces laterally.

In one case the apparatus comprises a closure element to selectively close the exit opening and/or the entry opening.

The housing portion may have a sleeve opening to facilitate a part of a surgical device extending out of the housing portion. The sleeve opening may be provided along at least part of the sidewall of the housing portion. The sleeve opening may face laterally.

In one case the housing portion has an opening which acts as both the sleeve opening and the exit opening. The housing portion may have an opening which acts as both the sleeve opening and the entry opening.

In a further case the conveying device comprises an ejector element to assist ejection of at least part of a surgical device from within the housing portion. The ejector element may comprise a plunger.

The housing portion may be substantially non-circular in cross-section. The housing portion may be substantially oval-shaped in cross-section.

In another embodiment the conveying device comprises an insertion element insertable at least partially through a wound opening and a drawing element to couple a surgical device to the insertion element for drawing of the surgical device at least partially through the wound opening. The drawing element may be substantially flexible. The drawing element may comprise a length of string. The insertion element may have an opening through which the drawing element extends to couple the drawing element to the insertion element. The opening may be provided in the region of a distal end of the insertion element.

The conveying device may be configured to convey a surgical device arranged concentrically with respect to a longitudinal axis of the conveying device. The conveying device may be configured to convey a surgical device arranged offset with respect to a longitudinal axis of the conveying device.

In one case the conveying device has a wound extending portion with a maximum transverse dimension of between 3 mm and 35 mm. The maximum transverse dimension of the wound extending portion may be between 5 mm and 12 mm.

In one case a distal end of the conveying device is substantially blunt. In another case a distal end of the conveying device is substantially rounded.

In one embodiment the apparatus comprises an opening device to create a wound opening.

The opening device may comprise an incising device. The incising device may be configured to create a wound opening by cutting tissue. The incising device may comprise a substantially sharp tip. The incising device may comprise a blade element. The incising device may comprise an electrocautery scalpel.

The opening device may be configured to create a wound opening by forcing tissue apart. The opening device may comprise a substantially blunt tip. The opening device may comprise a substantially bladeless tip.

The opening device may be mounted to the conveying device. The conveying device may comprise a lumen extending therethrough and the opening device may be extendable through the lumen to mount the opening device to the conveying device. The opening device may be mounted substantially concentrically with respect to a longitudinal axis of the conveying device.

The opening device may be attached to the conveying device. In one case the opening device is releasably attached to the conveying device. The apparatus may be configured to create a wound opening and convey a surgical device at least partially through the wound opening in a single step.

The opening device may be provided at a distal end of the conveying device.

In one case the opening device is movable relative to the conveying device between an extended configuration and a retracted configuration. The opening device may be manually movable relative to the conveying device between the extended configuration and the retracted configuration. The opening device may comprise a handle portion to facilitate manual movement of the opening device. The opening device may be biased towards the retracted configuration. The opening device may be biased towards the extended configuration.

In another case the opening device is detached from the conveying device.

The apparatus may be configured to create a wound opening in an opening step and to convey a surgical device at least partially through the wound opening in a separate conveying step. In one embodiment the conveying device is configured to be inserted at least partially through a wound opening after the opening device has been removed from the wound opening. In another embodiment the conveying device is configured to be inserted at least partially through a wound opening while the opening device remains in position extending through the wound opening. In the retracted configuration a distal end of the opening device may be covered. In the retracted configuration a distal end of the opening device may be housed within the conveying device. The opening device may have a wound extending portion with a substantially flattened cross-section. The conveying device may have a wound extending portion with a substantially flattened cross-section.

In a further embodiment the opening device comprises a cutting element for creating a wound opening and a shield element for shielding the cutting element. The shield element may be movable relative to the cutting element between a cutting configuration and a shielding configuration. The opening device may be biased towards the shielding configuration. The opening device may comprise a locking element to releasably lock the opening device in the shielding configuration.

The cutting element may be fixed to the conveying device. The shield element may be mounted to the conveying device. The shield element may be concentrically mounted around the conveying device.

In one case the opening device comprises a support element, the cutting element being fixedly attached to the support element and the shield element being movably attached to the support element.

In another case the opening device comprises a support element, the shield element being fixedly attached to the support element and the cutting element being movably attached to the support element.

In a further embodiment the opening device comprises a cutting element for creating a wound opening and a support element, the cutting element being releasably attached to the support element.

In one case the apparatus comprises a limiting element to limit the extent of passage of the opening device through tissue. The limiting element may comprise an abutment member for abutting an external surface of tissue adjacent a wound opening. The limiting element may be mounted to the opening device. The position of mounting of the limiting element on the opening device may be adjustable.

The limiting element may be movable relative to the opening device between a retracted configuration and an extended configuration. The limiting element may be biased towards the retracted configuration.

The opening device may have a wound extending portion with a maximum transverse dimension of between 3 mm and 35 mm. The maximum transverse dimension of the wound extending portion may be between 5 mm and 12 mm.

In another embodiment the apparatus comprises a guide device insertable at least partially through a wound opening to maintain the patency of the wound opening.

The guide device may be substantially flexible. The guide device may comprise a length of string.

The guide device may be substantially rigid. In one case the guide device is substantially tubular. The guide device may have a substantially flattened, oblong cross-section. The guide device may have a slot extending along a sidewall of the guide device.

The guide device may be mountable to the conveying device and/or to the opening device.

The guide device may have a wound extending portion with a maximum transverse dimension of between 3 mm and 35 mm. The maximum transverse dimension of the wound extending portion may be between 5 mm and 12 mm.

In another case the apparatus comprises a removal device to assist in removal of a surgical device from a wound opening. The removal device may be detached from a surgical device. The removal device may be configured to engage a surgical device to assist in removal of the surgical device from a wound opening. The removal device may be configured to engage a distal portion of a surgical device.

The removal device may comprise a hook element to engage a surgical device. A concave portion of the hook element may face proximally. The hook element may be provided in the region of a distal end of the removal device.

The removal device may comprise a gripping portion which may be gripped.

In one case the removal device comprises a connector element extendable at least partially through a wound opening. The connector element may be substantially flexible. The connector element may comprise a length of string.

The guide device and the removal device may be provided by a single device.

In another aspect of the invention there is provided a surgical assembly comprising: —
 a surgical device; and
 an apparatus of the invention for inserting the surgical device at least partially through a wound opening.

The surgical device may comprise a wound retractor device. The wound retractor device may comprise a distal retaining element for location distally of a wound opening to retain the wound retractor device in position retracting the wound opening.

In a further aspect, the invention provides a method of inserting a surgical device at least partially through a wound opening, the method comprising the steps of: —
 providing a surgical device;
 creating a wound opening; and
 conveying the surgical device at least partially through the wound opening.

The wound opening may be created and the surgical device may be conveyed at least partially through the wound opening in a single step.

In one embodiment the wound opening is created using an opening device, and the surgical device is conveyed at least partially through the wound opening using a conveying device. The method may comprise the step of moving the opening device relative to the conveying device between an extended configuration and a retracted configuration. The opening device may be moved relative to the conveying device from the extended configuration to the retracted configuration after the wound opening has been created. The opening device may be moved relative to the conveying device from the extended configuration to the retracted configuration before the surgical device has been conveyed fully through the wound opening.

In one case the opening device is manually moved relative to the conveying device between the extended configuration and the retracted configuration. The opening device may be pulled proximally relative to the conveying device from the extended configuration to the retracted configuration. The opening device may be moved relative to the conveying device from the extended configuration to the retracted configuration by a biasing element. The opening device may be moved while the conveying device remains in a fixed position.

The wound opening may be created in an opening step and the surgical device may be conveyed at least partially through the wound opening in a separate conveying step. In one case the wound opening is created using an opening device, and the surgical device is conveyed at least partially through the wound opening after the opening device has been removed from the wound opening. In another case the wound opening is created using an opening device, and the surgical device is conveyed at least partially through the wound opening while the opening device remains in position extending through the wound opening.

The surgical device may be conveyed at least partially through the wound opening by engaging the surgical device and pushing the surgical device distally. In one embodiment the method comprises the step of retaining the surgical device in engagement with a conveying device during the step of conveying at least partially through the wound opening.

The surgical device may be conveyed at least partially through the wound opening with at least part of the surgical device in a low-profile configuration. The method may comprise the step of holding at least part of the surgical device in the low-profile configuration during the step of conveying at least partially through the wound opening. The method may comprise the step of releasing the surgical device after conveying at least partially through the wound opening.

In one case the method comprises the step of holding a first part of the surgical device externally of the wound opening during conveying of a second part of the surgical device through the wound opening. Part of the surgical device may be maintained in tension.

The surgical device may be conveyed at least partially through the wound opening with at least part of the surgical device received in a housing portion of a conveying device. The method may comprise the step of inserting at least part of the surgical device into the housing portion before conveying at least partially through the wound opening. The method may comprise the step of ejecting at least part of the surgical device from within the housing portion after conveying at least partially through the wound opening.

The surgical device may be conveyed at least partially through the wound opening by drawing the surgical device distally.

In one case the wound opening is created by cutting tissue. In another case the wound opening is created by forcing tissue apart.

The wound opening may be created by advancing an opening device substantially distally through tissue. The wound opening may be created by rotating an opening device. The opening device may be rotated about an axis substantially parallel to the longitudinal axis of the wound opening.

In a further case the method comprises the steps of: —
providing a guide device; and
inserting the guide device at least partially through the wound opening to maintain the patency of the wound opening.

The wound opening may be created using an opening device, and the method may comprise the step of limiting the extent of passage of the opening device through tissue.

The wound opening may be created using an opening device, and the method may comprise the step of shielding a cutting element of the opening device after the wound opening has been created. The cutting element may be shielded before the surgical device has been conveyed fully through the wound opening. The method may comprise the step of exposing the cutting element to create the wound opening.

In one case the method comprises the step of removing the surgical device from the wound opening. The method may comprise the step of engaging the surgical device to remove the surgical device from the wound opening. A distal portion of the surgical device may be engaged.

The maximum transverse dimension of the wound opening is preferably between 3 mm and 35 mm. The maximum transverse dimension of the wound opening may be between 5 mm and 12 mm.

The invention also provides in another aspect a guide device insertable at least partially through a wound opening to maintain the patency of the wound opening.

In another aspect the invention provides a removal device to assist in removal of a surgical device from a wound opening.

According to another aspect the invention provides an opening device comprising a cutting element for creating a wound opening and a support element, the cutting element being releasably attached to the support element.

In a further aspect the invention provides an opening device to create a wound opening, the opening device comprising a limiting element to limit the extent of passage of the opening device through tissue.

According to another aspect the invention provides an opening device comprising a cutting element for creating a wound opening and a shield element for shielding the cutting element.

BRIEF DESCRIPTION OF THE DRAWINGS

The invention will be more clearly understood from the following description of some embodiments thereof, given by way of example only, with reference to the accompanying drawings, in which: —

FIG. 6 is a side view of another apparatus for inserting a surgical device at least partially through a wound opening according to the invention;

FIGS. 7 to 9 are partially cross-sectional, side views of the apparatus of FIG. 6, in use;

FIG. 10 is a side view of another apparatus for inserting a surgical device at least partially through a wound opening according to the invention and a surgical device;

FIG. 11 is a partially cut-away, side view of the apparatus and surgical device of FIG. 10;

FIGS. 12 to 15 are partially cross-sectional, side views of the apparatus of FIG. 10, in use;

FIGS. 16 to 21 are partially cross-sectional, side views of another apparatus for inserting a surgical device at least partially through a wound opening according to the invention, in use;

FIGS. 21(a) to 21(f) are views similar to FIGS. 10 to 15 of a further apparatus for inserting a surgical device at least partially through a wound opening according to the invention;

FIG. 21(q)(i) is a side view of another apparatus for inserting a surgical device at least partially through a wound opening according to the invention;

FIG. 21(q)(ii) is a perspective view of an opening device of the apparatus of FIG. 21(q)(i);

FIGS. 21(r)(i) to 21(v)(ii) are views similar to FIGS. 21(q)(i) and 21(q)(ii) of further apparatus for inserting a surgical device at least partially through a wound opening according to the invention;

FIGS. 24(e) to 24(j) are partially cut-away, perspective views of the apparatus of FIG. 24(a), in use;

FIGS. 24(l) and 24(m) are perspective views of the apparatus of FIG. 24(k) and a surgical device;

FIGS. 25 to 30 are partially cross-sectional, side views of another apparatus for inserting a surgical device at least partially through a wound opening according to the invention, in use;

FIGS. 31 to 36 are partially cross-sectional, side views of another apparatus for inserting a surgical device at least partially through a wound opening according to the invention, in use;

FIGS. 37 to 43 are partially cross-sectional, side views of a further apparatus for inserting a surgical device at least partially through a wound opening according to the invention, in use;

FIGS. 43(a) to 43(f) are partially cut-away, perspective views of the apparatus of FIGS. 24(a) to 24(j), in use;

FIGS. 44 to 49 are partially cross-sectional, side views of another apparatus for inserting a surgical device at least partially through a wound opening according to the invention, in use;

FIGS. 51 and 52 are perspective views of a guide device and an incising device of another apparatus for inserting a surgical device at least partially through a wound opening according to the invention;

FIGS. 53 to 58 are perspective views of the apparatus, in use;

FIGS. 58(a) to 58(d) are perspective views of another apparatus for inserting a surgical device at least partially through a wound opening according to the invention, in use;

FIGS. 58(e) to 58(h) are perspective views of another apparatus for inserting a surgical device at least partially through a wound opening according to the invention, in use;

FIGS. 58(i) to 58(n) are partially cut-away, perspective views of another apparatus for inserting a surgical device at least partially through a wound opening according to the invention, in use;

FIG. 66 is a side view of an incising device of another apparatus for inserting a surgical device at least partially through a wound opening according to the invention;

FIGS. 67 and 68 are partially cross-sectional, side views of the incising device of FIG. 66, in use;

FIG. 69 is a side view of a further apparatus for inserting a surgical device at least partially through a wound opening according to the invention;

FIG. 70 is an end view of the apparatus of FIG. 69;

FIG. 71 is a partially cross-sectional, side view of the apparatus of FIG. 69 in an extended configuration;

FIG. 72 is a partially cross-sectional, side view of the apparatus of FIG. 69 in a retracted configuration;

FIGS. 75 (j) and 75(k) are views similar to FIGS. 75(h) and 75(i) of a distal end of a further apparatus for inserting a surgical device at least partially through a wound opening according to the invention;

FIG. 75(k)(iii) is a front view of another apparatus for inserting a surgical device at least partially through a wound opening according to the invention in an obstructing configuration;

FIG. 75(k)(iv) is a side view of the apparatus of FIG. 75(k)(iii) in the obstructing configuration;

FIGS. 75(k)(v) and 75(k)(vi) are views similar to FIGS. 75(k)(iii) and 75(k)(iv) of the apparatus of FIG. 75(k)(iii) in a passage configuration;

FIGS. 75(k)(vii) and 75(k)(viii) are views similar to FIGS. 75(k)(iii) and 75(k)(iv) of the apparatus of FIG. 75(k)(iii) in the obstructing configuration and a surgical device;

FIGS. 76 to 81 are partially cross-sectional, side views of an incising device of another apparatus for inserting a surgical device at least partially through a wound opening according to the invention, in use;

FIGS. 82 and 83 are perspective views of another apparatus for inserting a surgical device at least partially through a wound opening according to the invention;

FIGS. 84 to 88 are partially cross-sectional, side views of the apparatus of FIGS. 82 and 83, in use;

FIGS. 94 to 102 are partially cross-sectional, front views of the apparatus of FIG. 89, in use;

FIG. 108 is a perspective view of a further apparatus for inserting a surgical device at least partially through a wound opening according to the invention in a shielding configuration;

FIGS. 109 and 110 are perspective views of the apparatus of FIG. 108 in a cutting configuration;

DETAILED DESCRIPTION

Figure 1:
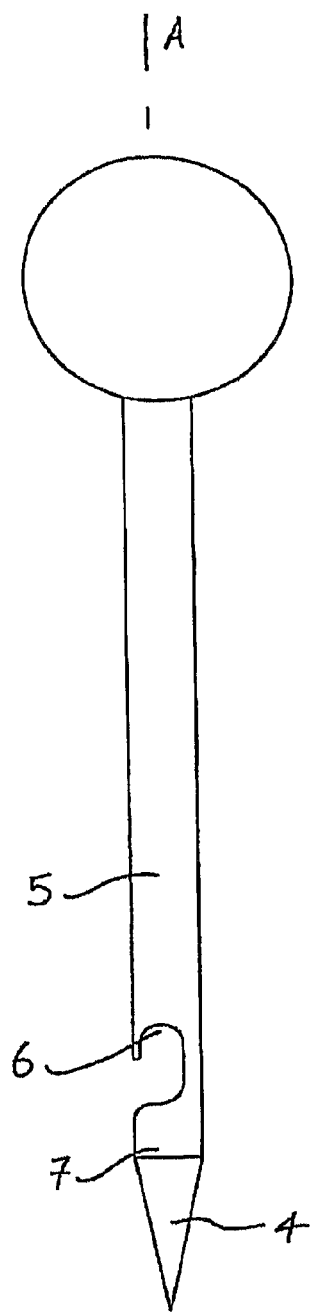
FIG. 1 is a side view of an apparatus for inserting a surgical device at least partially through a wound opening according to the invention.
Figure 2:
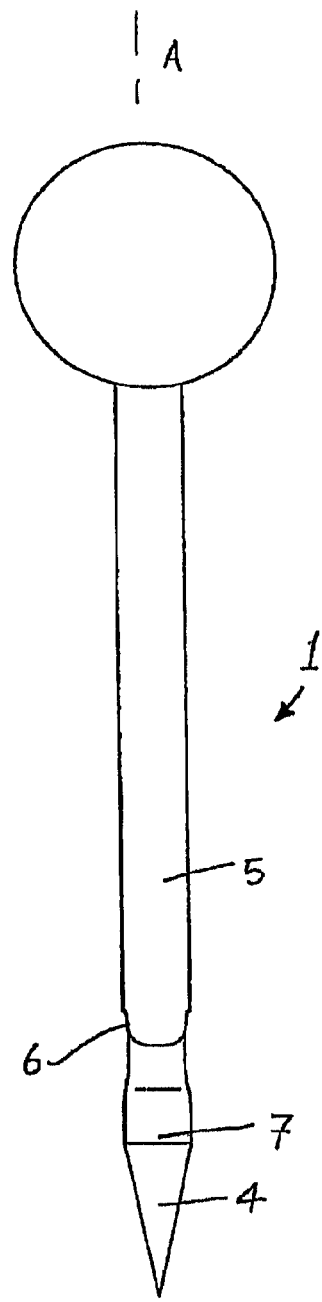
FIG. 2 is an end view of the apparatus of FIG. 1.

Referring to the drawings and initially to FIGS. 1 to 5 thereof, there is illustrated an apparatus 1 according to the invention suitable for inserting a surgical device, such as a wound retractor device 2, at least partially through a wound opening 3. Together the apparatus 1 and the wound retractor device 2 form a surgical assembly. The apparatus 1 comprises an incising device 4 for creating the wound opening 3, and a conveying device 5 insertable through the wound opening 3 to convey the wound retractor device 2 through the wound opening 3.

In this case the wound retractor device 2 has a distal retaining ring 9 for locating distally of the wound opening 3 to retain the wound retractor device 2 in position retracting the wound opening 3. However it will be appreciated that the apparatus 1 is suitable for conveying a variety of surgical devices at least partially through a wound opening 3. For example, the surgical device may be of any suitable construction such as the wound retractor devices described in US patent application published under No. 2001/0037053A, and/or U.S. Pat. No. 6,582,364, and/or U.S. patent application Ser. No. 10/678,653, the relevant contents of which are incorporated herein by reference.

In this case the incising device 4 is provided in the form of a sharpened blade element fixedly attached to the distal end 7 of the conveying device 5.

The conveying device 5 has a hook element 6 in the region of the distal end 7 for engaging a portion of the wound retractor device 2 to couple the wound retractor device 2 to the conveying device 5. As illustrated in FIG. 1, the concave portion of the hook element 6 faces distally.

The hook element 6 opens to a side of the conveying device 5. The wound retractor device 2 is therefore arranged offset with respect to the longitudinal axis A-A of the conveying device 5.

Figure 5:
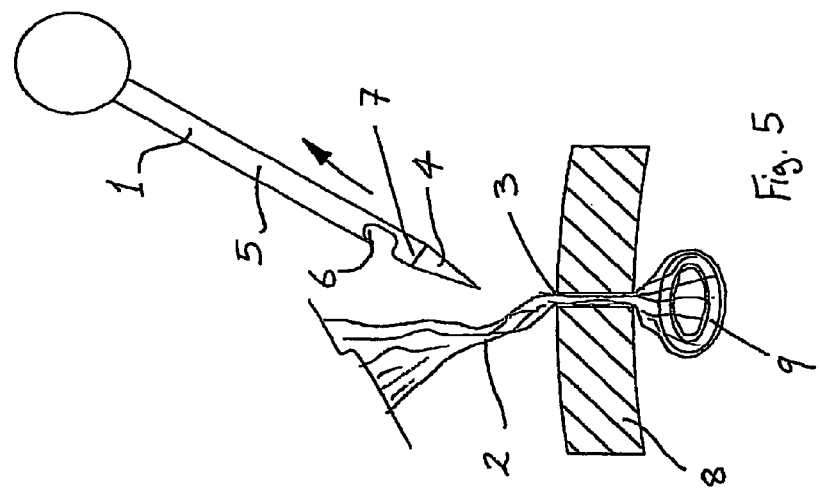
FIGS. 3 to 5 are partially cross-sectional, side views of the apparatus of FIG. 1, in use.
Figure 4:
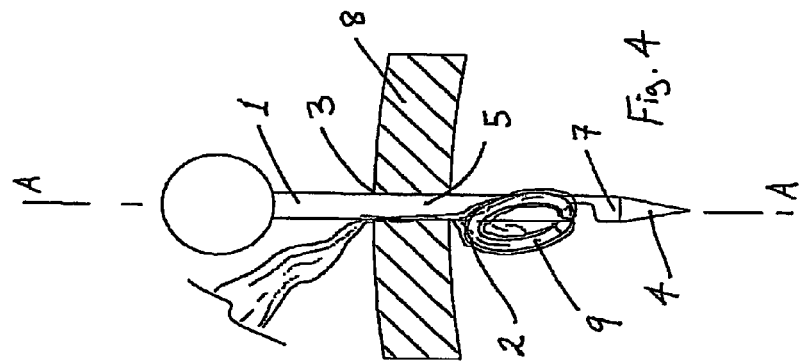
Figure 3:
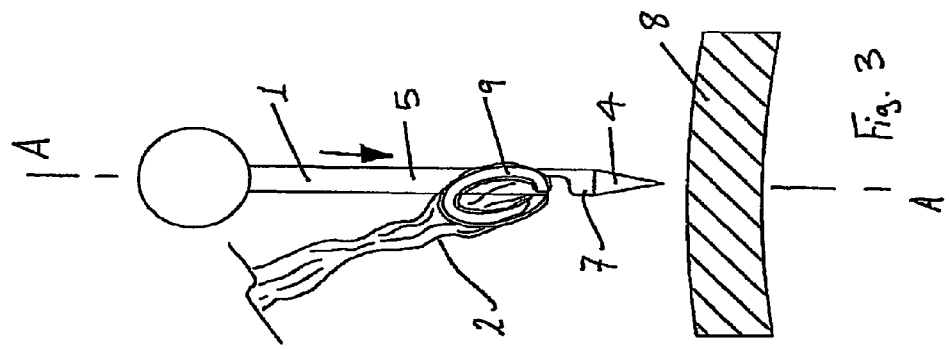

In use, the wound retractor device 2 is coupled to the conveying device 5 by engaging the distal ring 9 of the wound retractor device 2 with the hook element 6 (FIG. 3). The apparatus 1 is then passed through tissue 8 with the blade element 4 as the leading end to create the wound opening 3, and is advanced through the wound opening 3 to convey the wound retractor device 2 through the wound opening 3 by passing the distal ring 9 distally (FIG. 4). Thus the apparatus 1 may be used to create the wound opening 3 and convey the wound retractor device 2 through the wound opening 3 in a single step. The apparatus 1 may then be withdrawn from the wound opening 3 leaving the wound retractor device 2 in position extending through the wound opening 3 and with the distal ring 9 distally of the wound opening 3 (FIG. 5).

The maximum transverse dimension of the wound opening 3 is between 3 mm and 35 mm, preferably between 5 mm and 12 mm.

The maximum transverse dimension of the incising device 4 and of the portion of the conveying device 5 which extends through the wound opening 3 is between 3 mm and 35 mm, preferably between 5 mm and 12 mm.

In FIGS. 6 to 9 there is illustrated another apparatus 11 according to the invention, which is similar to the apparatus 1 of FIGS. 1 to 5, and similar elements in FIGS. 6 to 9 are assigned the same reference numerals.

In this case the incising device 12 is provided in the form of an electrocautery scalpel fixedly attached to the distal end 7 of the conveying device 5. The electrocautery scalpel 12 has a power connection lead 13 for connecting to a power supply.

FIGS. 10 to 15 illustrate a further apparatus 21 according to the invention, which is similar to the apparatus 1 of FIGS. 1 to 5, and similar elements in FIGS. 10 to 15 are assigned the same reference numerals.

In this case the conveying device 5 comprises a housing portion 22 for receiving the distal ring 9 of the wound retractor device 2. In this manner the wound retractor device 2 is coupled to the conveying device 5.

An entry/exit opening 23 is provided at the distal end of housing portion 22 facing distally. The opening 23 facilitates insertion of the distal ring 9 into and ejection of the distal ring 9 from within the housing portion 22.

A sleeve opening 25 is also provided through which a sleeve portion of the wound retractor device 2 may extend from the distal ring 9 proximally out of the housing portion 22. The sleeve opening 25 is provided along a part of the sidewall of the housing portion 22 and faces laterally.

The blade element 4 is hingeably attached to the housing portion 22. In this way the blade element 4 acts as a closure element to selectively close the opening 23 (FIG. 11) or selectively open the opening 23 (FIG. 14).

The conveying device also includes a plunger 24 which may be depressed to assist ejection of the distal ring 9 from within the housing portion 22 (FIG. 14).

In use, the wound retractor device 2 is coupled to the conveying device 5 by inserting the distal ring 9 into the housing portion 22 through the opening 23 and moving the blade element 4 across to close the opening 23. The sleeve portion of the wound retractor device 2 extends proximally out through the sleeve opening 25. The apparatus 21 is then passed through tissue 8 with the blade element 4 as the leading end to create the wound opening 3, and is advanced through the wound opening 3 to convey the wound retractor device 2 through the wound opening 3 (FIGS. 12 and 13). The plunger 24 is then depressed to push the distal ring 9 distally to engage against the blade element 4, and thus move the blade element 4 across to open the opening 23. Further depression of the plunger 24 ejects the distal ring 9 from within the housing portion 22 through the opening 23 (FIG. 14). The apparatus 21 may then be withdrawn from the wound opening 3 leaving the wound retractor device 2 in position extending through the wound opening 3 and with the distal ring 9 distally of the wound opening 3 (FIG. 15).

Referring to FIGS. 16 to 21 there is illustrated another apparatus 31 according to the invention, which is similar to the apparatus 21 of FIGS. 10 to 15, and similar elements in FIGS. 16 to 21 are assigned the same reference numerals.

In this case the housing portion 22 has an entry opening 32 in the form of an elliptical slot along a proximal part of the sidewall of the housing portion 22, and has an exit opening 33 in the form of an elliptical slot along a distal part of the sidewall. The slots 32, 33 face laterally. A narrow slot 34 joins the entry opening 32 to the exit opening 33. The narrow slot 34 allows the sleeve portion of the wound retractor device 2 to pass into the body (FIG. 20).

The blade element 4 is fixedly attached to the housing portion 22 in this case.

In use, the wound retractor device 2 is coupled to the conveying device 5 by inserting the distal ring 9 into the housing portion 22 through the proximal opening 32 (FIGS. 16 and 17). The apparatus 31 is then passed through tissue 8 with the blade element 4 as the leading end to create the wound opening 3, and is advanced through the wound opening 3 to convey the wound retractor device 2 through the wound opening 3 (FIGS. 18 and 19). The plunger 24 is depressed to eject the distal ring 9 from within the housing portion 22 through the exit opening 33 (FIG. 20). The sleeve of the wound retractor device 2 passes along the narrow slot 34. The apparatus 31 may then be withdrawn from the wound opening 3 leaving the wound retractor device 2 in position extending through the wound opening 3 and with the distal ring 9 distally of the wound opening 3 (FIG. 21).

FIGS. 21(a) to 21(f) illustrate another apparatus 230 according to the invention, which is similar to the apparatus 31 of FIGS. 16 to 21, and similar elements in FIGS. 21(a) to 21(f) are assigned the same reference numerals.

In this case the housing portion 22 has a single opening 231, which faces laterally, along the distal portion of the sidewall. The opening 231 acts as the entry opening to facilitate insertion of the distal ring 9 of the wound retractor device 2 into the housing portion 22 (FIGS. 21(a) and 21(b)), and acts as the exit opening to facilitate ejection of the distal ring 9 from within the housing portion 22 (FIG. 21(e)). The opening 231 also acts as the sleeve opening to facilitate extension the sleeve of the wound retractor device 2 out of the housing portion 22 during conveying through the wound opening 3 (FIG. 21(c) and FIG. 21(d)).

The method of using the apparatus 130 includes the following steps:
  Compress the distal ring 9 of the wound retractor device 2;
  Load the distal ring 9 through the cut-out 231 in the cannula 22 with the sleeve trailing out (FIGS. 21(a) and 21(b));
  Pierce the skin 8 with the blade 4 and advance the introducer 230 until the cut-out 231 is inside the abdomen (FIGS. 21(c) and 21(d));
  Depress the ejector plunger 24 to push out the distal ring 9 (FIG. 21(e));
  Remove the injector introducer 230 from the incision 3, leaving the distal ring 9 inside the abdomen (FIG. 21(f)).

Referring to FIGS. 21(g) to 21(k) there is illustrated another apparatus 600 according to the invention, which is similar to the apparatus 230 of FIGS. 21(a) to 21(f), and similar elements in FIGS. 21(g) to 21(k) are assigned the same reference numerals.

In this case the apparatus 600 comprises the conveying device 5 and an opening device 601 for creating the wound opening 3 by forcing the tissue 8 apart. The opening device 601 is provided in this case in the form of a substantially blunt, solid bladeless tip fixedly attached to the distal end 7 of the conveying device 5.

Figures 21A, 21B:
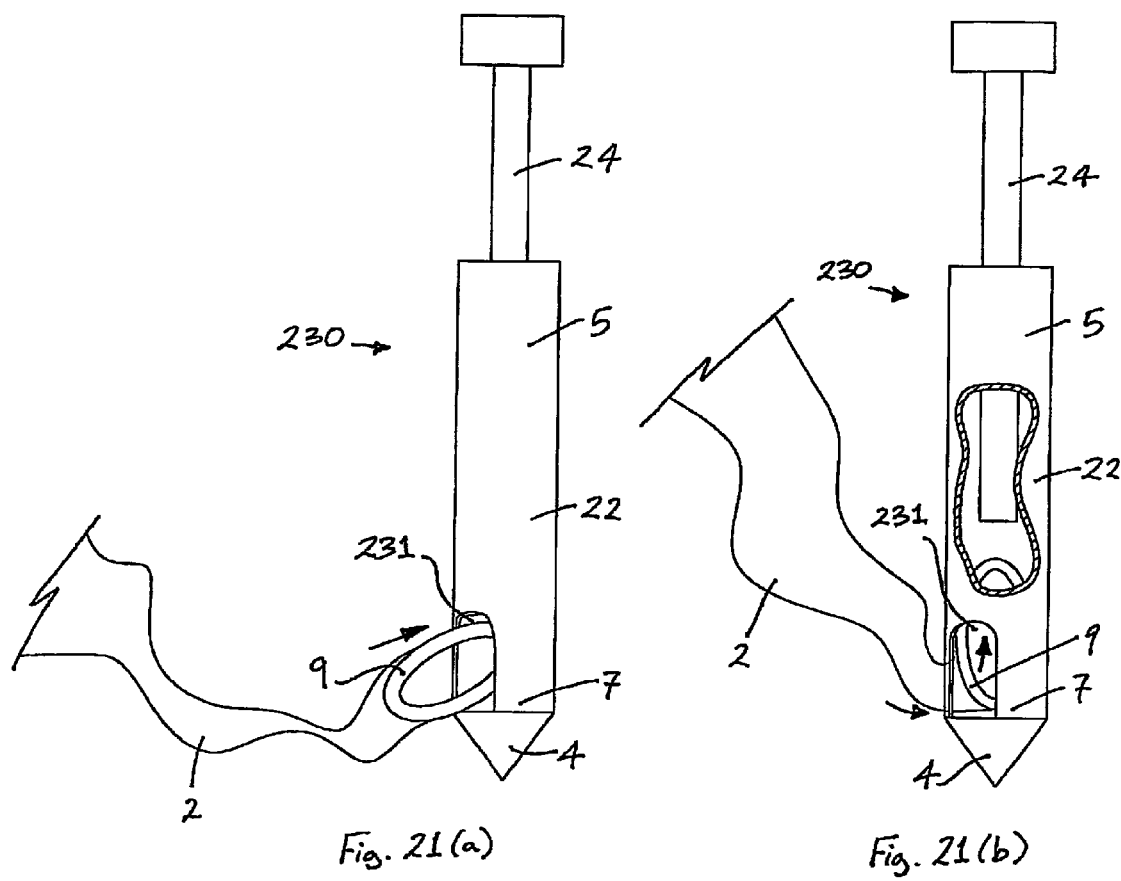
Figure 21C:
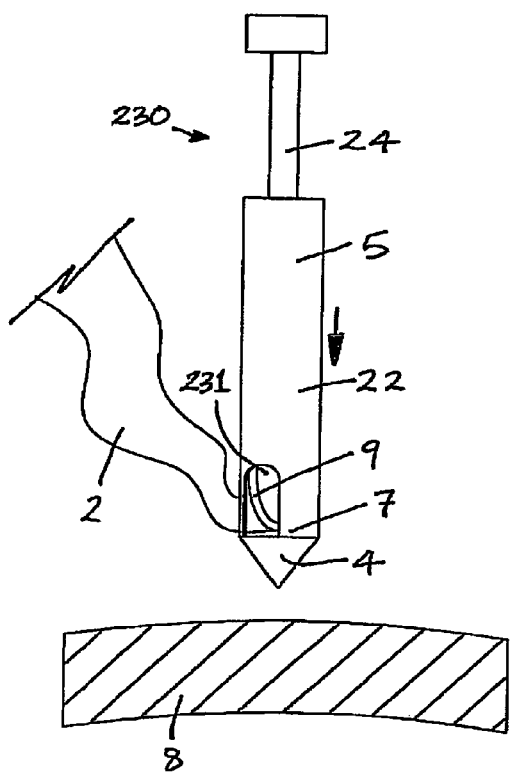
Figure 21D:
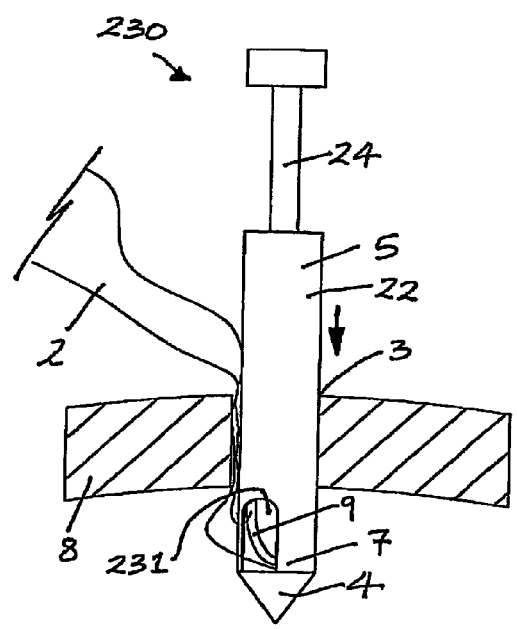
Figure 21G:
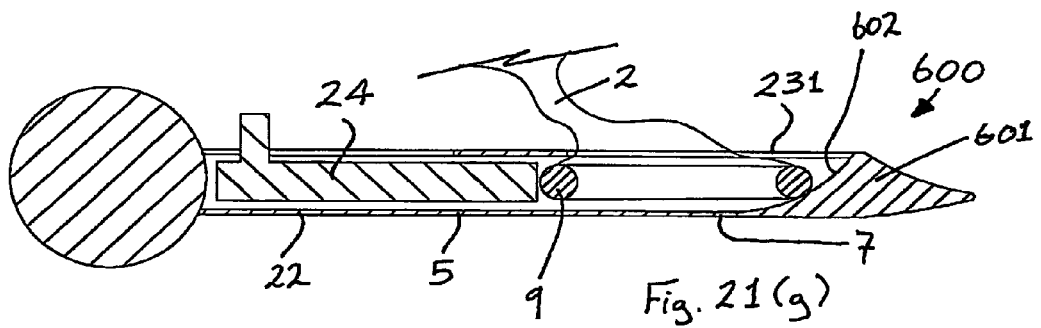
FIG. 21(g) is a cross-sectional, side view of another apparatus for inserting a surgical device at least partially through a wound opening according to the invention.
Figure 21H:
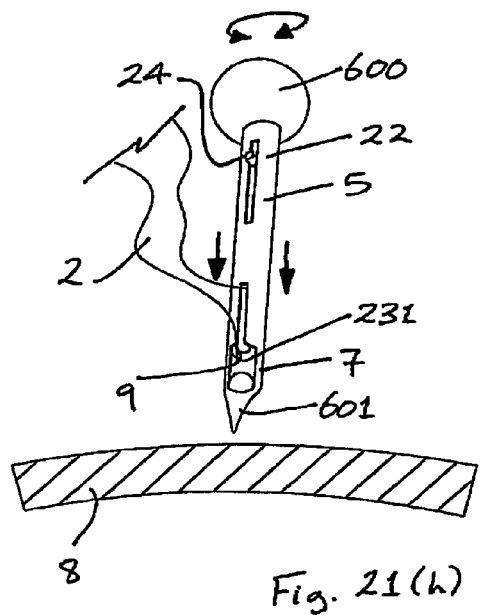
FIGS. 21(h) to 21(k) are partially cross-sectional, side views of the apparatus of FIG. 21(g), in use.
Figure 21I:
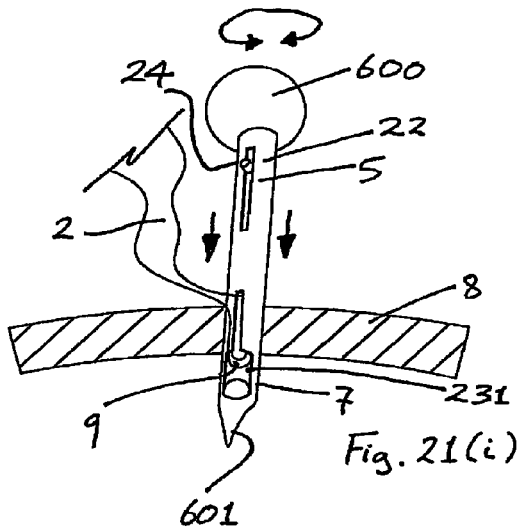
Figure 21J:
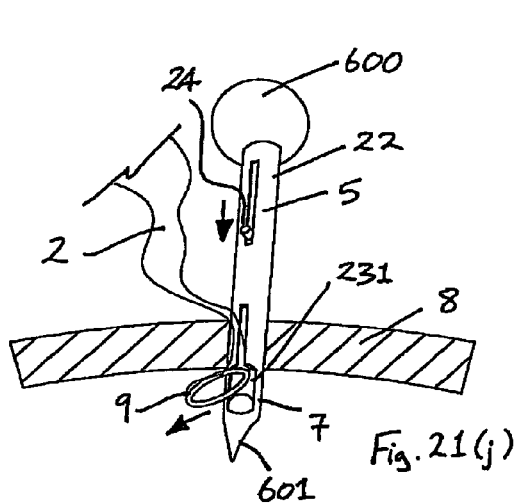
Figure 21K:
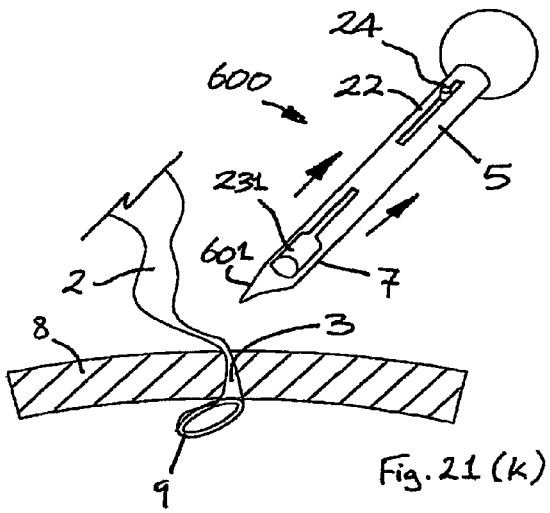
Figure 21L:
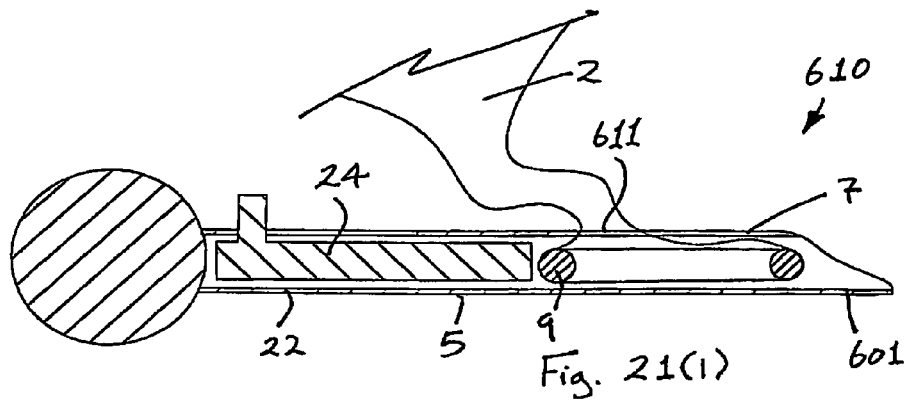
FIGS. 21(l) to 21(p) are views similar to FIGS. 21(g) to 21(k) of another apparatus for inserting a surgical device at least partially through a wound opening according to the invention.

In use the wound opening 3 is created by advancing the opening device 601 distally through the tissue 8 while simultaneously rotating the opening device 601 in a reciprocating clockwise—counter clockwise manner about an axis substantially parallel to the longitudinal axis of the wound opening 3 (FIGS. 21(h) and 21(i)).

FIGS. 21(g) to 21(k) show the ejector system 600. The 'O'-ring 9 is loaded through the side opening 231 of the shaft 22. This allows the tip 601 to be more substantial in size.

At the intersection of the housing portion 22 and the opening device 601 at the distal end 7 of the conveying device 5, there is provided a ramp 602 to facilitate ejection of the 'O'-ring 9. In use, the 'O'-ring 9 is pushed outwards with the ramp system 602 (FIG. 21(j)).

FIGS. 21(l) to 21(p) illustrate another apparatus 610 according to the invention, which is similar to the apparatus 600 of FIGS. 21(g) to 21(h), and similar elements in FIGS. 21(l) to 21(p) are assigned the same reference numerals.

In this case the opening device 601 is provided in the form of a substantially blunt, hollow bladeless tip fixedly attached to the distal end 7 of the conveying device 5.

Figure 21M:
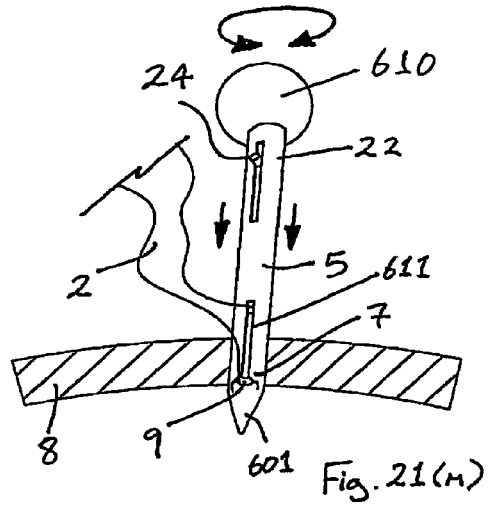
Figure 21N:
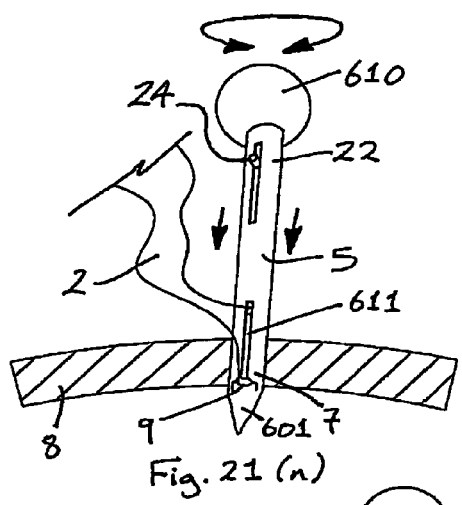

A sleeve opening 611 is provided in the sidewall of the housing portion 22 facing laterally to facilitate a sleeve portion of the wound retractor device 2 to extend out of the housing portion 22 while the distal ring 9 of the wound retractor device 2 is housed within the housing portion 22 (FIGS. 21(m) and 21(n)).

FIGS. 21(l) to 21(p) show the ejector type introducer 610 which is loaded from the front. The introducer 610 features the blunt, hollow, bladeless tip 601.

Figure 21O:
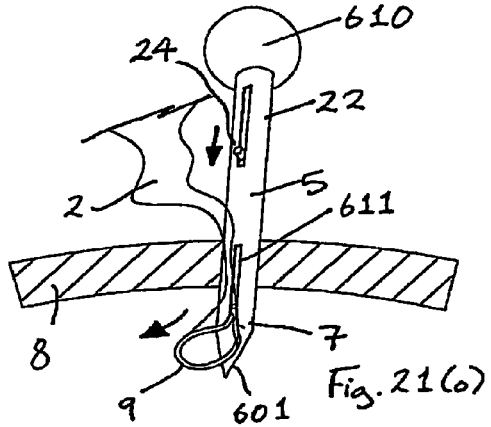
Figure 21P:
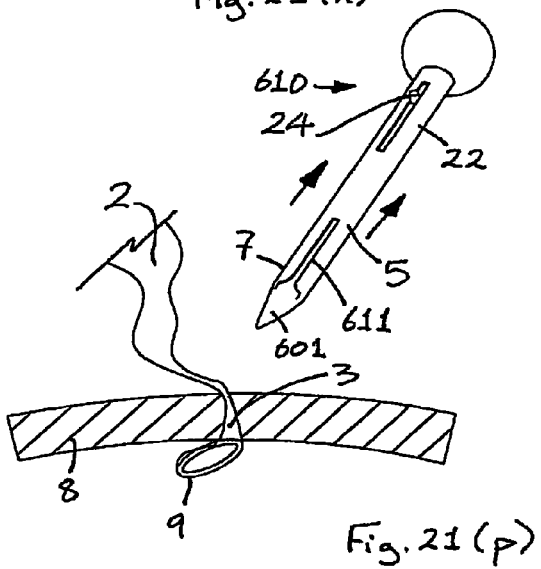

The buttonhole distal ring 9 is loaded up through the hollow bladeless tip 601, and subsequently ejected through the tip 601 (FIG. 21(o)). A back and forward motion together with a downwards pressure is employed to create the wound opening 3 (FIGS. 21(m) and 21(n)). The rod 24 is pushed down to eject the 'O'-ring 9, and as a result the 'O'-ring 9 is pushed downwards (FIG. 21(o)).

It will be appreciated that the blunt, bladeless tip opening device may have a variety of different configurations. For example, in the apparatus 620 according to the invention the opening device 621 comprises a winged tip configuration (FIGS. 21(q)(i) and 21(q)(ii)), in the apparatus 622 according to the invention the opening device 623 comprises an asymmetrical tip configuration (FIGS. 21(r)(i) and 21(r)(ii)), in the apparatus 624 according to the invention the opening device 625 comprises a four wing configuration (FIGS. 21(s)(i) and 21(s)(ii)), in the apparatus 626 according to the invention the opening device 627 comprises a flap tip configuration (FIGS. 21(t)(i) and 21(t)(ii)), in the apparatus 628 according to the invention the opening device 629 comprises a spiral tip configuration (FIGS. 21(u)(i) and 21(u)(ii)), in the apparatus 630 according to the invention the opening device 631 comprises a series of protrusions (FIGS. 21(v)(i) and 21(v)(ii)).

In the embodiments described previously with reference to FIGS. 21(g) to 21(p), the blunt, bladeless tip opening device was employed with a conveying device 5 in which the distal ring 9 of the wound retractor device 2 is received within the housing portion 22. In the embodiments described previously with reference to FIGS. 21(q)(i) to 21(v)(ii), the blunt, bladeless tip opening device was employed with a conveying device 5 in which the distal ring 9 of the wound retractor device 2 may be engaged by the hook element 6. It will be appreciated that for any of the embodiments disclosed in this patent specification in which the wound opening is created by an incising device which creates the wound opening by cutting tissue, a blunt, bladeless tip opening device may be employed in place of the incising device to create the wound opening by forcing tissue apart instead. It will also be appreciated that for any of the embodiments disclosed in this patent specification in which the wound opening is created by a blunt, bladeless tip opening device which creates the wound opening by forcing tissue apart, an incising device may be employed in place of the blunt, bladeless tip opening device to create the wound opening by cutting tissue instead.

Figure 22:
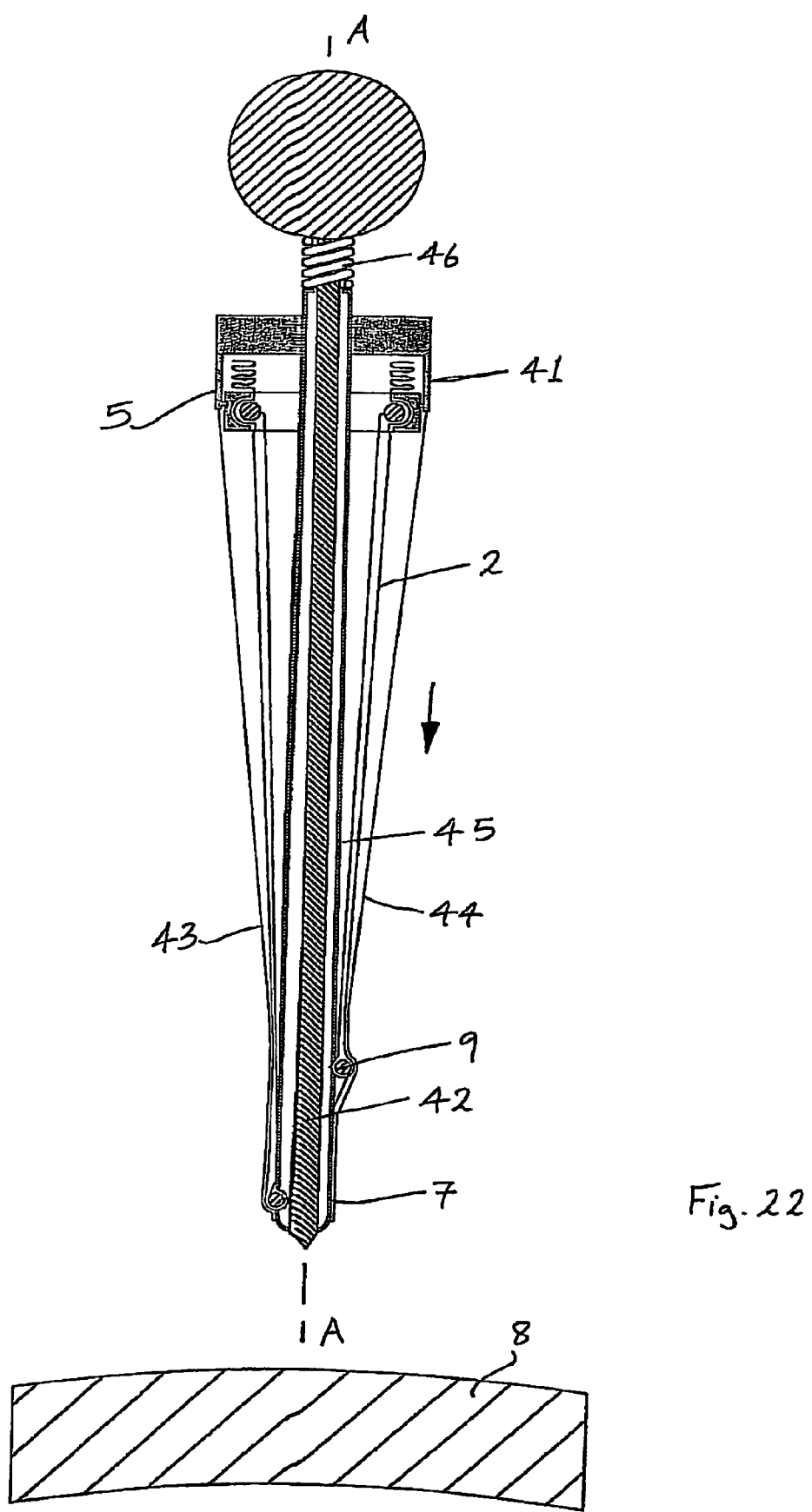
FIGS. 22 to 24 are partially cross-sectional, side views of a further apparatus for inserting a surgical device at least partially through a wound opening according to the invention, in use.
Figure 23:
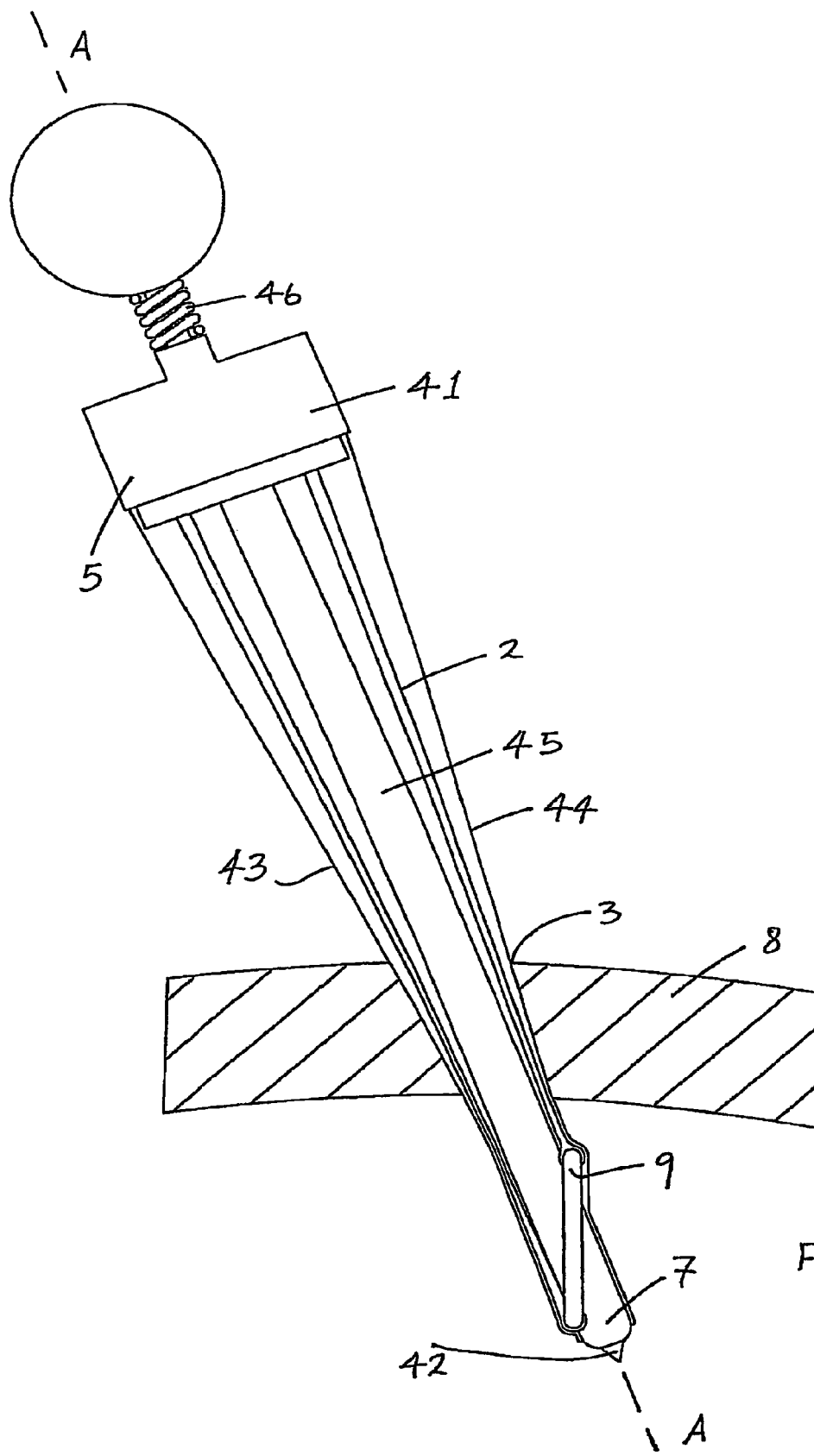
Figure 24:
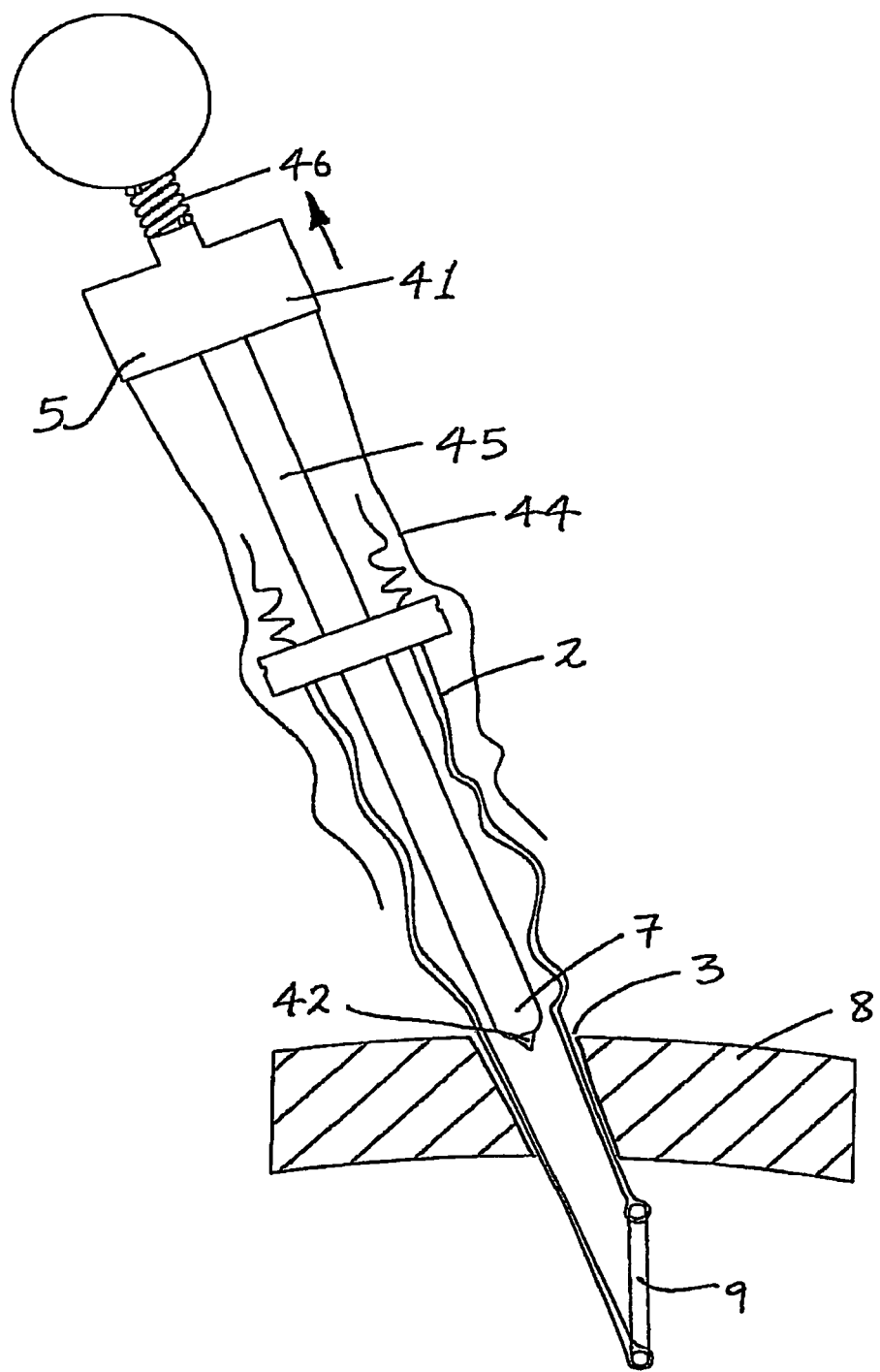
Figure 24A:
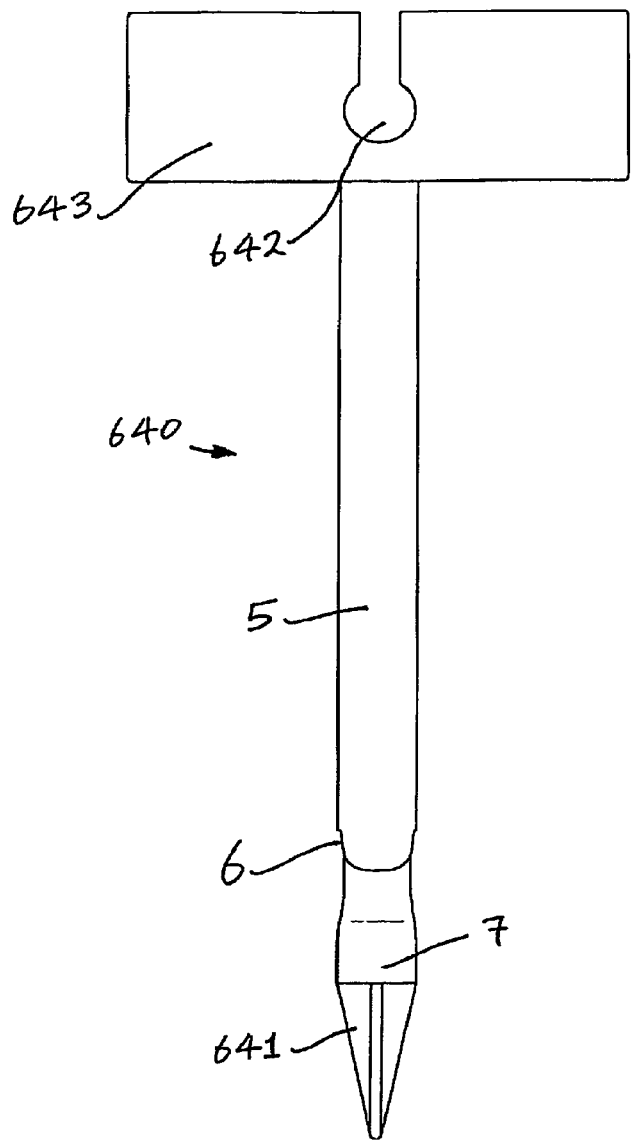
FIG. 24(a) is an end view of another apparatus for inserting a surgical device at least partially through a wound opening according to the invention.
Figure 24B:
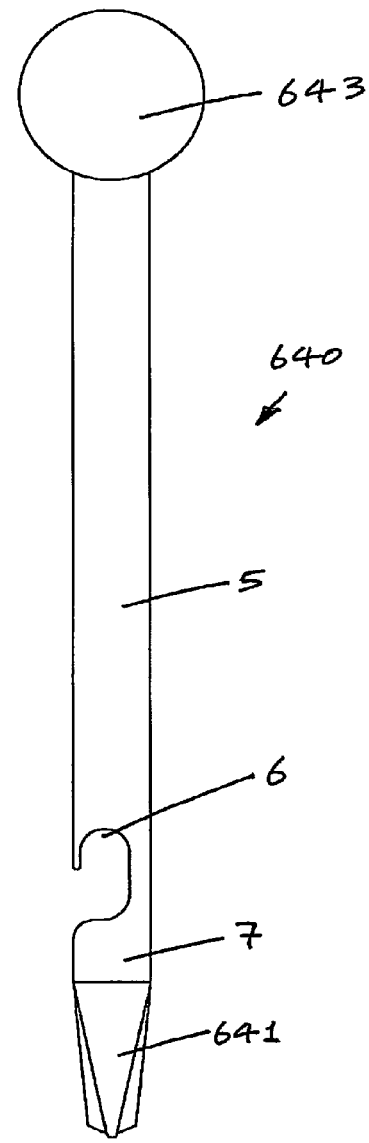
FIG. 24(b) is a side view of the apparatus of FIG. 24(a)

In FIGS. 22 to 24 there is illustrated another apparatus 41 according to the invention, which is similar to the apparatus 21 of FIGS. 10 to 15, and similar elements in FIGS. 22 to 24 are assigned the same reference numerals.

In this case the incising device 42 is provided in the form of a sharpened blade element extending concentrically through the conveying device 5.

The housing portion 43 of the conveying device 5 comprises a flexible sleeve 44 and an inner tubular member 45 with a proximal spring 46. The distal end of the sleeve 44 is releasably attached to the distal end of the tubular member 45 with the distal ring 9 of the wound retractor device 2 housed between the sleeve 44 and the tubular member 45 (FIG. 22). The wound retractor device 2 is arranged concentrically with respect to the longitudinal axis A-A of the conveying device 5.

In use, the apparatus 41 is passed through tissue 8 with the blade element 42 as the leading end to create the word opening 3, and is advanced through the wound opening 3 to convey the wound retractor device 2 through the wound opening 3 (FIGS. 22 and 23).

The apparatus 41 is inserted as a normal trocar. The distal ring 9 and sleeve portion of the wound retractor device 2 are held close to the tubular member 45 by the retaining sleeve 44, which may be made out of a plastic film material/stretchable film material, or woven material.

The attachment of the distal end of the sleeve 44 to the distal end of the tubular member 45 is then released. In particular, when the distal ring 9 is within the abdomen, the sleeve 44 is released at the distal end by a release mechanism within the tubular member 45.

The apparatus 41 is then withdrawn from the wound opening 3 leaving the wound retractor device 2 in position extending through the wound opening 3 and with the distal ring 9 distally of the wound opening 3 (FIG. 24). In particular, the piercing introducer 42 and retaining sleeve 44 are pulled proximally, leaving the wound retractor device 2 in position to be deployed and secured.

Referring to FIGS. 24(a) to 24(j) there is illustrated another apparatus 640 according to the invention, which is similar to the apparatus 1 of FIGS. 1 to 5, and similar elements in FIGS. 24(c) to 24(j) are assigned the same reference numerals.

In this case the apparatus 640 comprises an opening device 641 in the form of a blunt, bladeless tip similar to the tip 621 described previously with reference to FIGS. 21(q)(i) and 21(q)(ii).

The conveying device 5 comprises a receiver slot 642 at the proximal end 643 of the conveying device 5. The sleeve portion of the wound retractor device 2 may be received in the slot 642 to hold the sleeve portion externally of the wound opening 3, and thus maintain the sleeve portion in tension, during conveying of the distal ring 9 of the wound retractor device 2 through the wound opening 3.

In use the wound opening 3 is created by advancing the opening device 641 distally while rotating the opening device 641 in a reciprocating clockwise—counter clockwise manner to force the tissue 8 apart (FIGS. 24(f) to 24(i)), in a manner similar to that described previously with reference to FIGS. 21(g) to 21(p).

The slot 642 holds the sleeve portion of the wound retractor device 2 in tension externally of the wound opening 3, and thus maintain the sleeve portion in tension, during conveying of the distal ring 9 of the wound retractor device 2 through the wound opening 3 (FIGS. 24(e) to 24(i)).

Figure 24C:
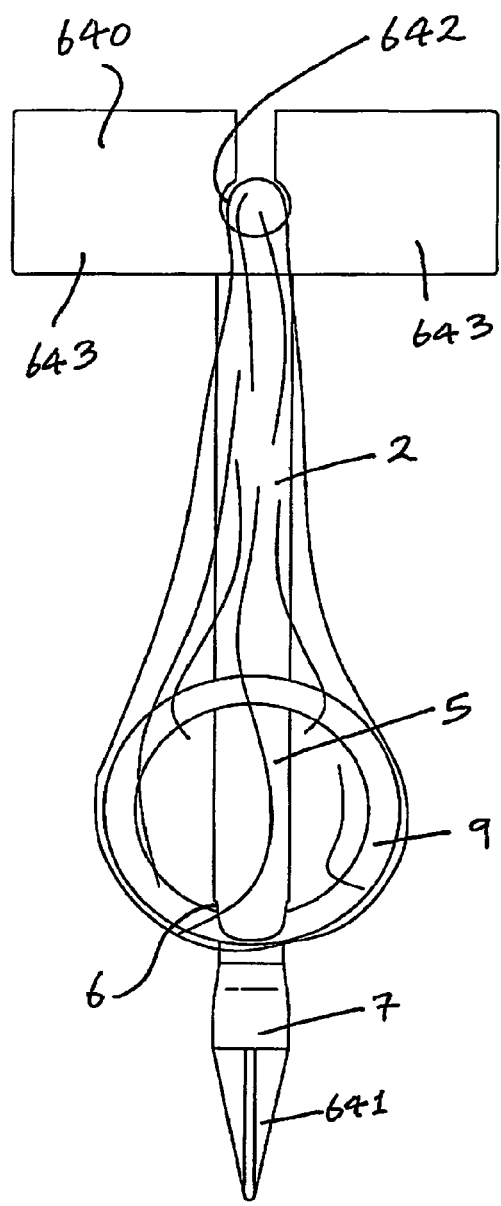
FIGS. 24(c) and 24(d) are views similar to FIGS. 24(a) and 24(b) of the apparatus of FIG. 24(a) and a surgical device.
Figure 24D:
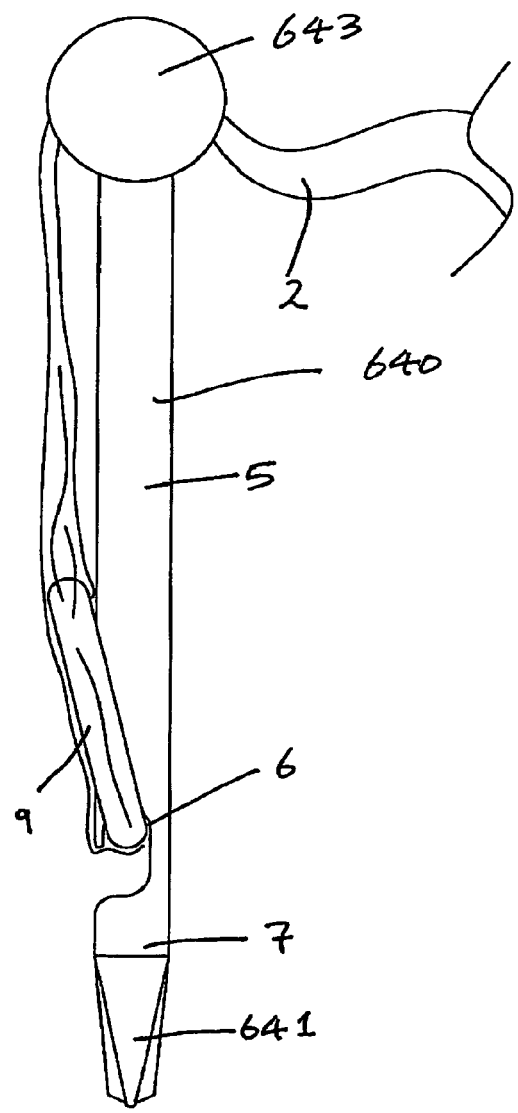
Figure 24F:
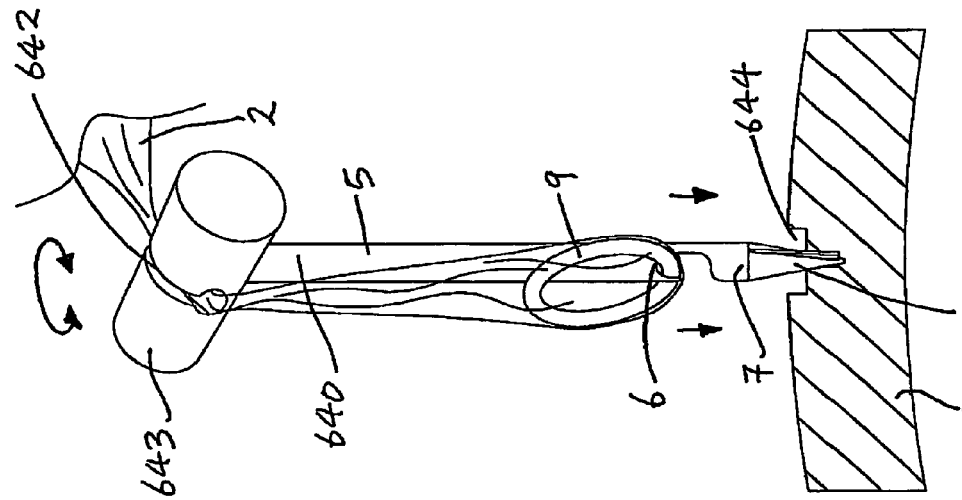
Figure 24E:
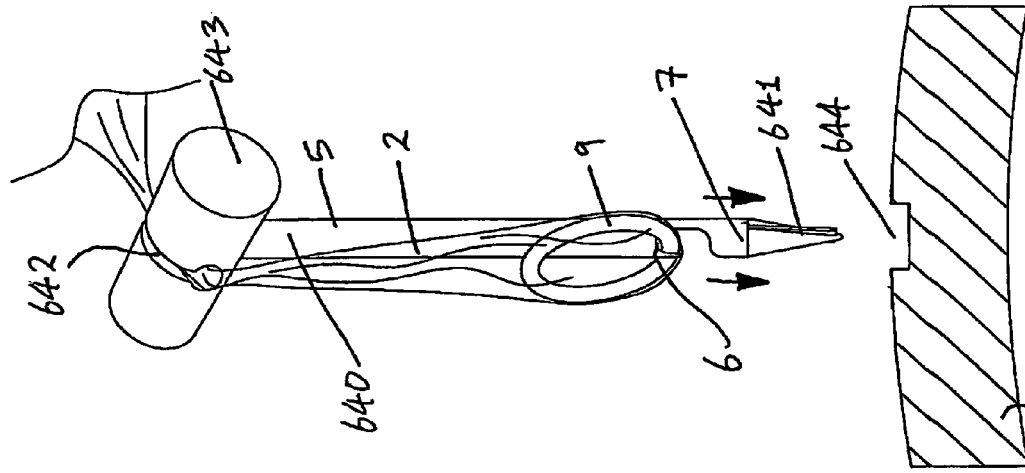

In use, the sleeve is tensioned and passed through the slot 641 in the handle to keep the sleeve taut and to keep the ring 9 on the hook 6 (FIG. 24(c)). The distal ring 9 is fixed on the hook 6 due to the sleeve being in tension (FIG. 24(d)). An incision 644 is made in the skin 8 using a scalpel. The depth of the incision 644 is just sufficient to break the skin surface (FIG. 24(e)). The introducer 5 is twisted back and forth as it advances through the abdominal wall 8. The blunt tip 641 passes through the skin layers dissecting as it goes (FIG. 24(f)). The opening device 641 is twisted and advanced (FIG. 24(g)) until the bladeless tip 641 enters the abdominal cavity (FIG. 24(h)). Because the tip 641 is blunt, the procedure is therefore particularly safe. In particular the risk of damage to internal organs due to inadvertent contact with the tip 641 is minimised. The introducer 5 is further advanced until all of the distal ring 9 is inside the abdomen (FIG. 24(i)). The sleeve is unhooked from the slot 642 in the introducer handle and the introducer 5 is removed leaving the distal ring 9 in the abdomen (FIG. 24(j)).

Figure 24K:
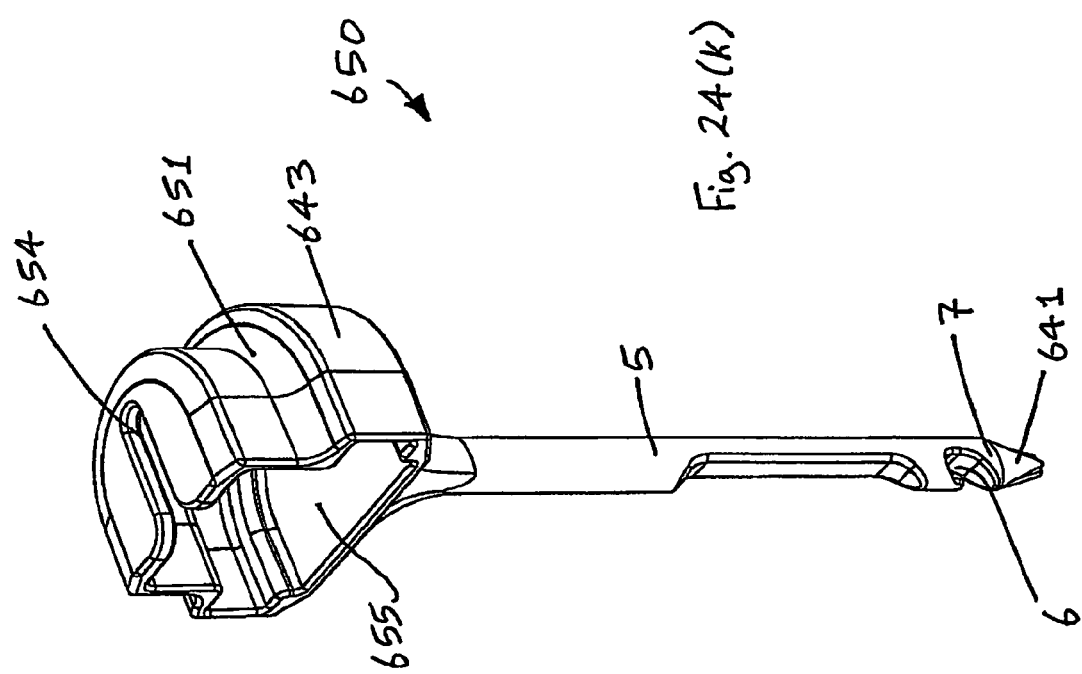
FIG. 24(k) is a perspective view of another apparatus for inserting a surgical device at least partially through a wound opening according to the invention.
Figure 24:
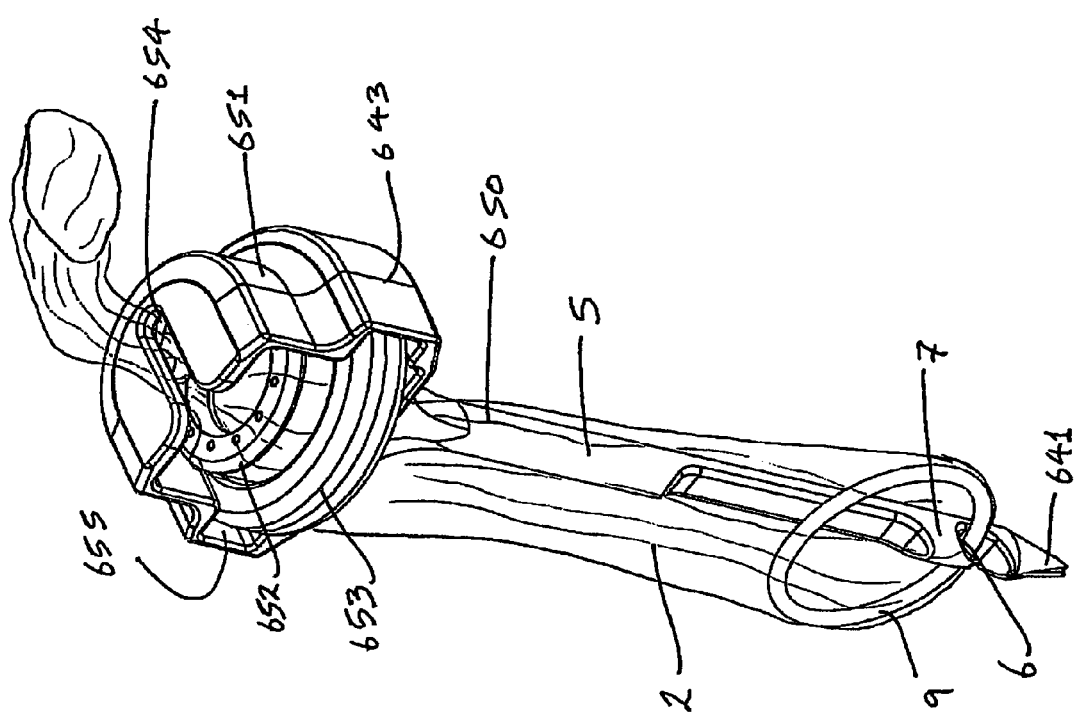
Figure 33:
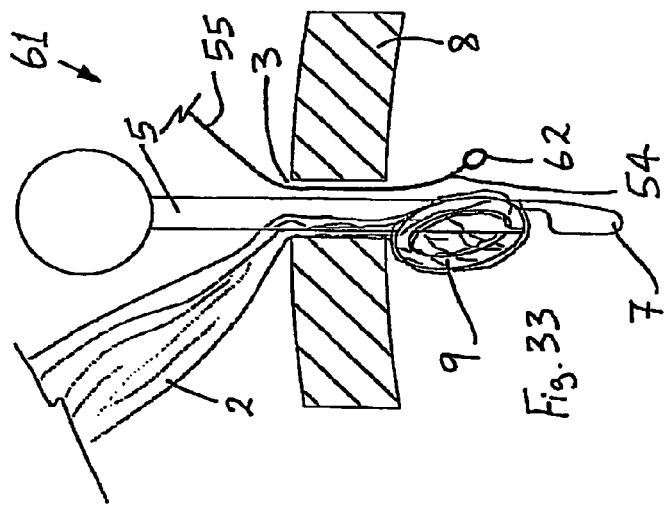
Figure 32:
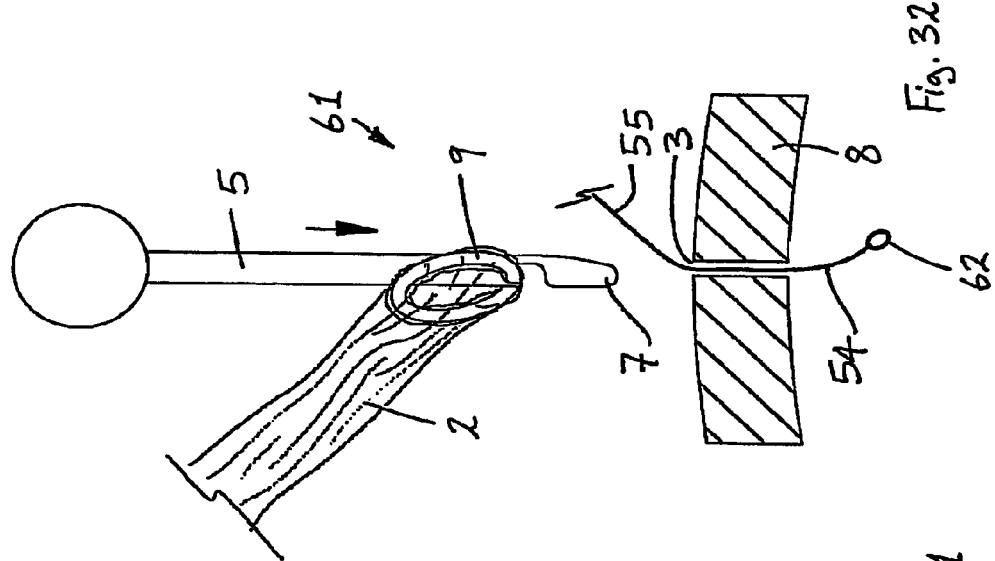
Figure 31:
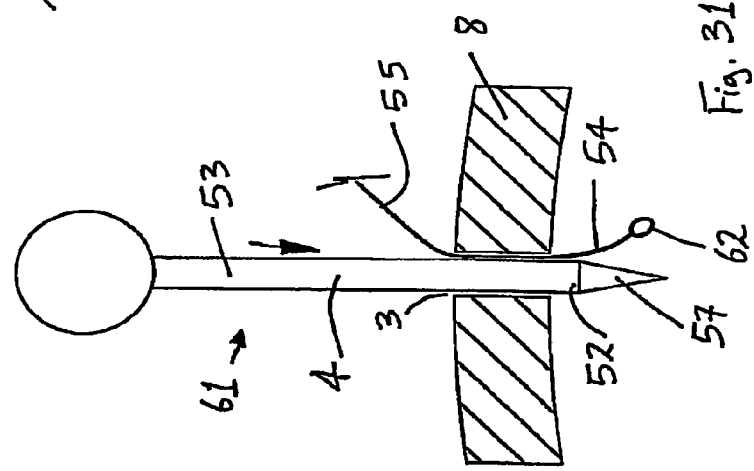

In FIGS. 24(k) to 24(m) there is illustrated a further apparatus 650 according to the invention, which is similar to the apparatus 640 of FIGS. 24(a) to 24(j), and similar elements in FIGS. 24 (k) and 24(m) are assigned the same reference numerals.

In this case the conveying device 5 comprises a receiver housing portion 651 at the proximal end 643 of the conveying device 5. A seal portion 652 and a proximal ring portion 653 of the wound retractor device 2 may be received in the housing portion 651 (FIG. 24(m)) to hold the seal portion 652 and the proximal ring portion 653 externally of the wound opening 3, and thus maintain the sleeve portion of the wound retractor device 2 in tension, during conveying of the distal ring 9 of the wound retractor device 2 through the wound opening 3.

FIG. 24(k) illustrates the introducer 650 which includes a slot 654 for the excess sleeve portion at the proximal top end of the buttonhole device 2, a reception space 655 for part of the buttonhole device 2, and the hook 6 for the distal ring 9.

In use, the distal ring 9 is attached to the hook 6 (FIG. 24(l)).

The seal portion 652 and the proximal ring portion 653 of the buttonhole device 2 are inserted into the housing 651 at the proximal top end of the introducer 650, and the excess sleeve material is passed out through the slot 654 in the top of the buttonhole device housing 651 (FIG. 24(m)). The sleeve portion is now kept in tension.

It will be appreciated that the apparatus according to the invention, as disclosed in this patent specification, may be employed to insert a variety of different types of surgical devices at least partially through a wound opening. The apparatus according to the invention may be employed to insert a variety of different types of wound retractor devices at least partially through a wound opening, for example the wound retractor devices disclosed in International patent application No. PCT/IE2003/000141 the relevant contents of which are incorporated herein by reference, and/or the wound retractor devices disclosed in International patent application No. PCT/IE2005/000113 the relevant contents of which are incorporated herein by reference.

FIGS. 25 to 30 illustrate a further apparatus 51 according to the invention, which is similar to the apparatus 1 of FIGS. 1 to 5, and similar elements in FIGS. 25 to 30 are assigned the same reference numerals.

In this case the incising device 4 comprises a sharpened blade element 57 fixedly attached to the distal end 52 of an elongate member 53. The incising device 4 remains detached from the conveying device 5.

In this case the conveying device 5 has a rounded/blunt distal end 7.

The apparatus 51 further comprises a guide device 54 insertable through the wound opening 3. The guide device 54 is provided in this case in the form of a length of flexible string/ribbon 55 with a hook element 56 attached to a distal end of the string 55. The concave portion of the hook element 56 faces proximally.

The string 55 and the hook element 56 also act as a removal device to assist in removal of the wound retractor device 2 from the wound opening 3. The hook element 56 is engagable with the distal ring 9 of the wound retractor device 2, and the string 55 extends proximally through the wound opening 3 for actuation by a user. In this manner the string 55 connects the hook element 56 to the user.

In use, the incising device 4 and the guide device 54 are passed through the tissue 8 with the blade element 57 as the leading end to create the wound opening 3 in an incision step (FIG. 25). The incising device 4 is then withdrawn from the wound opening 3 leaving the guide device 54 in position extending through the wound opening 3 and with the hook element 56 distally of the wound opening 3 (FIG. 26). Because the guide device 54 extends through the wound opening 3, this arrangement ensures that the patency of the wound opening 3 is maintained even when the incising device 4 has been withdrawn. In particular the string 55 ensures that the various layers of fat/muscle/fascia stay aligned as a straight incision.

The wound retractor device 2 is coupled to the conveying device 5 by engaging the distal ring 9 with the hook element 6 (FIG. 26). The conveying device 5 is then advanced though the wound opening 3 to convey the wound retractor device 2 through the wound opening 3 in a conveying step (FIG. 27).

Thus the incising device 4 of the apparatus 51 is used to create the wound opening 3 in an incision step (FIG. 25), and the conveying device 5 of the apparatus 51 is used to subsequently convey the wound retractor device 2 through the wound opening 3 in a conveying step (FIG. 27). These two steps are distinct and separate.

The conveying device 5 may be withdrawn from the wound opening 3 leaving the wound retractor device 2 in position extending through the wound opening 3 and with the distal ring 9 distally of the wound opening 3 (FIG. 28).

To assist in removal of the wound retractor device 2 from the wound opening 3, the hook element 56 may be engaged with the distal ring 9 and pulled proximally by pulling the string 55 proximally (FIG. 30). The wound retractor device 2 may thus be removed from the wound opening 3.

The string 55 and hook element 56 remain detached from the wound retractor device 2. This enables the string 55 and hook element 56 to be inserted into the wound opening 3 before insertion of the wound retractor device 2, and thus enables the string 55 and hook element 56 to act as the guide device. The hook element 56 contacts the distal ring 9 to aid removal of the wound retractor device 2, but remains detached from the distal ring 9.

The maximum transverse dimension of the portion of the incising device 4 which extends through the wound opening 3 is between 3 mm and 35 mm, preferably between 5 mm and 12 mm.

Referring to FIGS. 31 to 36 there is illustrated another apparatus 61 according to the invention, which is similar to the apparatus 51 of FIGS. 25 to 30, and similar elements in FIGS. 31 to 36 are assigned the same reference numerals.

In this case the guide device 54 comprises a loop 62 in the string 55 at the distal end of the string 55.

As illustrated in FIGS. 35 and 36, to assist in removal of the wound retractor device 2, the loop 62 may be gripped by a grasping instrument 63 and pulled proximally while also pulling the string 35 proximally. In this case the loop 62 and string 35 are not required to contact the distal ring 9 to effect removal of the wound retractor device 2.

In FIGS. 37 to 43 there is illustrated another apparatus 71 according to the invention, which is similar to the apparatus 51 of FIGS. 25 to 30, and similar elements in FIGS. 37 to 43 are assigned the same reference numerals.

In this case the blade element 57 is releasably attached to the distal end 52 of the elongate member 53, and the blade element 57 is fixedly attached to the distal end of the string 55. A proximal side of the blade element 57 has a hook formation 72.

Figure 40:
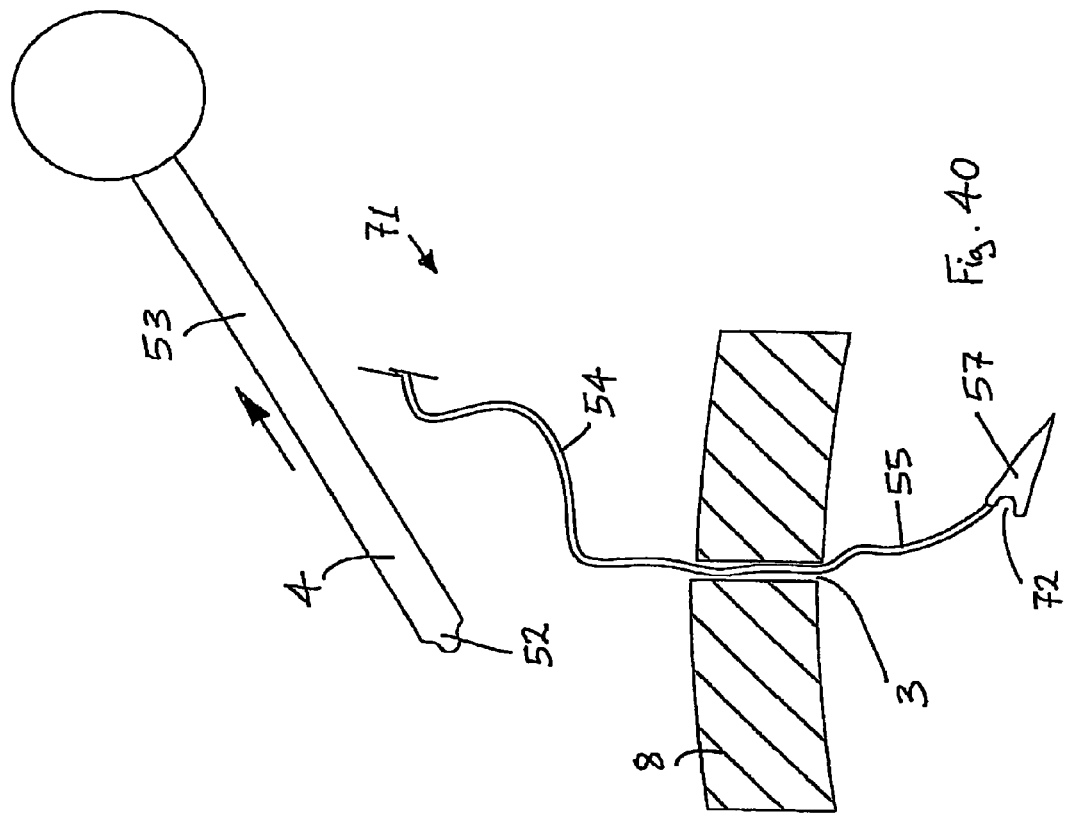
Figure 39:
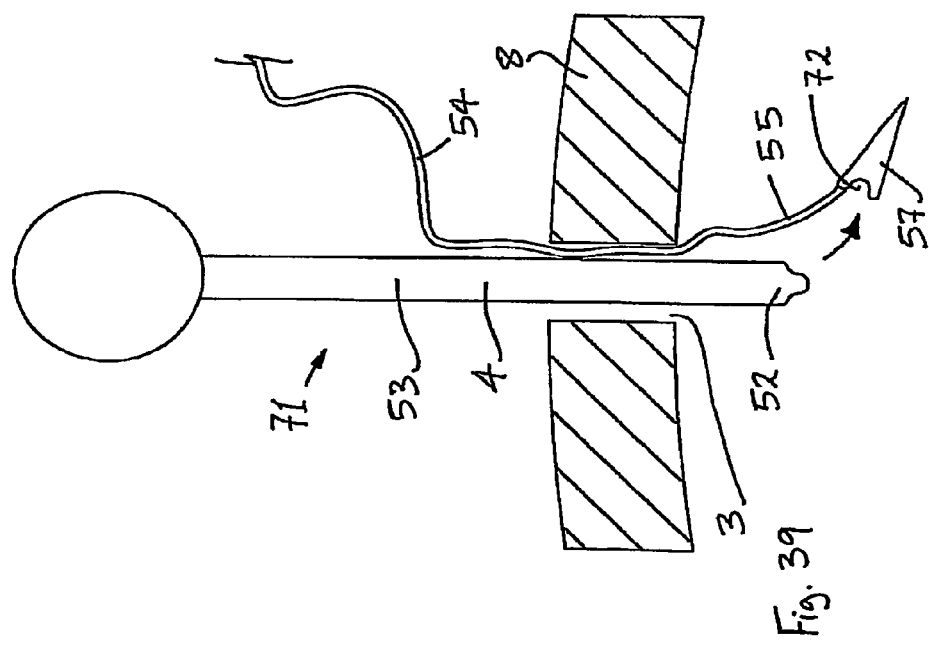

In use, the incising device 4, with the blade element 57 attached to the elongate member 53, and the string 55 are passed through tissue 8 with the blade element 57 as the leading end to create the wound opening 3 in an incision step (FIG. 38). The blade element 57 is detached from the elongate member 53 (FIG. 39), and the elongate member 53 is withdrawn from the wound opening 3 leaving the string 55 extending through the wound opening 3 and with the blade element 57 distally of the wound opening 3 (FIG. 40).

Figure 43:
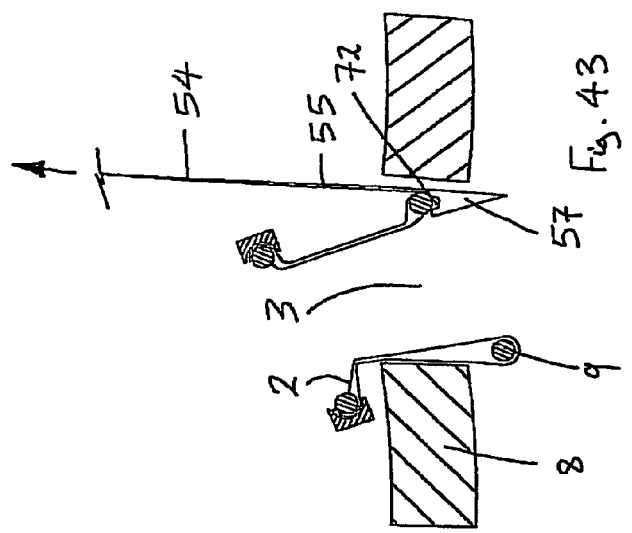
Figure 42:
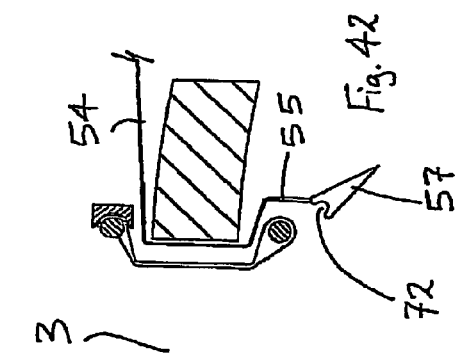
Figure 41:
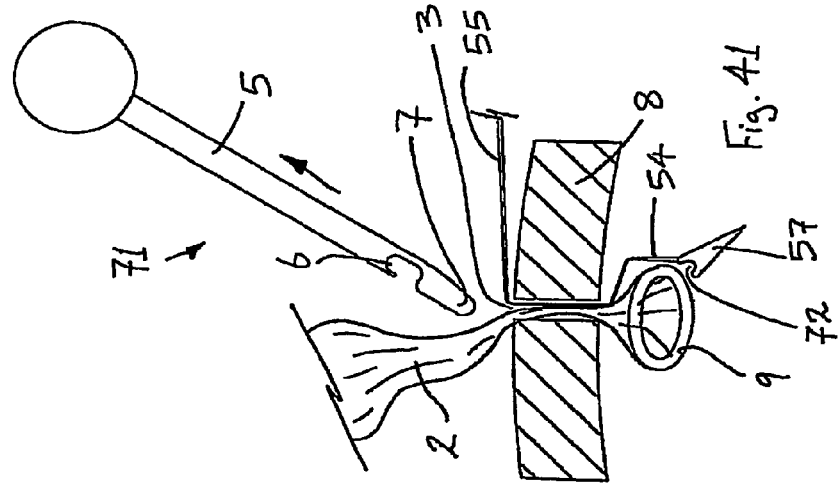

To assist in removal of the wound retractor device 2 from the wound opening 3, the hook formation 72 of the blade element 57 may be engaged with the distal ring 9 and pulled proximally by pulling the string 55 proximally (FIG. 43).

It will be appreciated that a surgical device, such as the wound retractor device 2, may be inserted at least partially through the wound opening 3 with the wound opening 3 being created and the wound retractor device 2 being conveyed at least partially through the wound opening 3 in a single step, or alternatively with the wound opening 3 being created in an opening step and with the wound retractor device 2 being conveyed at least partially through the wound opening 3 in a separate conveying step.

For example, with reference to FIGS. 24(e) to 24(j), the apparatus 640 is described and illustrated creating the wound opening 3 and conveying the wound retractor device 2 at least partially through the wound opening 3 in a single step. With reference to FIGS. 43(a) to 43(f), the apparatus 640 may alternatively be employed to create the wound opening 3 in an opening step (FIGS. 43(a) to 43(c)), and to subsequently convey the distal ring 9 of the wound retractor device 2 through the wound openign 3 is a separate conveying step (FIGS. 43(d) to 43(f)).

To create the wound opening 3, the opening device 641 is advanced distally while the opening device 641 is rotated in a reciprocating clockwise—counter clockwise manner about an axis substantially parallel to the longitudinal axis of the wound opening 3 (FIGS. 43(a) to 43(c)).

To convey the distal ring 9 through the wound opening 3, the conveying device 5 is advanced distally without rotating the conveying device 5 (FIGS. 43(d) and 43(e)). It will be appreciated that the conveying device 5 may alternatively be rotated in a reciprocating clockwise—counter clockwise manner about an axis substantially parallel to the longitudinal axis of the wound opening 3 while advancing distally through the wound opening 3 to convey the distal ring 9 through the wound opening 3. By rotating the conveying device 5 in this manner, this may assist in overcoming frictional resistance to passage of the distal ring 9 through the wound opening 3.

In FIGS. 43(*a*) to 43(*f*), the bladeless introducer 640 is employed to create the incision 3 prior to loading of the buttonhole distal ring 9 and delivery of the distal ring 9 through to the abdomen.

In use, the skin incision 644 is pre-made with a scalpel (FIG. 43(*a*)). The conveying device 641 is twisted back and forth and advanced (FIG. 43(*b*)). The blunt tip 641 enters the abdomen, and thus the incision 3 is created (FIG. 43(*c*)).

The introducer 640 is withdrawn, the buttonhole distal ring 9 is loaded on to the hook 6 and the sleeve is tensioned to keep the wound retractor device 2 fixed in position (FIG. 43(*d*)). The distal ring 9 is passed into the abdominal cavity (FIG. 43(*e*)). The sleeve is released, by untensioning the sleeve, from the introducer 640 which is then removed leaving the distal ring 9 in the abdomen (FIG. 43(*f*)). The buttonhole device 2 is now ready to be deployed.

FIGS. 44 to 49 illustrate a further apparatus 81 according to the invention, which is similar to the apparatus 71 of FIGS. 37 to 43, and similar elements in FIGS. 44 to 49 are assigned the same reference numerals.

In this case the incising device 4 is provided in the form of the blade element 57 releasably attached to the distal end 7 of the conveying device 5.

The distal end 7 of the conveying device 5 is rounded and blunt for added safety. The rounded/blunt distal end minimises the possibility of damage being caused to internal organs should the distal end 7 contact internal organs.

In use, the wound retractor device 2 is coupled to the conveying device 5 by engaging the distal ring 9 of the wound retractor device 2 with the hook element 6 (FIG. 44). The apparatus 81, with the blade element 57 attached to the conveying device 5, is passed through tissue 8 with the blade element 57 as the leading end to create the wound opening 3, and is advanced through the wound opening 3 to convey the wound retractor device 2 through the wound opening 3 (FIG. 45). Thus the apparatus 81 may be used to create the wound opening 3 and convey the wound retractor device 2 through the wound opening 3 in a single step.

In this case the string 55 and the blade element 57 are employed as the removal device 54 only, and not as the guide device. Because the wound opening 3 is created and the wound retractor device 2 is conveyed through the wound opening 3 in a single step, there is no requirement for a guide device in this case.

When the wound retractor device 2 is deployed to retract the wound opening 3, the blade element 57 remains distally of the wound opening 3 and the string 55 extends through the retracted wound opening 3 (FIG. 48).

Referring to FIGS. 51 to 58 there is illustrated another apparatus 91 according to the invention, which is similar to the apparatus 51 of FIGS. 25 to 30, and similar elements in FIGS. 51 to 58 are assigned the same reference numerals.

In this case the guide device 92 is provided in the form of a rigid tubular member 93. The tubular member 93 has a substantially circular cross-section. A slot 94 extends longitudinally along a sidewall of the tubular member 93.

As illustrated in FIG. 52, the tubular member 93 is mountable to the incising device 4. In this case the elongate member 53 of the incising device 4 has an elongate protrusion 95 for mating with the slot 94 in the tubular member 93.

In use the guide device 92 is mounted to the incising device 4 (FIG. 52), and the incising device 4 and the guide device 92 are passed through tissue 8 with the blade element 57 as the leading end to create the wound opening 3 in an incision step (FIG. 53). The incising device 4 is then withdrawn from the wound opening 3 leaving the guide device 92 in position extending through the wound opening 3 (FIG. 54).

Figure 58B:
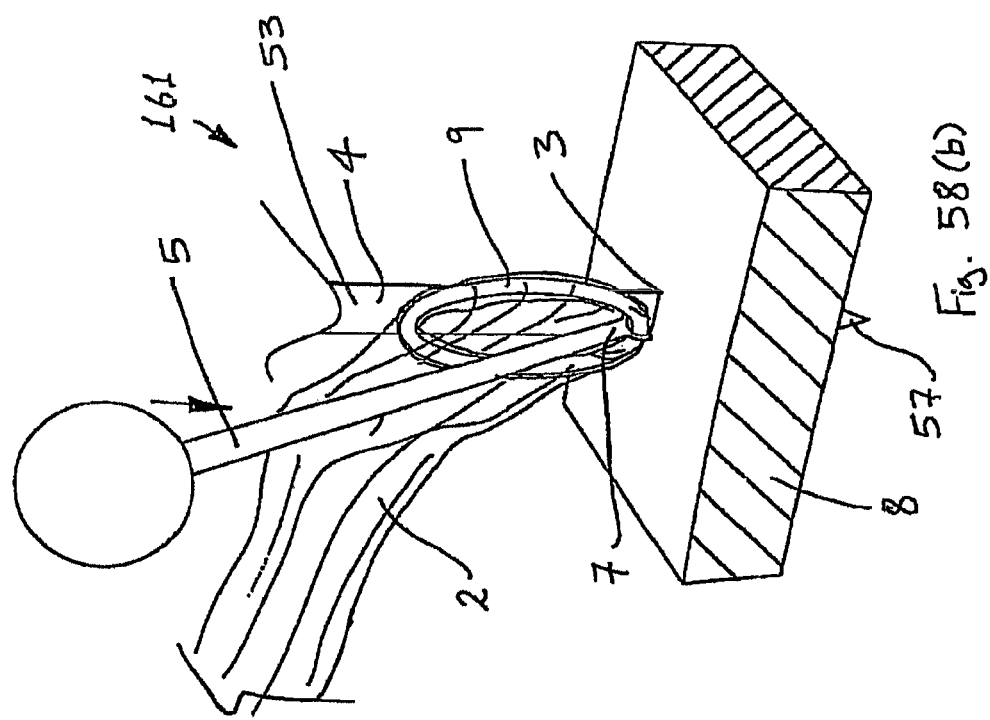
Figure 58A:
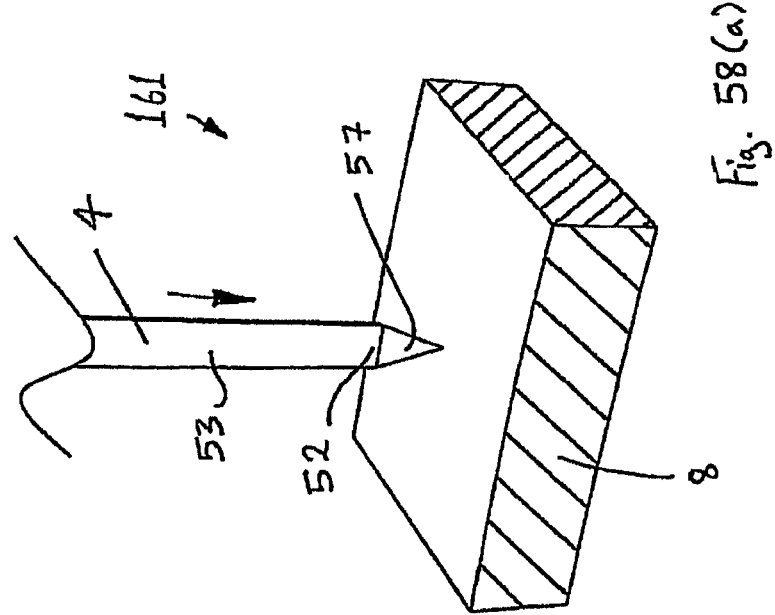
Figure 58:
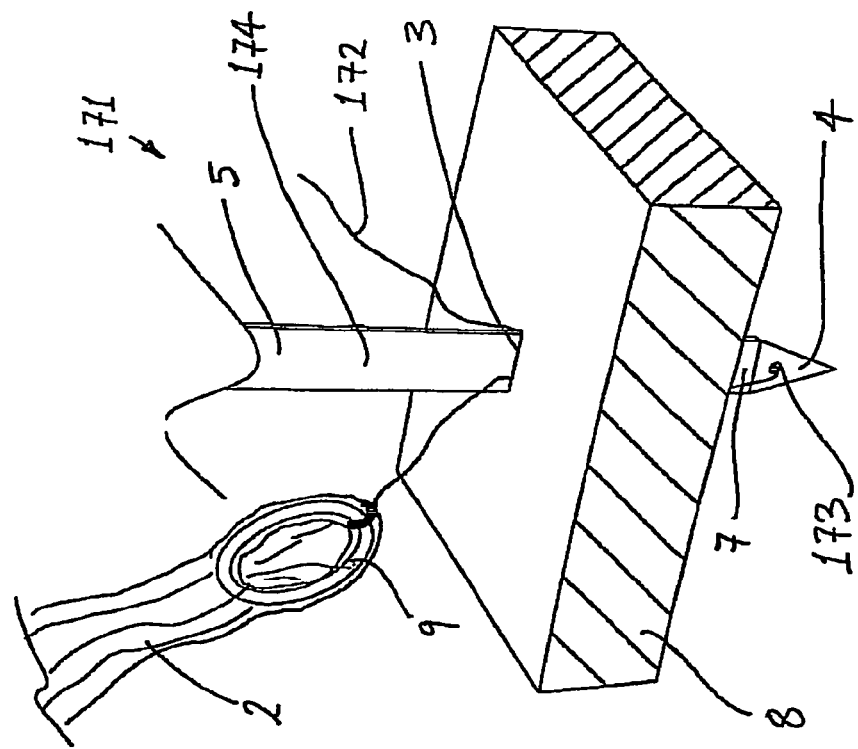
Figure 58:
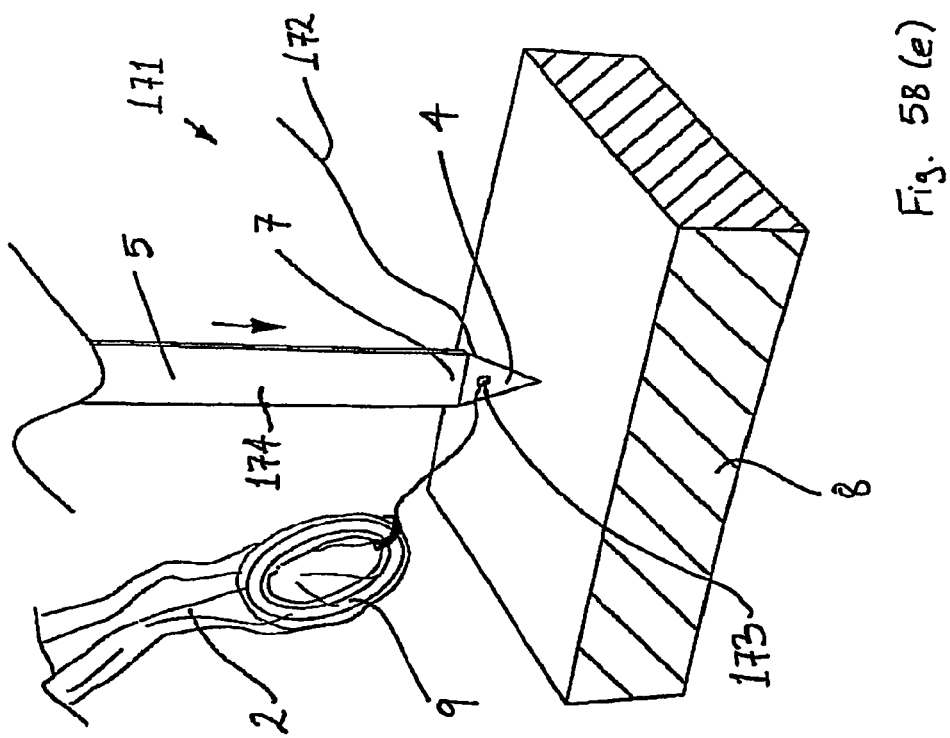
Figure 58J:
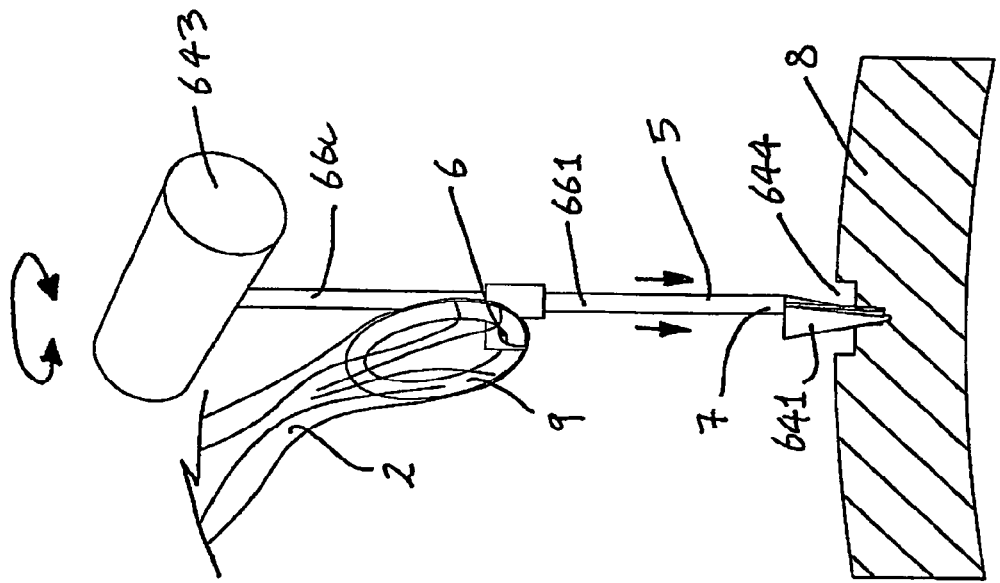
Figure 58I:
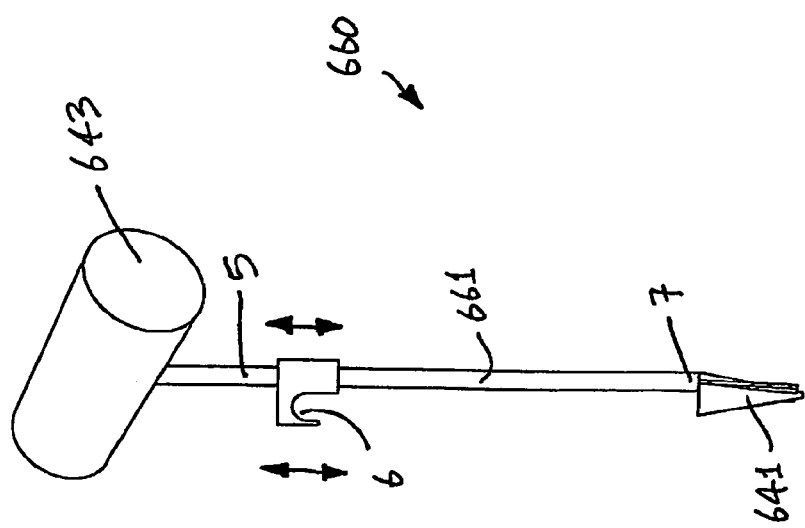

The wound retractor device 2 is coupled to the conveying device 5 by engaging the distal ring 9 with the hook element 6 (FIG. 55). The conveying device 5 is then advanced through the wound opening 3 to convey the wound retractor device 2 through the wound opening 3 in a conveying step (FIG. 56). The conveying device 5 and the guide device 92 may be withdrawn from the wound opening 3 leaving the wound retractor device 2 in position extending through the wound opening 3 and with the distal ring 9 distally of the wound opening 3 (FIGS. 57 and 58).

The open slot 94 of the guide device 92 facilitates removal of the guide device 92 over the sleeve portion of the wound retractor device 2.

The maximum transverse dimension of the portion of the guide device 92 which extends through the wound opening 3 is between 3 mm and 35 mm, preferably between 5 mm and 12 mm.

The guide device 92 does not act as a removal device to assist in removal of the wound retractor device 2 from the wound opening 3, in this case.

Figure 50:
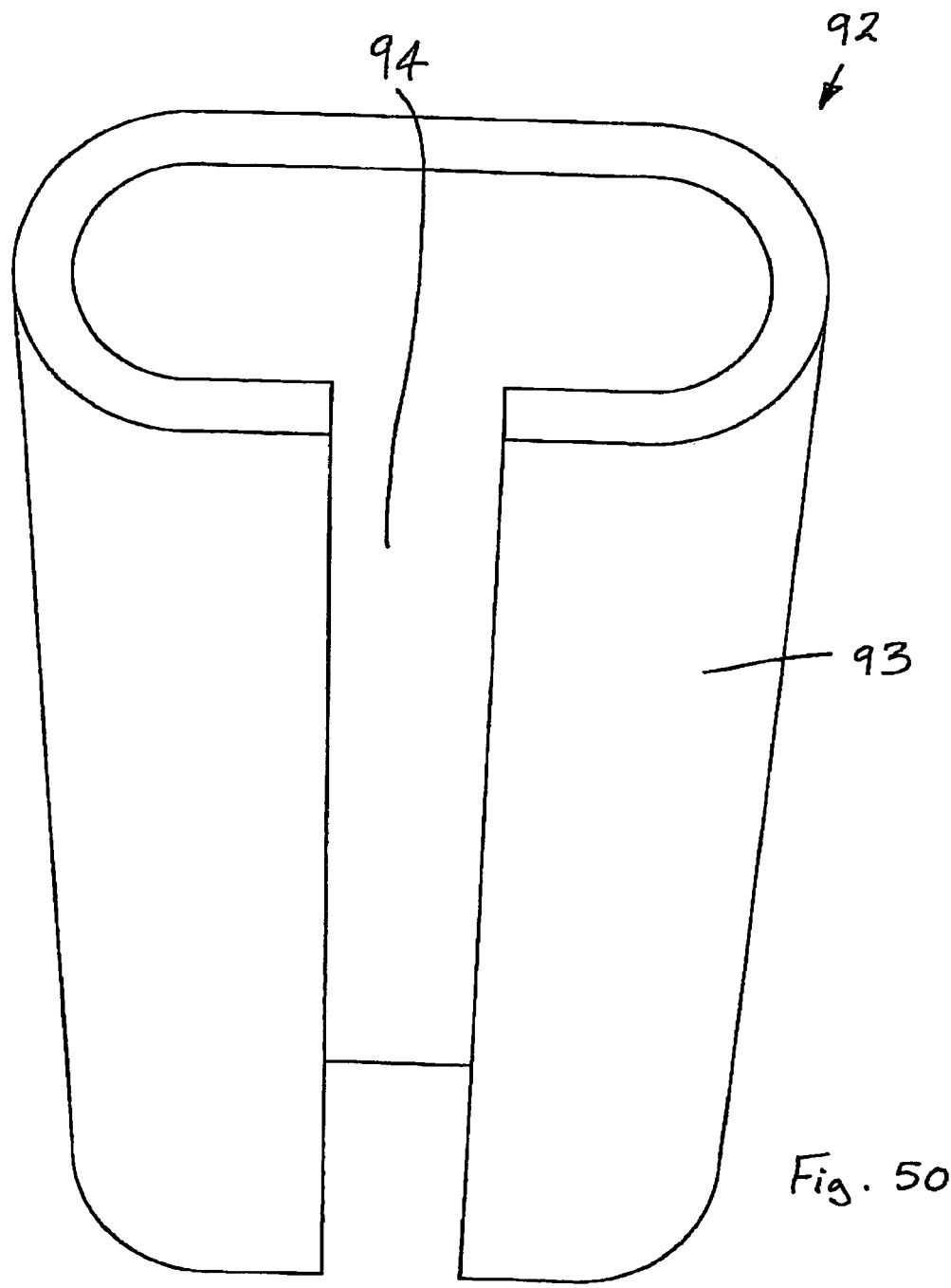
FIG. 50 is a perspective view of a guide device of another apparatus for inserting a surgical device at least partially through a wound opening according to the invention.

In an alternative embodiment the tubular member 93 may have a substantially flattened, oblong cross-section, as illustrated in FIG. 50. The flattened, oblong cross-section of the tubular member 93 may in certain cases be easier to accommodate in the wound opening 3, and/or may in certain cases be able to accommodate the squeezed distal ring 9 more easily.

FIGS. 58(*a*) to 58(*d*) illustrate another apparatus 161 according to the invention, which is similar to the apparatus 51 of FIGS. 25 to 30, and similar elements in FIGS. 58(*a*) to 58(*d*) are assigned the same reference numerals.

In this case both the incising device 4 and the conveying device 5 have substantially flattened cross-sections. The flattened incising device 4 is particularly easy to introduce compared to conventional trocar blades.

In use, the incising device 4 is passed through tissue 8 with the blade element 57 as the leading end to create the wound opening 3 in an incision step (FIG. 58(*a*)).

The wound retractor device 2 is coupled to the conveying device 5 by engaging the distal ring 9 with the hook element 6. The conveying device 5 is advanced through the wound opening 3 to convey the wound retractor device 2 through the wound opening 3 in a conveying step, while the incising device 4 remains in position extending through the wound opening 3 (FIG. 58(*b*)).

Because both the incising device 4 and the conveying device 5 have flattened cross-sections, both may be accommodated extending through the wound opening 3 at the same time. The elasticity of the tissue 8 and of the distal ring 9 facilitate introduction of the distal ring 9 through the wound opening 3 while the incising device 4 remains in position extending through the wound opening 3.

Because the incising device 4 is not removed from the wound opening 3 before insertion of the conveying device 5, there is no requirement for a separate guide device in this case. The incising device 4 effects the function of maintaining the patency of the wound opening 3.

Both the incising device 4 and the conveying device 5 may then be withdrawn from the wound opening 3 leaving the wound retractor device 2 in position extending through the wound opening 3 and with the distal ring 9 distally of the wound opening 3 (FIG. 58(*d*)).

Referring to FIGS. 58(*e*) to 58(*h*) there is illustrated another apparatus 171 according to the invention, which is similar to the apparatus 1 of FIGS. 1 to 5, and similar elements in FIGS. 58(*e*) to 58(*h*) are assigned the same reference numerals.

In this case the conveying device 5 comprises an insertion element 174 insertable through the wound opening 3, and a drawing element 172, provided in this case in the form of a length of flexible string. The string 172 is attached to the distal ring 9 of the wound retractor device 2 by means of a hook and extends through an opening 173 in the distal end 7 of the insertion element 174. In this manner the string 172 couples the distal ring 9 to the insertion element 174, and can be used to draw the distal ring 9 distally through the wound opening 3.

The blade element 4 is fixedly attached to the distal end 7 of the insertion element 174.

In use, the insertion element 174 is passed through tissue 8 with the blade element 4 as the leading end to create the wound opening 3 (FIG. 58(*e*)). The string 172 is then pulled proximally (FIG. 58(*g*)). Because the string 172 is looped through the opening 173, the string 172 acts as a pulley to draw the distal ring 9 distally through the wound opening 3. The insertion element 174 may then be withdrawn from the wound opening 3 leaving the wound retractor device 2 in position extending through the wound opening 3 and with the distal ring 9 distally of the wound opening 3 (FIG. 58(*h*)).

The string 172 may be left in position extending through the wound opening 3. The string 172 may be subsequently used to assist in removal of the wound retractor device 2.

In FIGS. 58(*i*) to 58(*n*) there is illustrated another apparatus 660 according to the invention, which is similar to the apparatus 640 of FIGS. 43(*a*) to 43(*f*), and similar elements in FIGS. 58(*i*) to 58(*n*) are assigned the same reference numerals.

In this case the conveying device 5 comprises a body portion 661 and the hook element 6 is slidably moveable along the body portion 661.

In use, the distal ring 9 of the wound retractor device 2 is coupled to the hook element 6 by engaging the hook element 6 with the distal ring 9 (FIG. 58(*j*)). The wound opening 3 is created in an opening step by advancing the opening device 641 distally while rotating the opening device 641 in a reciprocating clockwise—counter clockwise manner to force the tissue 8 apart (FIGS. 58(*k*) and 58(*l*)). The distal ring 9 remains externally of the wound opening 3 during the step of creating the wound opening 3.

The distal ring 9 is then conveyed through the wound opening 3 in a separate conveying step by sliding the hook element 6 distally along the body portion 661 of the conveying device 5 (FIG. 58(*m*)). During the step of conveying the distal ring 9 through the wound opening 3, the opening device 641 remains within the wound interior and the body portion 661 of the conveying device 5 remains extending through the wound opening 3.

The apparatus 660 is then removed from the wound opening 3 to leave the distal ring 9 within the wound interior and the sleeve portion extending proximally out through the wound opening 3 (FIG. 58(*n*)).

The apparatus 660 comprises the proximal handle 643, the hook 6 on the sliding member, and the bladeless introducer tip 641 (FIG. 58(*i*)).

The distal ring 9 is attached to the sliding hook 6, which is initially positioned away from the dissecting, leading edge 641 of the introducer 660 (FIG. 58(*j*)). This ensures that the ring 9 will not interfere with the twisting motion required by the bladeless tip 641.

The twisting motion advances the bladeless tip 641 through the abdominal wall 8 (FIG. 58(*k*)). The distal ring 9 does not interfere with the creation of the incision 3. In FIG. 58 (*l*), the bladeless tip 641 has entered the abdomen.

The sliding hook member 6 is then advanced down the shaft 661 of the introducer 660 to pass the distal ring 9 through the incision 3 (FIG. 58(*m*)). The introducer 660 is removed, leaving the distal ring 9 in the abdomen ready for deployment (FIG. 58(*n*)).

Figure 59:
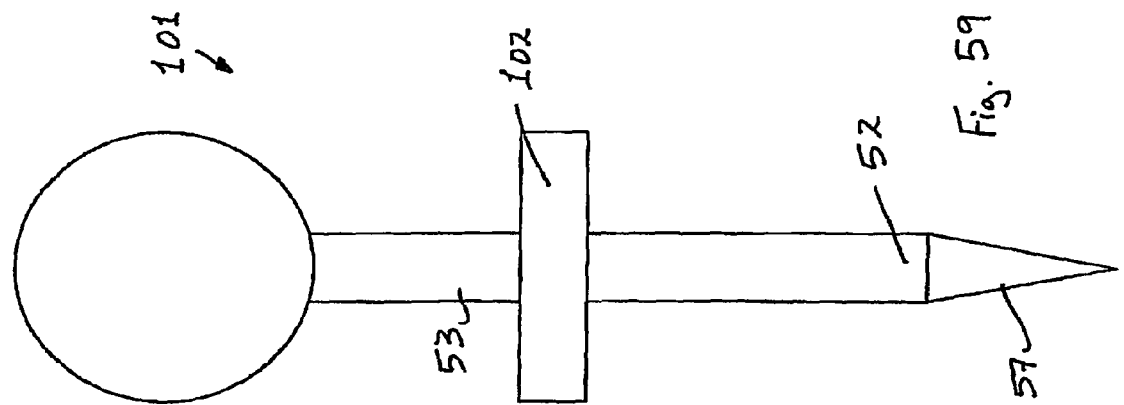

In FIG. 59 there is illustrated an incising device 101 of another apparatus according to the invention, which is similar to the incising device 4 of FIGS. 25 to 30, and similar elements in FIG. 59 are assigned the same reference numerals.

In this case the incising device 101 has an abutment member 102 fixedly mounted to the elongate member 53. The abutment member 102 is suitable for abutting an external surface of tissue 8 adjacent the wound opening 3. In this manner the abutment member 102 acts as a limiting element to limit the extent of passage of the incising device 101 through tissue 8. In particular the abutment member 102 prevents any sudden "jump-through" when the tissue 8 is pierced.

Figure 60:
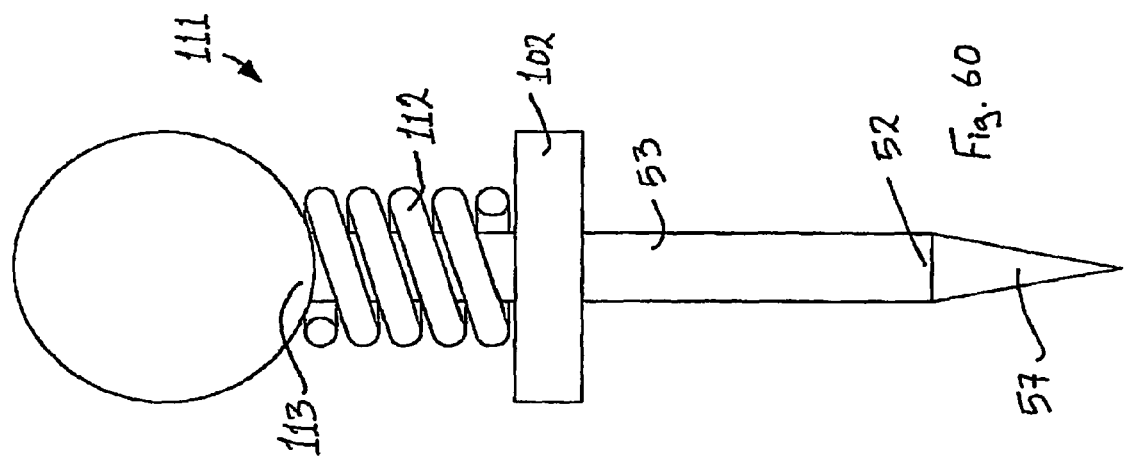

FIG. 60 illustrates a further incising device 111 of another apparatus according to the invention, which is similar to the incising device 101 of FIG. 59, and similar elements in FIG. 60 are assigned the same reference numerals.

In this case the abutment member 102 is mounted to the elongate member 53 by means of a coiled spring 112. The coiled spring 112 extends between the abutment member 102 and the proximal end 113 of the elongate member 53. The abutment member 102 is thus movable relative to the elongate member 53 between a retracted configuration (FIG. 60) and an extended configuration, in which the spring 112 is compressed. The spring 112 acts to bias the abutment member 102 away from the proximal end 113 of the elongate member 53 towards the retracted configuration.

Figure 61:
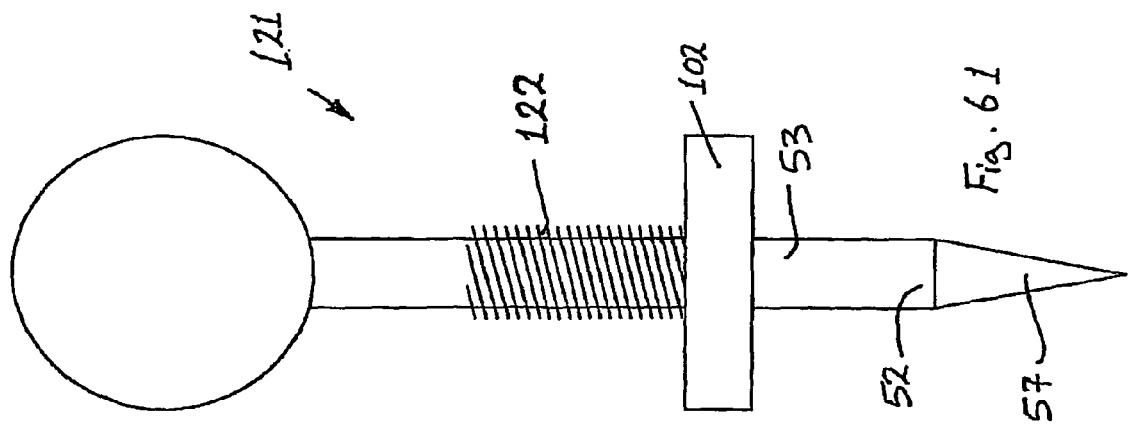
FIGS. 59 to 61 are side views of incising devices of other apparatus for inserting a surgical device at least partially through a wound opening according to the invention.
Figure 63:
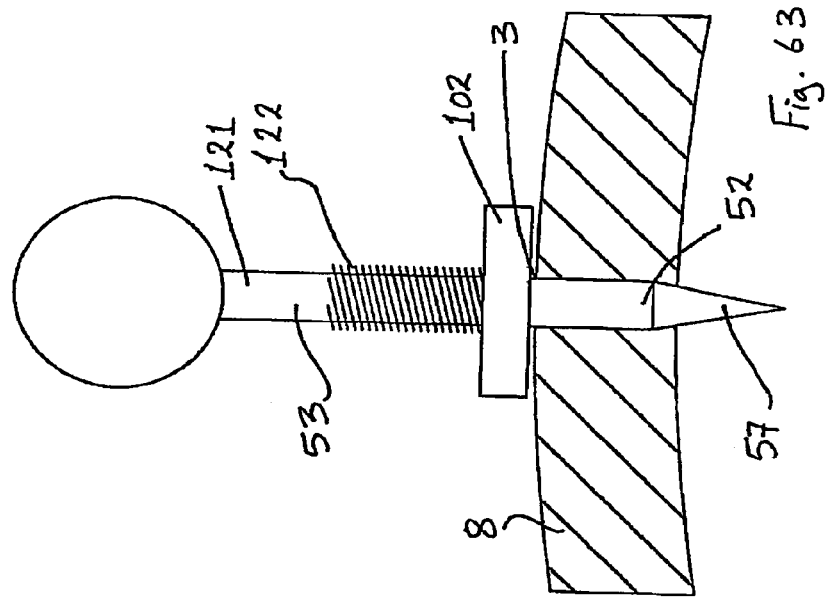
FIGS. 62 and 63 are partially cross-sectional, side views of the incising device of FIG. 61, in use.
Figure 62:
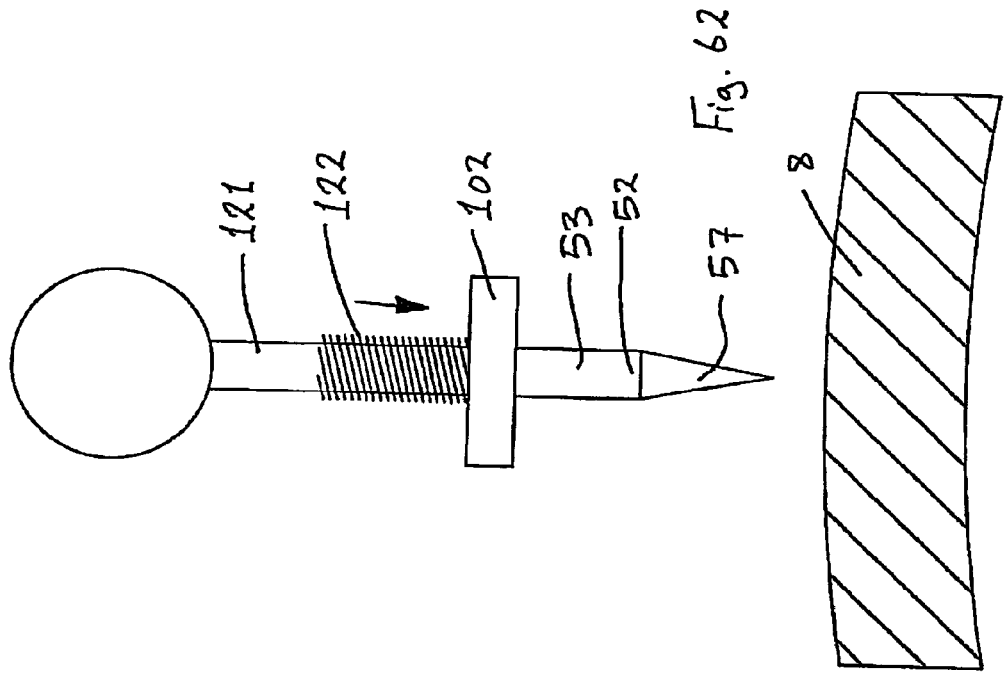

Referring to FIGS. 61 to 63 there is illustrated another incising device 121 of another apparatus according to the invention, which is similar to the incising device 101 of FIG. 59, and similar elements in FIGS. 61 to 63 are assigned the same reference numerals.

In this case the abutment member 102 is mounted to the elongate member 53 by means of a screw-thread arrangement 122. This arrangement facilitates adjustment of the position of mounting of the abutment member 102 on the elongate member 53. Thus the abutment member 102 is adjustable to accommodate different abdomen thickness.

The abutment member 102 prevents the blade element 57 entering too far into the abdomen (FIG. 63).

Figure 64:
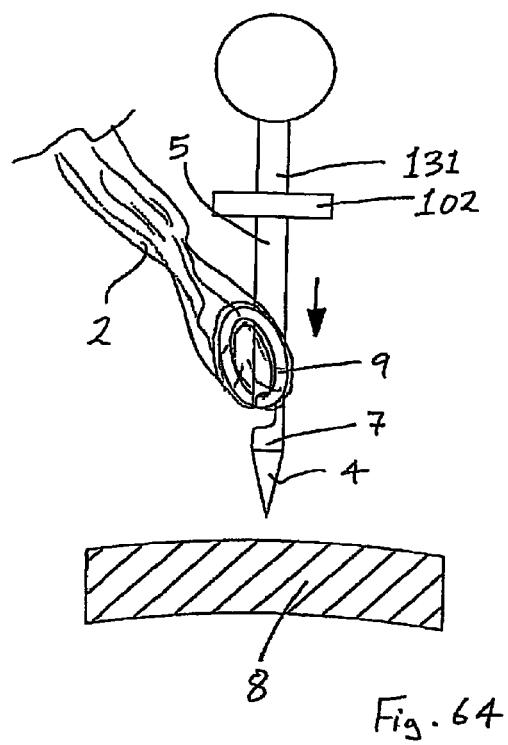
FIGS. 64 and 65 are partially cross-sectional, side views of another apparatus for inserting a surgical device at least partially through a wound opening according to the invention, in use.
Figure 65:
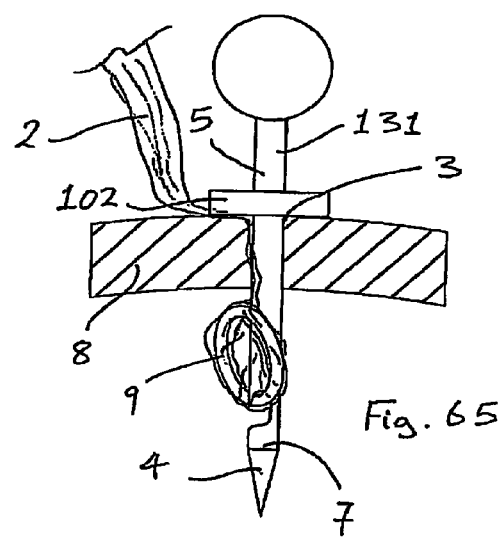
Figure 73:
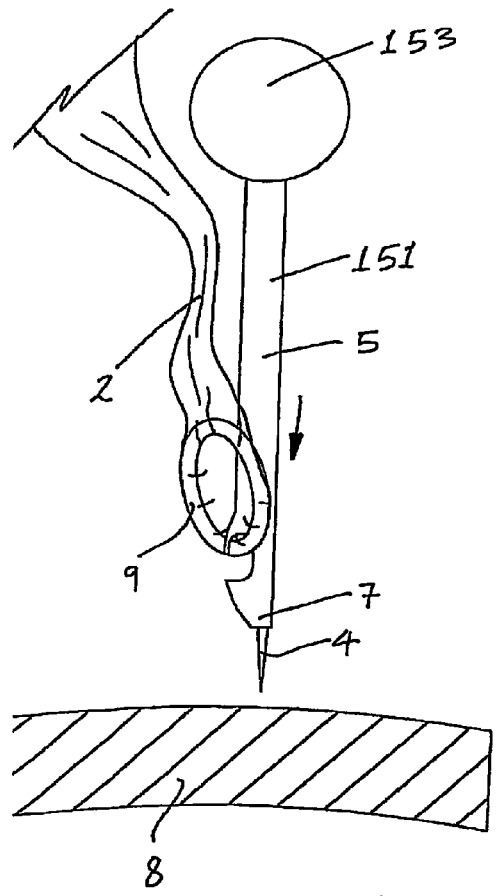
FIGS. 73 to 75 are partially cross-sectional, side views of the apparatus of FIG. 69, in use.

In FIGS. 64 and 65 there is illustrated another apparatus 131 according to the invention, which is similar to the apparatus 1 of FIGS. 1 to 5, and similar elements in FIGS. 64 and 65 are assigned the same reference numerals.

In this case the apparatus 131 has the abutment member 102, similar to that described previously with reference to FIG. 59, fixedly mounted to the conveying device 5.

FIGS. 66 to 68 illustrate a further incising device 141 of another apparatus according to the invention, which is similar to the incising device 111 of FIG. 60, and similar elements in FIGS. 66 to 68 are assigned the same reference numerals.

In this case the coiled spring 112 extends between the abutment member 102 and the distal end 52 of the elongate member 53. The abutment member 102 is thus movable relative to the elongate member 53 between a retracted configuration (FIG. 67) and an extended configuration (FIG. 68), in which the spring 112 is extended. The spring 112 acts to bias the abutment member 102 towards the distal end 52 of the elongate member 53 towards the retracted configuration.

In order to fully pierce the tissue 8, the spring 112 must be stretched. Hence the piercing operation is a controlled one. In this manner, the possibility of sudden "jump-through" when the blade element 57 breaks through is minimised.

Referring to FIGS. 69 to 75 there is illustrated another apparatus 151 according to the invention, which is similar to the apparatus 1 of FIGS. 1 to 5, and similar elements in FIGS. 69 to 75 are assigned the same reference numerals.

In this case the blade element 4 is attached to the conveying device 5 by means of a spring 152 extending between the blade element 4 and the proximal end 153 of the conveying device 5. The blade element 4 is movable relative to the conveying device 5 between an extended configuration (FIG. 71) and a retracted configuration (FIG. 72), in which the spring 152 is compressed. The spring 152 acts to bias the blade element 4 away from the proximal end 153 towards the extended configuration.

Figure 74:
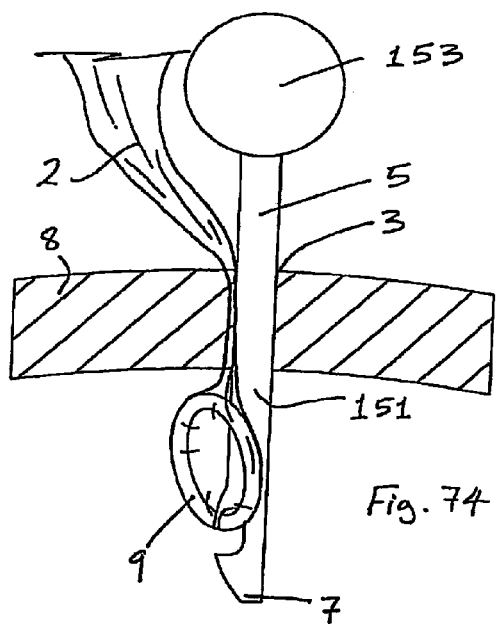

When the apparatus 151 pierces the tissue 8, the blade element 4 retracts into the conveying device 5 for safety (FIG. 74).

FIGS. 75(a) to 75(g) illustrate another apparatus 200 according to the invention, which is similar to the apparatus 151 of FIGS. 69 to 75, and similar elements in FIGS. 75(a) to 75(g) are assigned the same reference numerals.

In this case the blade element 4 is detached from the conveying device 5. The blade element 4 is mounted to the conveying device 5 by extending the blade element 4 through a lumen 201 in the conveying device 5. A handle portion 202 is provided at the proximal end of the blade element 4 to facilitate gripping of the blade element 4 and manual movement of the blade element 4 relative to the conveying device 5 between the extended configuration (FIG. 75(a)) and the retracted configuration (FIG. 75(b)). In the retracted configuration, the distal end of the blade element 4 is housed within the distal end 7 of the conveying device 5 to safely cover the distal end of the blade element 4.

As illustrated in FIG. 75(a) the blade element 4 is mounted substantially concentrically with respect to the longitudinal axis of the conveying device 5. In this concentric arrangement the longitudinal axis of the blade element 4 is substantially parallel to the longitudinal axis of the conveying device 5. The centre axis of the blade element 4 may be offset in the radial direction by a relatively small distance from the centre axis of the conveying device 5, in particular to accommodate the hook element 6 and a recess in the sidewall of the conveying device.

As illustrated in FIG. 75(b), the distal end 7 of the conveying device 5 is blunt and rounded for safety.

As illustrated in FIG. 75(b), lifting the blade element 4 by means of retraction of the handle 202 causes the blade 4 to move up into the body of the hook introducer 5.

Figure 75:
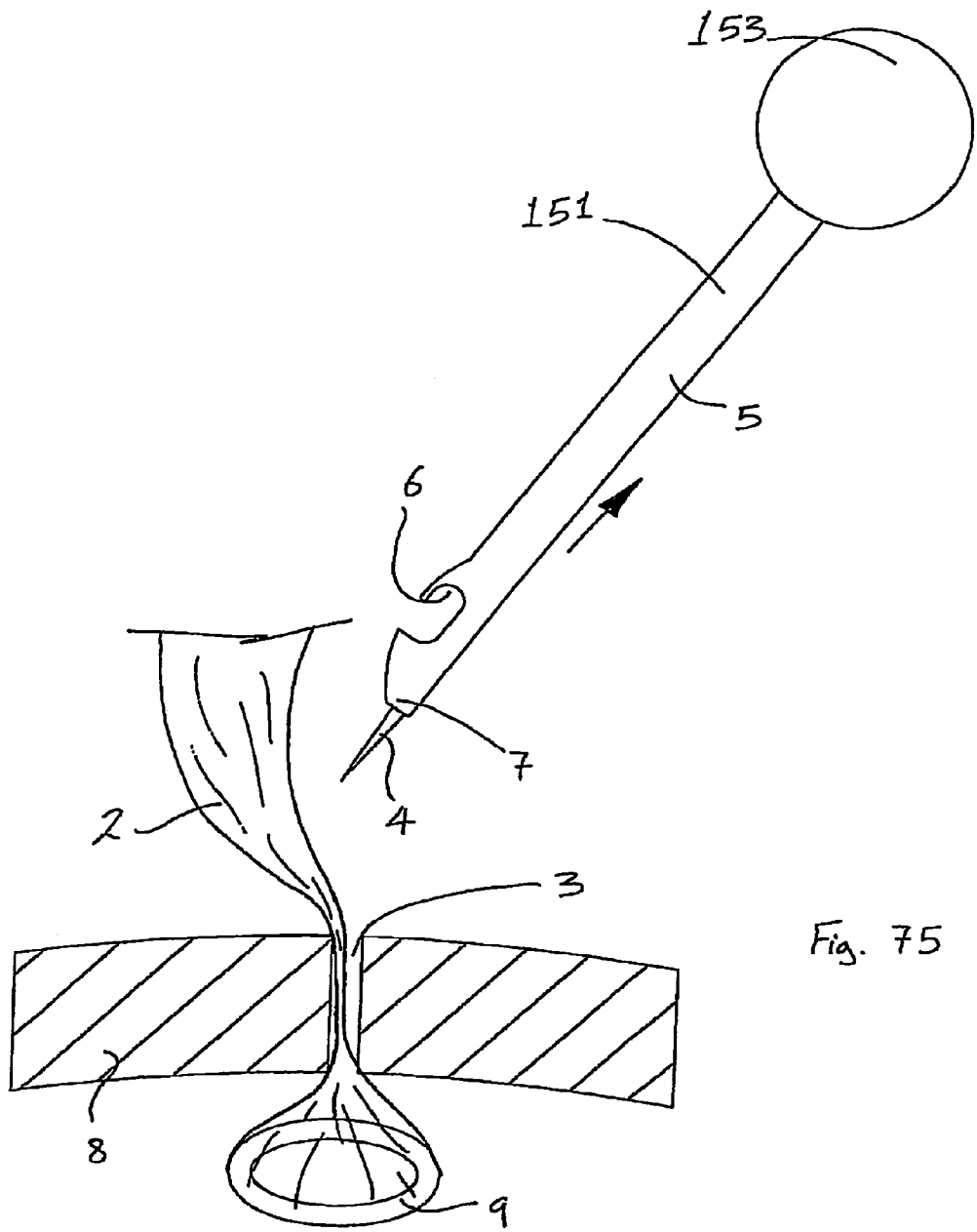
Figure 75D:
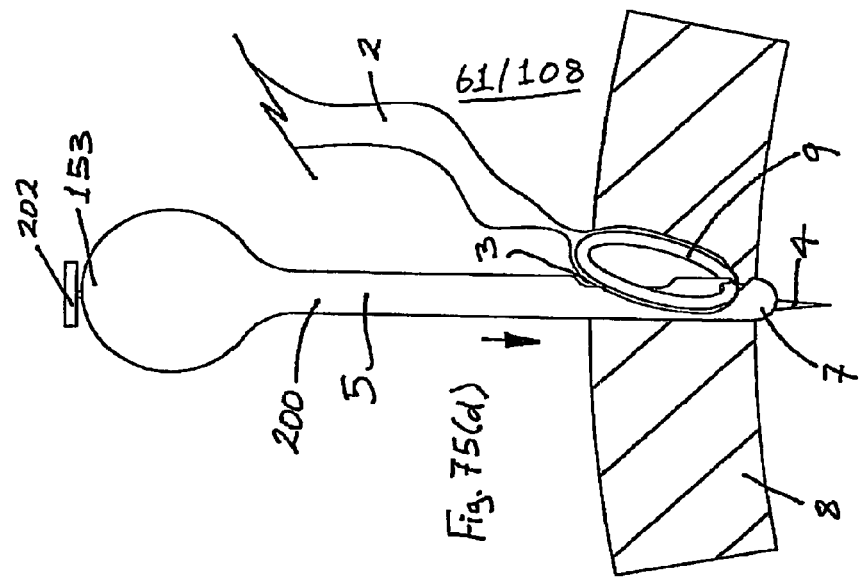
FIGS. 75(c) to 75(g) are partially cross-sectional, side views of the apparatus of FIGS. 75(a) and 75(b), in use.
Figure 75C:
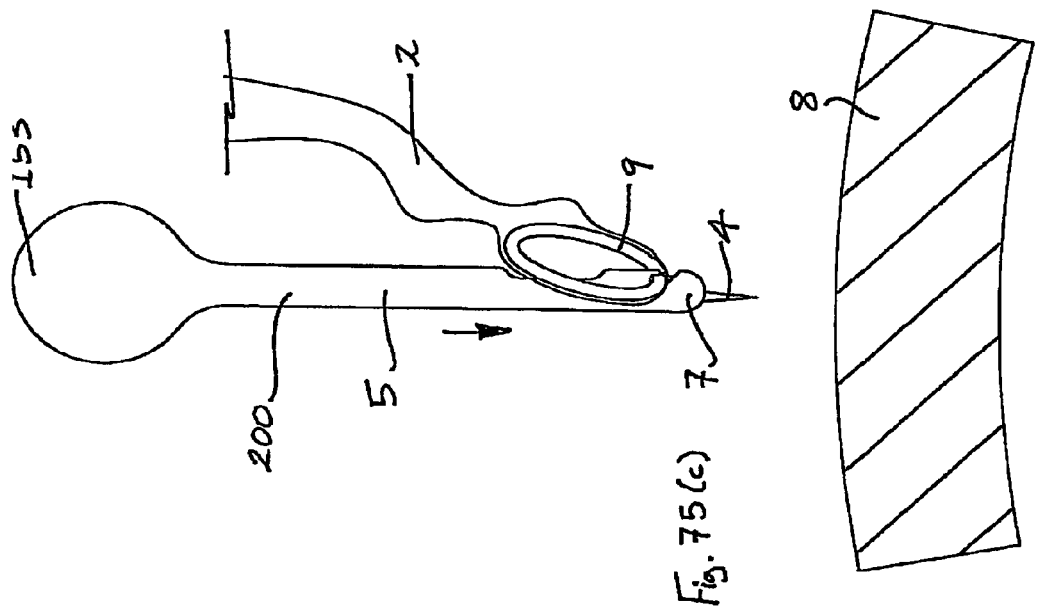
Figure 75G:
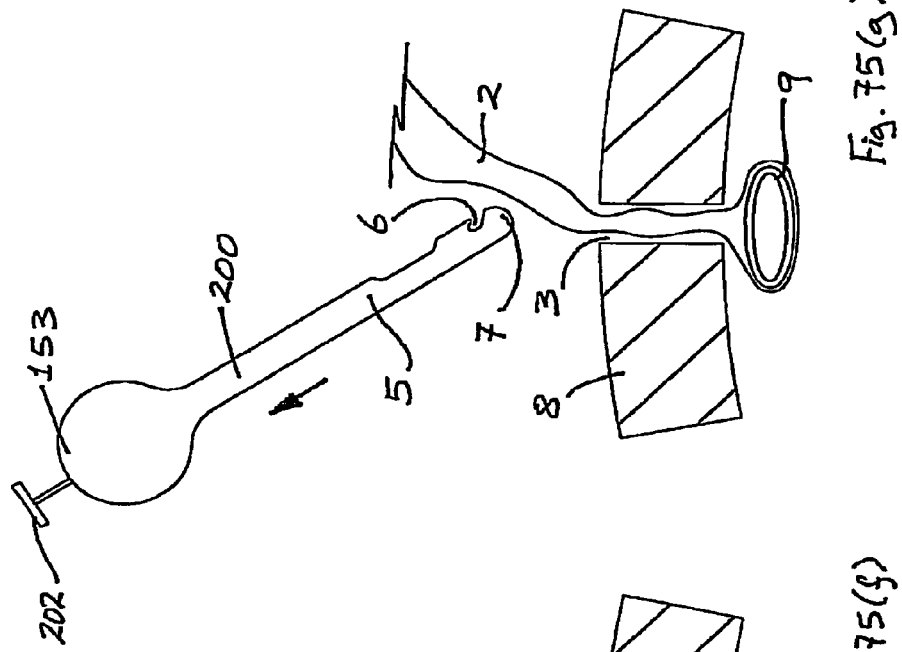

In use, the apparatus 200 with the blade element 4 in the extended configuration is pushed distally through the tissue 8 until the blade element 4 has passed through the tissue 8 to create the wound opening 3 (FIG. 75(d)). The blade 4 creates the incision 3 and the hook 6 drags the distal ring 9 through the incision 3. The pushing force is stopped once the blade 4 is seen entering the abdomen. The handle portion 202 of the blade element 4 is then gripped, and the blade element 4 is manually pulled proximally while the conveying device 5 remains in a fixed position to move the blade element 4 from the extended configuration to the retracted configuration (FIG. 75(e)). The blade retracting handle 202 is pulled up to hide the blade 4 in the introducer body 5 to result in a safe blunt introducer 5. It is noted that the wound retractor device 2 has only been conveyed partially through the wound opening 3 at the point where the blade element 4 is retracted into the conveying device 5.

Figure 75F:
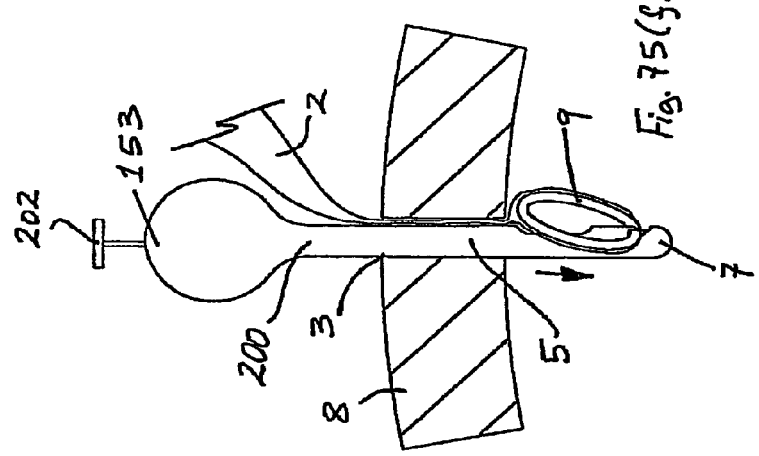
Figure 75E:
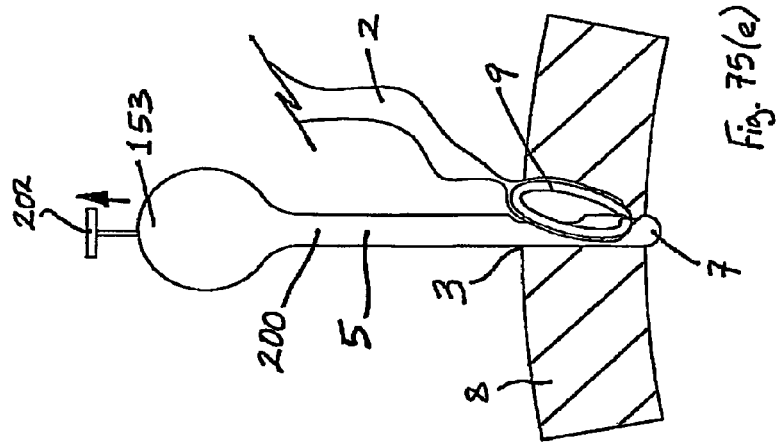
Figure 75:
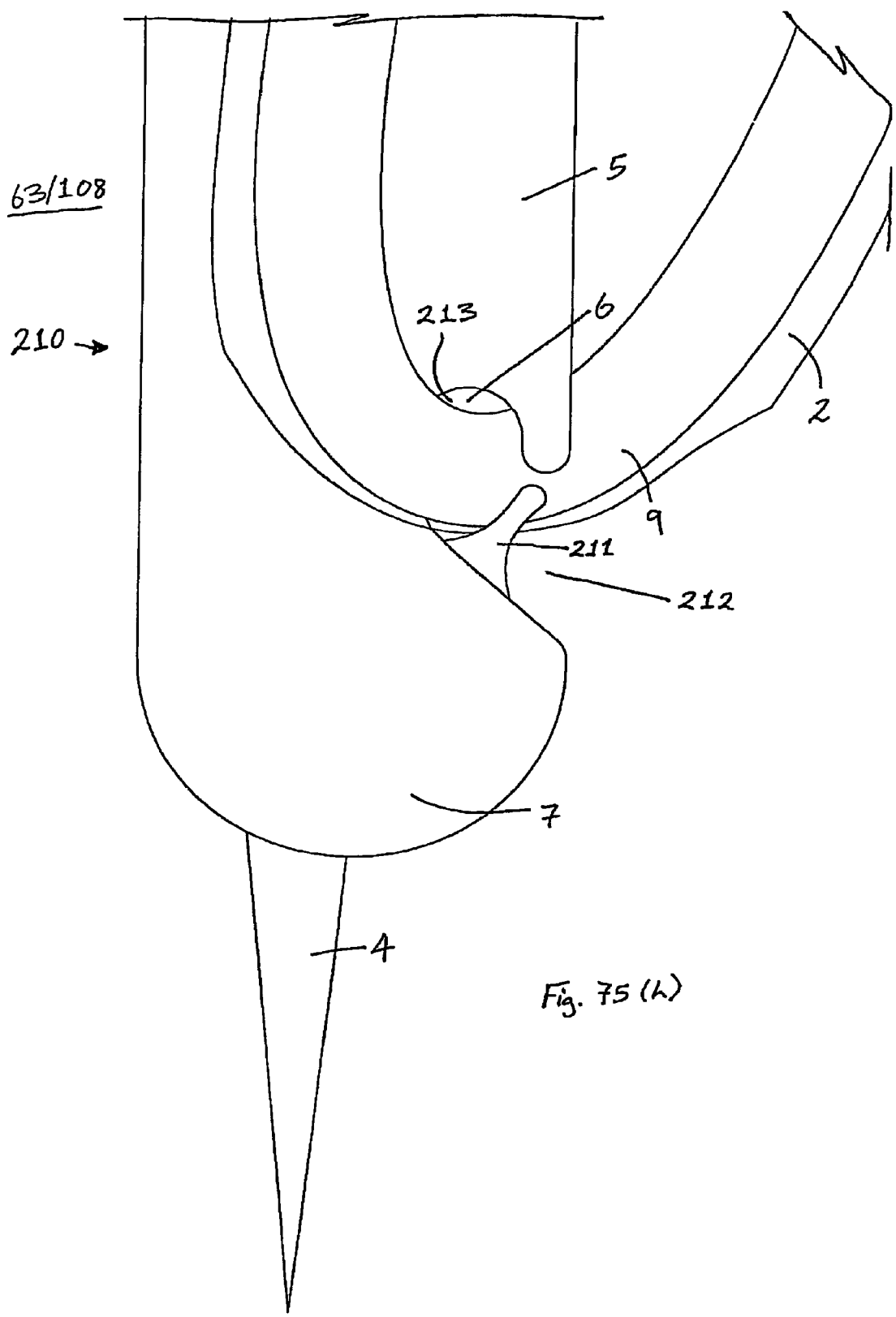

The conveying device 5 is then pushed further distally through the wound opening 3 until the distal ring 9 of the wound retractor device 2 has passed fully through the wound opening 3 into the abdomen (FIG. 75(f)). The introducer 5 is advanced until the distal ring 9 is fully inside the abdomen. The apparatus 200 is then withdrawn from the wound opening 3 leaving the wound retractor device 2 mounted in the wound opening 3 (FIG. 75(g)). The introducer 5 is removed to leave the distal ring 9 in the abdomen and the wound retractor device 2 ready to be used.

Figure 75I:
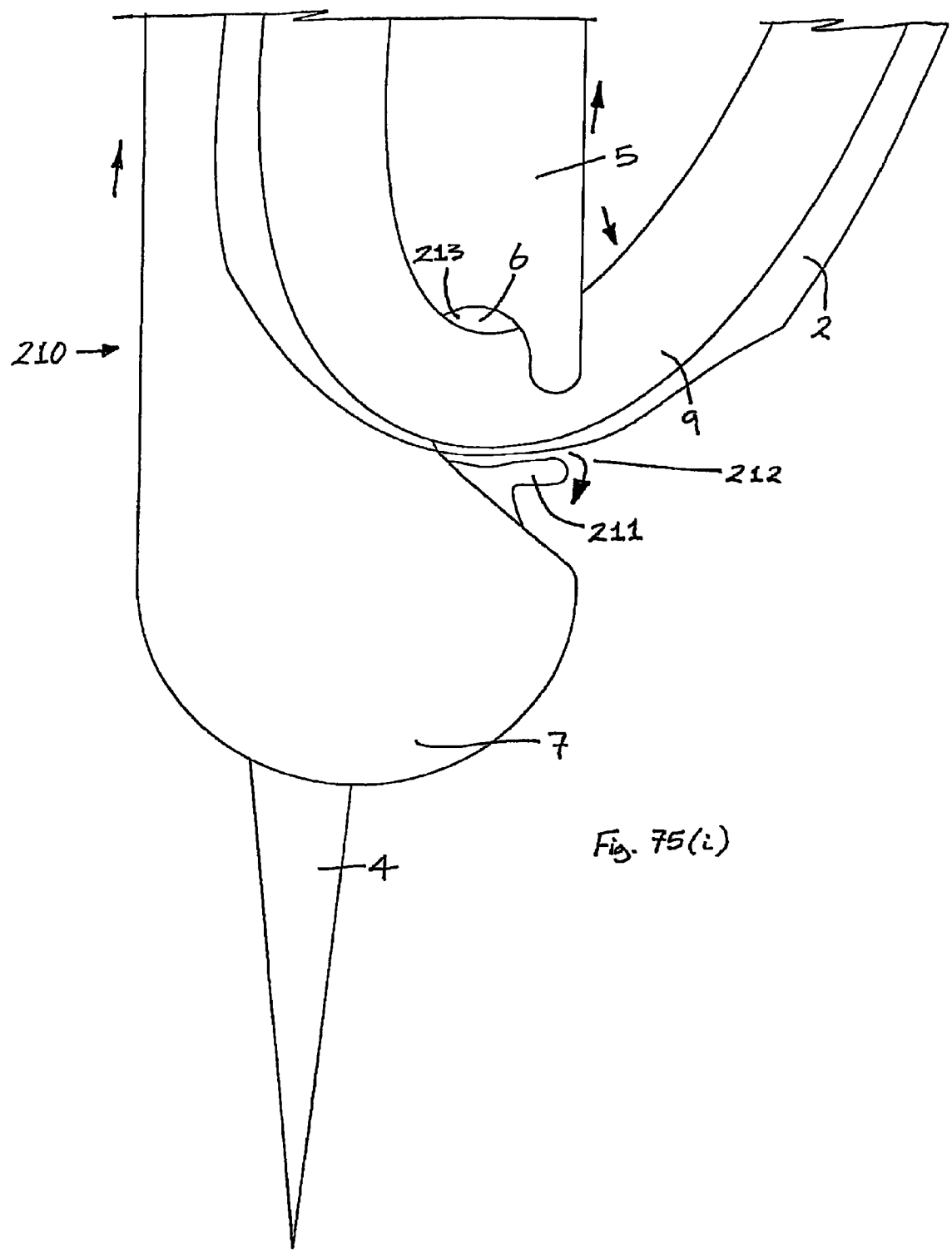
FIG. 75(i) is a side view of the apparatus of FIG. 75(h) in a passage configuration.

In FIGS. 75(h) and 75(i) there is illustrated another apparatus 210 according to the invention, which is similar to the apparatus 200 of FIGS. 75(a) to 75(g), and similar elements in FIGS. 75(h) and 75(i) are assigned the same reference numerals.

In this case the conveying device 5 comprises a resilient arm 211 which extends across the passageway 212 between the concave portion 213 of the hook element 6 and externally of the conveying device 5. The arm 211 is movable between an obstructing configuration in which the arm 211 extends across to obstruct part of the passageway 212 (FIG. 75(h)) and a passage configuration in which the arm 211 is bent back to facilitate passage of the distal ring 9 of the wound retractor device 2 through the passageway 212 into and out of the concave portion 213 of the hook element 6 (FIG. 75(i)). In the obstructing configuration, the arm 211 retains the distal ring 9 in engagement with the hook element 6 during insertion of the wound retractor device 2 through a wound opening 3. The resilient nature of the arm 211 biases the arm 211 towards the obstructing configuration.

The soft rubber distal ring retainer 211 has enough strength to hold the distal ring 9 in place during delivery through the abdominal wall 8, but bends out of the way to deposit the ring 9 in the abdomen when the hook introducer 5 is being withdrawn.

As illustrated in FIG. 75(i), the soft rubber distal ring retainer 211 collapses to either load or deposit the distal ring 9 into/from the hook 213.

Figure 75K:
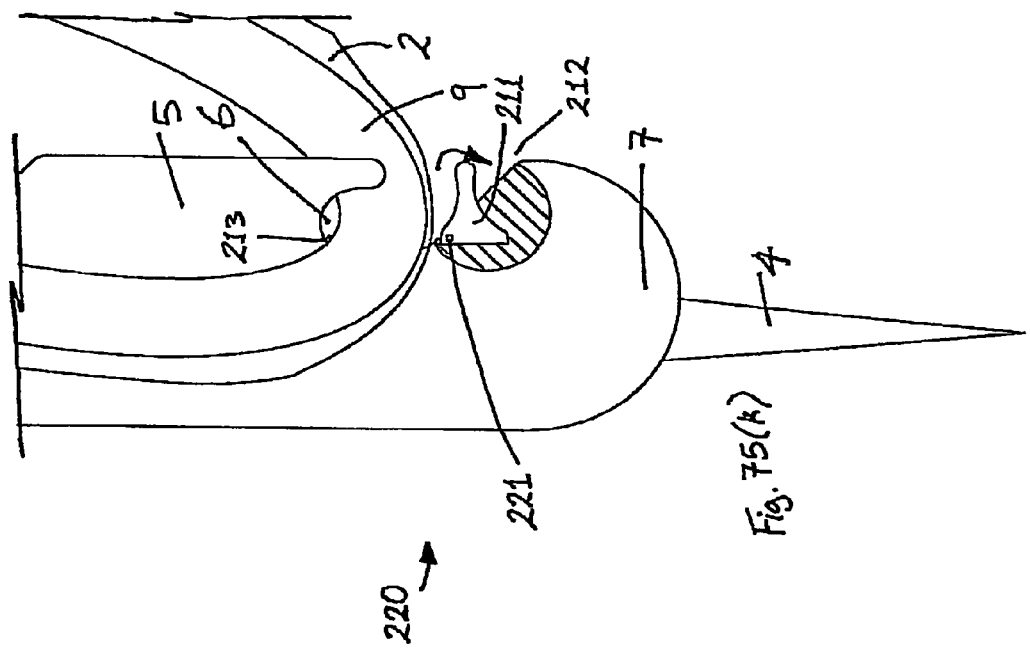
FIGS. 75(k)(i) and 75(k)(ii) are side views of part of another apparatus for inserting a surgical device at least partially through a wound opening according to the invention.
Figure 75J:
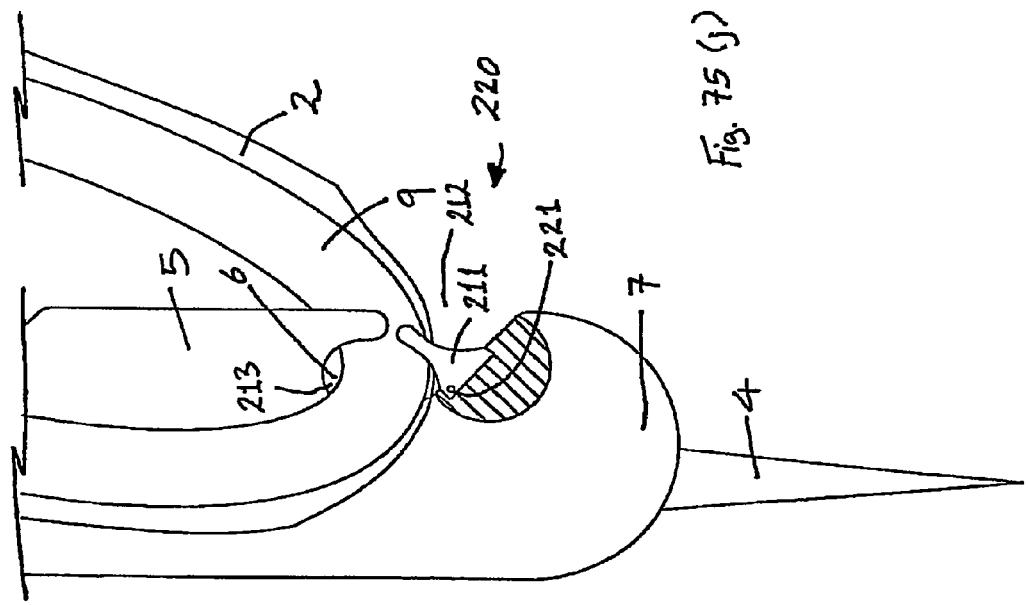
FIGS. 75(a) and 75(b) are views similar to FIGS. 71 and 72 of another apparatus for inserting a surgical device at least partially through a wound opening according to the invention.
FIG. 75(h) is a side view of a distal end of another apparatus for inserting a surgical device at least partially through a wound opening according to the invention in an obstructing configuration.
FIG. 75(l) is a perspective view of another apparatus for inserting a surgical device at least partially through a wound opening according to the invention in an extended configuration.
FIG. 75(m) is a side view of the apparatus of FIG. 75(l) in the extended configuration.
FIG. 75(n) is a partially cross-sectional, side view of the apparatus of FIG. 75(l) in the extended configuration.
FIG. 75(o) is a plan view from below of the apparatus of FIG. 75(l) in the extended configuration.
FIGS. 75(p) and 75(q) are views similar to FIGS. 75(m) and 75(n) of the apparatus of FIG. 75(l) in a retracted configuration.
FIG. 75(r) is a side view of a conveying device of the apparatus of FIG. 75(l)
FIG. 75(s) is a cross-sectional, side view of the conveying device of FIG. 75(p)
FIG. 75(t) is a perspective view of an incising device of the apparatus of FIG. 75(l)
FIGS. 75(u) to 75(y) are partially cross-sectional, side views of the apparatus of FIG. 75(l), in use.
Figure 75:
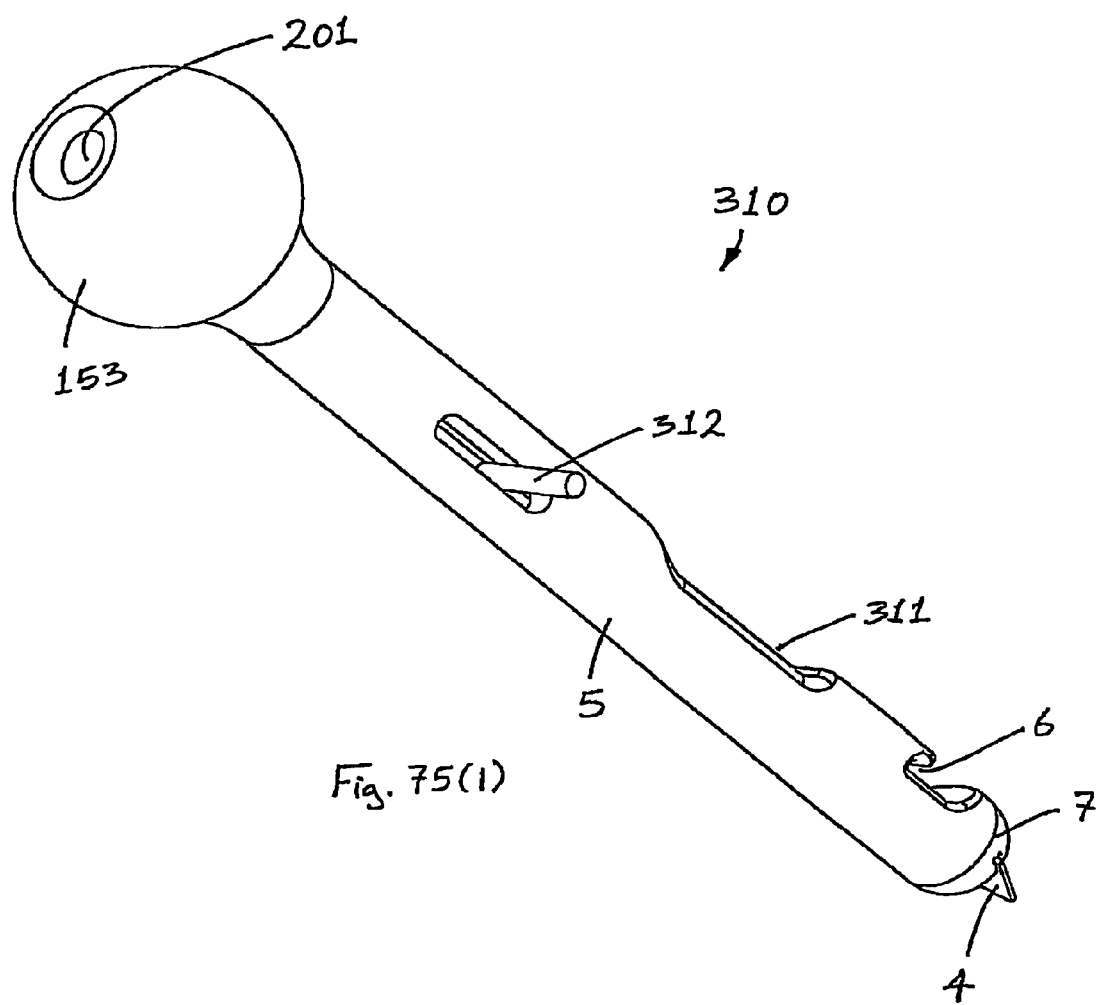
Figure 75M:
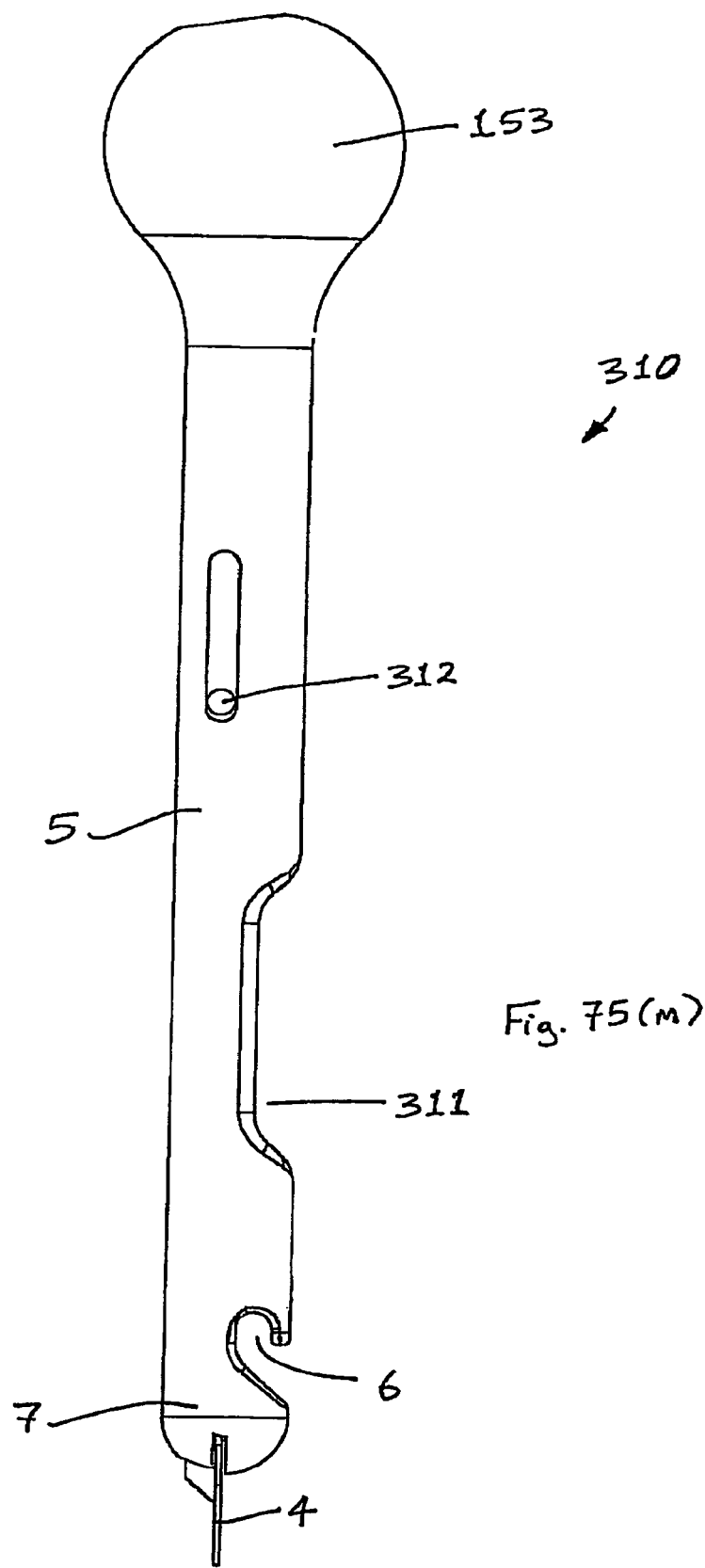
Figure 75N:
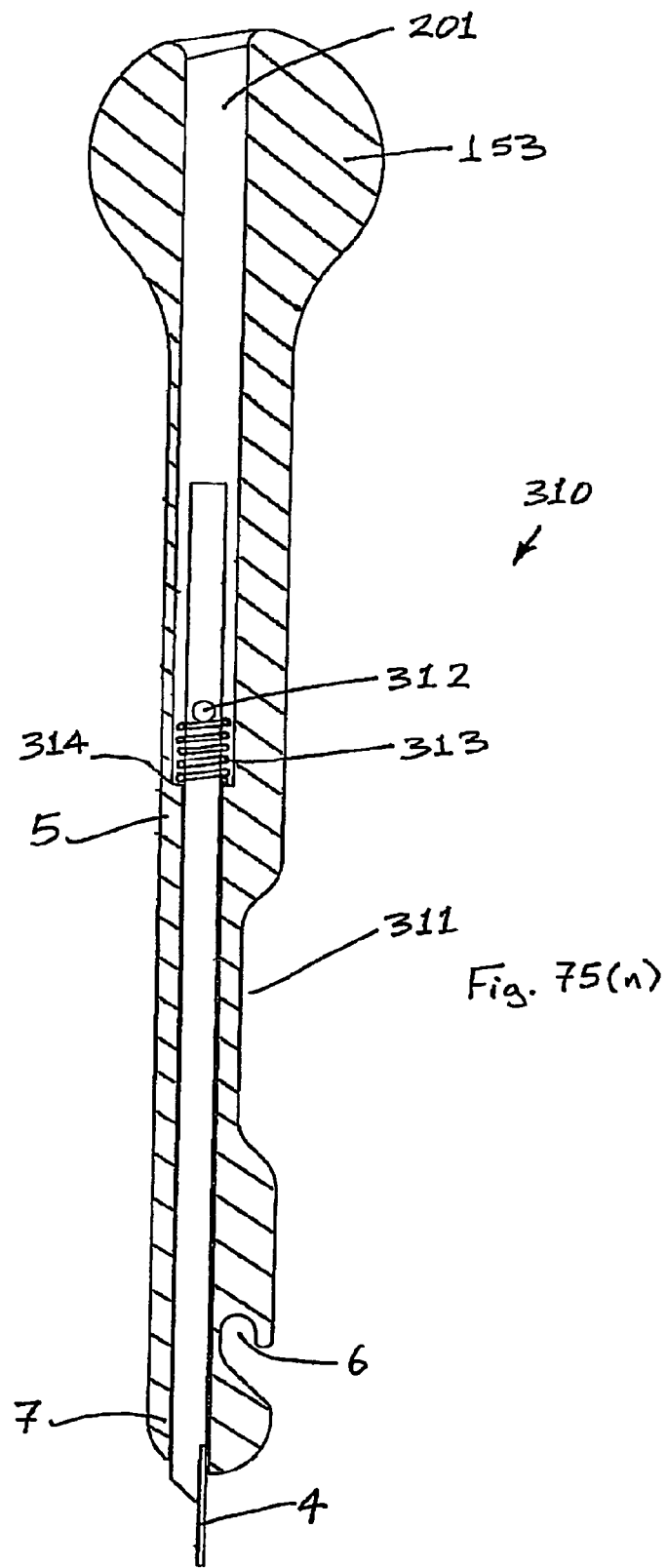
Figure 75O:
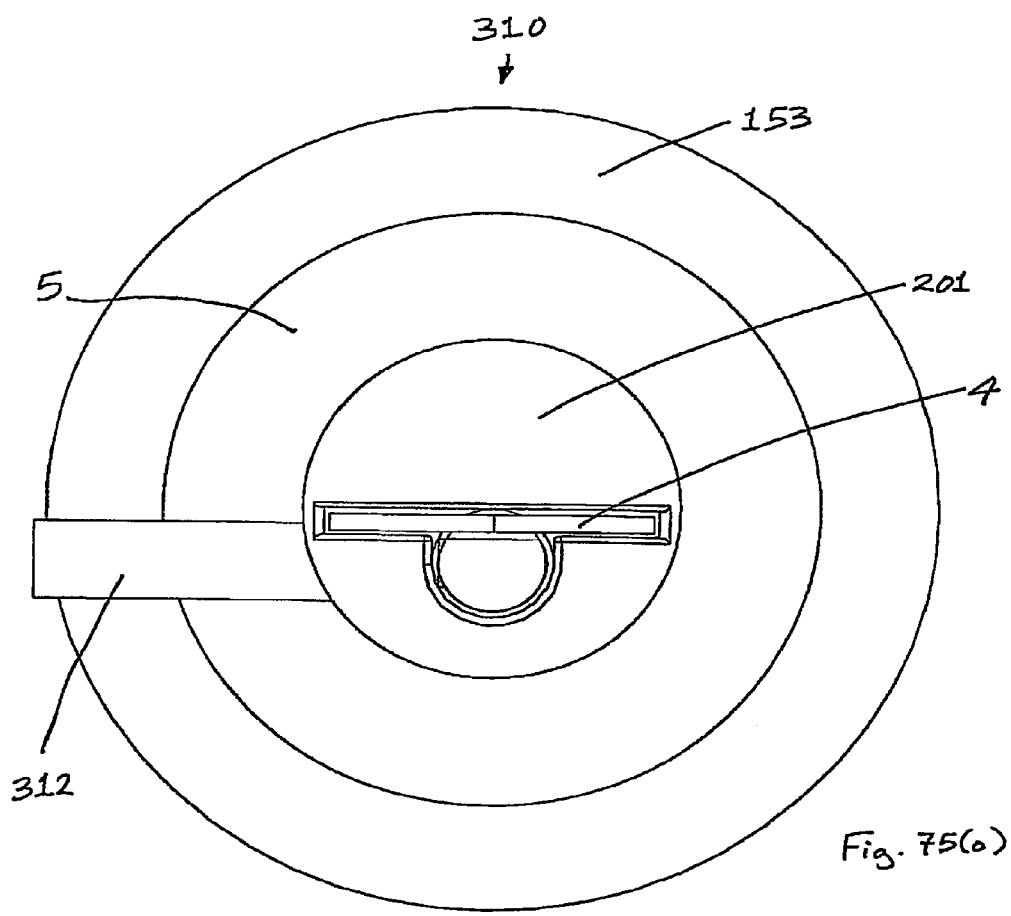
Figure 75P:
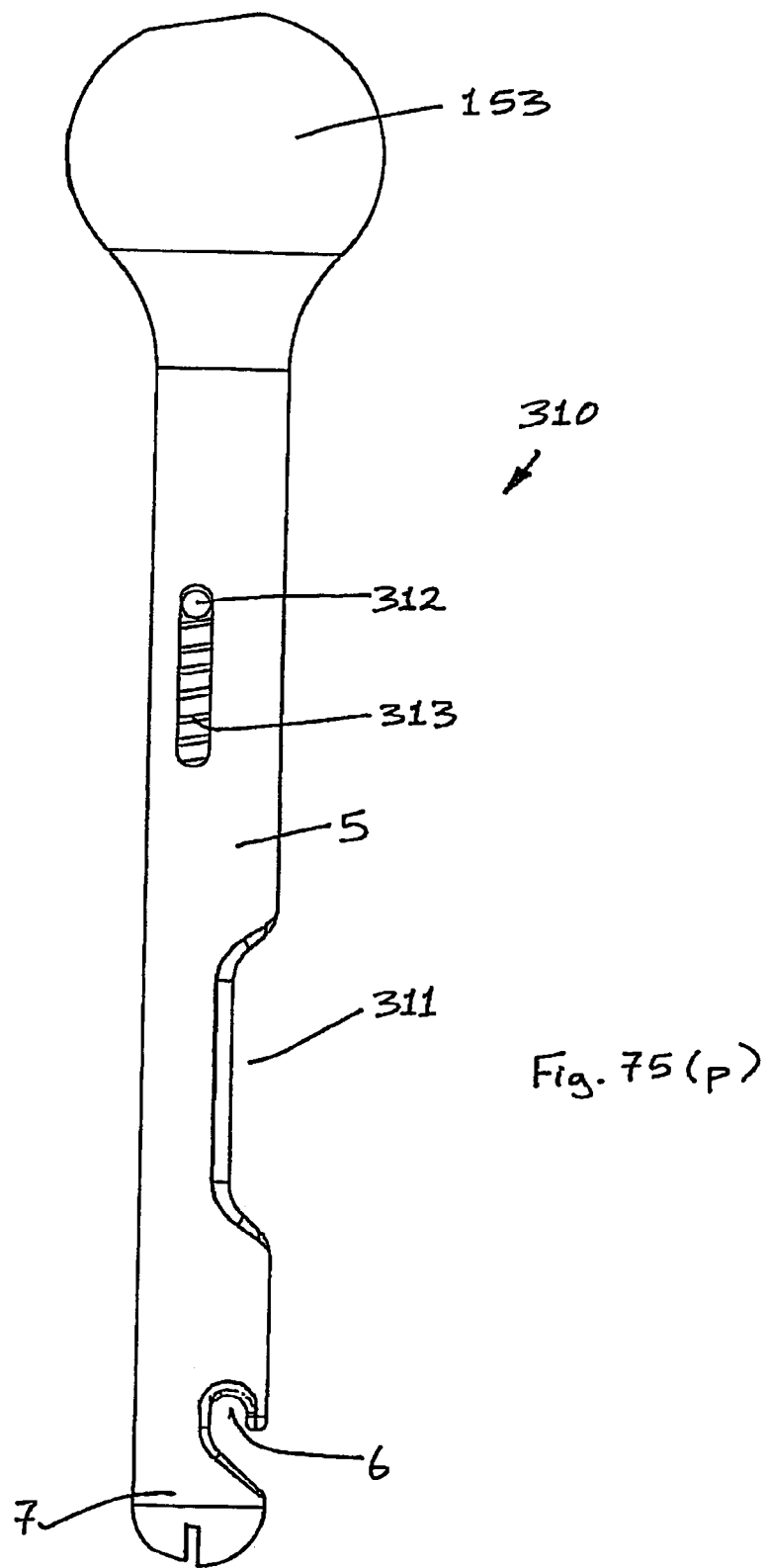
Figure 75Q:
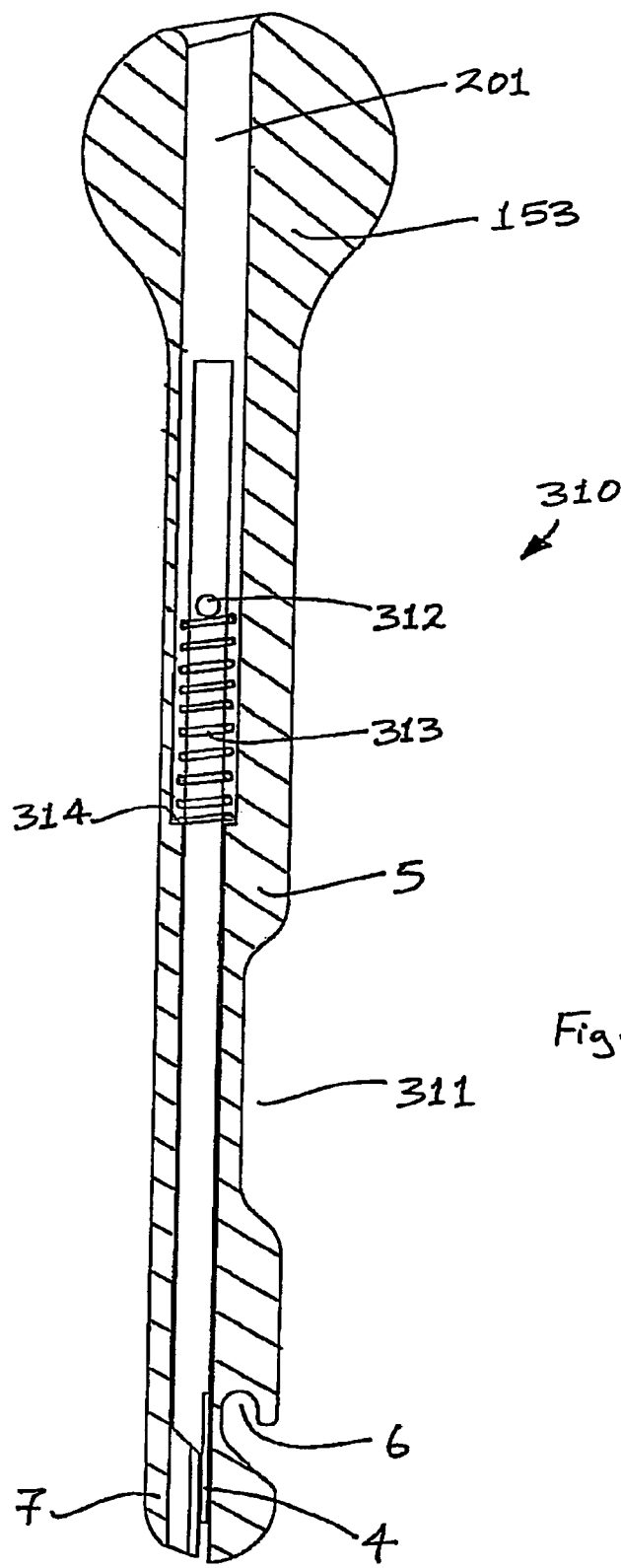

Referring to FIGS. 75(j) and 75(k) there is illustrated a further apparatus 220 according to the invention, which is similar to the apparatus 210 of FIGS. 75(h) and 75(i), and similar elements in FIGS. 75(j) and 75(l) are assigned the same reference numerals.

In this case the arm 211 is substantially rigid and is pivotably attached to the body of the conveying device 5 by means of a hinge 221. The arm 211 is pivotably movable between the obstructing configuration (FIG. 75 (j)) and the passage configuration (FIG. 75(k)).

The pivot hook 211 is moved to (i) load the distal ring 9 into the concave position 213, or (ii) allow the distal ring 9 to be removed from the concave portion 213. The addition of the pivot hook 211 ensures that the distal ring 9 is fully held in the hook 213 of the introducer 5. When required the arm 211 is moved out of the way to load or deliver the distal ring 9.

FIGS. 75(k)(i) and 75(k)(ii) illustrate another apparatus 670 according to the invention, which is similar to the apparatus 220 of the FIGS. 75(j) and 75(k), and similar elements in FIGS. 75(k)(i) and 75(k)(ii) are assigned the same reference numerals.

In this case the apparatus 670 comprises an opening device 671, in the form of a blunt, bladeless tip, fixedly attached to the distal end 7 of the conveying device 5.

The tip 671 is similar to the tip 621 described previously with reference to FIGS. 21(*q*)(i) and 21(*q*)(ii).

FIGS. 75(*k*)(i) and 75(*k*)(ii) show the hook introducer 670 with the mechanical clasp 211 to hold the 'O'-ring 9 in place. The clasp 211 could be spring loaded or controlled via a lever.

FIGS. 75 (*k*)(i) and 75(*k*)(ii) show the blunt tip 671 with two wings for serration of the tissue.

Referring to FIGS. 75(*k*)(iii) to 75(*k*)(viii) there is illustrated a further apparatus 680 according to the invention, which is similar to the apparatus 670 of FIGS. 75(*k*)(i) and 75(*k*)(ii), and similar elements in FIGS. 75(*k*)(iii) to 75(*k*)(viii) are assigned the same reference numerals.

In this case the conveying device 5 comprises a rigid arm 681 movable, under the control of a thumbswitch 682, between the obstructing configuration in which the arm 681 obstructs part of the passageway 212 (FIGS. 75(*k*)(iii) and 75(*k*)(iv)), and the passage configuration in which the arm 681 is moved distally to facilitate passage of the distal ring 9 of the wound retractor device 2 through the passageway 212 into and out of the concave portion 213 of the hook element 6 (FIGS. 75(*k*)(v) and 75(*k*)(vi)).

The locking bar feature 681 may be employed to secure the distal ring 9 to the hook 6. The apparatus 680 comprises the proximal handle 683, the shaft 5, the thumbswitch 682, the hook 6, the locking bar 681, and the bladeless tip 671. The thumbswitch 682 is spring-loaded towards the obstructing position, in which the locking bar 681 is moved proximally (FIGS. 75(*k*)(iii) and 75(*k*)(iv)).

In FIG. 75(*k*)(vi), the thumbswitch 682 is pushed down distally. This causes the locking bar 681 to move down distally also. The distal ring 9 may now be fitted onto the hook 6 (FIGS. 75(*k*)(vii) and 75(*k*)(viii)).

After the buttonhole distal ring 9 is placed on to the hook 6, the thumbswitch 682 is released. This causes the locking bar 681 to lock the ring 9 in place (FIGS. 75(*k*)(vii) and 75(*k*)(viii)). To release the ring 9, for example in the abdomen, the thumbswitch 682 may be pressed distally down again.

In FIGS. 75(*l*) to 75(*v*) there is illustrated a further apparatus 310 for inserting a surgical device at least partially through a wound opening according to the invention, which is similar to the apparatus 200 of FIGS. 75(*a*) to 75(*g*), and similar elements in FIGS. 75(*l*) to 75(*v*) are assigned the same reference numerals.

In this case the blade element 4 is biased towards the retracted configuration by means of a compression spring 313. The spring 313 is located between and engaging against an internal ledge 314 in the lumen 201 of the conveying device 5 and a laterally protruding handle 312 on the blade element 4 (FIG. 75(*n*)). In the extended configuration the spring 313 is compressed (FIG. 75(*n*)), and in the retracted configuration the spring 313 is in an uncompressed, at-rest state (FIG. 75(*q*)).

The blade element 4 is moved relative to the conveying device 5 from the retracted configuration to the extended configuration by manually pushing the handle 312 distally, for example using a thumb. To move the blade element 4 relative to the conveying device 5 from the extended configuration to the retracted configuration, the handle 312 is released and the biasing force of the spring 313 pushes the blade element 4 proximally.

A recess 311 is provided at a lateral side of the conveying device 5 to minimise the profile of the distal ring 9 during conveying through the wound opening 3 (FIGS. 75(*u*) to 75(*x*)).

In use, the distal ring 9 of the wound retractor device 2 is hooked onto the introducer handle 5 by means of the hook 6 (FIG. 75(*u*)). The blade 4 is exposed by the surgeon depressing the thumb switch 312. The introducer 5 is advanced until the surgeon sees the blade 4 appearing through abdominal wall 8 on his monitor (FIG. 75(*v*)).

The surgeon removes his thumb from the thumb switch 312. The spring 313 extends, causing the blade 4 to retract safely into the introducer handle 5 (FIG. 75(*w*)). There is thus provided a safe, blunt introducer 5 which the surgeon advances into the abdomen until the distal ring 9 is fully inside (FIG. 75(*x*)).

The introducer 5 is withdrawn from the incision 3 leaving the distal ring 9 in the abdomen and the wound retractor device 2 is ready to be deployed to retract the incision 3 (FIG. 75(*y*)).

In FIGS. 76 to 81 there is illustrated a further incising device 181 of another apparatus according to the invention, which is similar to the incising device 4 of FIGS. 25 to 30, and similar elements in FIGS. 76 to 81 are assigned the same reference numerals.

Figure 77:
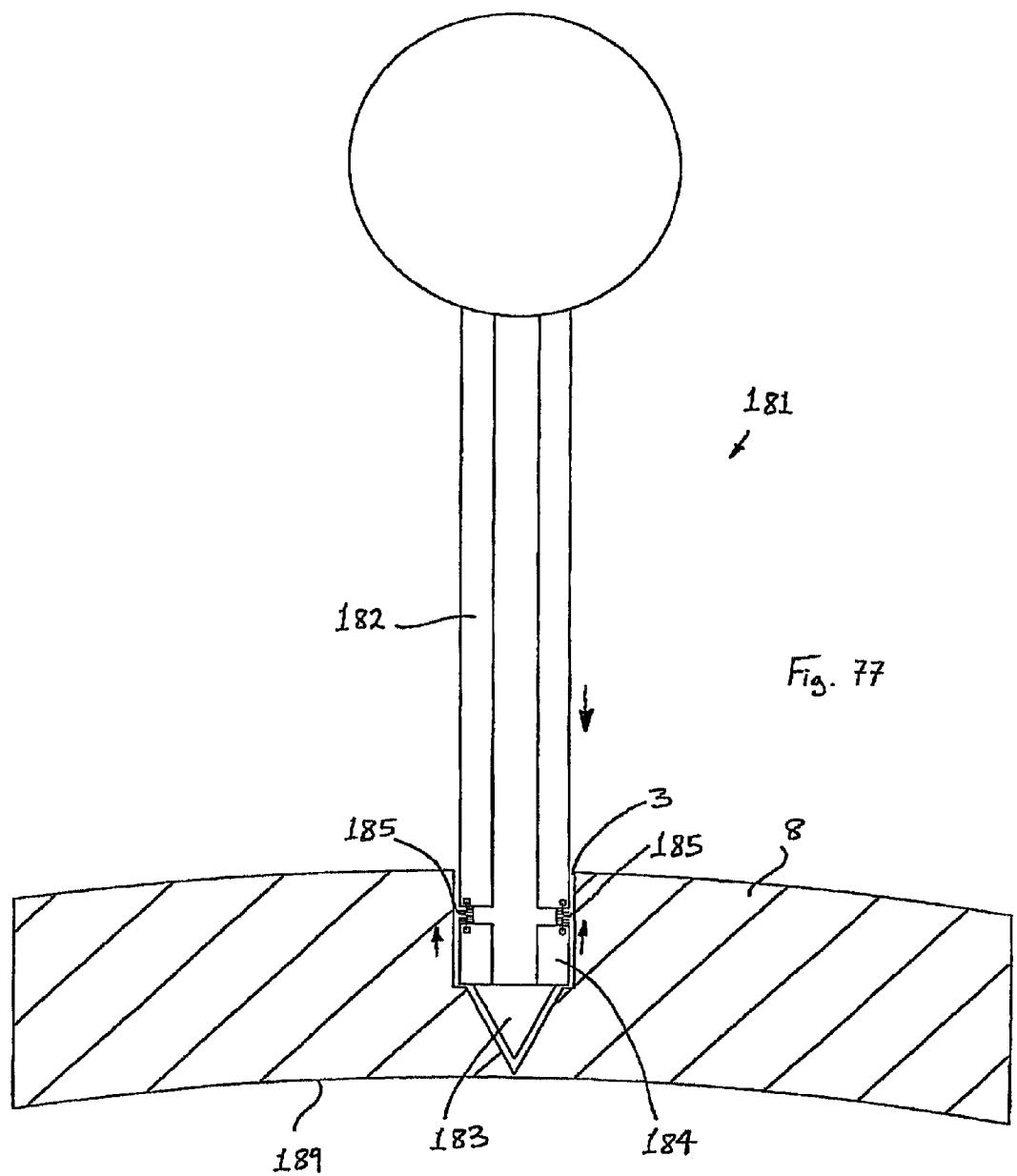

In this case the incising device 181 comprises a support element 182, a cutting element 183 for creating the wound opening 3 fixedly attached to the support element 182, and a shield element 184 for shielding the cutting element 183 movably attached to the support element 182 by means of two springs 185. The shield element 184 is movable relative to the cutting element 183 between an extended shielding configuration (FIGS. 76, 78, 79, 81) and a retracted cutting configuration (FIGS. 77 and 80). The springs 185 act to bias the shield element 184 towards the extended shielding configuration.

As illustrated in FIGS. 79 to 81, the shield element 182 has a cantilever arm 186 with a radially inwardly protruding finger 187 at a proximal end of the arm 186. The finger 187 is engageable in a recess 188 in the cutting element 183 to releasably lock the shield element 182 in the extended shielding configuration (FIG. 81).

In use, the incising device 181 is configured with the shield element 184 in the extended shielding configuration and with the finger 187 disengaged from the recess 188 (FIGS. 76 and 79). The incising device 181 is then moved distally towards the tissue 8 so that the cutting element 183 and the shield element 184 engage the tissue 8. Further movement of the incising device 181 distally causes the shield element 184 to move proximally relative to the cutting element 183 against the biasing force of the springs 185 due to the frictional resistance of the tissue 8 (FIGS. 77 and 80). The proximal movement of the shield element 184 exposes the cutting element 183. The sharpened cutting element 183 passes through the tissue 8 to create the wound opening 3 (FIG. 77).

Figure 78:
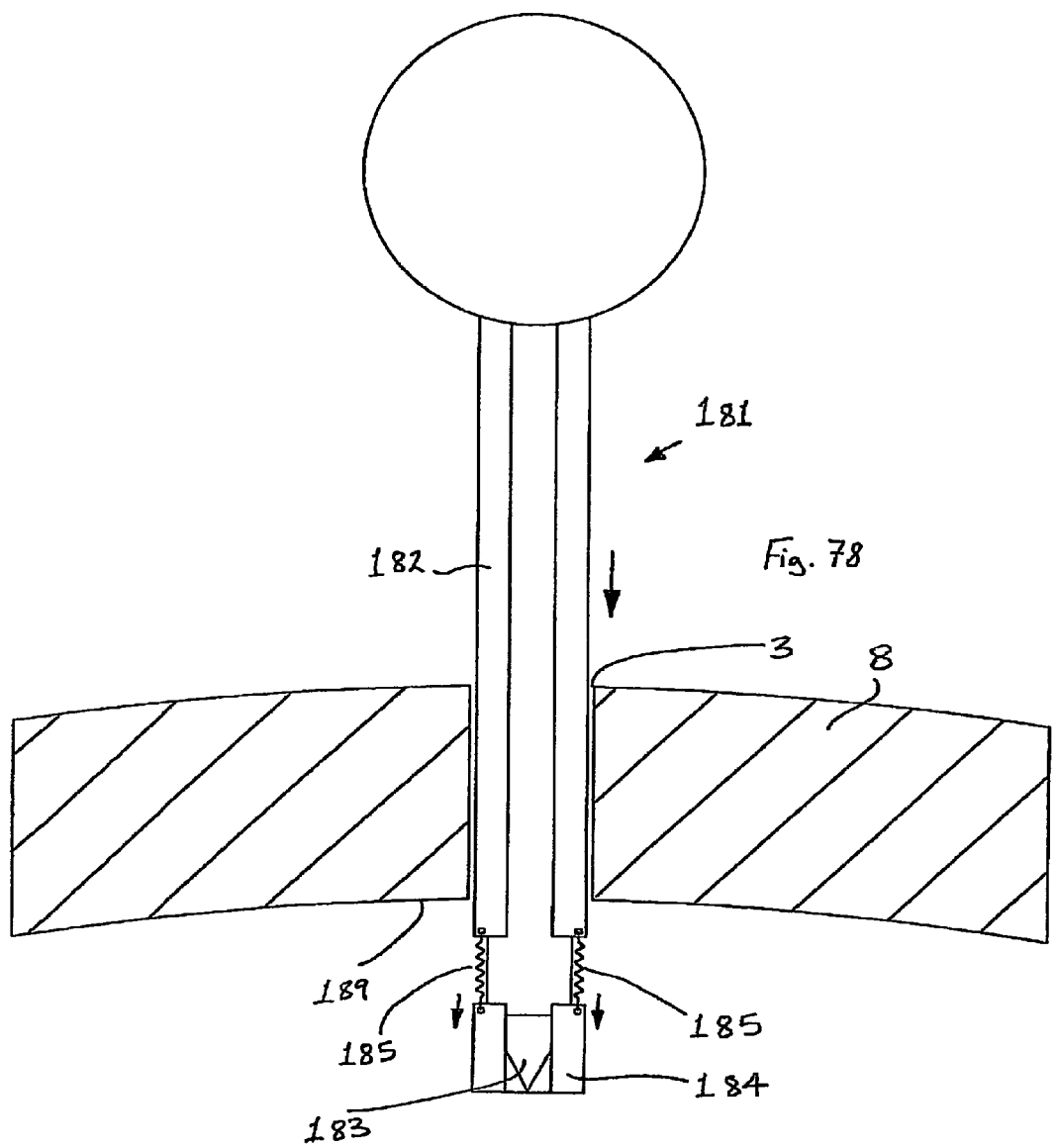

The cutting element 183 breaks through to the distal side 189 of the tissue 8, and the shield element 184 then reaches the distal side 189 of the tissue 8. When the shield element 184 reaches the distal side 189, there is no further frictional resistance to advancement of the shield element 184 and thus the shield element 184 moves distally relative to the cutting element 183 to the extended shielding configuration under the biasing force of the springs 185 (FIG. 78). As the shield element 184 moves distally, the finger 187 engages the recess 188 to lock the shield element 184 in the extended shielding configuration (FIG. 81).

In this extended shielding configuration, the shield element 184 shields the cutting element 183 and thus prevents the sharpened cutting element 183 from inadvertently contacting and potentially damaging any internal organs or tissue.

It will be appreciated that in an alternative embodiment of the invention, the shield element may be fixedly attached to the support element, and the cutting element may be movably attached to the support element, for example by means of springs.

FIGS. 82 to 88 illustrate another apparatus 300 for inserting a surgical device at least partially through a wound opening according to the invention, which is similar to the apparatus 230 of FIGS. 21(a) to 21(f), and similar elements in FIGS. 82 to 88 are assigned the same reference numerals.

In this case the apparatus 300 comprises a shield element 184 attached to the housing portion 22 by means of two compression springs 185, in a manner similar to that described previously with reference to FIGS. 76 to 81.

The shield element 184 is movable relative to the blade element 4 between an extended shielding configuration (FIG. 83) and a retracted cutting configuration (FIG. 82). The springs 185 act to bias the shield element 184 towards the extended shielding configuration.

In use, the apparatus 300 is configured with the shield element 184 in the extended shielding configuration (FIG. 84). The apparatus 300 is then moved distally towards the tissue 8 so that the blade element 4 and the shield element 184 engage the tissue 8. Further movement of the apparatus 300 distally causes the shield element 184 to move proximally relative to the blade element 4 against the biasing force of the springs 185 due to the frictional resistance of the tissue 8 (FIG. 85). The proximal movement of the shield element 184 exposes the blade element 4. The sharpened blade element 4 passes through the tissue 8 to create the wound opening.

The blade element 4 breaks through to the distal side of the tissue 8, and the shield element 184 then reaches the distal side of the tissue 8. When the shield element 184 reaches the distal side, there is no further frictional resistance to advancement of the shield element 184 and thus the shield element 184 moves distally relative to the blade element 4 to the extended shielding configuration under the biasing force of the springs 185 (FIG. 86).

In this extended shielding configuration, the shield element 184 shields the blade element 4 and thus prevents the sharpened blade element 4 from inadvertently contacting and potentially damaging any internal organs or tissue (FIG. 87). The distal ring 9 of the surgical device 2 may then be ejected from the housing portion 22 (FIG. 88).

FIGS. 82 to 88 illustrate the spring shield system. The springs 185 are configured so that the shield 184 is biased to slide forward to cover the blade 4.

The shield system protects organs from stabbing or other inadvertent damage due to introduction of the surgical device 2.

In FIG. 84 the protective shield 184 covers the blade 4 when not in use. In FIG. 85, when the introducer 5 is pushed against the skin, the shield 184 begins to retract exposing the blade 4. In FIG. 86, as soon as the blade 4 passes through the abdomen wall, the shield 184 springs back to cover the blade 4. In FIGS. 87 and 88, the introducer 5 can now be pushed further inside to release the O-ring 9.

Figure 75Y:
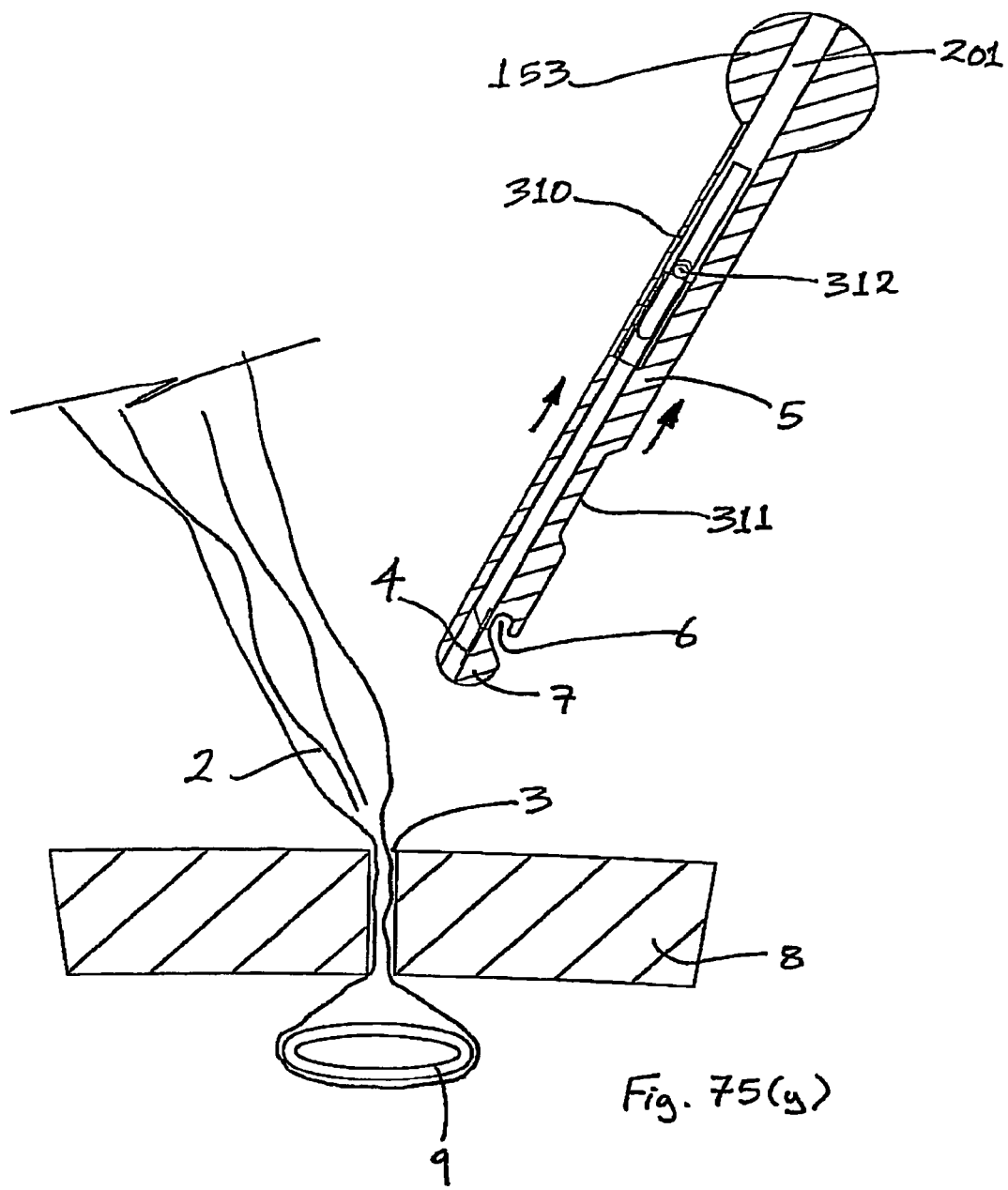

Referring to FIGS. 89 to 102 there is illustrated another apparatus 500 for inserting a surgical device at least partially through a wound opening according to the invention, which is similar to the apparatus 310 of FIGS. 75(l) to 75(y), and similar elements in FIGS. 89 to 102 are assigned the same reference numerals.

In this case the apparatus 500 comprises a holder element 501 concentrically mounted around the conveying device 5. The holder element 501 is suitable for holding the distal ring 9 of the wound retractor device 2 in a low-profile configuration, in this case an oval-shaped configuration (FIG. 95), during insertion of the distal ring 9 through the wound opening 3.

Figure 94:
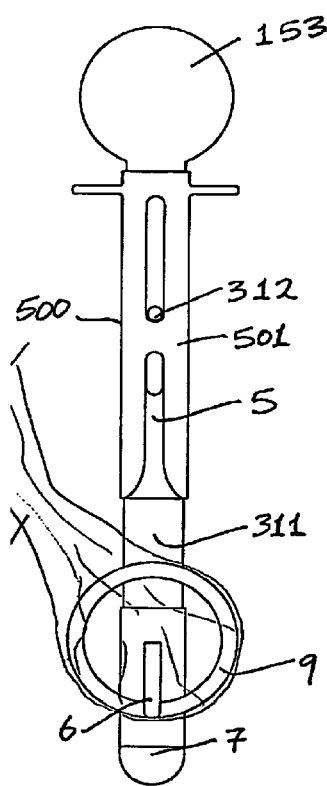
Figure 95:
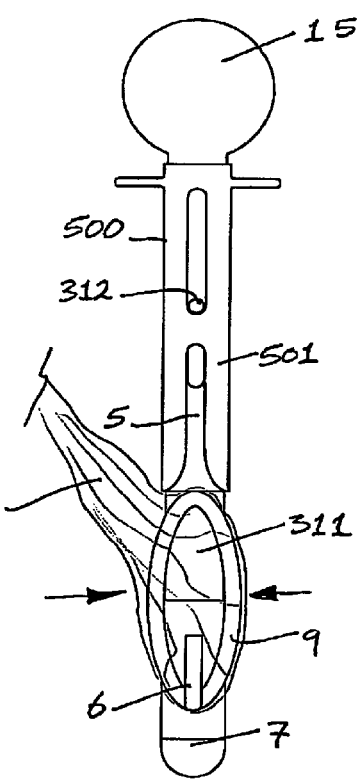

The holder element 501 is longitudinally slidable relative to the conveying device 5 between a holding configuration in which the distal ring 9 is held in the low-profile, oval configuration (FIG. 96), and a release configuration in which the distal ring 9 is released (FIG. 94).

Figure 96:
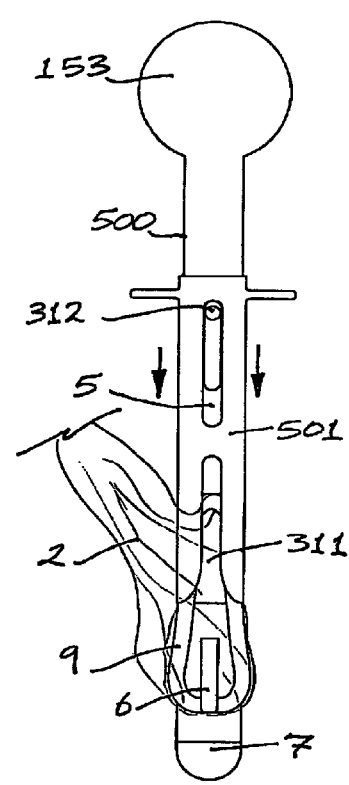

In use the distal ring 9 of the wound retractor device 2 is hooked onto the introducer handle 5 by means of the hook 6 (FIG. 94). The distal ring 9 is compressed into the low-profile, oval configuration (FIG. 95), and the holder element 501 is slid distally along the conveying device 5 from the release configuration to the holding configuration to hold the distal ring 9 in the low-profile, oval configuration (FIG. 96). The blade 4 is exposed by the surgeon depressing the thumb switch 312 (FIG. 97). The introducer 5 is advanced until the surgeon sees the blade 4 appearing through the abdominal wall 8 on his monitor (FIG. 98). The surgeon removes his thumb from the thumb switch 312. The spring 313 extends, causing the blade 4 to retract safely into the introducer handle 5 (FIG. 99). There is thus provided a safe, blunt introducer 5 which the surgeon advances into the abdomen until the distal ring 9 in the low-profile, oval configuration is fully inside (FIG. 100). The holder element 501 is slid proximally along the conveying device 5 from the holding configuration to the release configuration to release the distal ring 9 (FIG. 101). The introducer 5 is withdrawn from the incision 3 leaving the distal ring 9 in the abdomen and the wound retractor device 2 is ready to be deployed to retract the incision 3 (FIG. 102).

Figure 89:
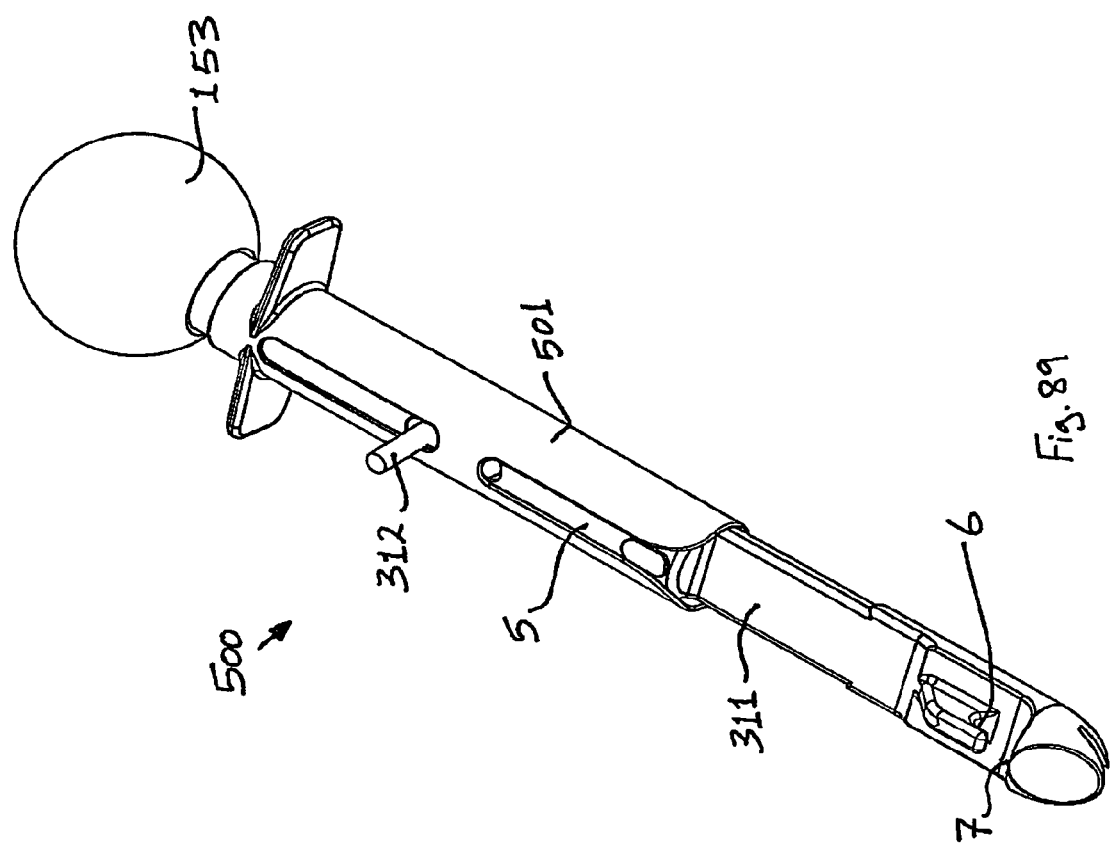
FIG. 89 is a perspective view of another apparatus for inserting a surgical device at least partially through a wound opening according to the invention with a holder element in a release configuration and with an incising device in a retracted configuration.
Figure 90:
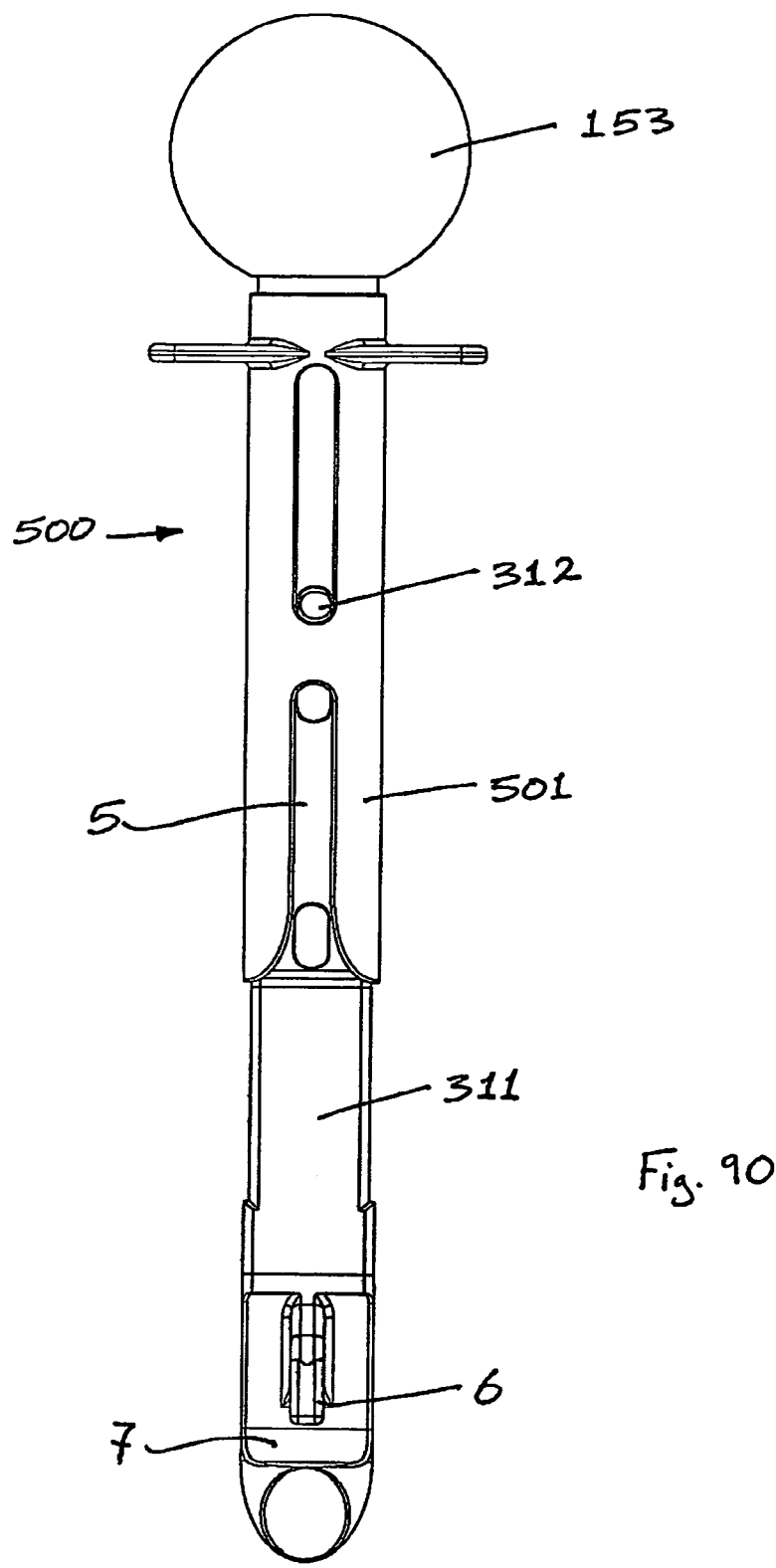
FIG. 90 is a front view of the apparatus of FIG. 89.
Figure 91:
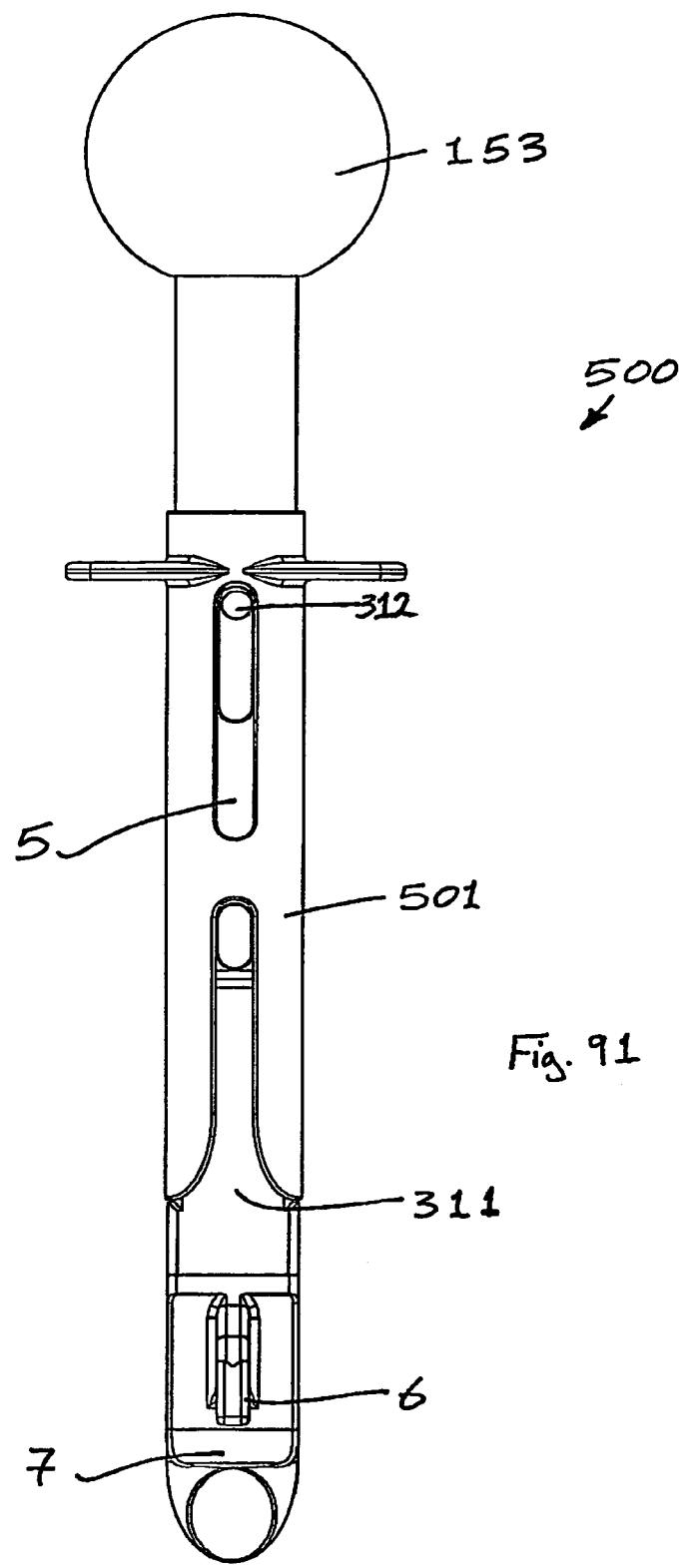
FIG. 91 is a front view of the apparatus of FIG. 89 with the holder element in a holding configuration and with the incising device in the retracted configuration.

In FIG. 89, the ring retainer 501 is fully retracted and the blade 4 is fully retracted.

Figure 92:
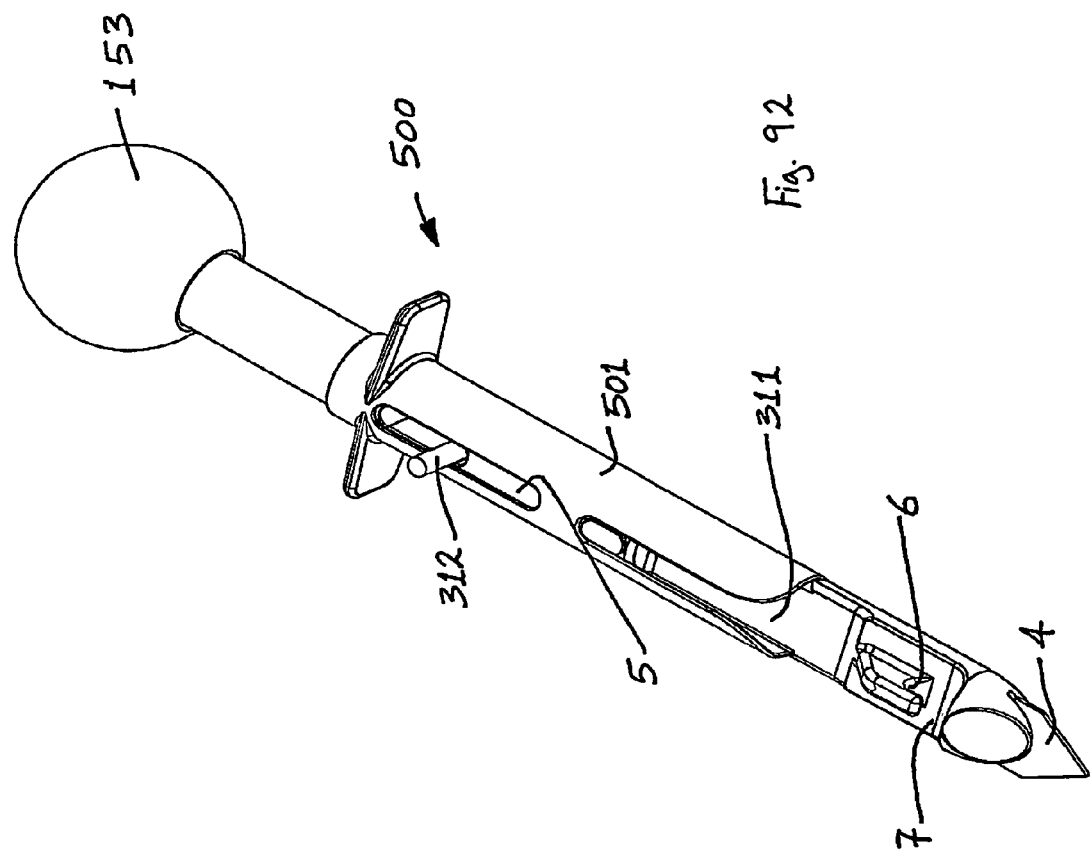
FIG. 92 is a perspective view of the apparatus of FIG. 89 with the holder element in the holding configuration and with the incising device in an extended configuration.
Figure 93:
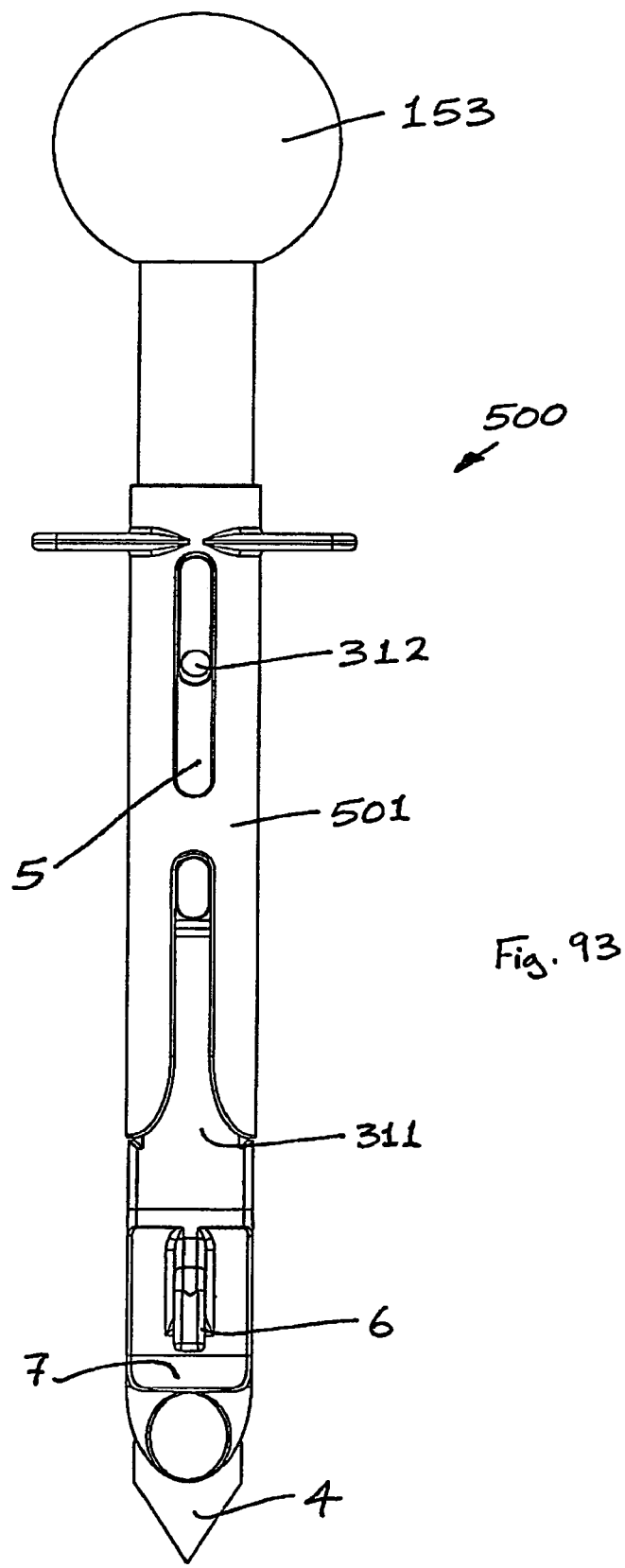
FIG. 93 is a front view of the apparatus of FIG. 92.

In FIG. 92 the ring retainer 501 is fully advanced and the blade 4 is fully exposed.

In FIG. 97 the thumb switch 312 is pushed down to expose the blade 4.

In FIG. 98 the introducer 500 easily advances through the abdominal wall 8 because the distal ring 9 is compressed and does not present any excess width. The blade 4 is seen on a laparoscope to be just extending into the abdomen.

In FIG. 99 the surgeon removes his finger from the thumb-switch 312. The internal spring now automatically retracts the blade 4.

In FIG. 100 the introducer 500 can now be safely advanced into the abdomen.

In FIG. 101, the ring retainer 501 is pulled back up. The distal ring 9 is released and is no longer compressed. Alternatively the distal ring 9 could be ejected instead of withdrawing the holder element 501.

In FIG. 102, the introducer 500 is withdrawn from the incision 3. The distal ring 9 simply falls off the hook 6 and remains in the abdomen. The buttonhole device 2 is ready to be fired.

In FIGS. 103 to 107, there is illustrated another apparatus 510 for inserting a surgical device at least partially through a wound opening according to the invention, which is similar to the apparatus 230 of FIGS. 21(a) to 21(f), and similar elements in FIGS. 103 to 107 are assigned the same reference numerals.

Figure 104:
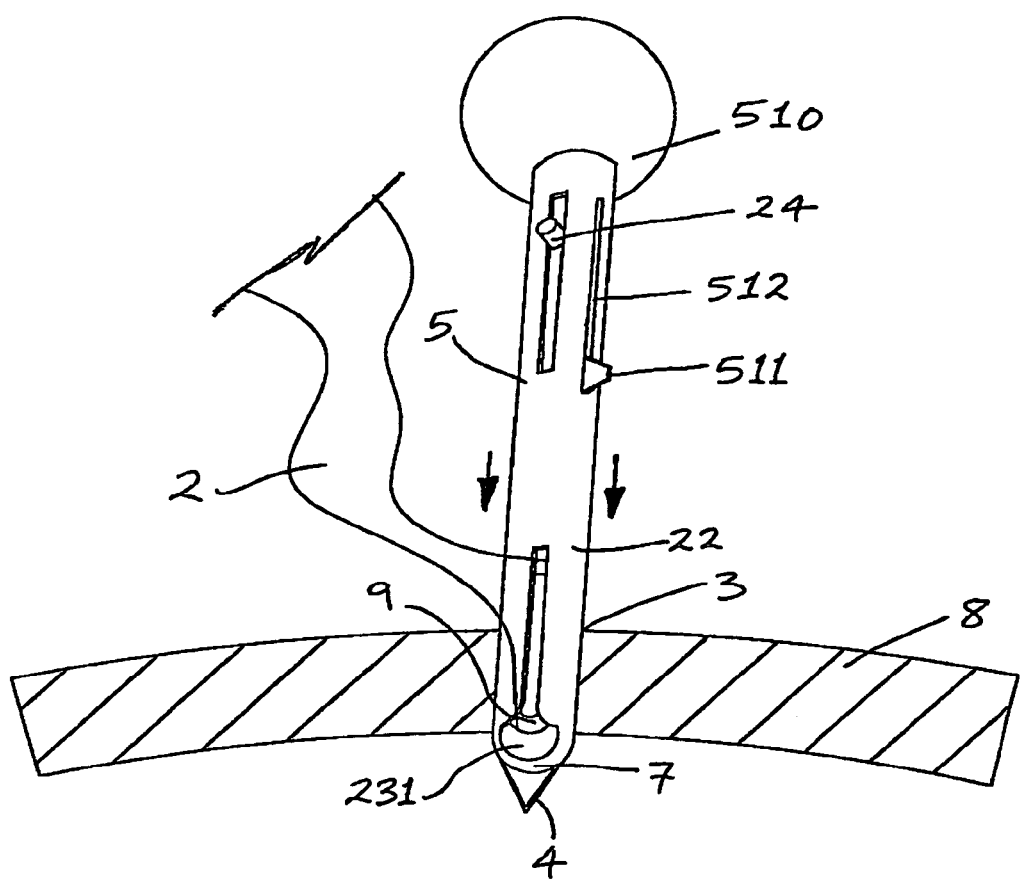
FIGS. 104 to 107 are partially cut-away, perspective views of the apparatus of FIG. 103, in use.
Figure 105:
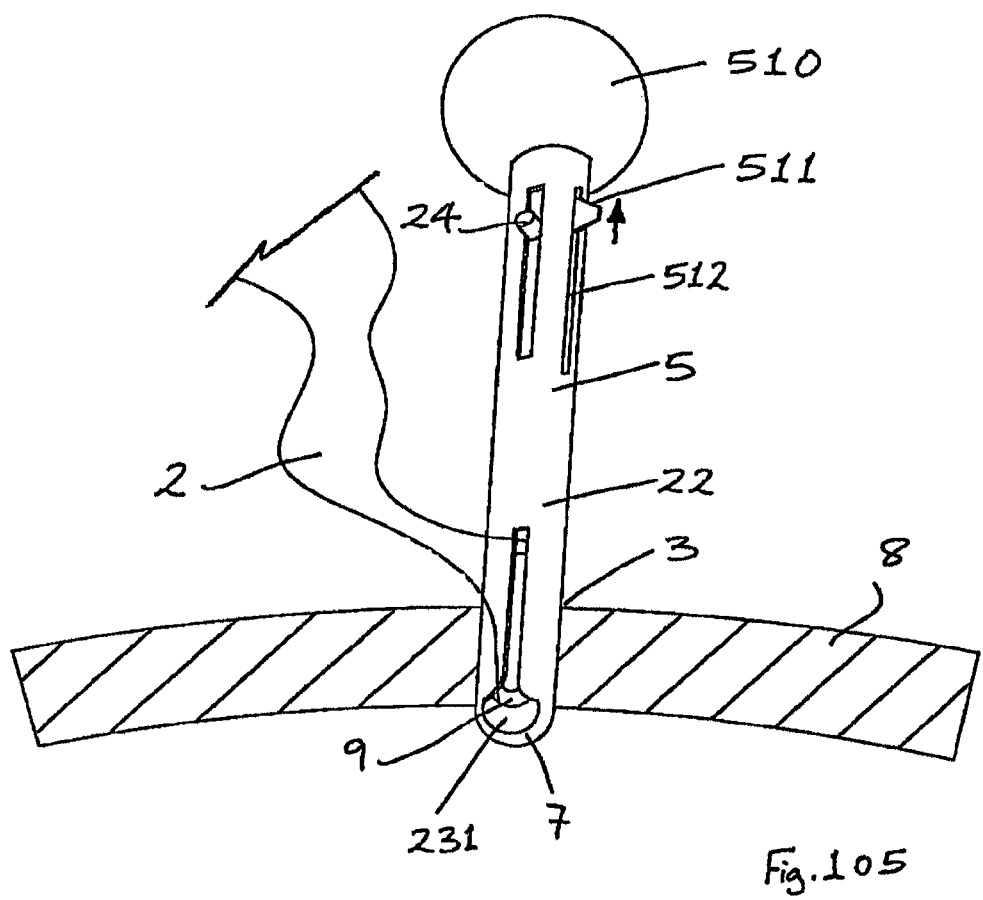

In this case the blade element 4 is movable relative to the housing portion 22 between an extended configuration (FIG. 104) and a retracted configuration (FIG. 105). An actuator 511 is provided extending through a slot 512 in the housing portion 22 to facilitate movement of the blade element 4 between the extended configuration and the retracted configuration.

In use, the distal ring 9 of the wound retractor device 2 is compressed and inserted through the opening 231 into the housing portion 22 with the sleeve of the wound retractor device 2 extending out of the housing portion 22 through the opening 231. The apparatus 510 is extended through the tissue 8 with the blade element 4 in the extended configuration to create the wound opening 3 (FIG. 104). When the blade element 4 has passed fully through the tissue 8 and is located within the wound interior, the blade element 4 is moved proximally to the retracted configuration by means of the actuator 511 while the housing portion 22 is held in a fixed position (FIG. 105). It is noted that the distal ring 9 has been conveyed only partially through the wound opening 3 when the blade element 4 is retracted.

Figure 106:
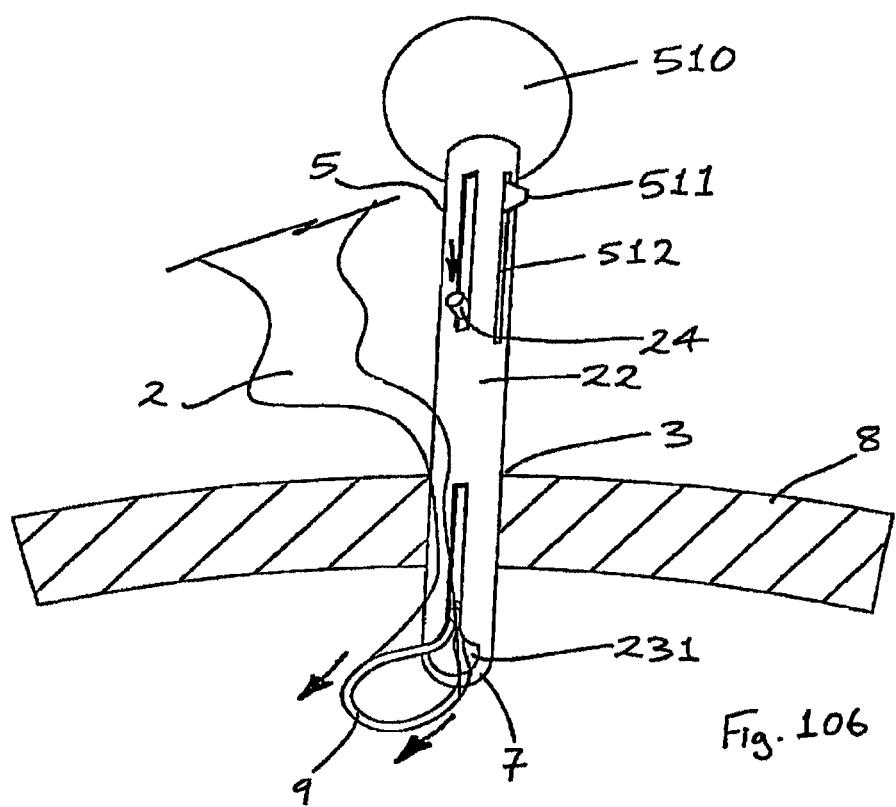
Figure 107:
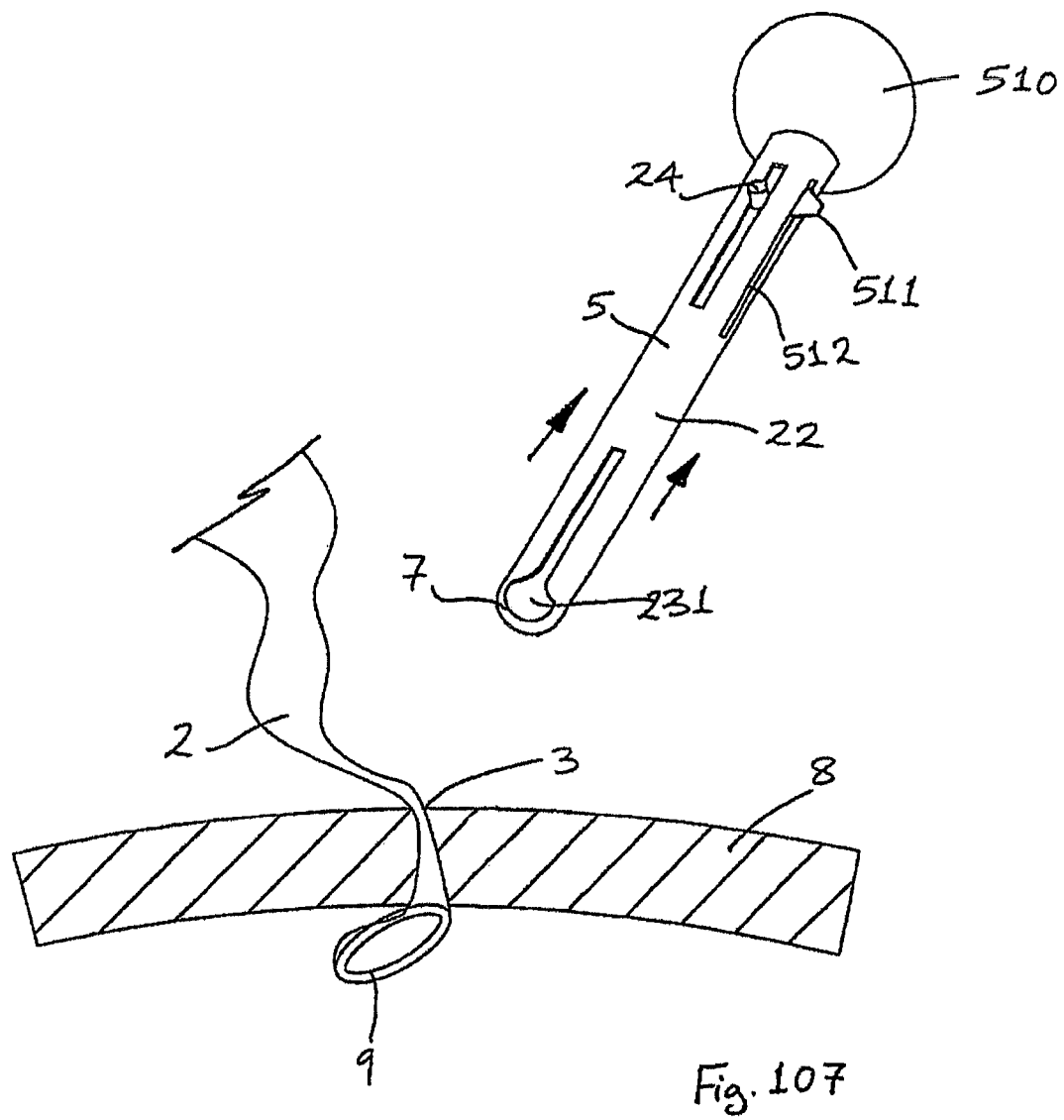
Figure 110:
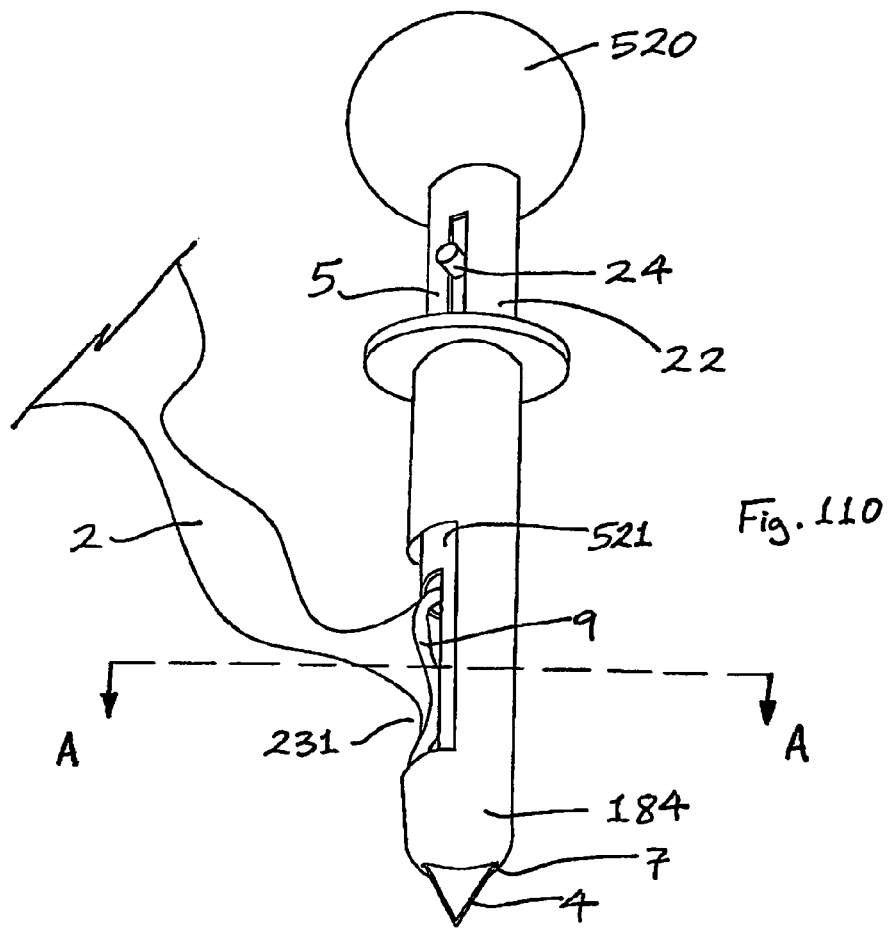

The apparatus 510 is then advanced further through the wound opening 3, and the plunger 24 is depressed to eject the distal ring 9 from within the housing portion 22 (FIG. 106). The apparatus 510 is withdrawn from the wound opening 3 leaving the wound retractor device 2 in position extending through the wound opening 3 and with the distal ring 9 distally of the wound opening 3 (FIG. 107).

The introducer 510 involves crushing the "O"-ring 9 down and sliding it into a slot 231 in the shaft 22 of the introducer 510. The slot 231 is at the distal tip of the shaft 22 so as to make firing the distal ring 9 safer.

Figure 103:
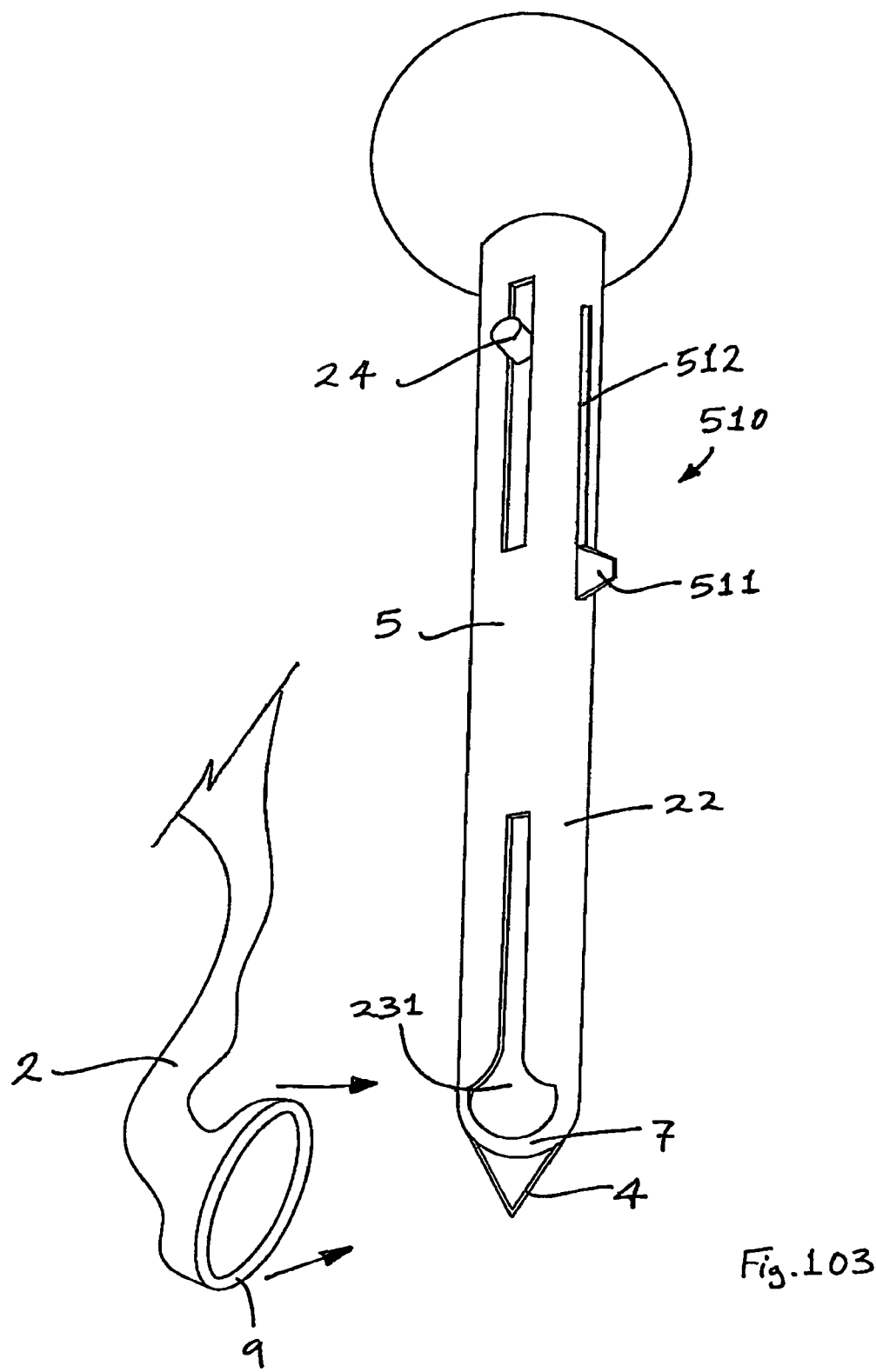
FIG. 103 is a perspective view of another apparatus for inserting a surgical device at least partially through a wound opening according to the invention.

In FIG. 103, the "O"-ring 9 is compressed and slid inside the shaft 22. The housing portion 22 may have an oval-shaped cross-section.

In FIG. 104 the introducer 510 is pushed into the abdomen wall 8. When the blade 4 is visible, the blade activation lever 511 is pulled up (FIG. 105) and the introducer 510 can be pushed in further if needed.

In FIG. 106 the plunger activation lever 24 is pushed downwards releasing the "O"-ring 9 and sleeve into the abdomen.

FIGS. 108 to 115 illustrate another apparatus 520 according to the invention, which is similar to the apparatus 300 of FIGS. 82 to 88, and similar elements in FIGS. 108 to 115 are assigned the same reference numerals.

In this case the blade element 4 is fixedly attached to the distal end 7 of the housing portion 22. The shield element 184 is provided in the form of a tubular element concentrically mounted around the housing portion 22. The shield element 184 is manually movable relative to the housing portion 22 between the extended shielding configuration (FIG. 108) and the retracted cutting configuration (FIG. 109).

A cut-out portion 521 is provided in the shield element 184 to facilitate access to the opening 231 in the housing portion 22.

Figure 111:
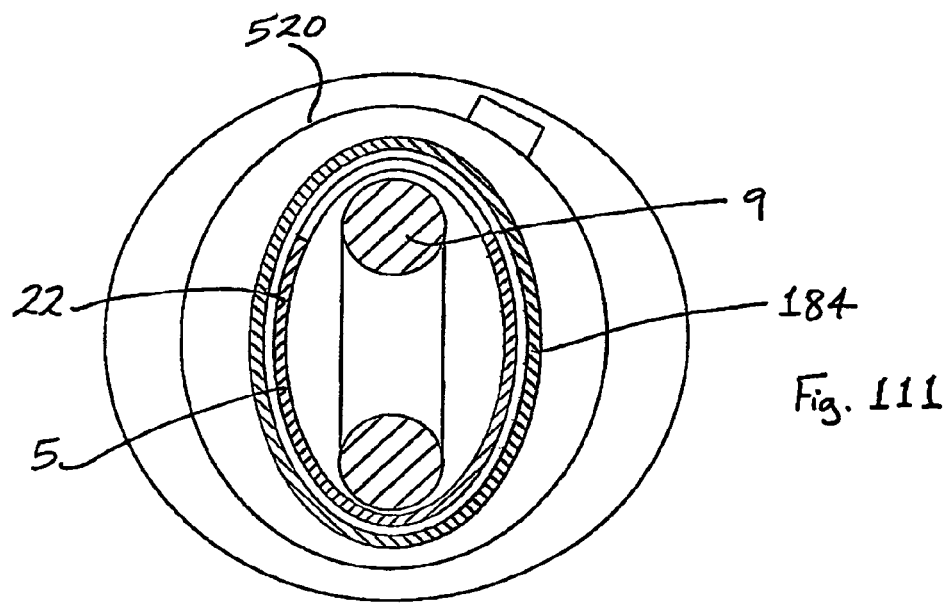
FIG. 111 is a view along line A-A in FIG. 110.

In this case the housing portion 22 has a substantially oval-shaped cross-section, as illustrated in FIG. 111. By streamlining the distal ring 9 into a compressed, oblong configuration, it may be easier to pass the distal ring 9 through the incision 3.

Figure 112:
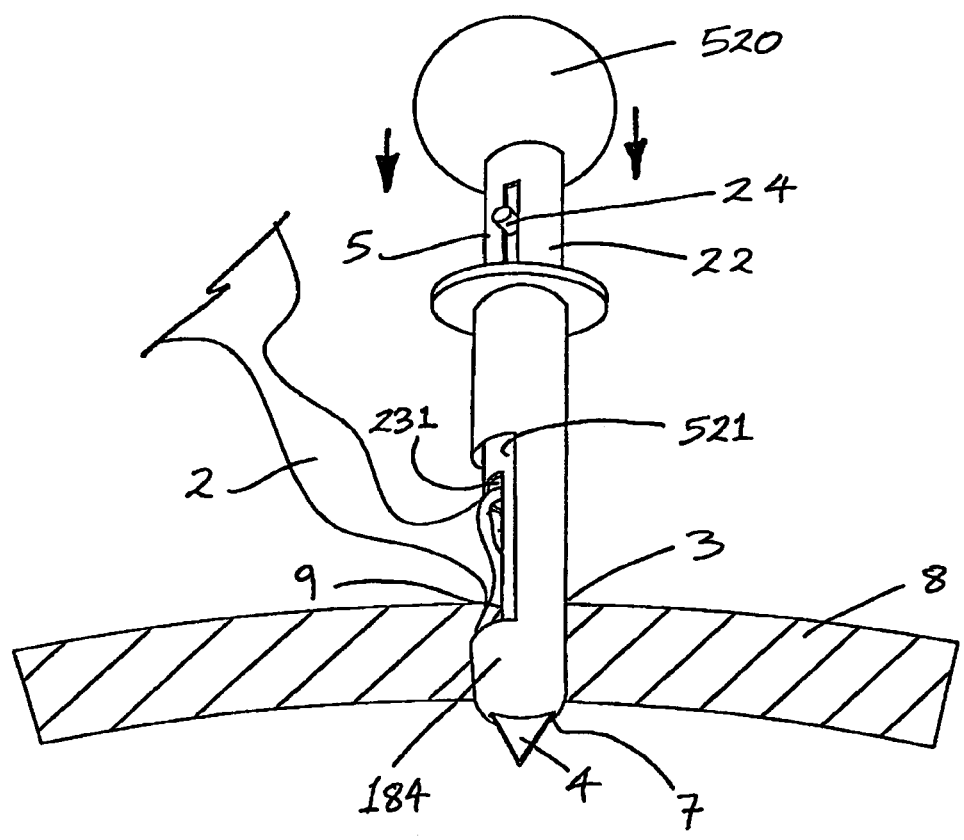
FIGS. 112 to 115 are partially cut-away, perspective views of the apparatus of FIG. 108, in use.
Figure 113:
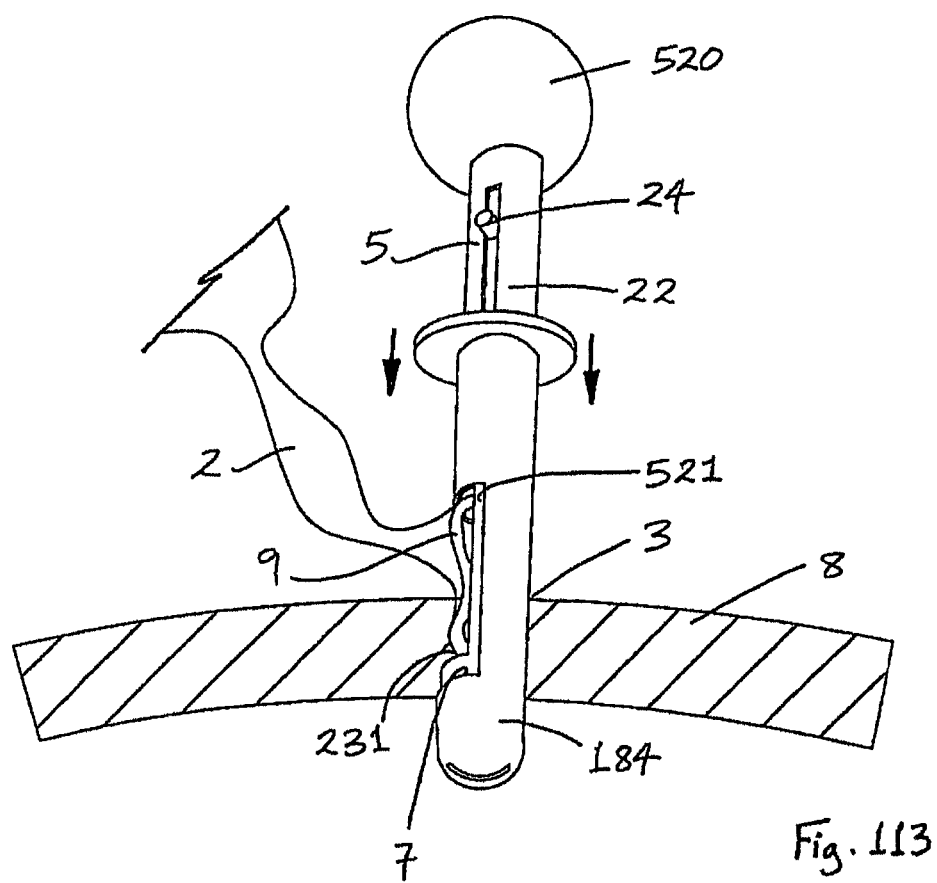

In use, the distal ring 9 of the wound retractor device 2 is compressed and inserted through the cut-away portion 521 in the shield element 184 and through the opening 231 into the housing portion 22 (FIGS. 108 and 109). The apparatus 520 is passed through the tissue 8 with the shield element 184 in the retracted cutting configuration to create the wound opening 3 through the tissue 8 (FIG. 112). When the blade element 4 has passed fully through the tissue 8 and is located within the wound interior, the shield element 184 is pushed distally while holding the housing portion 22 in a fixed position to move the shield element 184 to the extended shielding configuration (FIG. 113). It is noted that the blade element 4 is shielded before the distal ring 9 has been conveyed fully through the wound opening 3.

Figure 114:
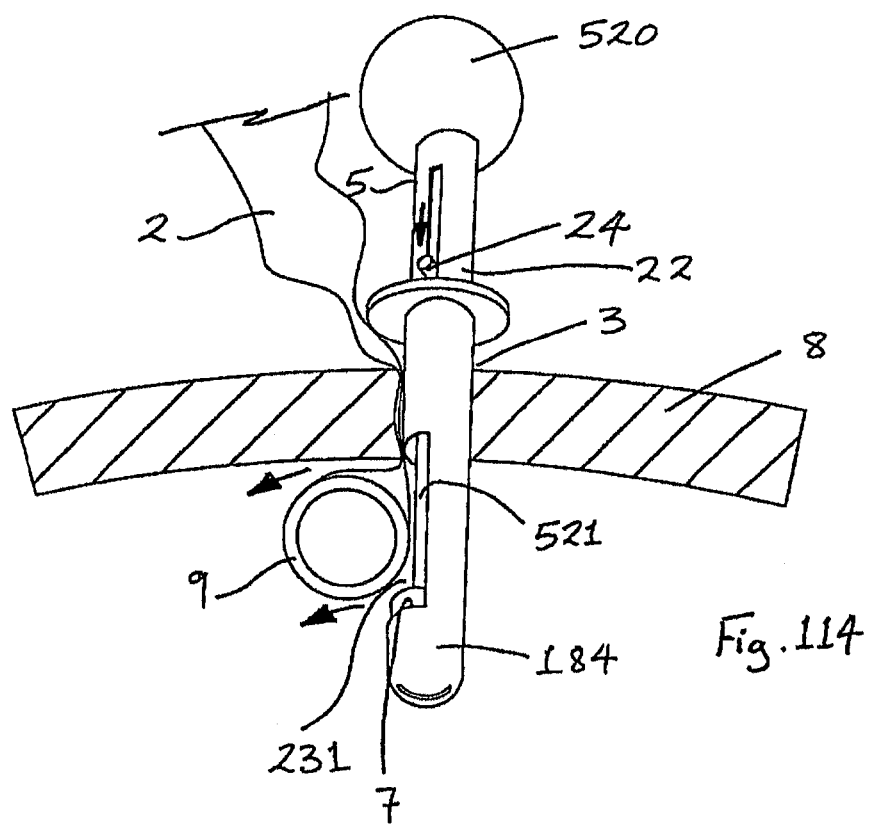
Figure 115:
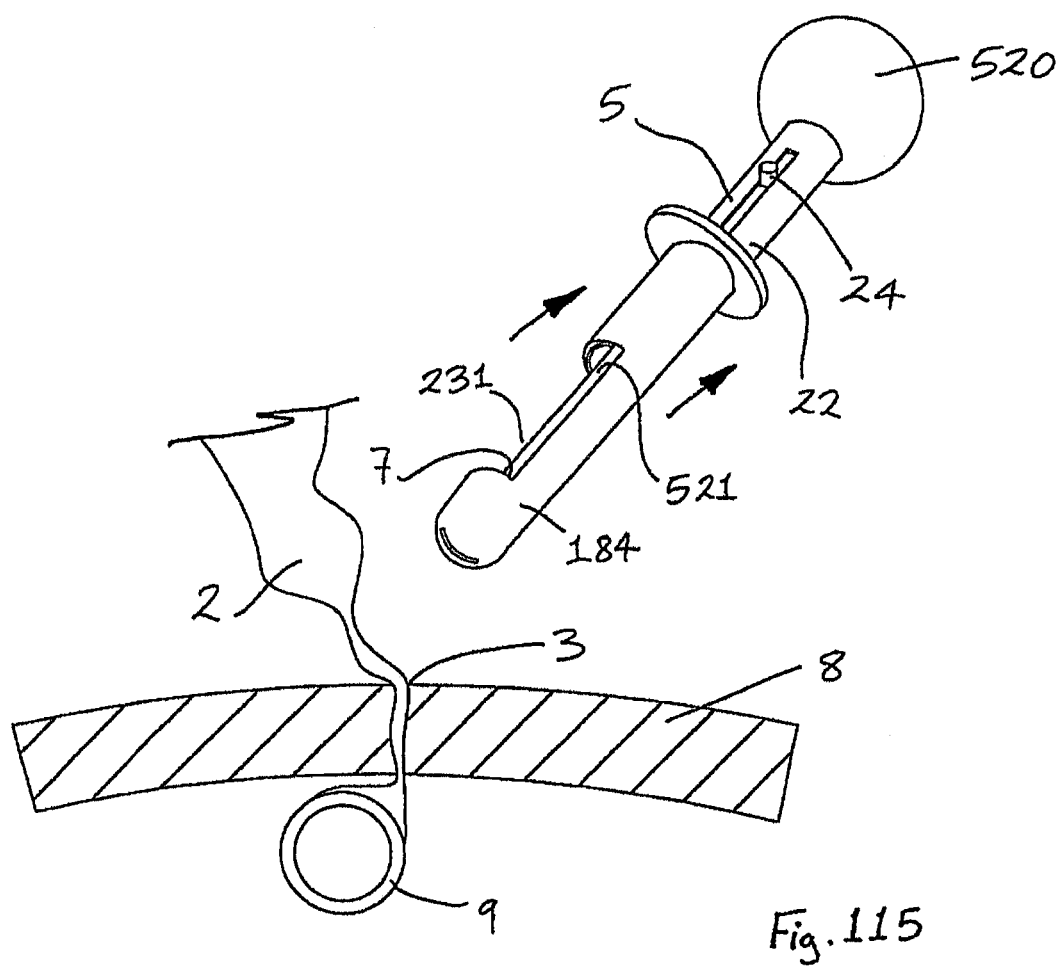

The apparatus 520 is inserted further through the wound opening 3 until the opening 231 is fully within the wound interior. The plunger 24 is then depressed to eject the distal ring 9 out of the housing portion 22 through the opening 231 and through the cut-away portion 521 (FIG. 114). The apparatus 520 is removed from the wound opening 3 leaving the distal ring 9 within the wound interior and the wound retractor device 2 extending through the wound opening 3 (FIG. 115).

The introducer 520 uses a system where the "O"-ring 9 and the sleeve are encapsulated inside the shaft 22. The sliding sheath 184 holds the "O"-ring 9 in place inside the shaft 22 and pushes forward to cover the blade 4 and release the "O"-ring 9.

The shaft 22 of the introducer 520 is oval in shape allowing easier compression of the "O"-ring 9.

When the blade 4 is visible through the underside of the abdomen wall 8, the sliding sheath 184 can be pushed forward to cover the blade element 4 (FIG. 113).

When the blade 4 is protected, the introducer 520 can be pushed in further if desired. When in far enough, the plunger 24 can be pushed down via the plunger lever to release the "O"-ring 9 and sleeve into the abdomen (FIG. 114).

Figures 116, 117:
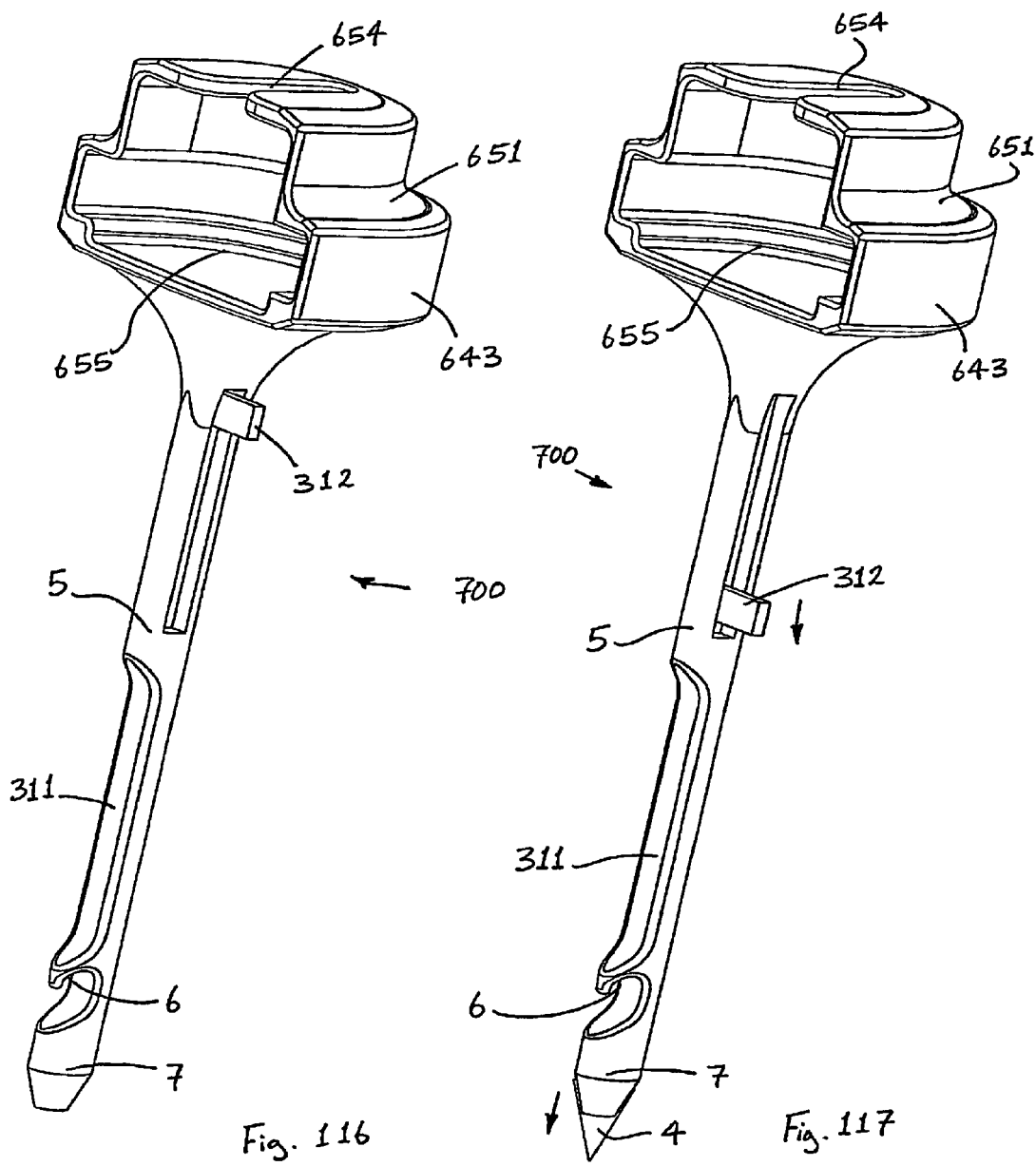
FIG. 116 is a perspective view of another apparatus for inserting a surgical device at least partially through a wound opening according to the invention in a retracted configuration.
FIG. 117 is a perspective view of the apparatus of FIG. 116 in an extended configuration.

FIGS. 116 and 117 illustrate another apparatus 700 according to the invention, which is similar to the apparatus 310 of FIGS. 75(*l*) to 75(*v*), and similar elements in FIGS. 116 and 117 are assigned the same reference numerals.

In this case the apparatus 700 comprises a receiver housing portion 651 similar to that described previously with reference to FIGS. 24(*k*) to 24(*m*). The apparatus 700 comprises the housing 651 for the outer proximal ring and seal of the wound retractor 2, the hook 6 and the blade 4. In use the handle 312 may be pushed down to expose the blade 4.

It will be appreciated that the apparatus of the invention are suitable for inserting a variety of surgical devices at least partially through a wound opening. For example the surgical device could be a wound retractor device as described previously. A sealing valve may be mounted to the wound retractor device. The sealing valve could be at least partially of a gelatinous elastomeric material. The sealing valve could be mounted to the wound retractor device before insertion through the wound opening or after insertion through the wound opening.

It will be appreciated that the apparatus of the invention may comprise an incising device in any suitable form. For example, the incising device may comprise a flat-tipped blade element or a pyramid-tipped blade element, or any other suitable blade element.

In the embodiments of the invention described above, the cutting element/blade element of the conveying device is pushed fully through the thickness of the tissue to create a wound opening. However it will be appreciated that the invention also provides a method of creating a wound opening in tissue in which the cutting element/blade element is pushed through the tissue only until the leading tip emerges on the interior side of the tissue. The cutting element/blade element may then be withdrawn and the distal ring of the surgical device pushed distally through the partially created wound opening. As the distal ring is pushed distally, the sides of the partially created wound opening are forced apart to create a wound opening. This method results in a smaller incision size and reduces the risk of herniation, by relying on the elasticity of the tissue to create the wound opening rather than relying on a larger incision size.

The invention is not limited to the embodiments hereinbefore described, with reference to the accompanying drawings, which may be varied in construction and detail.

The invention claimed is:

1. An apparatus for inserting a surgical device at least partially through a wound opening, the apparatus comprising:
    a holder including:
        a proximal portion having a proximal opening,
        a side portion having a slot,
        a distal portion having a distal opening, and a passage configured to receive at least a portion of the surgical device; and a movable member coupled to the holder and movable relative to the holder, the movable member including:
a proximal portion,
a shaft extending from the proximal portion of the movable member, the shaft entering the holder through the proximal opening and being received in the passage of the holder,
a protrusion formed on an outer surface of the shaft, the protrusion extending into the slot of the holder, wherein the protrusion and the slot selectively limit relative motion between the movable member and the holder, and
a distal portion configured to engage the surgical device.

2. The apparatus of claim 1, wherein the slot extends longitudinally along the side portion of the holder.

3. The apparatus of claim 1, wherein a proximal portion of the slot limits proximal movement of the shaft relative to the holder.

4. The apparatus of claim 1, wherein edges of the side portion that form the slot engage side portions of the protrusion.

5. The apparatus of claim 1, wherein the shaft is selectively slidable into and out of the proximal opening of the holder.

6. The apparatus of claim 1, wherein the distal portion of the movable member is selectively slidable into and out of the distal opening.

7. The apparatus of claim 1, wherein the movable member is movable to a distalmost position relative to the holder, and at least a portion of the protrusion extends into the slot when the movable member is in the distalmost position.

8. An apparatus for inserting a surgical device at least partially through a wound opening, the apparatus comprising:
a holder including:
a proximal portion having a proximal opening,
a distal portion having a distal opening,
a side portion having a slot connected to the distal opening, wherein edges of the slot adjacent the distal opening diverge, and
a passage configured to receive at least a portion of the surgical device; and
a movable member coupled to the holder and movable relative to the holder, the movable member including:
a proximal portion including a protrusion forming a proximal end,
a shaft extending from the protrusion, the shaft entering the holder through the proximal opening and being slidably received in the passage of the holder, the shaft including a longitudinal axis, wherein the protrusion is aligned with the longitudinal axis, and
a distal portion configured to engage the surgical device, wherein the distal portion is selectively extendable out of and retractable into the distal opening.

9. The apparatus of claim 8, wherein a width of the slot increases as the slot approaches the distal opening.

10. The apparatus of claim 8, wherein a portion of the slot has edges that are substantially parallel.

11. The apparatus of claim 8, wherein the shaft includes a protrusion extending into the slot, the shaft protrusion being formed on an outer surface of the shaft.

12. The apparatus of claim 8, wherein the proximal end protrusion is wider than the shaft.

13. An apparatus for inserting a surgical device at least partially through a wound opening, the surgical device including at least a distal ring and a sleeve, the apparatus comprising:
a holder including:
a proximal portion having a proximal opening and at least one gripping protrusion extending from an outer surface of the proximal portion of the holder,
a passage configured to receive at least a portion of the distal ring of the surgical device,
a distal portion having a distal opening configured to allow at least a portion of the distal ring to enter into and exit from the passage, and
a side portion having a slot connected to the distal opening, wherein edges of the slot adjacent the distal opening diverge, and the slot is configured to receive at least a portion of the sleeve of the surgical device; and
a movable member coupled to the holder and movable relative to the holder, the movable member being movable relative to the holder between a first position allowing at least a portion of the distal ring of the surgical device to enter into the passage of the holder, and a second position for deploying at least a portion of the distal ring from the holder, the movable member including:
a proximal portion including a protrusion forming a proximal end, and
a shaft extending from the protrusion, the shaft entering the holder though the proximal opening and being slidably received in the passage of the holder, the shaft including a longitudinal axis, and the protrusion being aligned with the longitudinal axis of the shaft.

14. The apparatus of claim 13, wherein a width of the slot increases as the slot approaches the distal opening.

15. The apparatus of claim 13, wherein a distal portion of the movable member is selectively extendable out of and retractable into the distal opening.

16. The apparatus of claim 13, wherein the movable member includes a shaft protrusion extending into the slot, the shaft protrusion being formed on an outer surface of the shaft.

17. The apparatus of claim 13, wherein the movable member includes a distally facing surface configured to push the distal ring out of the passage as the movable member moves to the second position.

18. The apparatus of claim 13, wherein the at least one gripping protrusion includes a first gripping protrusion extending from a first side of the outer surface of the holder, and a second gripping protrusion extending from a second side of the outer surface of the holder, the second side being opposite the first side.

19. The apparatus of claim 13, wherein the at least one gripping protrusion extends substantially perpendicular to a longitudinal axis of the holder.

* * * * *